United States Patent
Brodney et al.

(10) Patent No.: US 11,312,713 B2
(45) Date of Patent: *Apr. 26, 2022

(54) IMIDAZO[4,5-C]QUINOLINE DERIVATIVES AS LRRK2 INHIBITORS

(71) Applicant: Pfizer Inc., New York, NY (US)

(72) Inventors: Michael Aaron Brodney, Newton, MA (US); Thomas Allen Chappie, Carlisle, MA (US); Jinshan Michael Chen, Madison, CT (US); Jotham Wadsworth Coe, Niantic, CT (US); Karen Jean Coffman, Pawcatuck, CT (US); Paul Galatsis, Newton, MA (US); Michelle Renee Garnsey, Providence, RI (US); Christopher John Helal, Mystic, CT (US); Jaclyn Louise Henderson, Cambridge, MA (US); Bethany Lyn Kormos, Somerville, MA (US); Ravi G. Kurumbail, East Lyme, CT (US); Luis Angel Martinez-Alsina, Gales Ferry, CT (US); Martin Youngjin Pettersson, Littleton, MA (US); Matthew Richard Reese, Mystic, CT (US); Colin Richard Rose, Quaker Hill, CT (US); Antonia Friederike Stepan, Biberach an der Riss (DE); Patrick Robert Verhoest, Newton, MA (US); Travis T. Wager, Brookline, MA (US); Joseph Scott Warmus, Ledyard, CT (US); Yuan Zhang, East Lyme, CT (US)

(73) Assignee: Pfizer Inc., New York, NY (US)

( * ) Notice: Subject to any disclaimer, the term of this patent is extended or adjusted under 35 U.S.C. 154(b) by 39 days.

This patent is subject to a terminal disclaimer.

(21) Appl. No.: 16/492,558

(22) PCT Filed: Mar. 6, 2018

(86) PCT No.: PCT/IB2018/051439
§ 371 (c)(1),
(2) Date: Sep. 9, 2019

(87) PCT Pub. No.: WO2018/163066
PCT Pub. Date: Sep. 13, 2018

(65) Prior Publication Data
US 2021/0355117 A1    Nov. 18, 2021

Related U.S. Application Data

(60) Provisional application No. 62/629,152, filed on Feb. 12, 2018, provisional application No. 62/469,756, filed on Mar. 10, 2017.

(51) Int. Cl.
*C07D 471/04*    (2006.01)

(52) U.S. Cl.
CPC ............... *C07D 471/04* (2013.01)

(58) Field of Classification Search
CPC .................................. C07D 471/04
USPC ........................................ 514/303
See application file for complete search history.

(56) References Cited

U.S. PATENT DOCUMENTS

2020/0039977 A1* 2/2020 Chappie .................. A61P 25/28

FOREIGN PATENT DOCUMENTS

| EP | 0329073 | 8/1989 |
|---|---|---|
| EP | 2462921 A1 | 6/2012 |
| WO | WO2005003064 | 1/2005 |
| WO | WO2005054238 | 6/2005 |
| WO | 2008136034 A2 | 11/2008 |
| WO | WO2014060113 | 4/2014 |
| WO | 2016108130 A1 | 7/2016 |
| WO | 2017046675 * | 9/2016 |
| WO | WO2017046675 | 3/2017 |
| WO | 2017210158 | 12/2017 |

OTHER PUBLICATIONS

Meinert et al., "Semifluorinated alkanes—a new class of compounds with outstanding properties for use in ophthalmology." European Journal of Ophthalmology, 10(3):189-197 (2000).

Szumny et al., "The influence of new beta-adrenolytics nebivolol and carvedilol on intraocular pressure and iris blood flow in rabbits," Graefe's Archive for Clinical and Experimental Ophthalmology, 252(6): 917-923 (2014).

(Continued)

*Primary Examiner* — Niloofar Rahmani
(74) *Attorney, Agent, or Firm* — Haley Guiliano LLP; James F. Haley, Jr.; Jacob E. Dander

(57) ABSTRACT

The present invention provides novel imidazo[4,5-c]quinoline derivatives of Formula (I), and the pharmaceutically acceptable salts thereof I wherein $R^1$, $R^2$ and $R^3$ are as defined in the specification. The invention is also directed to pharmaceutical compositions comprising the compounds of Formula I and to use of the compounds in the treatment of diseases associated with LRRK2, such as neurodegenerative diseases including Parkinson's disease or Alzheimer's disease, cancer, Crohn's disease or leprosy.

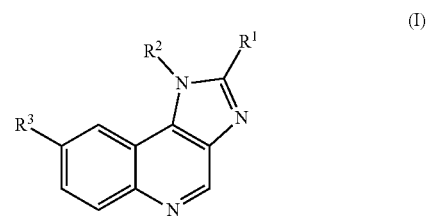

(I)

18 Claims, No Drawings

(56) References Cited

OTHER PUBLICATIONS

Takada, et al., "Synthesis and structure—activity relationships of fused imidazopyridines: a new series of benzodiazepine receptor ligands," Journal of Medicinal Chemistry, 39(14):2844-2851 (1996).

* cited by examiner

IMIDAZO[4,5-C]QUINOLINE DERIVATIVES AS LRRK2 INHIBITORS

CROSS-REFERENCE TO RELATED APPLICATIONS

This application is a United States National Phase Application filed under 35 U.S.C. § 371 from International Patent Application No. PCT/IB2018/051439, filed Mar. 6, 2018, which claims the benefit of priority to U.S. Provisional Patent Application Ser. Nos. 62/629,152, Feb. 12, 2018, and 62/469,756, filed Mar. 10, 2017, the disclosures of which are hereby incorporated by reference in their entireties.

FIELD OF THE INVENTION

The present invention relates to small molecule inhibitors of leucine-rich repeat kinase 2 (LRRK2). This invention also relates to methods of inhibiting, in mammals, including humans, LRRK2 by administration of the small molecule LRRK2 inhibitors. The present invention also relates to the treatment of Parkinson's disease (PD) and other neurodegenerative and/or neurological disorders in mammals, including humans, with the LRRK2 inhibitors. More particularly, this invention relates to novel imidazo[4,5-c]quinoline compounds useful for the treatment of neurodegenerative and/or neurological disorders, such as PD, Alzheimer's disease (AD) and other LRRK2 associated disorders.

BACKGROUND OF THE INVENTION

LRRK2 is a 286 kDa protein in the ROCO protein family with a complex multidomain structure. Protein motifs that have been established for LRRK2 include an armadillo-like (ARM) domain, an ankyrin-like (ANK) domain, a leucine-rich repeat (LRR) domain, a Ras (renin-angiotensin system) of complex (ROC) domain, a C-terminal of ROC (COR) domain, a kinase domain, and a C-terminal WD40 domain. The ROC domain binds guanosine triphosphate (GTP) and the COR domain may be a regulator of the ROC domain's GTPase activity. The kinase domain has structural homology to the MAP kinase kinase kinases (MAPKKK) and has been shown to phosphorylate a number of cellular proteins in vitro, but the endogenous substrate has yet to be determined. LRRK2 has been found in various regions of the brain as well as in a number of peripheral tissues including heart, lung, spleen, and kidney.

LRRK2 has the ability to potentially play a complex role in multiple cellular processes as a consequence of its multi-domain construct, each associated with putative protein-protein interactions, guanosine triphosphatase (GTPase) activity, and kinase activity. For example, LRRK2 has been associated with NFAT inhibition in the immune system and has been linked to vesicle trafficking, presynaptic homeostasis, mammalian target of rapamycin (mTOR) signaling, signaling through the receptor tyrosine kinase MET in papillary renal and thyroid carcinomas, cytoskeletal dynamics, the mitogen-activated protein kinase (MAPK) pathway, the tumor necrosis factor-α (TNF-α) pathway, the Wnt pathway and autophagy. Recent genome-wide association (GWA) genetic studies have implicated LRRK2 in the pathogenesis of various human diseases such as PD, inflammatory bowel disease (Crohn's disease), cancer and leprosy (Lewis, P. A. and Manzoni, C. Science Signaling 2012, 5(207), pe2).

Parkinson's disease (PD) is a relatively common age-related neurodegenerative disorder resulting from the progressive loss of dopamine-producing neurons and which affects up to 4% of the population over age 80. PD is characterized by both motor symptoms, such as tremor at rest, rigidity, akinesia and postural instability as well as non-motor symptoms such as impairment of cognition, sleep and sense of smell. GWA studies have linked LRRK2 to PD and many patients with point mutations in LRRK2 present symptoms that are indistinguishable from those with idiopathic PD. Over 20 LRRK2 mutations have been associated with autosomal-dominant Parkinsonism, and the R1441C, R1441G, R1441H, Y1699C, G2019S, I2020T and N1437H missense mutations are considered to be pathogenic. The LRRK2 R1441G mutation has been shown to increase the release of proinflammatory cytokines (higher levels of TNF-α, IL-1β, IL-12 and lower levels of IL-10) in microglial cells from transgenic mice and thus may result in direct toxicity to neurons (Gillardon, F. et al. Neuroscience 2012, 208, 41-48). In a murine model of neuroinflammation, induction of LRRK2 in microglia was observed and inhibition of LRRK2 kinase activity with small molecule LRRK2 inhibitors (LRRK2-IN-1 or sunitinib) or LRRK2 knockout resulted in attenuation of TNF-α secretion and nitric oxide synthase (iNOS) induction (Moehle, M. et al. J. Neurosci. 2012, 32(5), 1602-1611). The most common of the LRRK2 mutations, G2019S, is present in more than 85% of PD patients carrying LRRK2 mutations. This mutation, which is present in the LRRK2 kinase domain, leads to an enhancement of LRRK2 kinase activity. In the human brain LRRK2 expression is highest in the same regions of the brain that are impacted by PD, and LRRK2 is found in Lewy Bodies, a hallmark of PD. Recent studies indicate that a potent, selective, brain-penetrant kinase inhibitor for LRRK2 could be a therapeutic treatment for PD.

Dementia results from a wide variety of distinctive pathological processes. The most common pathological processes causing dementia are AD, cerebral amyloid angiopathy (CM) and prion-mediated diseases (see, e.g., Haan et al., Clin. Neurol. Neurosurg. 1990, 92(4):305-310; Glenner et al., J. Neurol. Sci. 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050. LRRK2 mutations have been associated with AD-like pathology, which suggests that there may be a partial overlap between the neurodegenerative pathways in both AD and PD (Zimprach, A. et al. Neuron 2004, 44, 601-607). In addition, the LRRK2 R1628P variant (COR domain) has been associated with an increased incidence of AD in a certain population, perhaps resulting from increased apoptosis and cell death (Zhao, Y. et al.; Neurobiology of Aging 2011, 32, 1990-1993).

An increased incidence of certain non-skin cancers such as renal, breast, lung and prostate cancers, as well as acute myelogenous leukemia (AML), has been reported in Parkinson's disease patients with the LRRK2 G2019S mutation (Saunders-Pullman, R. et al.; Movement Disorders, 2010, 25(15), 2536-2541). Since the G2019S mutation is associated with increased LRRK2 kinase activity, inhibition of this activity may be useful in the treatment of cancer, such as kidney, breast, lung, prostate and blood cancers.

Inflammatory bowel disease (IBD) or Crohn's disease (CD) is a complex disease and is believed to result from an inappropriate immune response to microbiota in the intestinal tract. GWA studies have recently identified LRRK2 as a major susceptibility gene for Crohn's disease, particularly the M2397T polymorphism in the WD40 domain (Liu, Z. et al. Nat. Immunol. 2011, 12, 1063-1070). In a recent study LRRK2 deficient mice were found to be more susceptible to dextran sodium sulfate induced colitis than their wild-type counterparts, indicating that LRRK2 may play a role in the pathogenesis of IBD (Liu, Z. and Lenardo, M.; Cell Research 2012, 1-3).

Both non-selective and selective small molecule compounds with LRRK2 inhibitory activity such as staurosporine, sunitinib, LRRK2-IN-1, CZC-25146, TAE684 and those in WO 2011/141756, WO 2012/028629 and WO 2012/058193 have been described. It is desirable to provide compounds which are potent and selective inhibitors of LRRK2 with a favorable pharmacokinetic profile and the ability to traverse the blood-brain barrier. Accordingly, the present invention is directed to novel imidazo[4,5-c]quinoline compounds with LRRK2 inhibitory activity and the use of these compounds in the treatment of diseases associated with LRRK2, such as neurodegenerative diseases, including PD.

SUMMARY OF THE INVENTION

The present invention is directed at compounds of Formula I

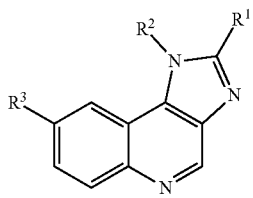

wherein
$R^1$ is selected from the group consisting of methyl, ethyl, cyclobutyl, cyclopentyl,

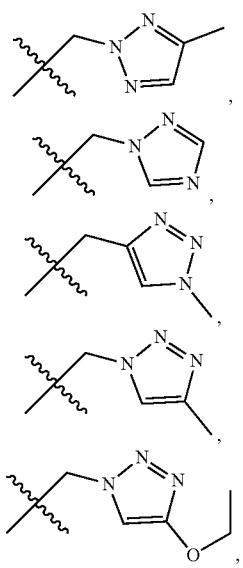

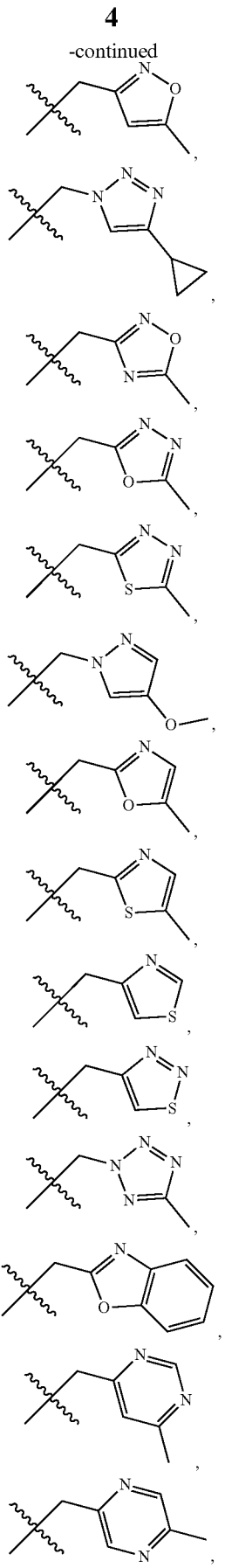

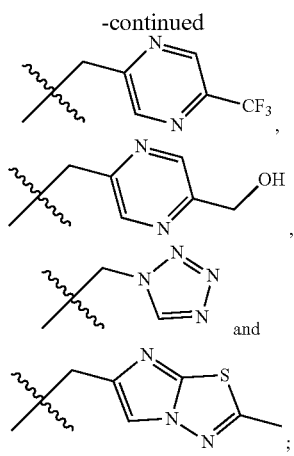

$R^2$ is selected from the group consisting of 2,2-difluoropropyl,

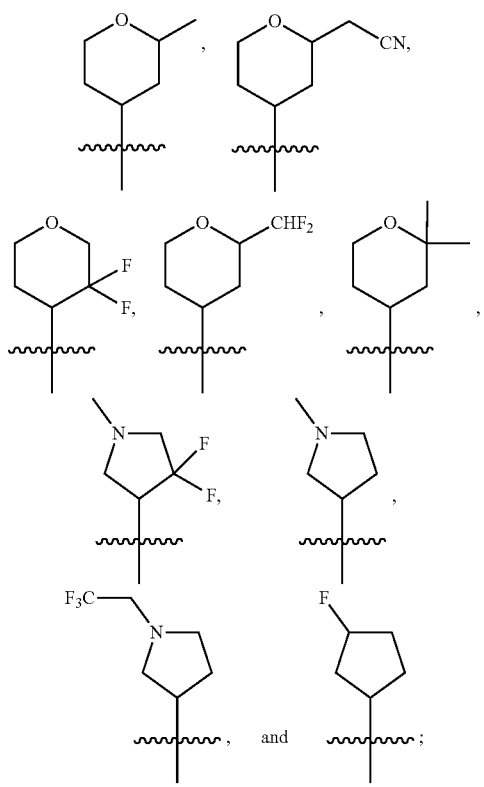

and $R^3$ is selected from the group consisting of fluoro, chloro, cyano, difluoromethyl and trifluoromethyl; or a pharmaceutically acceptable salt thereof.

The present invention is also directed at pharmaceutical compositions which include a pharmaceutically acceptable carrier and a compound of Formula I or a pharmaceutically acceptable salt thereof, present in a therapeutically effective amount.

The present invention is also directed at a method for the treatment of disorder or condition selected from Parkinson's disease (but also including other neurological diseases which may include migraine; epilepsy; Alzheimer's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS) premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema) and pediatric psychiatric disorders (including attention deficit disorder, attention deficit/hyperactive disorder, conduct disorder, and autism) in a mammal, preferably a human, comprising administering to a subject a therapeutically effective amount of a composition comprising a compound of Formula I or a pharmaceutically acceptable salt thereof.

It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

"Therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. By "pharmaceutically acceptable" is meant that the substance or composition must be compatible chemically and/or toxicologically, with the other ingredients comprising a formulation, and/or the mammal being treated therewith.

As used herein, the expressions "reaction-inert solvent" and "inert solvent" refer to a solvent or a mixture thereof which does not interact with starting materials, reagents, intermediates or products in a manner which adversely affects the yield of the desired product.

The term "neurological" refers to the central nervous system. The treatment of neurological conditions refers to the treatment of a condition, disease, ailment, etc. impacting the central nervous system ("CNS"). Such diseases can impact tissues in the periphery as well as the central nervous system.

If substituents are described as being "independently selected" from a group, each substituent is selected independent of the other. Each substituent therefore may be identical to or different from the other substituent(s).

As used herein the terms "formula I", "Formula I", "formula (I)" or "Formula (I)" may be referred to as a "compound(s) of the invention." Such terms are also defined to include all forms of the compound of formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention may have asymmetric carbon atoms. The carbon-carbon bonds of the compounds of the invention may be depicted herein using a solid line (———) a solid wedge (◥◣), or a dotted wedge (⋯⫶⫶⫶⫶⫶). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula (I) may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula (I) can exist as enantiomers and diastereomers or as racemates and mixtures thereof. The use of a solid line to depict bonds to one or more asymmetric carbon atoms in a compound of Formula (I) and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation. The present invention comprises the tautomeric forms of compounds of the invention. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, β-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula (I) with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remington's Pharmaceutical Sciences" Mack Pub. Co., New Jersey (1991). The formulations of the invention can be designed to be short-acting, fast-releasing, long-acting, and sustained-releasing. Thus, the pharmaceutical formulations can also be formulated for controlled release or for slow release.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In such solid dos-age forms, a compound of the present invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-sol™), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i) one or more lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug may also be in microencapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and dicalcium phosphate. The filler/diluent mixtures typically comprise less than 98% of the formulation and preferably less than 95%, for example 93.5%. Preferred disintegrants include Ac-di-sol™, Explotab™, starch and sodium lauryl sulphate. When present a disintegrant will usually comprise less than 10% of the formulation or less than 5%, for example about 3%. A preferred lubricant is magnesium stearate. When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

In another embodiment, oral administration may be in a liquid dose form. Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyole® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Capmul™ MCM (medium chain mono- and diglycerides, from Abitec), Migyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about $C_8$ to $C_{10}$) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents. Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin. In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and nonbiodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, (hydroxypropyl)methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal or vaginal dose form. Such rectal dose form may be in the form of, for example, a suppository. Cocoa butter, polyethylene glycol and suppository wax are traditional suppository bases, but various alternatives may be used as appropriate. These bases are solid at ordinary room temperature, but liquid at body temperature, and therefore, melt in the rectum or vaginal cavity thereby re-leasing the active component(s).

Many of the present compounds are poorly soluble in water, e.g., less than about 1 µg/mL. Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. Patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt 10 wt %, 25 wt 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(R0-102) (15.8%), sodium starch (7%), sodium lauryl sulfate (2%) and magnesium stearate (1%).

The HPMCAS polymers are available in low, medium and high grades as Aqoa.sup.(R)-LF, Aqoat.sup.(R)-MF and Aqoat.sup.(R)-HF respectively from Shin-Etsu Chemical Co., LTD, Tokyo, Japan. The higher MF and HF grades are generally preferred.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination. The present invention includes the use of a combination of a LRRK2 inhibitor compound as provided in Formula (I) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula (I), depending on the disease, disorder, or condition to be treated. For example, a pharmaceutical composition for use in treating Parkinson's disease may comprise a compound of Formula (I) or a pharmaceutically acceptable salt thereof together with another agent such as a dopamine (levodopa, either alone or with a DOPA decarboxylase inhibitor), a monoamine oxidase (MAO) inhibitor, a catechol O-methyltransferase (COMT) inhibitor or an anticholinergic agent, or any combination thereof. Particularly preferred agents to combine with the compounds of Formula (I) for use in treating Parkinson's disease include levodopa, carbidopa, tolcapone, entacapone, selegiline, benztropine and trihexyphenidyl, or any combination thereof. Pharmaceutically active agents that may be used in combination with the compounds of Formula (I) and compositions thereof include, without limitation:

(i) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(ii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(iii) catechol O-methyltransferase (COMT) inhibitors, such as nitecapone, tolcapone (TASMAR), entacapone (COMTAN), and tropolone;

(iv) monoamine oxidase (MAO) inhibitors, such as selegiline (EMSAM), selegiline hydrochloride (I-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-β (or fragments thereof), such as $A\beta_{1-15}$ to pan HLA DRbinding epitope (PADRE®), ACC-001 (Elan/Wyeth), and Affitope;

(vii) antibodies to amyloid-β (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate, celecoxib, lovastatin, anapsos, colostrinin, pioglitazone, clioquinol (also known as PBT1), PBT2 (Prana Biotechnology), flurbiprofen (ANSAID®, FROBEN®) and its Renantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulindegrading enzyme (also known as insulysin), the Gingko biloba extract EGb-761 (ROKAN®, TEBONIN®), tramiprosate (CEREBRIL®, ALZHEMED®), KIACTA®), neprilysin (also known as neutral endopeptidase (NEP)), scylloinositol (also known as scyllitol), atorvastatin (LIPITOR®), simvastatin (ZOCOR®), ibutamoren mesylate, BACE inhibitors such as LY450139 (Lilly), BMS-782450, GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-am inobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) phosphodiesterase (PDE) inhibitors, including (a) PDE1 inhibitors; (b) PDE2 inhibitors; (c) PDE3 inhibitors; (d) PDE4 inhibitors; (e) PDE5 inhibitors; (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008); and (g) PDE10 inhibitors such as 2-({4-[1-methyl-4-(pyridin-4-yl)-1H-pyrazol-3-yl]phenoxy}methyl)quinoline (PF-2545920);

(xiii) serotonin (5-hydroxytryptamine) 1A (5-HT$_{1A}$) receptor antagonists, such as spiperone, levo-pindolol, lecozotan;
(xiv) serotonin (5-hydroxytryptamine) 2C (5-HT$_{2c}$) receptor agonists, such as vabicaserin, and zicronapine; serotonin (5-hydroxytryptamine) 4 (5-HT$_4$) receptor agonists/antagonists, such as PRX-03140 (Epix) and PF-04995274;
(xv) serotonin (5-hydroxytryptamine) 3C (5-HT$_{3c}$) receptor antagonists, such as Ondansetron (Zofran);
(xvi) serotonin (5-hydroxytryptamine) 6 (5-HT$_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck NS), SAM-760, and PRX-07034 (Epix);
(xvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;
(xviii) Glycine transporter-1 inhibitors such as paliflutine, ORG-25935, and ORG26041; and mGluR modulators such as AFQ-059 and amantidine;
(xix) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;
(xx) P450 inhibitors, such as ritonavir;
(xxi) tau therapy targets, such as davunetide;
and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

In one embodiment, the compound of the present invention is:

[(2S,4R)-4-(8-chloro-2-ethyl-1H-imidazo[4,5-c]quinolin-1-yl)tetrahydro-2H-pyran-2-yl]acetonitrile;
[(2R,4S)-4-(8-chloro-2-ethyl-1H-imidazo[4,5-c]quinolin-1-yl)tetrahydro-2H-pyran-2-yl]acetonitrile;
1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 1;
1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 2;
8-chloro-1-[(4S)-3,3-difluorotetrahydro-2H-pyran-4-yl]-2-[(5-methyl-1,2-oxazol-3-yl)methyl]-1H-imidazo[4,5-c]quinoline;
2-[(6-methylpyrimidin-4-yl)methyl]-1-[(3R)-1-methylpyrrolidin-3-yl]-1H-imidazo [4,5-c]quinoline-8-carbonitrile;
8-chloro-1-(3,3-difluorotetrahydro-2H-pyran-4-yl)-2-[(5-methylpyrazin-2-yl) methyl]-1H-imidazo[4,5-c]quinoline, ENT 1;
8-chloro-1-(3,3-difluorotetrahydro-2H-pyran-4-yl)-2-[(5-methylpyrazin-2-yl) methyl]-1H-imidazo[4,5-c]quinoline, ENT 2;
1-[(2R,4R)-2-methyltetrahydro-2H-pyran-4-yl]-2-[(1-methyl-1H-1,2,3-triazol-4-yl) methyl]-8-(trifluoromethyl)-1H-imidazo[4,5-c]quinoline;
[cis-4-(8-chloro-2-cyclobutyl-1H-imidazo[4,5-c]quinolin-1-yl)tetrahydro-2H-pyran-2-yl]acetonitrile, ENT 1;
[cis-4-(8-chloro-2-cyclobutyl-1H-imidazo[4,5-c]quinolin-1-yl)tetrahydro-2H-pyran-2-yl]acetonitrile, ENT 2;
8-(difluoromethyl)-2-[(4-methoxy-1H-pyrazol-1-yl) methyl]-1-[(2R,4R)-2-methyl tetrahydro-2H-pyran-4-yl]-1H-imidazo[4,5-c]quinoline;
8-(difluoromethyl)-2-[(5-methylpyrazin-2-yl)methyl]-1-[(2R,4R)-2-methyltetrahydro-2H-pyran-4-yl]-1H-imidazo[4,5-c]quinoline;
{8-chloro-1-[(2R,4R)-2-methyltetrahydro-2H-pyran-4-yl]-1H-imidazo[4,5-c]quinolin-2-yl}(5-methylpyrazin-2-yl)methanol, DIAST 1;
{8-chloro-1-[(2R,4R)-2-methyltetrahydro-2H-pyran-4-yl]-1H-imidazo[4,5-c]quinolin-2-yl}(5-methylpyrazin-2-yl)methanol, DIAST 2;
1-(4,4-difluoro-1-methylpyrrolidin-3-yl)-8-fluoro-2-(1H-1,2,4-triazol-1-ylmethyl)-1H-imidazo[4,5-c]quinoline, ENT 1;
1-(4,4-difluoro-1-methylpyrrolidin-3-yl)-8-fluoro-2-(1H-1,2,4-triazol-1-ylmethyl)-1H-imidazo[4,5-c]quinoline, ENT 2;
1-(4,4-difluoro-1-methylpyrrolidin-3-yl)-8-fluoro-2-[(4-methyl-1H-1,2,3-triazol-1-yl) methyl]-1H-imidazo[4,5-c]quinoline, ENT 1;
1-(4,4-difluoro-1-methylpyrrolidin-3-yl)-8-fluoro-2-[(4-methyl-1H-1,2,3-triazol-1-yl) methyl]-1H-imidazo[4,5-c]quinoline, ENT 2;
1-(4,4-difluoro-1-methylpyrrolidin-3-yl)-8-fluoro-2-[(5-methylpyrazin-2-yl)methyl]-1H-imidazo[4,5-c]quinoline, ENT 1;
1-(4,4-difluoro-1-methylpyrrolidin-3-yl)-8-fluoro-2-[(5-methylpyrazin-2-yl)methyl]-1H-imidazo[4,5-c]quinoline, ENT 2;
8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 1;
8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 2;
8-chloro-1-(4,4-difluoro-1-methylpyrrolidin-3-yl)-2-(1H-1,2,4-triazol-1-ylmethyl)-1H-imidazo[4,5-c]quinoline, ENT 1;
8-chloro-1-(4,4-difluoro-1-methylpyrrolidin-3-yl)-2-(1H-1,2,4-triazol-1-ylmethyl)-1H-imidazo[4,5-c]quinoline, ENT 2;
8-chloro-1-(3,3-difluorotetrahydro-2H-pyran-4-yl)-2-[(4-methoxy-1H-pyrazol-1-yl) methyl]-1H-imidazo[4,5-c] quinoline, ENT 1;
8-chloro-1-(3,3-difluorotetrahydro-2H-pyran-4-yl)-2-[(4-methoxy-1H-pyrazol-1-yl) methyl]-1H-imidazo[4,5-c] quinoline, ENT 2;
8-fluoro-2-[(2-methylimidazo[2,1-b][1,3,4]thiadiazol-6-yl) methyl]-1-[(2R,4R)-2-methyltetrahydro-2H-pyran-4-yl]-1H-imidazo[4,5-c]quinoline;
2-[(5-methylpyrazin-2-yl)methyl]-1-[(2R,4R)-2-methyltetrahydro-2H-pyran-4-yl]-8-(trifluoromethyl)-1H-imidazo [4,5-c]quinoline;
2-cyclopentyl-1-[(2R,4R)-2-methyltetrahydro-2H-pyran-4-yl]-1H-imidazo[4,5-c]quinoline-8-carbonitrile;

[cis-4-(8-chloro-2-methyl-1H-imidazo[4,5-c]quinolin-1-yl) tetrahydro-2H-pyran-2-yl]acetonitrile, ENT 1;

1-(4,4-difluoro-1-methylpyrrolidin-3-yl)-2-[(5-methyl-1,2,4-oxadiazol-3-yl)methyl]-1H-imidazo[4,5-c]quinoline-8-carbonitrile, ENT 1;

2-[(5-methylpyrazin-2-yl)methyl]-1-[(3R)-1-methylpyrrolidin-3-yl]-1H-imidazo[4,5-c]quinoline-8-carbonitrile;

1-[(3R)-1-methylpyrrolidin-3-yl]-2-[(5-methyl-2H-tetrazol-2-yl)methyl]-1H-imidazo [4,5-c]quinoline-8-carbonitrile;

2-[(3-methyl-1,2-oxazol-5-yl)methyl]-1-[(3R)-1-methylpyrrolidin-3-yl]-1H-imidazo [4,5-c]quinoline-8-carbonitrile;

2-[(4-methoxy-1H-pyrazol-1-yl)methyl]-1-[(3R)-1-methylpyrrolidin-3-yl]-1H-imidazo[4,5-c]quinoline-8-carbonitrile;

1-[(3R)-1-methylpyrrolidin-3-yl]-2-[(5-methyl-1,3,4-thiadiazol-2-yl)methyl]-1H-imidazo[4,5-c]quinoline-8-carbonitrile;

2-[(5-methyl-1,3-oxazol-2-yl)methyl]-1-[(3R)-1-methylpyrrolidin-3-yl]-1H-imidazo [4,5-c]quinoline-8-carbonitrile;

1-[(2R,4R)-2-methyltetrahydro-2H-pyran-4-yl]-2-{[5-(trifluoromethyl)pyrazin-2-yl]methyl}-1H-imidazo[4,5-c]quinoline-8-carbonitrile;

8-chloro-2-[(6-methylpyrimidin-4-yl)methyl]-1-[(3R)-1-methylpyrrolidin-3-yl]-1H-imidazo[4,5-c]quinoline;

2-[(4-methoxy-1H-pyrazol-1-yl)methyl]-1-[(2R,4R)-2-methyltetrahydro-2H-pyran-4-yl]-8-(trifluoromethyl)-1H-imidazo[4,5-c]quinoline;

8-chloro-2-[(5-methyl-1,2,4-oxadiazol-3-yl)methyl]-1-[(3R)-1-methylpyrrolidin-3-yl]-1H-imidazo[4,5-c]quinoline;

8-chloro-1-(4,4-difluoro-1-methylpyrrolidin-3-yl)-2-(1H-1,2,4-triazol-1-ylmethyl)-1H-imidazo[4,5-c]quinoline;

8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline;

8-chloro-1-(4,4-difluoro-1-methylpyrrolidin-3-yl)-2-[(5-methyl-1,2,4-oxadiazol-3-yl) methyl]-1H-imidazo[4,5-c]quinoline;

8-chloro-1-(3,3-difluorotetrahydro-2H-pyran-4-yl)-2-[(4-methyl-1H-1,2,3-triazol-1-yl)methyl]-1H-imidazo[4,5-c]quinoline, ENT 1;

8-chloro-2-[(4-cyclopropyl-1H-1,2,3-triazol-1-yl)methyl]-1-(4,4-difluoro-1-methylpyrrolidin-3-yl)-1H-imidazo[4,5-c]quinoline, ENT 2;

8-chloro-1-(4,4-difluoro-1-methylpyrrolidin-3-yl)-2-[(4-methyl-1H-1,2,3-triazol-1-yl) methyl]-1H-imidazo[4,5-c]quinoline, ENT 2;

8-chloro-1-(4,4-difluoro-1-methylpyrrolidin-3-yl)-2-[(5-methyl-2H-tetrazol-2-yl) methyl]-1H-imidazo[4,5-c]quinoline, ENT 1;

8-chloro-1-(4,4-difluoro-1-methylpyrrolidin-3-yl)-2-[(5-methylpyrazin-2-yl)methyl]-1H-imidazo[4,5-c]quinoline, ENT 1;

8-chloro-1-(4,4-difluoro-1-methylpyrrolidin-3-yl)-2-[(5-methyl-1,2-oxazol-3-yl) methyl]-1H-imidazo[4,5-c]quinoline, ENT 1;

8-chloro-1-(4,4-difluoro-1-methylpyrrolidin-3-yl)-2-[(5-methyl-1,2-oxazol-3-yl) methyl]-1H-imidazo[4,5-c]quinoline, ENT 2;

1-(4,4-difluoro-1-methylpyrrolidin-3-yl)-8-fluoro-2-{[4-(methoxymethyl)-1H-1,2,3-triazol-1-yl]methyl}-1H-imidazo[4,5-c]quinoline, ENT 2;

8-chloro-1-(3,3-difluorotetrahydro-2H-pyran-4-yl)-2-(1H-1,2,4-triazol-1-ylmethyl)-1H-imidazo[4,5-c]quinoline, ENT 2;

8-chloro-1-(3,3-difluorotetrahydro-2H-pyran-4-yl)-2-{[4-(methoxymethyl)-1H-1,2,3-triazol-1-yl]methyl}-1H-imidazo[4,5-c]quinoline, ENT 1;

2-[(5-methyl-1,2,4-oxadiazol-3-yl)methyl]-1-[(3R)-1-(2,2,2-trifluoroethyl)pyrrolidin-3-yl]-1H-imidazo[4,5-c]quinoline-8-carbonitrile;

2-[(4-methoxy-1H-pyrazol-1-yl)methyl]-1-[(2R,4R)-2-methyltetrahydro-2H-pyran-4-yl]-1H-imidazo[4,5-c]quinoline-8-carbonitrile;

8-chloro-1-[(2R,4R)-2-methyltetrahydro-2H-pyran-4-yl]-2-(1,3-thiazol-2-ylmethyl)-1H-imidazo[4,5-c]quinoline;

8-chloro-1-[cis-2-(difluoromethyl)tetrahydro-2H-pyran-4-yl]-2-[(5-methyl-1,2-oxazol-3-yl)methyl]-1H-imidazo[4,5-c]quinoline, ENT 1;

8-chloro-1-(3,3-difluorotetrahydro-2H-pyran-4-yl)-2-[(5-methyl-1,2-oxazol-3-yl) methyl]-1H-imidazo[4,5-c]quinoline, ENT 1;

1-[(2R,4R)-2-methyltetrahydro-2H-pyran-4-yl]-2-(1,3-thiazol-2-ylmethyl)-1H-imidazo[4,5-c]quinoline-8-carbonitrile;

8-chloro-1-[(3R)-1-methylpyrrolidin-3-yl]-2-[(4-methyl-1H-1,2,3-triazol-1-yl) methyl]-1H-imidazo[4,5-c]quinoline;

1-[(2R,4R)-2-methyltetrahydro-2H-pyran-4-yl]-2-(1,2,3-thiadiazol-4-ylmethyl)-8-(trifluoromethyl)-1H-imidazo[4,5-c]quinoline;

8-fluoro-1-[(2R,4R)-2-methyltetrahydro-2H-pyran-4-yl]-2-(1,3-thiazol-2-ylmethyl)-1H-imidazo[4,5-c]quinoline;

2-(1,3-benzoxazol-2-ylmethyl)-1-[cis-3-fluorocyclopentyl]-1H-imidazo[4,5-c]quinoline-8-carbonitrile;

1-[(2R,4R)-2-methyltetrahydro-2H-pyran-4-yl]-2-(1H-1,2,4-triazol-1-ylmethyl)-8-(trifluoromethyl)-1H-imidazo[4,5-c]quinoline;

8-chloro-2-[(5-methylpyrazin-2-yl)methyl]-1-[(3R)-1-methylpyrrolidin-3-yl]-1H-imidazo[4,5-c]quinoline;

1-[cis-3-fluorocyclopentyl]-2-[(5-methyl-1,2-oxazol-3-yl) methyl]-1H-imidazo[4,5-c]quinoline-8-carbonitrile;

1-[(2R,4R)-2-methyltetrahydro-2H-pyran-4-yl]-2-(1,3-thiazol-4-ylmethyl)-8-(trifluoromethyl)-1H-imidazo[4,5-c]quinoline;

2-[(5-methyl-1,3,4-oxadiazol-2-yl)methyl]-1-[(2R,4R)-2-methyltetrahydro-2H-pyran-4-yl]-8-(trifluoromethyl)-1H-imidazo[4,5-c]quinoline;

8-chloro-1-(2,2-dimethyltetrahydro-2H-pyran-4-yl)-2-(1H-1,2,4-triazol-1-ylmethyl)-1H-imidazo[4,5-c]quinoline;

8-chloro-1-(2,2-difluoropropyl)-2-[(4-methoxy-1H-pyrazol-1-yl)methyl]-1H-imidazo[4,5-c]quinoline;

8-fluoro-1-[(2R,4R)-2-methyltetrahydro-2H-pyran-4-yl]-2-{[5-(trifluoromethyl)pyrazin-2-yl]methyl}-1H-imidazo[4,5-c]quinoline;

1-[(2R,4R)-2-methyltetrahydro-2H-pyran-4-yl]-2-[(5-methyl-1,3,4-thiadiazol-2-yl) methyl]-8-(trifluoromethyl)-1H-imidazo[4,5-c]quinoline;

8-chloro-1-(3,3-difluorotetrahydro-2H-pyran-4-yl)-2-[(5-methyl-1,2,4-oxadiazol-3-ylmethyl]-1H-imidazo[4,5-c]quinoline, ENT 1;

2-[(6-methylpyrimidin-4-yl)methyl]-1-[(2R,4R)-2-methyltetrahydro-2H-pyran-4-yl]-8-(trifluoromethyl)-1H-imidazo[4,5-c]quinoline;

8-chloro-1-[cis-3-fluorocyclopentyl]-2-[(5-methylpyrazin-2-yl)methyl]-1H-imidazo[4,5-c]quinoline;

3-{8-chloro-1-[(2R,4R)-2-methyltetrahydro-2H-pyran-4-yl]-1H-imidazo[4,5-c]quinolin-2-yl}-2-methylpropanenitrile, DIAST 2;

8-fluoro-1-[cis-3-fluorocyclopentyl]-2-(1,2,3-thiadiazol-4-ylmethyl)-1H-imidazo[4,5-c]quinoline, ENT 2;

3-{8-chloro-1-[(2R,4R)-2-methyltetrahydro-2H-pyran-4-yl]-1H-imidazo[4,5-c]quinolin-2-yl}propanenitrile;
1-[(2R,4R)-2-methyltetrahydro-2H-pyran-4-yl]-2-[(5-methyl-2H-tetrazol-2-yl)methyl]-8-(trifluoromethyl)-1H-imidazo[4,5-c]quinoline;
8-chloro-1-(4,4-difluoro-1-methylpyrrolidin-3-yl)-2-[(4-methyl-1H-1,2,3-triazol-1-yl)methyl]-1H-imidazo[4,5-c]quinoline;
8-chloro-1-(4,4-difluoro-1-methylpyrrolidin-3-yl)-2-(1H-tetrazol-1-ylmethyl)-1H-imidazo[4,5-c]quinoline;
8-chloro-1-(4,4-difluoro-1-methylpyrrolidin-3-yl)-2-[(1-methyl-1H-1,2,4-triazol-3-yl) methyl]-1H-imidazo[4,5-c]quinoline;
1-(4,4-difluoro-1-methylpyrrolidin-3-yl)-8-fluoro-2-[(2-methylimidazo[2,1-b][1,3,4]thiadiazol-6-yl)methyl]-1H-imidazo[4,5-c]quinoline, ENT 1;
8-chloro-1-(4,4-difluoro-1-methylpyrrolidin-3-yl)-2-(1H-tetrazol-1-ylmethyl)-1H-imidazo[4,5-c]quinoline, ENT 2;
8-chloro-1-(4,4-difluoro-1-methylpyrrolidin-3-yl)-2-[(4-methyl-2H-1,2,3-triazol-2-yl) methyl]-1H-imidazo[4,5-c]quinoline, ENT 1;
8-chloro-1-(4,4-difluoro-1-methylpyrrolidin-3-yl)-2-[(5-methyl-1,2,4-oxadiazol-3-yl) methyl]-1H-imidazo[4,5-c]quinoline, ENT 1;
8-chloro-1-(4,4-difluoro-1-methylpyrrolidin-3-yl)-2-[(5-methyl-1,3,4-thiadiazol-2-yl) methyl]-1H-imidazo[4,5-c]quinoline, ENT 2;
8-(difluoromethyl)-1-[(2R,4R)-2-methyltetrahydro-2H-pyran-4-yl]-2-[(4-methyl-1H-1,2,3-triazol-1-yl)methyl]-1H-imidazo[4,5-c]quinoline;
8-(difluoromethyl)-2-[(5-methyl-1,2-oxazol-3-yl)methyl]-1-[(2R,4R)-2-methyltetrahydro-2H-pyran-4-yl]-1H-imidazo[4,5-c]quinoline;
8-chloro-1-(3,3-difluorotetrahydro-2H-pyran-4-yl)-2-[(5-methyl-1,3,4-thiadiazol-2-yl)methyl]-1H-imidazo[4,5-c]quinoline, ENT 1;
8-chloro-1-(3,3-difluorotetrahydro-2H-pyran-4-yl)-2-(1H-1,2,4-triazol-1-ylmethyl)-1H-imidazo[4,5-c]quinoline, ENT 1;
8-chloro-2-[(4-cyclopropyl-1H-1,2,3-triazol-1-yl)methyl]-1-(3,3-difluorotetrahydro-2H-pyran-4-yl)-1H-imidazo[4,5-c]quinolone, ENT 1; or
[5-({8-chloro-1-[(2R,4R)-2-methyltetrahydro-2H-pyran-4-yl]-1H-imidazo[4,5-c]quinolin-2-yl}methyl)pyrazin-2-yl]methanol or a pharmaceutically acceptable salt thereof.

In another embodiment, the compound of the present invention is:
8-chloro-2-{[5-($^2$H$_3$)methylpyrazin-2-yl]methyl}-1-[(2R,4R)-2-methyltetrahydro-2H-pyran-4-yl]-1H-imidazo[4,5-c]quinoline;
8-chloro-2-{[5-($^2$H$_3$)methylpyrazin-2-yl]($^2$H$_2$)methyl}-1-[(2R,4R)-2-methyltetrahydro-2H-pyran-4-yl]-1H-imidazo[4,5-c]quinoline;
8-chloro-2-{[5-($^2$H$_2$)methylpyrazin-2-yl]methyl}-1-[(2R,4R)-2-methyltetrahydro-2H-pyran-4-yl]-1H-imidazo[4,5-c]quinoline;
8-chloro-2-{[5-($^2$H$_1$)methylpyrazin-2-yl]methyl}-1-[(2R,4R)-2-methyltetrahydro-2H-pyran-4-yl]-1H-imidazo[4,5-c]quinoline;
[5-({8-chloro-1-[(2R,4R)-2-methyltetrahydro-2H-pyran-4-yl]-1H-imidazo[4,5-c]quinolin-2-yl}methyl)pyrazin-2-yl]($^2$H$_2$)methanol; or
[5-({8-chloro-1-[(2R,4R)-2-methyltetrahydro-2H-pyran-4-yl]-1H-imidazo[4,5-c]quinolin-2-yl}methyl)pyrazin-2-yl]($^2$H$_1$)methanol,
or a pharmaceutically acceptable salt thereof.

In another embodiment of the present invention, the compound of Formula I has
$R^1$ is ethyl or

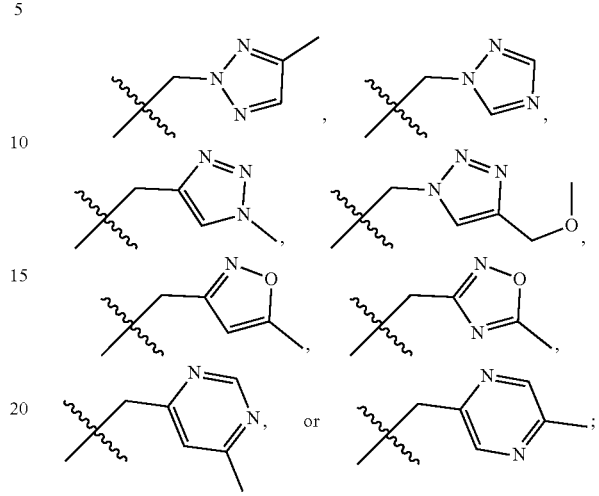

$R^2$ is

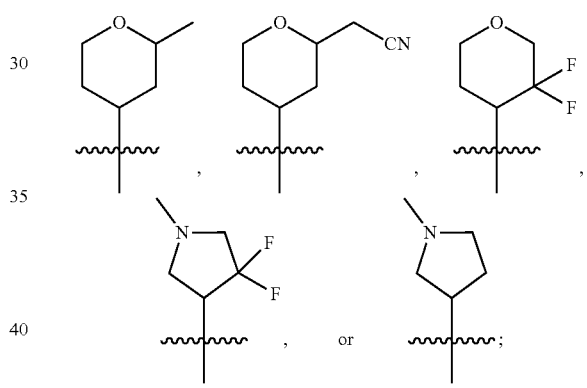

and
$R^3$ is chloro, cyano, difluoromethyl, or trifluoromethyl,
or a pharmaceutically acceptable salt thereof.

In another embodiment, the compound of Formula I has
$R^1$ is

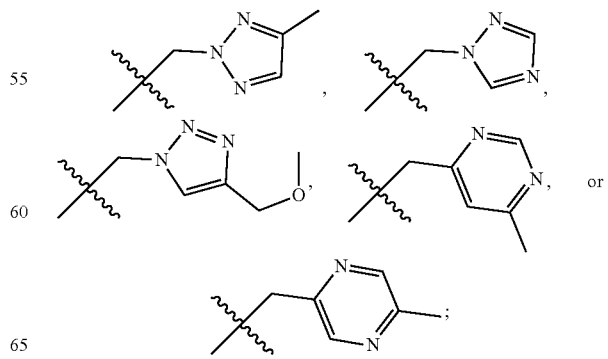

$R^2$ is

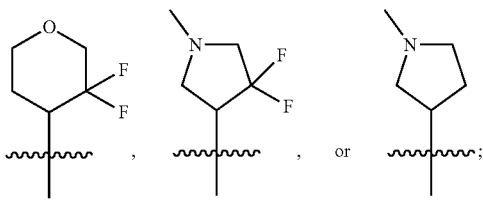

and
$R^3$ is chloro or cyano,
or a pharmaceutically acceptable salt thereof.

In another embodiment, the compound of the present invention of Formula I has
$R^1$ is

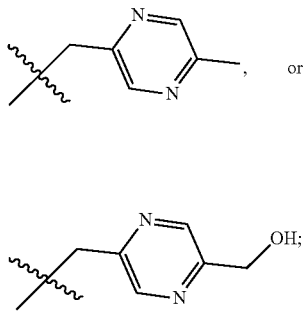

$R^2$ is

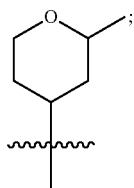 [SMILES: *C1CCOC(C)C1]

and
$R^3$ is chloro,
or a pharmaceutically acceptable salt thereof.

In yet another embodiment, the compound of the present invention of Formula I has
$R^1$ is

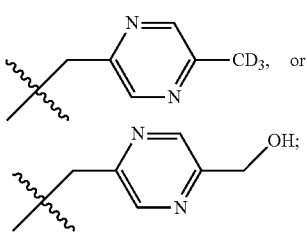

$R^2$ is

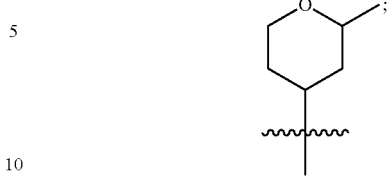

and
$R^3$ is chloro,
or a pharmaceutically acceptable salt thereof.

In another embodiment, the present invention directed at a method of treating a disease or disorder selected from the group consisting of Crohn's disease, Parkinson's disease, Lewy body dementia, frontotemporal dementia, corticobasal dementia, progressive supranuclear palsy, leprosy, Alzheimer's disease, tauopathy disease and Alpha-synucleinopathy in a patient, the method comprising administering to a patient in need of treatment thereof a therapeutically effective amount of a compound of Formula (I) or pharmaceutically acceptable salt thereof.

In yet another embodiment of the present invention, the treatment of a disease or disorder is selected from the group consisting of Crohn's disease, Parkinson's disease, Lewy body dementia, frontotemporal dementia, corticobasal dementia, progressive supranuclear palsy, leprosy, Alzheimer's disease, tauopathy disease and Alpha-synucleinopathy.

In another embodiment, the treatment of a disease or disorder is selected from the group consisting of Lewy body dementia, frontotemporal dementia, corticobasal dementia, progressive supranuclear palsy, leprosy, inflammatory bowel disease, inflammatory bowel syndrome, Alzheimer's disease, tauopathy diseases, Alpha-synucleinopathy, Parkinson's disease, Parkinson's disease with dementia, Parkinson's disease at risk syndrome, Lewy body variant of Alzheimer's disease, combined Parkinson's disease and Alzheimer's disease, multiple system atrophy, striatonigral degeneration, olivopontocerebellar atrophy, Shy-Drager syndrome, ulcerative colitis, juvenile parkinsonism, Steele-Richardson-Olszewski disease, Lytico-Bodig or parkinsonism-dementia-ALS complex of Guam, cortical basal ganglionic degeneration, progressive pallidal atrophy, Parkinsonism-dementia complex, pallidopyramidal disease, hereditary juvenile dystonia-parkinsonism, autosomal dominant Lewy body disease, Huntington disease, Wilson disease, hereditary ceruloplasmin deficiency, Hallervorden-Spatz disease, olivopontocerebellar and spinocerebellar degenerations, Machado-Joseph disease, familial amyotrophy-dementia-parkinsonism, disinhibitiondementia-parkinsonism-amyotrophycomplex, Gerstmann-Strausler-Scheinker disease, familial progressive subcortical gliosis, Lubag (x-linked dystonia parkinsonism), familial basal ganglia calcification, mitochondrial cytopathies with striatal necrosis, ceroid lipofuscinosis, familial Parkinsonism with peripheral neuropathy, Parkinsonism-pyramidal syndrome, neuroacanthocytosis and hereditary hemochromatosis.

In yet another embodiment of the present invention, the treatment of a disease or disorder is selected from a neurological disorder, most preferably Parkinson's disease, (but also other neurological disorders such as migraine; epilepsy; Alzheimer's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence;

eating disorder; and pediatric psychiatric disorder) in a mammal, preferably a human, comprising administering to said mammal a therapeutically effective amount of a compound of Formula I or pharmaceutically acceptable salt thereof. In addition, the compounds of Formula I and pharmaceutically acceptable salts thereof may also be employed in methods of treating other disorders associated with LRRK2 such as Crohn's disease, leprosy and certain cancers, such as kidney, breast, lung, prostate, lung and blood cancer.

The text revision of the fourth edition of the Diagnostic and Statistical Manual of Mental Disorders (DSM-IV-TR) (2000, American Psychiatric Association, Washington D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress.

General Synthetic Schemes

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. 1-XIII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the Reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in many cases, the compounds in Reaction Schemes 1 through 9 may be generated as a mixture of diastereomers and/or enantiomers; these may be separated at various stages of the synthetic schemes using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compounds of Formula I and intermediates thereof may be prepared according to the following reaction schemes and accompanying discussion. Unless otherwise indicated, $R^1$, $R^2$ and $R^3$ in the reaction schemes and discussions that follow are as defined as the same as hereinabove. In general the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes may be described in the experimental section. The schemes and examples provided herein (including the corresponding description) are for illustration only, and not intended to limit the scope of the present invention.

Reaction Scheme 1

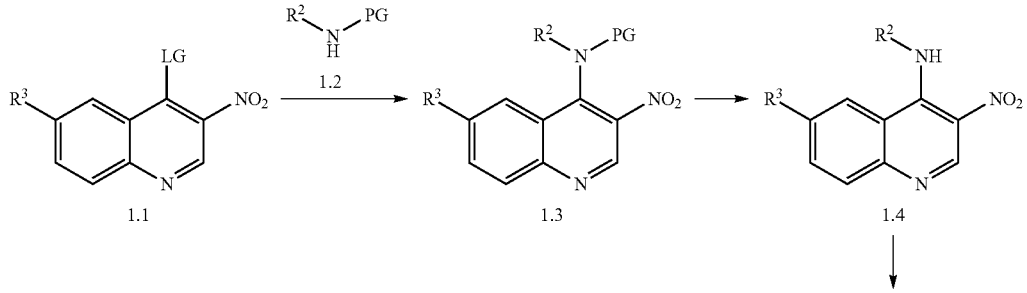

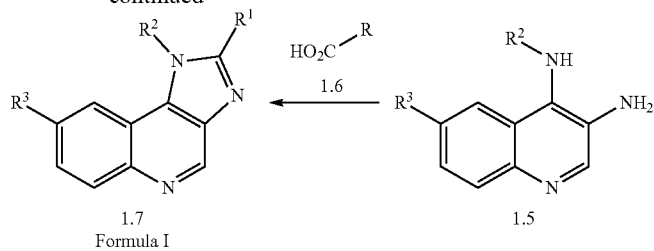

Reaction Scheme 1 depicts the preparation of compounds of Formula (I). Referring to Scheme 1, compounds 1.1 and 1.2 are either commercially available or can be made by methods described herein or other methods well known to those skilled in the art. In the compound of formula 1.1 the group designated LG represents an appropriate leaving group such as a halide (e.g., chloro or bromo) or triflate which is suitable to undergo nucleophilic displacement when reacted with the amine of formula 1.2. In the amine compound of formula 1.2, the group designated PG represents an appropriate amine protecting group such as an acid-labile protecting group selected from 2,4-dimethoxybenzyl (DMB), 4-methoxybenzyl (PMB) and t-butoxycarbonyl (Boc). The compounds of formulae 1.1 and 1.2 can be reacted, for example, in the presence of an appropriate base such as N,N-diisopropylethylamine (Hunig's base) or triethylamine in a suitable solvent such as acetonitrile or N,N-dimethylformamide (DMF) to afford the compound of formula 1.3. The reaction is typically carried out at an elevated temperature, such as 50 to 100° C. for a period of 1 to 48 hours. Removal of the protecting group, such as an acid-labile protecting group (PG) from the compound of formula 1.3 can typically be accomplished by treatment of 1.3 with an appropriate acid such as acetic acid, trifluoroacetic acid or hydrochloric acid to provide the compound of formula 1.4. Also, it is to be understood that in certain instances the compound of formula 1.1 can be reacted with an unprotected amine of formula $R^2$—$NH_2$ to arrive directly to a compound of formula 1.4. Reduction of the nitro group in the compound of formula 1.4 using conditions congruent with the functionality present affords the compound of formula 1.5. For example, the nitro group in the compound of formula 1.4 can be reduced to the corresponding amine of formula 1.5 by treatment of 1.4 with zinc dust and ammonium hydroxide in methanol or alternatively by hydrogenation of 1.4 using an appropriate catalyst such as platinum (IV) oxide in an appropriate solvent such as methanol, acetonitrile or a mixture thereof. Coupling the diamine compound 1.5 with the carboxylic acid of formula 1.6 then provides the desired compound of Formula I, also denoted as 1.7. The coupling reaction with the diamine of formula 1.5 and the carboxylic acid of formula 1.6 can be carried out in an appropriate solvent such as N,N-dimethylformamide or N-propylacetate in the presence of an appropriate base such as N,N-diisopropylethylamine and a coupling reagent such as 2,4,6-tripropyl-1,3,5,2,4,6-trioxatriphosphirane 2,4,6-trioxide or 1-ethyl-3-(3-dimethylaminopropyl)carbodiimide (EDCI). The coupling reaction is often heated between 60° C. and 110° C.

Reaction Scheme 2

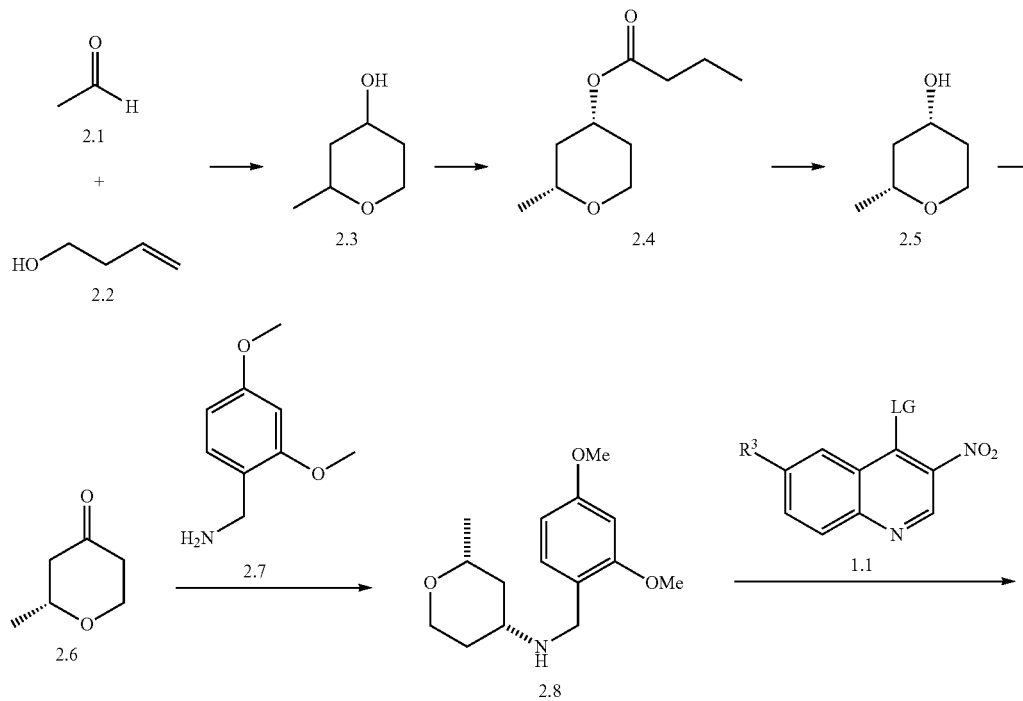

-continued

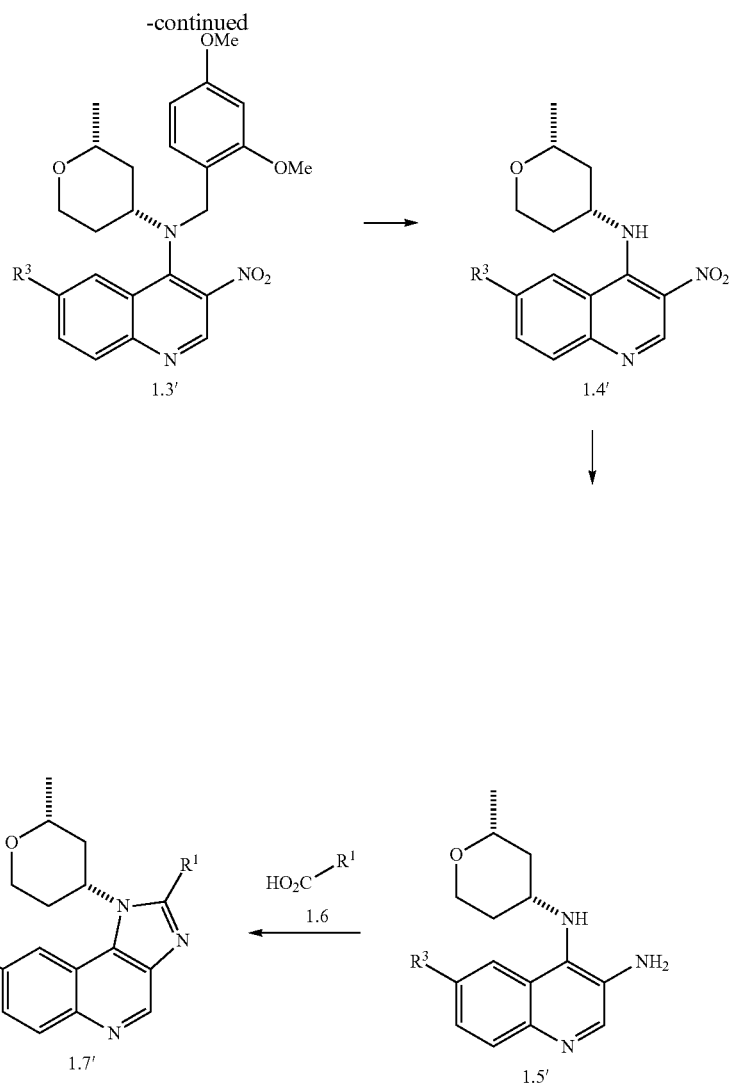

Reaction Scheme 2 depicts the preparation of compounds of formula 1.7', which is a compound of Formula I in which R² is the chiral 2-methyltetrahydropyran-4-yl moiety as shown. Using a published procedure, Prins reaction of the compound 2.1 with the compound 2.2 generates the pyran 2.3. Chiral resolution to produce the separated enantiomers, using an enzyme-based method, affords the compound of formula 2.5 after hydrolysis of the resolved ester 2.4. Oxidation of 2.5 provides ketone 2.6, which is reacted with the compound of formula 2.7 using reductive amination chemistry to provide the protected amine of formula 2.8. The protected amine of formula 2.8 can be reacted with the compound of formula 1.1 in a manner analogous to that previously described in Scheme 1 to provide the compound of formula 1.3'. The compounds of formulae 1.4', 1.5' and 1.7' can then be prepared in a manner analogous to the methods described in Scheme 1 for the compounds of formulae 1.4, 1.5 and 1.7, respectively.

Reaction Scheme 3

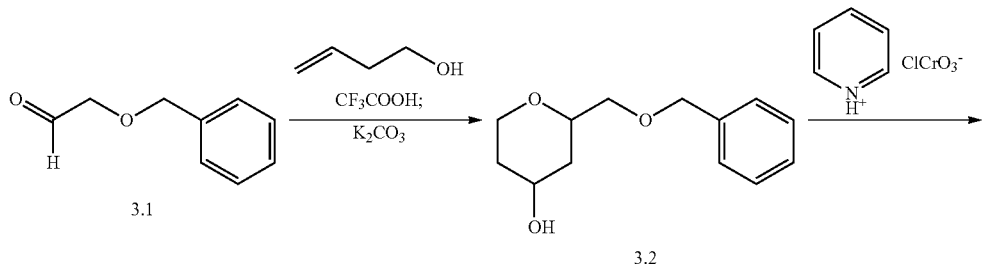

-continued
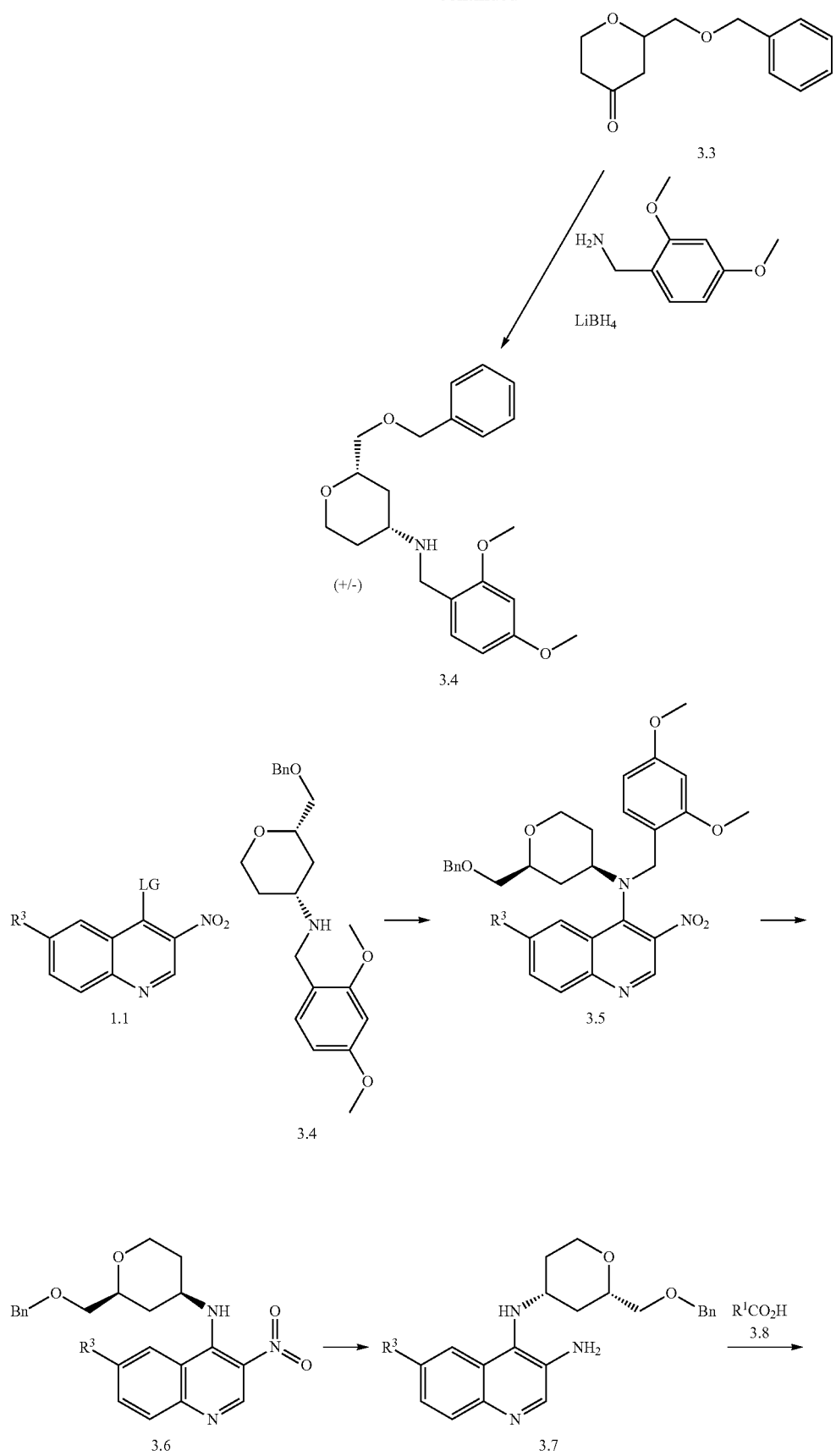

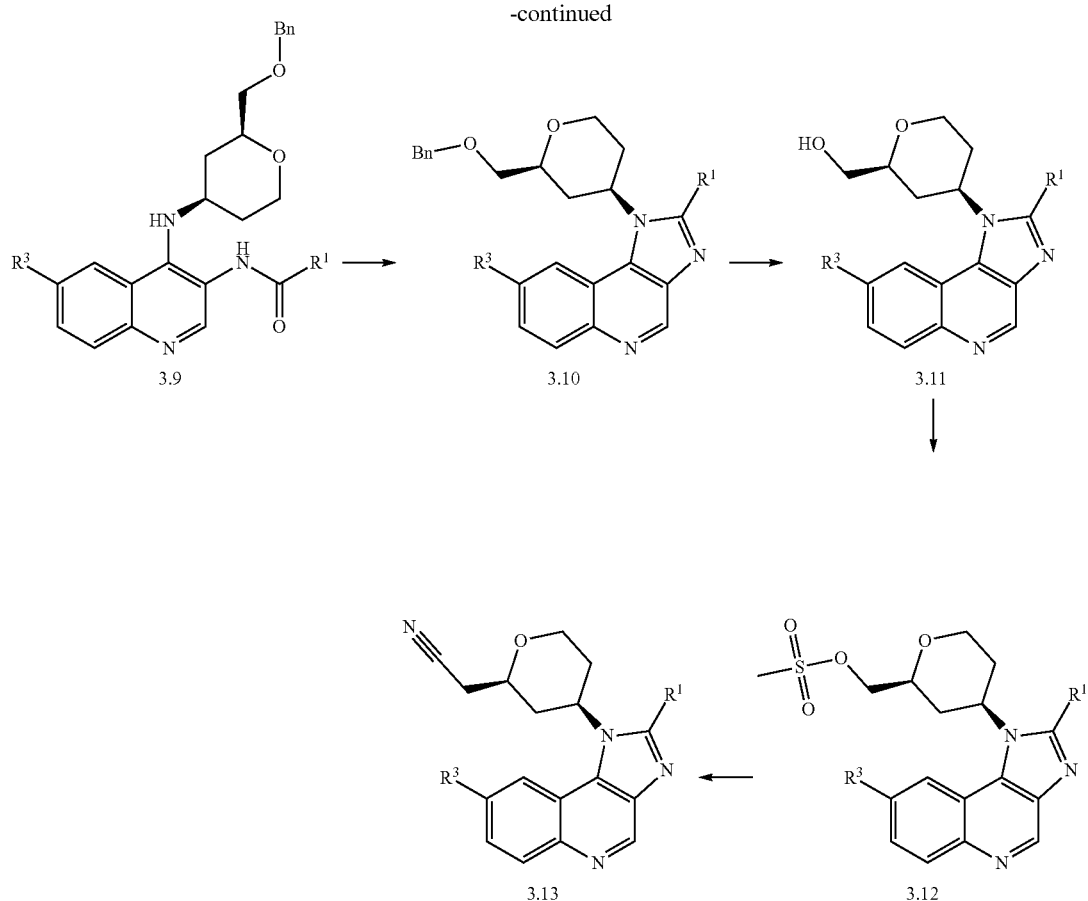

Reaction Scheme 3 depicts the preparation of compounds of formula 3.13, which is a compound of Formula I in which $R^2$ is the chiral 2-cyanomethyltetrahydropyran-4-yl moiety as shown. Using a published procedure, Prins reaction of the compound 3.1 with but-3-en-1-ol generated the pyran 3.2. Oxidation of 3.2 gave ketone 3.3 which was reacted with dimethoxybenzylamine using reductive amination chemistry to provide the protected amine of formula 3.4. The protected amine of formula 3.4 can be reacted with the compound of formula 1.1 in a manner analogous to that previously described in Scheme 1 to provide the compound of formula 3.5. Removal of the protecting group under acidic conditions afforded 3.6. The nitro group of 3.6 is reduced by catalytic hydrogenation or by treatment with a metal such as zinc or iron to afford the diamine 3.7. Acylation of 3.7 with acid 3.8 under a variety of coupling conditions known to those skilled in the art affords 3.9. The amide 3.9 can be dehydrated under thermal conditions to afford 3.10. Deprotection of 3.10 with a Lewis acid such as $BCl_3$, TMSI, $AlCl_3$ or through palladium-catalyzed hydrogenolysis afford the alcohol 3.11. The alcohol 3.11 can be converted to an activated leaving group such as, but not limited to, a sulfonate such as the mesylate 3.12. The compounds of formulae 3.13 can then be prepared by nucleophilic displacement of the mesylate with cyanide anion.

Reaction Scheme 4

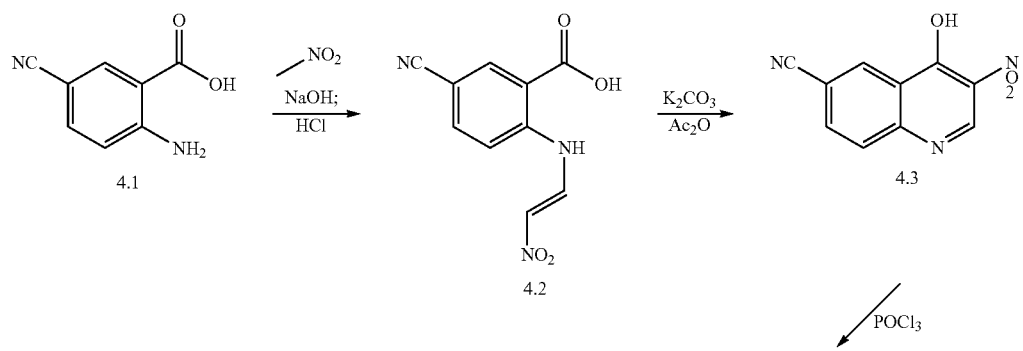

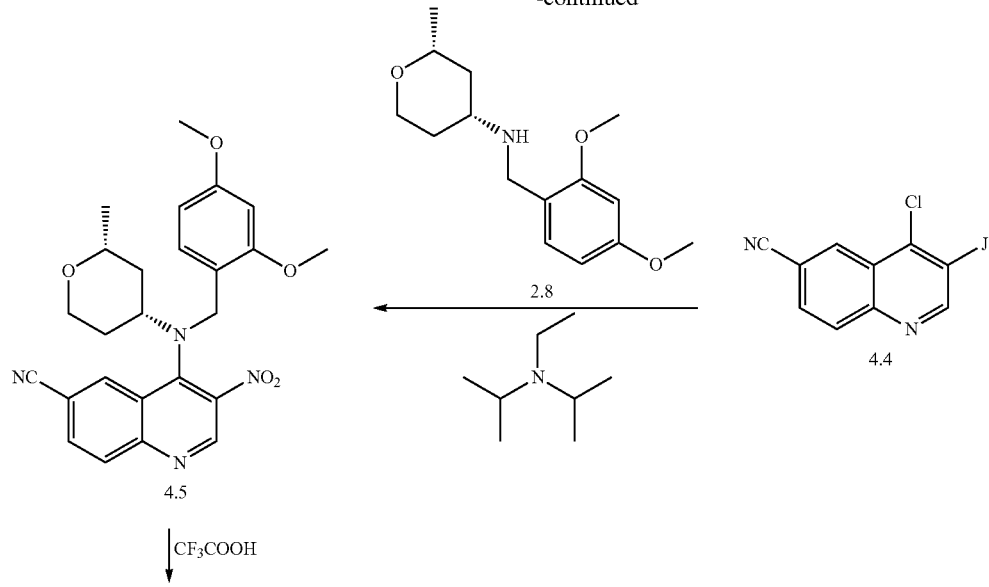

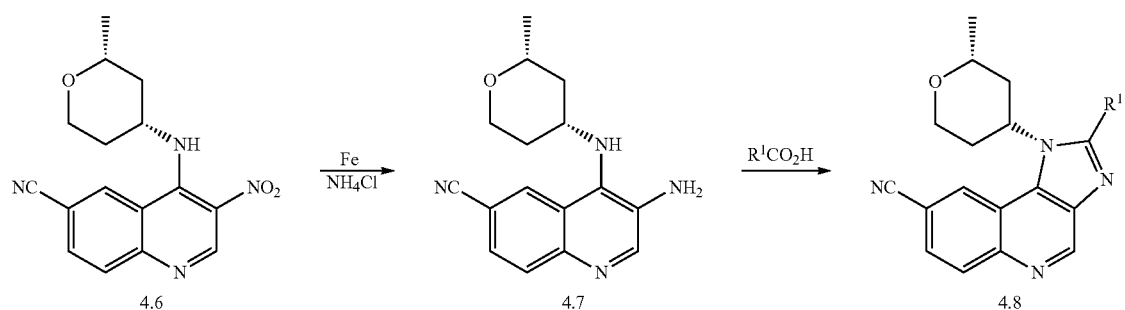

Reaction Scheme 4 depicts the preparation of compounds of formula 4.8, which is a compound of Formula I in which $R^2$ is the chiral 2-methyltetrahydropyran-4-yl moiety and $R^3$ is cyano as shown. The reaction begins from known acid 4.1, which is reacted with N-hydroxy-2-nitroethenamine prepared in situ to afford 4.2. The nitroamine 4.2 was treated with an agent that activated the carboxylic acid followed by condensation to afford quinolone 4.3. The phenol of 4.3 can be converted to the activated chloride 4.4 with phosphorous oxychloride or thionyl chloride. Chloride 4.4 can undergo nucleophilic displacement with an appropriate amine such as 2.8 to afford 4.5. 4.5 can be deprotected to provide 4.6 which, in turn, is reduced to provide diamine 4.7. Compounds of formula 4.8 can be made from 4.7 by condensation with an appropriate acid $R^1CO_2H$ in a manner similar to that previously described.

Reaction Scheme 5

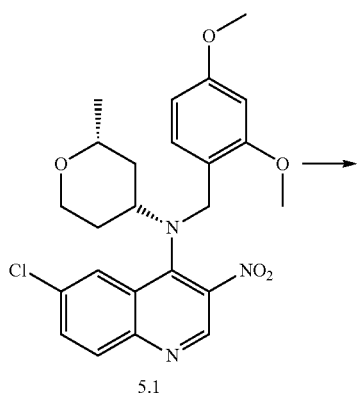

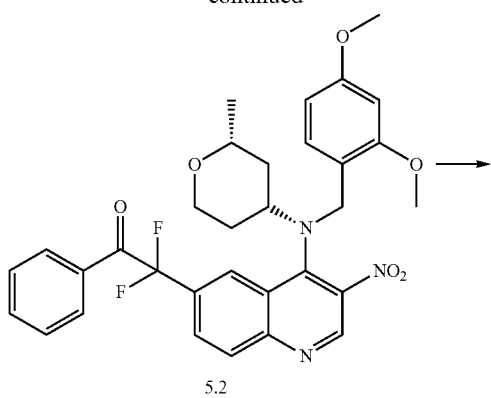

5.2

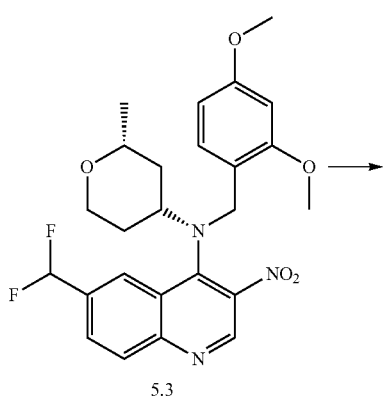

5.3

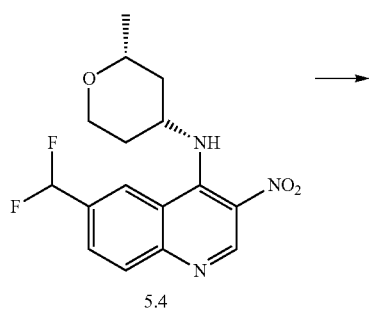

5.4

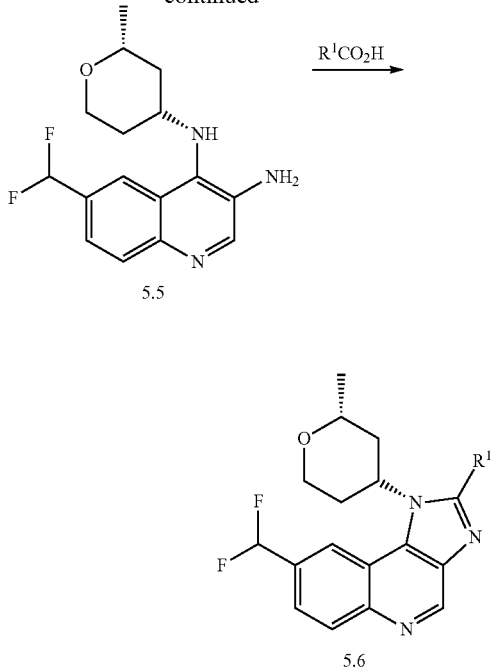

5.5

5.6

Reaction Scheme 5 depicts the preparation of compounds of the formula 5.6, which is a compound of Formula I in which $R^2$ is the chiral 2-methyltetrahydropyran-4-yl moiety and $R^3$ is the difluoromethyl group as shown. Compound 5.1 is treated with 2,2-difluoro-1-phenylethan-1-one and a suitable palladium complex such as cataCXium A Pd G2 and base such as tri-potassium phosphate n-hydrate in an inert solvent such as toluene to afford compound 5.2. The benzoyl group of 5.2 can be removed with a base such as sodium hydroxide or potassium hydroxide in water or other similar conditions. Alternatively the benzoyl is removed in alcohol solvent with sodium methoxide. The protecting group of 5.3 (such as a DMB group) can be removed as previously described and the nitro group of 5.4 can be reduced to provide the diamine 5.5. Compounds of formula 5.6 can be made from 5.5 in a manner similar to that previously described by condensation of 5.5 with an appropriate acid $R^1CO_2H$.

Reaction Scheme 6

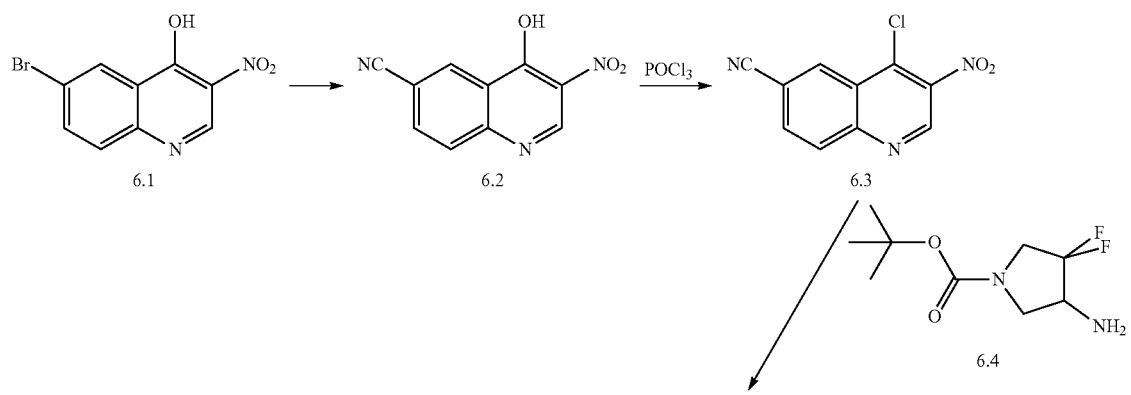

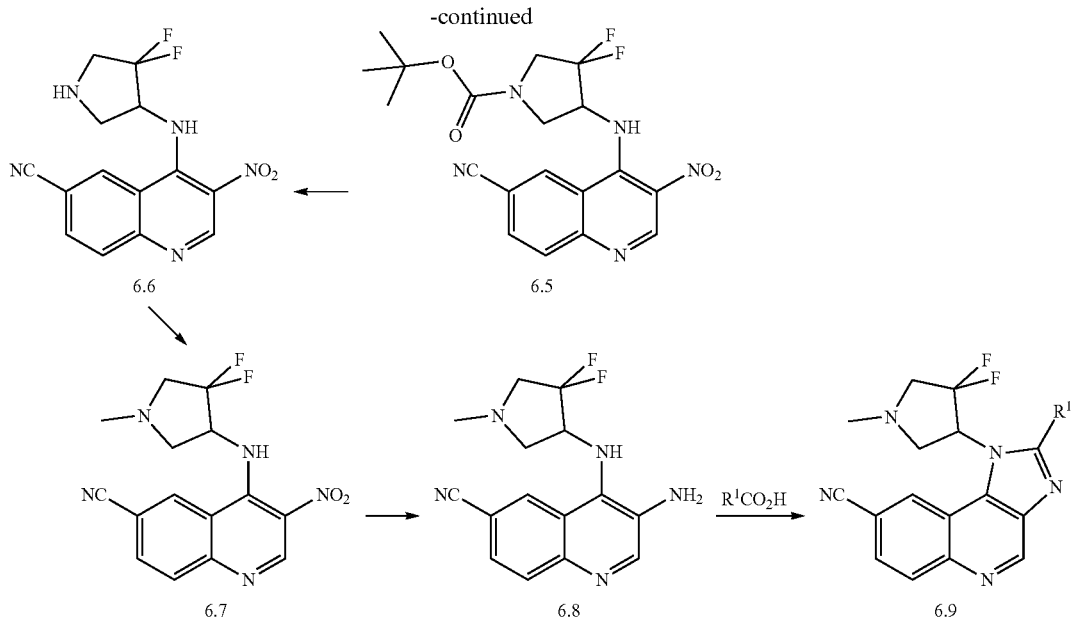

Reaction Scheme 6 depicts the preparation of compounds of the formula 6.9, which is a compound of Formula I in which $R^2$ is the chiral 4,4-difluoro-1-methylpyrrolidin-3-yl moiety and $R^3$ is cyano as shown. This amine is available through a procedure described in US Published Patent Application 20150141402. This series of compounds may be prepared as in the examples above, through formation of the chloride 6.3 through reaction of 6.2 with phosphorous oxychloride or thionyl chloride in a suitable inert solvent. The chloride was treated with amine 6.4 in the presence of a suitable base such as Hunig's base (N,N-diisopropylethylamine) or triethylamine to afford 6.5. The protecting group is removed by treatment of 6.5 with an acid such as trifluoroacetic acid or hydrochloric acid. The secondary amine 6.6 can be methylated through a standard reductive amination using formaldehyde and a reducing agent such as sodium triacetoxyborohydride or sodium cyanoborohydride. The nitro group of compound 6.7 can be reduced through hydrogenation over a platinum catalyst or alternatively the nitro group can be reduced with a suitable metal such as iron or zinc. The claimed compounds 6.9 can be made from 6.8 through condensations with a suitable acid $R^1CO_2H$ under the conditions described previously.

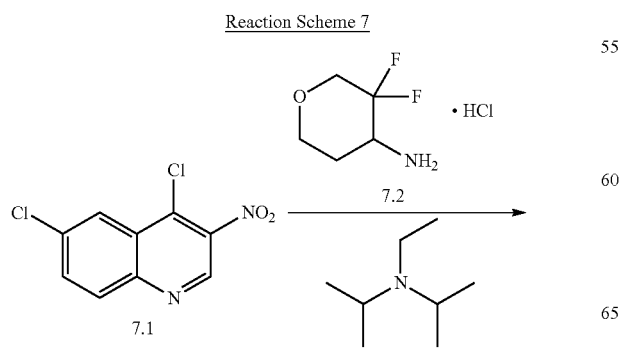

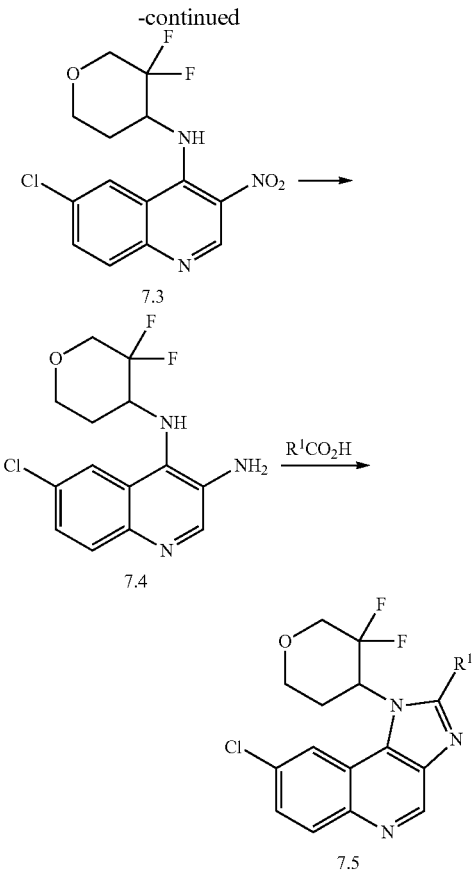

Reaction Scheme 7 depicts the preparation of compounds of the formula 7.5, which is a compound of Formula I in which $R^2$ is the chiral 3,3-difluorotetrahydro-2H-pyran-4-amine moiety as shown. The chloride 7.1 is treated with amine 7.2 in the presence of a suitable base such as Hunig's base or triethylamine to afford 7.3. The nitro group of compound 7.3 can be reduced through hydrogenation over a platinum catalyst or alternatively the nitro group can be reduced with a suitable metal such as iron or zinc. The compounds 7.5 can then be made from 7.4 through condensation with a suitable acid R¹CO₂H under the conditions described previously.

Reaction Scheme 8

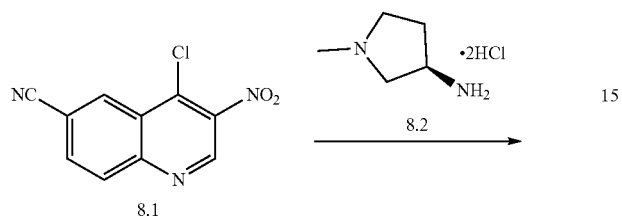

8.1

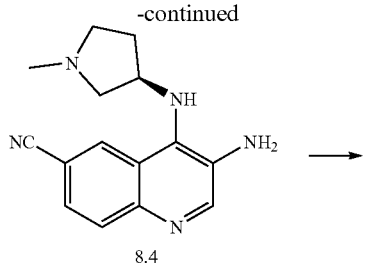

8.4

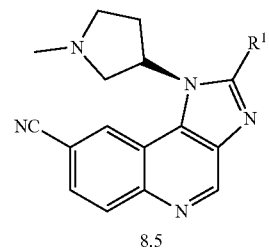

8.5

Reaction Scheme 8 depicts the preparation of compounds of the formula 8.5, which is a compound of Formula I in which R² is the chiral (R)-1-methylpyrrolidin-3-amine moiety and R³ is cyano as shown. The chloride was treated with chiral amine 8.2 in the presence of a suitable base such as Hunig's base or triethylamine to afford 8.3. The nitro group of compound 8.3 can be reduced through hydrogenation over a platinum catalyst or alternatively the nitro group can be reduced with a suitable metal such as iron or zinc. The compounds 8.5 can be made from 8.4 through condensation with a suitable acid R¹CO₂H under the conditions described previously.

Reaction Scheme 9

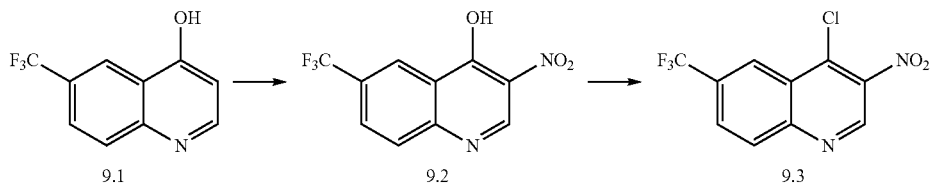

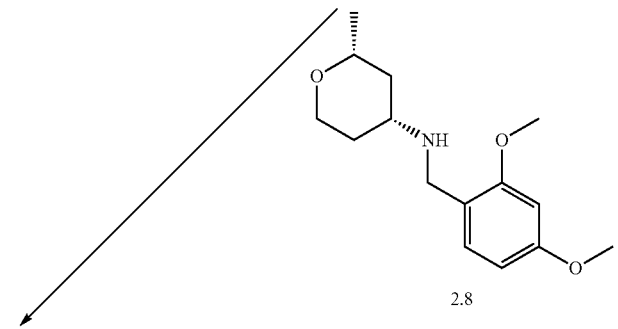

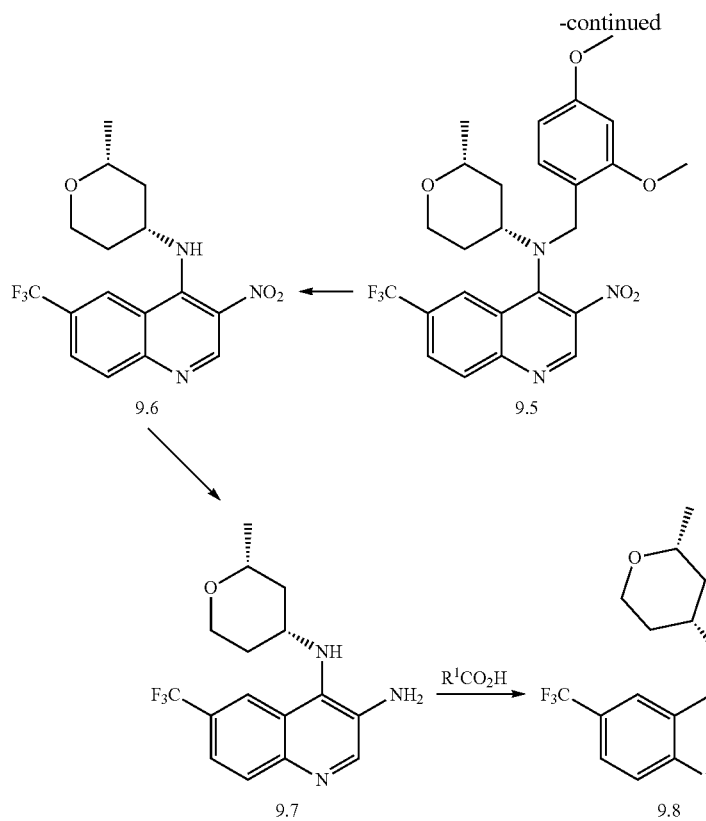

Reaction Scheme 9 depicts the preparation of compounds of the formula 9.8, which is a compound of Formula I in which $R^2$ is the chiral 2-methyltetrahydropyran-4-yl moiety and $R^3$ is trifluoromethyl as shown. The chloride 9.3 was treated with amine 2.8 in the presence of a suitable base such as Hunig's base or triethylamine to afford 9.5. Removal of the protecting group under acidic conditions affords 9.6. The nitro group of compound 9.6 can be reduced through hydrogenation over a platinum catalyst or alternatively the nitro group can be reduced with a suitable metal such as iron or zinc. The claimed compounds 9.8 can be made from 9.7 through condensation with a suitable acid $R^1CO_2H$ under the conditions described previously.

The methods generically described in Schemes 1 through 9 are not to be construed in a limiting manner. It is to be understood by one skilled in the art that variation in the order of certain reaction steps and conditions may be employed to provide compounds of Formula I. The selection of which approach is best to utilize can be made by one skilled in the art of organic synthesis. More specific examples of the methods used to prepare compounds of Formula I are provided below in the Examples, and likewise these methods are also not to be construed by one skilled in the art in a limiting manner.

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics, Aldrich Sure/Sear™ from SigmaAldrich, or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers or diastereomers of certain compounds of the invention (in some examples, the separated enantiomers are designated as ENT 1 and ENT 2, according to their order of elution, and the separated diastereomers are designated as DIAST 1 and DIAST 2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times. All starting materials in these Preparations and Examples are either commercially available or can be prepared by methods known in the art or as described herein.

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wis. or DriSolv™ products from EMD Chemicals, Gibbstown, N.J.) were employed. Commercial solvents and reagents were used without further purification. When indicated, reactions were heated by microwave irradiation using Biotage Initiator or Personal Chemistry Emrys Optimizer microwaves or the like. Reaction progress was monitored using thin layer chromatography (TLC), liquid chromatography-mass spectrometry (LCMS) and high performance liquid chromatography (HPLC), analyses. TLC was performed on pre-coated silica gel plates with a fluorescence indicator (254 nm excitation wavelength) and visualized under UV light and/or with I2, KMnO−4, CoCl2, phosphomolybdic acid, and/or ceric ammonium molybdate stains. LCMS data were acquired on an Agilent 1100 Series instrument with a Leap Technologies autosampler, Gemini C18 columns, MeCN/water gradients, and either TFA, formic acid, or ammonium hydroxide modifiers or similar equipment. The column eluent was analyzed using Waters ZQ mass spectrometer scanning in both positive and negative ion modes from 100 to 1200 Da. Other similar instruments were also used. HPLC data were acquired on an Agilent 1100 Series instrument using Gemini or XBridge C18 columns, MeCN/water gradients, and either TFA or ammonium hydroxide modifiers and comparable equipment. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges and the like. Chiral purifications were performed by chiral supercritical fluid chromatography (SFC) using Berger or Thar instruments and similar instruments; Chi-ralPAK-AD, -AS, -IC, Chiralcel-OD, or -OJ columns; and CO2 mixtures with MeOH, EtOH, iPrOH, or MeCN, alone or modified using TFA or iPrNH2. UV detection was used to trigger fraction collection.

Mass spectrometry data are reported from LCMS analyses. Mass spectrometry (MS) was performed via atmospheric pressure chemical ionization (APCI), electrospray Ionization (ESI), electron impact ionization (EI) or electron scatter (ES) ionization sources. Proton nuclear magnetic spectroscopy (1H NMR) chemical shifts are given in parts per million downfield from tetramethylsilane and were recorded on on 300, 400, 500, or 600 MHz Varian spectrometers. Chemical shifts are expressed in parts per million (ppm, δ) referenced to the deuterated solvent residual peaks. The peak shapes are described as follows: s, singlet; d, doublet; t, triplet; q, quartet; quin, quintet; m, multiplet; br s, broad singlet; app, apparent. Analytical SFC data were acquired on a Berger analytical instrument as described above. Optical rotation data were acquired on a PerkinElmer model 343 polarimeter using a 1 dm cell. Silica gel chromatography was performed primarily using a medium pressure Biotage or ISCO systems using columns pre-packaged by various commercial vendors including Biotage and ISCO.

Unless otherwise noted, chemical reactions were performed at room temperature (about 23 degrees Celsius).

The compounds and intermediates described below were named using the naming convention provided with ACD/ChemSketch 2012, File Version C10H41, Build 69045 (Advanced Chemistry Development, Inc., Toronto, Ontario, Canada). The naming convention provided with ACD/ChemSketch 2012 is well known by those skilled in the art and it is believed that the naming convention provided with ACD/ChemSketch 2012 generally comports with the IUPAC (International Union for Pure and Applied Chemistry) recommendations on Nomenclature of Organic Chemistry and the CAS Index rules.

In the experimental sections that follow the following abbreviations may be used. ACN is acetonitrile; $Ac_2O$ is acetic anhydride; br is broad; ° C. is degrees Celsius; $CDCl_3$ is deutero chloroform; $CD_3OD$ is deutero methanol; $CH_3NO_2$ is nitromethane; d is doublet; DCM is dichloromethane; DEA is diethylamine; DIAST is diastereomer; DIEA is N,N-diisopropylethylamine; DMB is dimethoxybenzyl; DMSO is dimethyl sulfoxide, EDCI is 1-(3-dimethylaminopropyl)-3-ethylcarbodiimide hydrochloride; ENT is enantiomer; EtOAc is ethyl acetate; EtOH is ethanol; ES is electrospray; FA is formic acid; g is gram; h is hour; HCl is hydrochloric acid; $H_2$ is hydrogen; $H_2O$ is water; HPLC is high performance liquid chromatography; Hz is hertz; $K_2CO_3$ is potassium carbonate; L is liter; LC is liquid chromatography; LCMS is liquid chromatography mass spectrometry; m is multiplet; M is molar; MeOH is methanol; $MgSO_4$ is magnesium sulfate; MHz is megahertz; min is minute; mL is milliliter, mM is millimole; μL is microliter; μM is micromole; MS is mass spectrometry; MsCl is methane sulfonyl chloride; MTBE is methyl tert-butyl ether; NADPH is nicotinamide adenine dinucleotide phosphate; $N_2$ is nitrogen; NEt₃ is triethylamine; $NaHCO_3$ is sodium bicarbonate; $Na_2SO_4$ is sodium sulfate; $NH_4Cl$ is ammonium chloride; $NH_4HCO_3$ is ammonium hydrogen carbonate; $NH_4OH$ is ammonium hydroxide; NMR is nuclear magnetic resonance, PE is petroleum ether; PSI is pounds per square inch; Pt/C is platinum on carbon; RT is retention time or room temperature depending on context; s is singlet; SFC is super critical fluid chromatography; t is triplet; TFA is trifluoroacetic acid; THF is tetrahydrofuran; TLC is thin-layer chromatography; and T3P is propyl phosphonic anhydride.

Preparation P1

(2R,4R)—N-(2,4-Dimethoxybenzyl)-2-methyltetrahydro-2H-pyran-4-amine (P1)

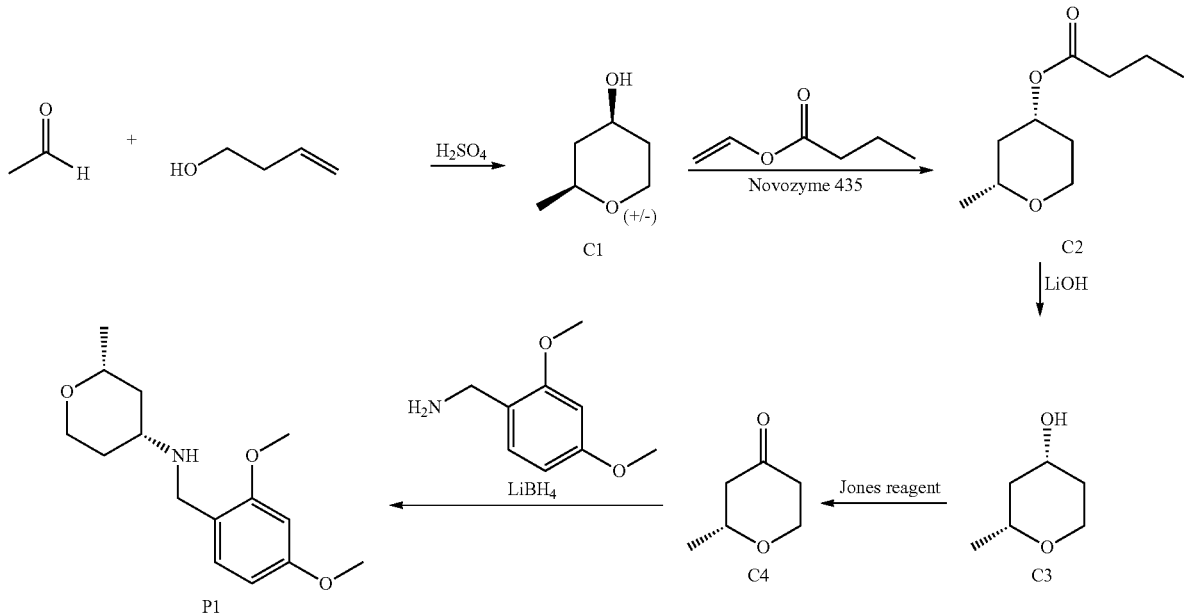

Step 1. Synthesis of cis-2-methyltetrahydro-2H-pyran-4-ol (C1)

But-3-en-1-ol (39.0 mL, 453 mmol) and acetaldehyde (25.5 mL, 454 mmol) were combined in aqueous sulfuric acid (20% w/w, 565 g) and stirred at 80° C. for 5 days. The reaction mixture was cooled to room temperature and extracted with diethyl ether, and then with dichloromethane; the combined organic layers were dried over magnesium sulfate, filtered, and concentrated in vacuo. Silica gel chromatography (Gradient: 0% to 25% ethyl acetate in heptane) afforded the product as a colorless oil. Yield: 11.2 g, 96.4 mmol, 21%. $^1$H NMR (400 MHz, CDCl$_3$) δ 3.99 (ddd, J=11.8, 4.9, 1.7 Hz, 1H), 3.71-3.80 (m, 1H), 3.35-3.46 (m, 2H), 1.82-1.98 (m, 3H), 1.48 (dddd, J=12.5, 12.4, 11.1, 4.9 Hz, 1H), 1.21 (d, J=6.2 Hz, 3H), 1.14-1.24 (m, 1H).

Step 2. Synthesis of (2R,4R)-2-methyltetrahydro-2H-pyran-4-yl butanoate (C2)

Ethenyl butanoate (78.6 mL, 620 mmol) and Novozyme 435 (immobilized *Candida antarctica* lipase B, 25 g) were added to a solution of C1 (150 g, 1.29 mol) in tetrahydrofuran (1.3 L). The reaction mixture was stirred at room temperature for 2 hours, whereupon it was filtered through a pad of diatomaceous earth, which was then rinsed twice with dichloromethane. The combined filtrates were concentrated in vacuo and purified via silica gel chromatography (Gradient: 0% to 10% ethyl acetate in heptane), providing the product as an oil. Yield: 51.5 g, 276 mmol, 45%. The absolute configurations of C2 and subsequent intermediates were confirmed via an X-ray structural determination carried out on C32 (see Preparation P10). $^1$H NMR (400 MHz, CDCl$_3$) δ 4.82-4.92 (m, 1H), 3.99 (ddd, J=11.9, 4.9, 1.7 Hz, 1H), 3.42-3.52 (m, 2H), 2.25 (t, J=7.4 Hz, 2H), 1.92-2.00 (m, 1H), 1.84-1.91 (m, 1H), 1.52-1.69 (m, 3H), 1.28 (ddd, J=12, 11, 11 Hz, 1H), 1.20 (d, J=6.2 Hz, 3H), 0.94 (t, J=7.4 Hz, 3H).

Step 3. Synthesis of (2R,4R)-2-methyltetrahydro-2H-pyran-4-ol (C3)

A solution of C2 (51.5 g, 276 mmol) in methanol and tetrahydrofuran (1:1, 700 mL) was treated with a solution of lithium hydroxide (19.9 g, 831 mmol) in water (120 mL), and the reaction mixture was stirred overnight at room temperature. After removal of the organic solvents via concentration under reduced pressure, the aqueous residue was extracted 4 times with dichloromethane; the combined organic layers were dried over magnesium sulfate, filtered, and concentrated in vacuo to afford the product as a colorless oil. Yield: 27.3 g, 235 mmol, 85%. $^1$H NMR (400 MHz, CDCl$_3$) δ 3.99 (ddd, J=11.8, 4.8, 1.7 Hz, 1H), 3.71-3.80 (m, 1H), 3.35-3.47 (m, 2H), 1.82-1.98 (m, 3H), 1.48 (dddd, J=12.5, 12.4, 11.1, 4.8 Hz, 1H), 1.21 (d, J=6.2 Hz, 3H), 1.14-1.24 (m, 1H).

Step 4. Synthesis of (2R)-2-methyltetrahydro-4H-pyran-4-one (C4)

A solution of C3 (27.3 g, 235 mmol) in acetone (980 mL) was cooled in an ice bath and treated drop-wise with Jones reagent (2.5 M, 103 mL, 258 mmol). The reaction mixture was stirred for 10 minutes at 0° C., then warmed to room temperature, stirred for a further 30 minutes, and cooled to 0° C. 2-Propanol (18 mL, 240 mmol) was added, and stirring was continued for 30 minutes. After the mixture had been concentrated in vacuo, the residue was partitioned between water and dichloromethane; the aqueous layer was extracted 3 times with dichloromethane, and the combined organic layers were dried over magnesium sulfate, filtered, and concentrated under reduced pressure to provide the product as a light yellow oil. Yield: 23 g, 200 mmol, 85%. $^1$H NMR (400 MHz, CDCl$_3$) δ 4.25 (ddd, J=11.5, 7.4, 1.3 Hz, 1H), 3.70 (dqd, J=12.2, 6.1, 2.7 Hz, 1H), 3.64 (ddd, J=12.2, 11.6, 2.8 Hz, 1H), 2.55 (dddd, J=14.6, 12.4, 7.4, 1.0 Hz, 1H), 2.37 (ddd, J=14.4, 2.3, 2.3 Hz, 1H), 2.21-2.31 (m, 2H), 1.29 (d, J=6.2 Hz, 3H).

Step 5. Synthesis of (2R,4R)—N-(2,4-dimethoxybenzyl)-2-methyltetrahydro-2H-pyran-4-amine (P1)

1-(2,4-Dimethoxyphenyl)methanamine (20.3 mL, 135 mmol) was added to a solution of C4 (10.3 g, 90.2 mmol) in methanol (200 mL), and the reaction mixture was stirred for 1 hour at room temperature. It was then cooled to −78° C.; lithium borohydride solution (2 M in tetrahydrofuran, 45.1 mL, 90.2 mmol) was added drop-wise, and stirring was continued at −78° C. for 2 hours. After slowly warming to room temperature overnight, the reaction mixture was quenched via careful addition of saturated aqueous sodium bicarbonate solution. Ethyl acetate (250 mL) and sufficient water to solubilize the precipitate were added, and the aqueous layer was extracted with ethyl acetate; the combined organic layers were dried over magnesium sulfate, filtered, and concentrated in vacuo. Silica gel chromatography (Gradient: 0% to 5% methanol in dichloromethane) provided the product as a colorless oil (10.4 g). Similar purification of mixed fractions afforded additional product (3.7 g). Combined yield: 14.1 g, 53.1 mmol, 59%. $^1$H NMR (400 MHz, CDCl$_3$) δ 7.13 (d, J=8.0 Hz, 1H), 6.42-6.47 (m, 2H), 3.99 (ddd, J=11.6, 4.6, 1.5 Hz, 1H), 3.82 (s, 3H), 3.80 (s, 3H), 3.76 (s, 2H), 3.36-3.45 (m, 2H), 2.63-2.73 (m, 1H), 1.85-1.92 (m, 1H), 1.78-1.85 (m, 1H), 1.38 (dddd, J=13, 12, 11, 4.7 Hz, 1H), 1.20 (d, J=6.2 Hz, 3H), 1.10 (ddd, J=11, 11, 11 Hz, 1H).

Preparation P2 cis-2-[(Benzyloxy)methyl]-N-(2,4-dimethoxybenzyl)tetrahydro-2H-pyran-4-amine (P2)

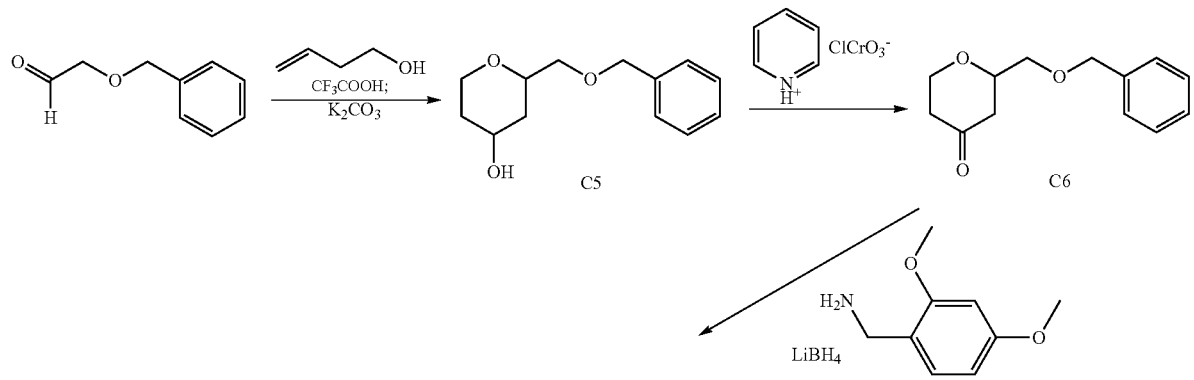

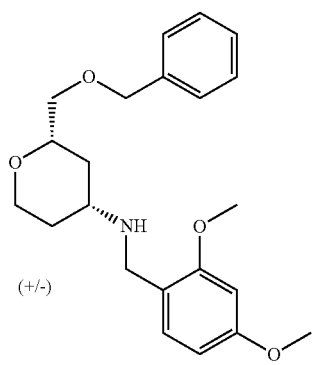

P2

Step 1. Synthesis of 2-[(benzyloxy)methyl]tetrahydro-2H-pyran-4-ol (C5)

A solution of (benzyloxy)acetaldehyde (25.0 g, 166 mmol) and but-3-en-1-ol (12.0 g, 166 mmol) in dichloromethane (550 mL) was added in a drop-wise manner to a 0° C. solution of trifluoroacetic acid (57 g, 500 mmol) in dichloromethane (500 mL). The reaction mixture was stirred at room temperature (20° C.) for 18 hours, whereupon it was concentrated in vacuo. After the residue had been dissolved in methanol (450 mL), it was treated with potassium carbonate (80 g, 580 mmol), and the reaction mixture was stirred for 5 hours at 20° C. A reaction mixture from a similar reaction employing (benzyloxy)acetaldehyde (20.0 g, 133 mmol) was added, and the combined mixtures were filtered. The filtrate was concentrated under reduced pressure, and partitioned between water (500 mL) and ethyl acetate (200 mL). The aqueous layer was then extracted with ethyl acetate (2×150 mL), and the combined organic layers were concentrated in vacuo. Silica gel chromatography (Gradient: 20% to 25% ethyl acetate in petroleum ether) provided the product as a yellow oil. From examination of the $^1$H NMR spectrum this material was assumed to be a mixture of the cis and trans isomers. Combined yield: 42.9 g, 193 mmol, 64%. $^1$H NMR (400 MHz, CDCl$_3$) δ 7.39-7.26 (m, 5H), 4.64-4.53 (m, 2H), [4.29-4.25 (m), 4.11-3.76 (m), and 3.59-3.40 (m), total 6H], [1.96-1.83 (m), 1.71-1.48 (m), and 1.36-1.24 (m), total 4H, assumed; partially obscured by water peak].

Step 2. Synthesis of 2-[(benzyloxy)methyl]tetrahydro-4H-pyran-4-one (C6)

Pyridinium chlorochromate (48 g, 220 mmol) was added to a solution of C5 (22.9 g, 103 mmol) in dichloromethane (350 mL), and the reaction mixture was stirred at room temperature (20° C.) for 18 hours. It was then combined with a similar reaction carried out using C5 (20 g, 90 mmol), and the mixture was filtered, then concentrated in vacuo. The residue was purified via chromatography on silica gel (Eluent: 20% ethyl acetate in petroleum ether), affording the product as a colorless oil. Combined yield: 36.2 g, 164 mmol, 85%. $^1$H NMR (400 MHz, CDCl$_3$) δ 7.40-7.27 (m, 5H), 4.65-4.58 (m, 2H), 4.36 (ddd, J=11.5, 7.5, 1.5 Hz, 1H), 3.85 (dddd, J=11, 5, 4, 3 Hz, 1H), 3.72 (ddd, J=12.3, 11.5, 2.8 Hz, 1H), 3.58 (dd, half of ABX pattern, J=10.5, 4.0 Hz, 1H), 3.55 (dd, half of ABX pattern, J=10.3, 5.3 Hz, 1H), 2.63 (dddd, J=15, 12, 7.5, 1 Hz, 1H), 2.56-2.47 (m, 1H), 2.40-2.32 (m, 2H).

Step 3. Synthesis of cis-2-[(benzyloxy)methyl]-N-(2,4-dimethoxybenzyl)tetrahydro-2H-pyran-4-amine (P2)

1-(2,4-Dimethoxyphenyl)methanamine (23 g, 140 mmol) was added to a solution of C6 (20 g, 91 mmol) in methanol (275 mL). The reaction mixture was stirred at room temperature (20° C.) for 24 hours, whereupon it was cooled to −78° C. and treated in a drop-wise manner with lithium borohydride (2 M solution in tetrahydrofuran; 46.0 mL 92.0 mmol). The reaction mixture was allowed to slowly warm to room temperature, and was then stirred at room temperature overnight. This was combined with a similar reaction mixture that employed C6 (16.18 g, 73.5 mmol) and concentrated in vacuo. The residue was mixed with saturated aqueous sodium bicarbonate solution (300 mL) and water (200 mL), and extracted with ethyl acetate (4×200 mL). The combined organic layers were dried over sodium sulfate, filtered, concentrated under reduced pressure, and purified via chromatography on silica gel (Gradient: 0% to 9% methanol in dichloromethane) to provide the product as a light yellow oil. Combined yield: 52.0 g, 140 mmol, 85%. LCMS m/z 371.9 [M+H]$^+$. $^1$H NMR (400 MHz, CDCl$_3$) δ 7.38-7.25 (m, 5H), 7.12 (d, J=8.0 Hz, 1H), 6.46 (d, half of AB quartet, J=2.5 Hz, 1H), 6.43 (dd, half of ABX pattern, J=8.0, 2.5 Hz, 1H), 4.58 (AB quartet, J$_{AB}$=12.0 Hz, Δv$_{AB}$=23.2 Hz, 2H), 4.07 (ddd, J=11.5, 4.5, 1.5 Hz, 1H), 3.81 (s, 3H), 3.80 (s, 3H), 3.75 (s, 2H), 3.59-3.39 (m, 4H), 2.75-2.65 (m, 1H), 1.91-1.80 (m, 2H), 1.48-1.35 (m, 1H), 1.23-1.12 (m, 1H).

Preparation P3

N$^4$-{cis-2-[(Benzyloxy)methyl]tetrahydro-2H-pyran-4-yl}-6-chloroquinoline-3,4-diamine (P3)

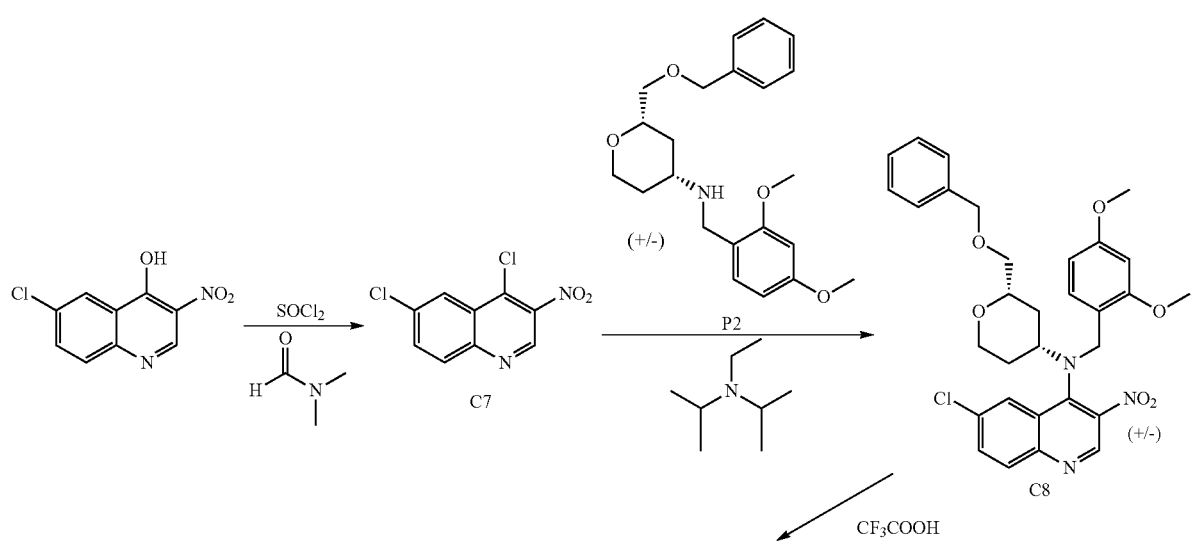

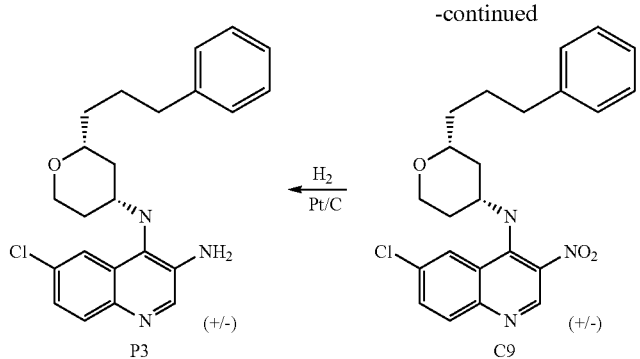

Step 1. Synthesis of 4,6-dichloro-3-nitroquinoline (C7)

N,N-Dimethylformamide (3.1 mL, 40 mmol) and thionyl chloride (97%, 6.9 mL, 93 mmol) were added to a suspension of 6-chloro-3-nitroquinolin-4-ol (15.38 g, 68.48 mmol) in dichloromethane (140 mL), and the reaction mixture was heated at reflux. After 5 hours, it was cooled to room temperature, diluted with additional dichloromethane (25 mL), and poured into saturated aqueous sodium bicarbonate solution (250 mL). The aqueous layer was extracted with dichloromethane (100 mL), then passed through a plug of diatomaceous earth, which was subsequently rinsed with dichloromethane (50 mL). The combined organic layers and organic filtrate were dried over magnesium sulfate, filtered, and concentrated in vacuo to afford the product as a pale tan solid. Yield: 16.8 g, quantitative. $^1$H NMR (400 MHz, CDCl$_3$) δ 9.25 (s, 1H), 8.42 (d, J=2.2 Hz, 1H), 8.17 (d, J=8.9 Hz, 1H), 7.89 (dd, J=9.0, 2.2 Hz, 1H).

Step 2. Synthesis of N-{cis-2-[(benzyloxy)methyl]tetrahydro-2H-pyran-4-yl}-6-chloro-N-(2,4-dimethoxybenzyl)-3-nitroquinolin-4-amine (C8)

Compound C7 (17.2 g, 70.8 mmol) was slowly added to a solution of P2 (20.8 g, 56.0 mmol) and N,N-diisopropylethylamine (21.7 g, 168 mmol) in acetonitrile (300 mL). The reaction mixture was stirred for 16 hours at room temperature (25° C.), at which time LCMS analysis indicated conversion to the product: LCMS m/z 578.0 (chlorine isotope pattern observed) [M+H]$^+$. The reaction mixture was concentrated to half its original volume, diluted with water (400 mL), and extracted with ethyl acetate (2×300 mL). The combined organic layers were dried over sodium sulfate, filtered, concentrated in vacuo, and purified via silica gel chromatography (Gradient: 0% to 25% ethyl acetate in petroleum ether) to provide the product as a yellow solid. Yield: 26.1 g, 45.2 mmol, 81% yield. $^1$H NMR (400 MHz, CDCl$_3$) δ 9.02 (s, 1H), 8.22 (d, J=2.5 Hz, 1H), 7.98 (d, J=9.0 Hz, 1H), 7.69 (dd, J=9.0, 2.5 Hz, 1H), 7.36-7.25 (m, 5H), 6.82 (br d, J=8.5 Hz, 1H), 6.22-6.18 (m, 2H), 4.57 (AB quartet, J$_{AB}$=12.3 Hz, Δv$_{AB}$=9.1 Hz, 2H), 4.40-4.27 (m, 2H), 4.15-4.07 (m, 1H), 3.83-3.73 (m, 1H), 3.69 (s, 3H), 3.59-3.40 (m, 4H), 3.54 (s, 3H), 2.00-1.91 (m, 3H), 1.78-1.66 (m, 1H).

Step 3. Synthesis of N-{cis-2-[(benzyloxy)methyl]tetrahydro-2H-pyran-4-yl}-6-chloro-3-nitroquinolin-4-amine (C9)

Trifluoroacetic acid (11.8 g, 103 mmol) was slowly added drop-wise to a 20° C. solution of C8 (6.00 g, 10.4 mmol) in dichloromethane (50 mL). The reaction mixture was stirred for 1 hour, whereupon LCMS analysis indicated conversion to the product: LCMS m/z 427.9 (chlorine isotope pattern observed) [M+H]$^+$. It was then combined with the reaction mixture from a similar transformation of C8 (1.95 g, 3.37 mmol) and concentrated in vacuo. The residue was diluted with saturated aqueous sodium bicarbonate solution (200 mL) and extracted with ethyl acetate (4×100 mL); the combined organic layers were dried over sodium sulfate, filtered, and concentrated under reduced pressure, providing the product as a yellow solid (6.40 g) that contained some ethyl acetate by $^1$H NMR analysis. Combined yield, corrected for solvent: 5.69 g, 13.3 mmol, 96%. $^1$H NMR (400 MHz, CDCl$_3$) δ 9.36 (s, 1H), 9.07 (br d, J=9.0 Hz, 1H), 8.10 (d, J=2.0 Hz, 1H), 7.97 (d, J=9.0 Hz, 1H), 7.73 (dd, J=9.0, 2.0 Hz, 1H), 7.38-7.26 (m, 5H), 4.59 (AB quartet, J$_{AB}$=12.0 Hz, Δv$_{AB}$=7.2 Hz, 2H), 4.34-4.22 (m, 1H), 4.18 (ddd, J=12.0, 4.5, 1.5 Hz, 1H), 3.69-3.62 (m, 1H), 3.62-3.52 (m, 2H), 3.49 (dd, component of ABC pattern, J=10.3, 4.3 Hz, 1H), 2.21-2.12 (m, 2H), 1.88-1.76 (m, 1H), 1.66-1.55 (m, 1H).

Step 4. Synthesis of N$^4$-{cis-2-[(benzyloxy)methyl]tetrahydro-2H-pyran-4-yl}-6-chloroquinoline-3,4-diamine (P3)

Platinum on carbon (5%; 1.37 g) was added in one portion to a 20° C. solution of C9 (6.0 g, 14 mmol) in tetrahydrofuran (200 mL). The reaction mixture was purged with argon, then saturated with hydrogen and stirred under 50 psi of hydrogen for 3 hours at 20° C. Filtration and concentration of the filtrate in vacuo provided the product as a brown solid. Yield: 5.75 g, 14.4 mmol, quantitative. LCMS m/z 397.8 (chlorine isotope pattern observed) [M+H]$^+$. $^1$H NMR (400 MHz, CDCl$_3$) δ 8.47 (s, 1H), 7.90 (d, J=9.0 Hz, 1H), 7.73 (d, J=2.0 Hz, 1H), 7.39 (dd, J=9.0, 2.0 Hz, 1H), 7.36-7.24 (m, 5H), 4.56 (AB quartet, J$_{AB}$=12.3 Hz, Δv$_{AB}$=9.9 Hz, 2H), 4.09 (ddd, J=12, 4.5, 1 Hz, 1H), 3.90 (br s, 2H), 3.57-3.40 (m, 5H), 3.39-3.31 (br m, 1H), 1.91-1.82 (m, 2H), 1.66-1.53 (m, 1H), 1.43-1.33 (m, 1H).

Preparation P4

3-Amino-4-[(4,4-difluoro-1-methylpyrrolidin-3-yl)amino]quinoline-6-carbonitrile (P4)

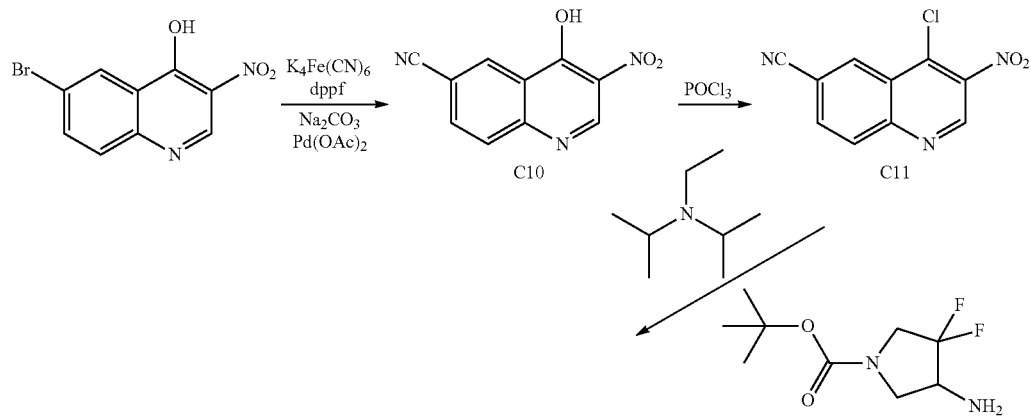

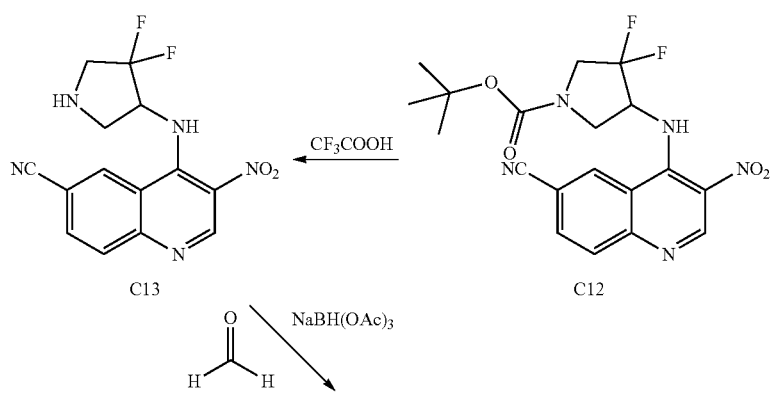

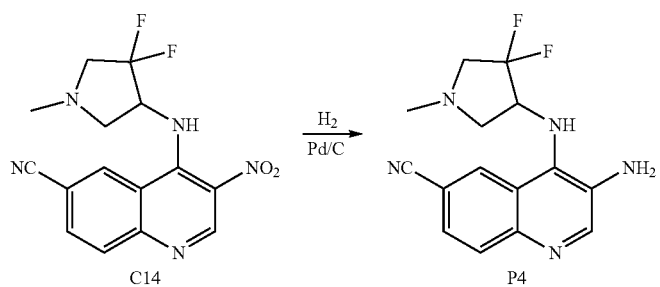

Step 1. Synthesis of 4-hydroxy-3-nitroquinoline-6-carbonitrile (C10)

This reaction was run in two identical batches. A mixture of 6-bromo-3-nitroquinolin-4-ol (25.0 g, 92.9 mmol), potassium hexacyanoferrate(II) trihydrate (13.7 g, 32.4 mmol), 1,1'-bis(diphenylphosphino)ferrocene (5.15 g, 9.29 mmol), sodium carbonate (11.8 g, 111 mmol), and palladium(II) acetate (1.04 g, 4.63 mmol) in N,N-dimethylformamide (350 mL) was heated at 140° C. for 16 hours. The reaction mixture was cooled to room temperature, and the two batches were combined and filtered through diatomaceous earth. The filter cake was slowly rinsed with N,N-dimethylformamide (200 mL) and tert-butyl methyl ether (3.0 L) while the filtrate was stirred. A dark solid precipitated from the filtrate during the stirring, and the resulting mixture was stirred at 20° C. for 15 minutes, and then filtered. This second filtrate was concentrated in vacuo to a volume of approximately 40 mL; the residue was diluted with tert-butyl methyl ether (~200 mL), and the resulting yellow precipitate was collected by filtration, and then triturated with ethyl acetate (~200 mL). The product was obtained as a deep yellow solid. Combined yield: 20 g, 93 mmol, 50%. LCMS m/z 216.0 [M+H]$^+$. $^1$H NMR (400 MHz, DMSO-d$_6$) δ 9.00 (s, 1H), 8.51 (d, J=2.0 Hz, 1H), 7.83 (dd, J=8.5, 1.5 Hz, 1H), 7.69 (d, J=8.5 Hz, 1H).

Step 2. Synthesis of
4-chloro-3-nitroquinoline-6-carbonitrile (C11)

To a 15° C. solution of C10 (5.00 g, 23.2 mmol) in N,N-dimethylformamide (30 mL) was added phosphorus oxychloride (9.85 g, 64.2 mmol), and the reaction mixture was stirred at 15° C. for 1.5 hours. It was then poured into ice water (100 mL) and the resulting suspension was filtered. The collected solids were dissolved in tetrahydrofuran (100 mL) and filtered through a pad of silica gel. Concentration of the filtrate in vacuo afforded the product as a white solid. Yield: 3.10 g, 13.3 mmol, yield 57%. $^1$H NMR (400 MHz, CDCl$_3$) δ 9.39 (s, 1H), 8.83 (d, J=1.8 Hz, 1H), 8.35 (d, J=8.8 Hz, 1H), 8.10 (dd, J=8.8, 1.8 Hz, 1H).

Step 3. Synthesis of tert-butyl 4-[(6-cyano-3-nitroquinolin-4-yl)amino]-3,3-difluoro pyrrolidine-1-carboxylate (C12)

tert-Butyl 4-amino-3,3-difluoropyrrolidine-1-carboxylate (prepared using the method described by D. C. Behenna et al., in U.S. Patent Application 2015 0141402 A1, May 21, 2015; 2.30 g, 10.3 mmol) was dissolved in acetonitrile (20 mL). N,N-Diisopropylethylamine (2.01 g, 15.5 mmol) and C11 (3.04 g, 13.0 mmol) were added to this solution, and the reaction mixture was stirred for 14 hours at 20° C. After removal of volatiles in vacuo, purification via silica gel chromatography (Gradient: 9% to 17% tetrahydrofuran in petroleum ether) provided the product as a pale yellow solid. Yield: 3.20 g, 7.63 mmol, 74%. $^1$H NMR (400 MHz, CDCl$_3$) δ 9.52 (s, 1H), 9.21-9.04 (br m, 1H), 8.48 (br s, 1H), 8.20 (d, J=8.8 Hz, 1H), 8.00 (dd, J=8.6, 1.5 Hz, 1H), 4.88-4.74 (m, 1H), 4.23 (br dd, J=9.7, 8.8 Hz, 1H), 4.05-3.89 (br m, 1H), 3.89-3.75 (m, 1H), 3.60 (ddd, J=11.4, 8.4, 1.3 Hz, 1H), 1.51 (s, 9H).

Step 4. Synthesis of 4-[(4,4-difluoropyrrolidin-3-yl)amino]-3-nitroquinoline-6-carbonitrile (C13)

Trifluoroacetic acid (1 mL) was added to a 15° C. solution of C12 (1.10 g, 2.62 mmol) in dichloromethane (2 mL). After the reaction mixture had been stirred for 1 hour at 15° C., at which time LCMS analysis indicated conversion to the product: LCMS m/z 320.1 [M+H]$^+$, it was concentrated in vacuo and neutralized via addition of aqueous sodium bicarbonate solution (60 mL). The resulting mixture was extracted with ethyl acetate (3×50 mL), and the combined organic layers were concentrated under reduced pressure to afford the product as a pale yellow solid. Yield: 810 mg, 2.54 mmol, 97%. $^1$H NMR (400 MHz, DMSO-d$_6$) δ 9.19 (s, 1H), 9.00 (s, 1H), 8.68-8.57 (br m, 1H), 8.13 (br AB quartet, J$_{AB}$=8.5 Hz, Δν$_{AB}$=48.4 Hz, 2H), 4.61-4.43 (m, 1H), 3.58 (dd, J=12.0, 7.5 Hz, 1H), 3.41-3.28 (m, 1H), 3.26-3.12 (m, 1H), 3.12 (dd, J=11.8, 7.3 Hz, 1H).

Step 5. Synthesis of 4-[(4,4-difluoro-1-methylpyrrolidin-3-yl)amino]-3-nitroquinoline-6-carbonitrile (C14)

Sodium triacetoxyborohydride (2.15 g, 10.1 mmol) was added to a 0° C. mixture of C13 (810 mg, 2.54 mmol) in acetonitrile (5 mL). An aqueous solution of formaldehyde (37%, 824 mg, 10.2 mmol) was added to the 0° C. reaction mixture over 20 minutes, and stirring was then continued at room temperature for 1 hour, at which time LCMS analysis indicated conversion to the product: LCMS m/z 334.1 [M+H]$^+$. After solvents had been removed via concentration in vacuo, the residue was basified to pH 8 by addition of aqueous sodium bicarbonate solution, filtered, and concentrated under reduced pressure, providing the product as a red solid. Yield: 780 mg, 2.34 mmol, 92%. $^1$H NMR (400 MHz, CDCl$_3$), characteristic peaks: δ 9.59 (br d, J=8.8 Hz, 1H), 9.48 (s, 1H), 8.55 (br s, 1H), 8.14 (d, J=8.4 Hz, 1H), 7.96 (dd, J=8.8, 1.3 Hz, 1H), 3.29-3.03 (m, 3H), 2.86 (ddd, J=9.9, 5.1, 2.0 Hz, 1H), 2.47 (s, 3H).

Step 6. Synthesis of 3-amino-4-[(4,4-difluoro-1-methylpyrrolidin-3-yl)amino]quinoline-6-carbonitrile (P4)

Palladium on carbon (10%; 1 g) was added to a solution of C14 (3.00 g, 9.00 mmol) in methanol (30 mL), and the reaction mixture was hydrogenated under a balloon of hydrogen for 2 hours at 25° C. It was then filtered through diatomaceous earth, concentrated in vacuo, and purified via silica gel chromatography (Gradient: 17% to 33% tetrahydrofuran in petroleum ether), providing the product as a pale yellow solid. Yield: 1.30 g, 4.29 mmol, 48%. $^1$H NMR (400 MHz, CDCl$_3$) δ 8.59 (s, 1H), 8.24 (d, J=1.8 Hz, 1H), 8.03 (d, J=8.8 Hz, 1H), 7.60 (dd, J=8.8, 1.8 Hz, 1H), 4.32-4.19 (m, 1H), 4.09-3.96 (m, 3H), 3.18-2.97 (m, 3H), 2.64 (ddd, J=9.7, 6.6, 1.8 Hz, 1H), 2.41 (s, 3H).

Preparation P5

6-Chloro-N⁴-(3,3-difluorotetrahydro-2H-pyran-4-yl)quinoline-3,4-diamine (P5)

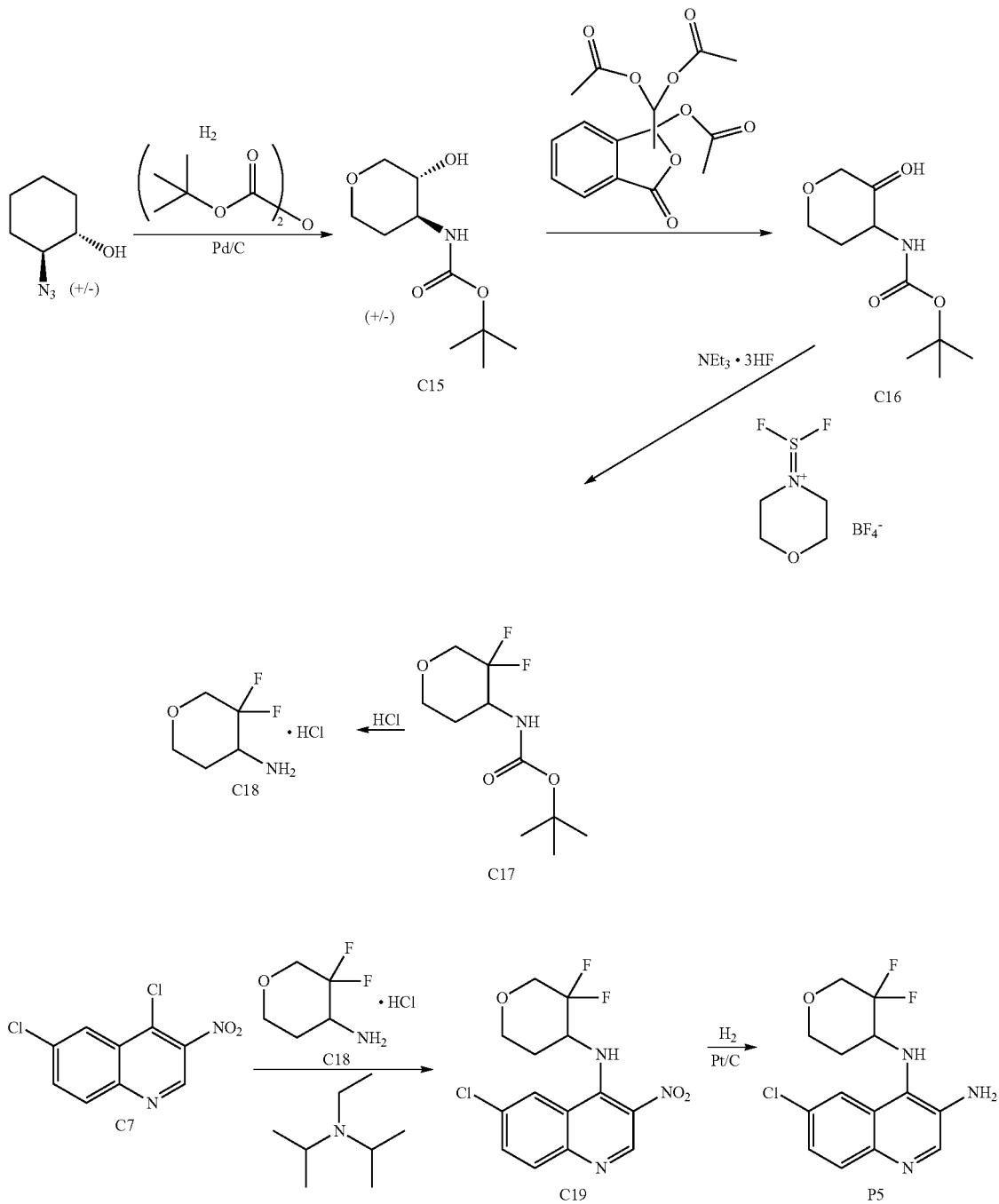

Step 1. Synthesis of tert-butyl (trans-3-hydroxytetrahydro-2H-pyran-4-yl)carbamate (C15)

A solution of trans-4-azidotetrahydro-2H-pyran-3-ol (see M. Chini et al., *Tetrahedron* 1994, 50, 1261-1274) (14.8 g, 103 mmol) and di-tert-butyl dicarbonate (23.0 g, 105 mmol) in ethyl acetate (345 mL) was added to palladium on carbon (10%, 1.5 g) and the reaction mixture was stirred under 50 psi of hydrogen at 20° C. to 25° C. for 22 hours. It was then filtered through diatomaceous earth and the filter pad was rinsed with ethyl acetate and methanol. The combined filtrates were concentrated in vacuo and the residue was triturated once with a mixture of dichloromethane (10 mL) and [9:1 petroleum ether/tetrahydrofuran] (60 mL), affording the product as a white solid. Yield: 15.8 g. 72.7 mmol, 71%. ¹H NMR (400 MHz, CDCl₃) δ 4.71-4.62 (br s, 1H), 4.01 (dd, J=11, 4 Hz, 1H), 3.98-3.87 (m, 2H), 3.57-3.42 (m, 2H), 3.40 (ddd, J=12, 12, 2 Hz, 1H), 3.13 (dd, J=11.0, 9.5 Hz, 1H), 1.96-1.88 (m, 1H), 1.59-1.47 (m, 1H, assumed; partially obscured by water peak), 1.47 (s, 9H).

Step 2. Synthesis of tert-butyl (3-oxotetrahydro-2H-pyran-4-yl)carbamate (C16)

A solution of C15 (35.1 g, 162 mmol) in dichloromethane (540 mL) was treated with [1,1,1-tris(acetyloxy)-1,1-dihydro-1,2-benziodoxol-3-(1H)-one] (Dess-Martin periodinane; 81.6 g, 192 mmol) and stirred at 25° C. for 18 hours. The reaction mixture was treated with saturated aqueous sodium bicarbonate solution and saturated aqueous sodium thiosulfate solution (250 mL); after stirring for 30 minutes, the layers were separated and the aqueous layer was extracted twice with dichloromethane (200 mL). The combined organic layers were dried over sodium sulfate, filtered, and concentrated in vacuo. Silica gel chromatography (Gradient: 10% to 30% ethyl acetate in petroleum ether) afforded the product as a yellow oil (27.95 g) that contained some aromatic material derived from the oxidizing reagent. This material was taken directly to the following step. $^1$H NMR (400 MHz, CDCl$_3$), product peaks only: δ 5.49-5.38 (br s, 1H), 4.55-4.42 (m, 1H), 4.08 (AB quartet, $J_{AB}$=14.8 Hz, $\Delta\nu_{AB}$=40.3 Hz, 2H), 4.07-3.99 (m, 1H), 3.89 (ddd, J=12.0, 11.5, 3.0 Hz, 1H), 2.75-2.63 (m, 1H), 1.96-1.81 (m, 1H), 1.44 (s, 9H).

Step 3. Synthesis of tert-butyl (3,3-difluorotetrahydro-2H-pyran-4-yl)carbamate (C17)

A solution of C16 (from the previous step; 27.95 g) in dichloromethane (124 mL) was slowly added to a 0° C. suspension of difluoro-4-morpholinylsulfonium tetrafluoroborate (XtalFluor-M®; 39.5 g, 163 mmol) and triethylamine trihydrofluoride (28.6 g, 177 mmol) in dichloromethane (384 mL), and the reaction mixture was allowed to slowly warm to 25° C. After three days, the reaction mixture was treated with saturated aqueous sodium bicarbonate solution (500 mL) and extracted with dichloromethane (500 mL). The organic layer was dried over sodium sulfate, filtered, and concentrated in vacuo. Chromatography on silica gel (Eluent: 10% ethyl acetate in petroleum ether) provided the product as a yellow solid. Yield: 8.93 g, 37.6 mmol, 23% over two steps. $^1$H NMR (400 MHz, CDCl$_3$) δ 4.91-4.75 (br m, 1H), 4.18-3.94 (m, 3H), 3.55-3.43 (m, 1H), 3.46 (dd, J=30.4, 12.8 Hz, 1H), 2.07-1.97 (m, 1H), 1.86-1.71 (m, 1H), 1.47 (s, 9H).

Step 4. Synthesis of 3,3-difluorotetrahydro-2H-pyran-4-amine, hydrochloride salt (C18)

A solution of hydrogen chloride in methanol (4 M, 16.8 mL, 67.2 mmol) was added to a 10° C. solution of C17 (3.18 g, 13.4 mmol) in methanol (35 mL). After the reaction mixture had stirred at 10° C. for 1 hour, it was concentrated in vacuo to afford the product as a white solid. Yield: 2.32 g, 13.4 mmol, quantitative. $^1$H NMR (400 MHz, DMSO-d$_6$) δ 9.03-8.89 (br s, 3H), 4.06-3.57 (m, 4H, assumed; partially obscured by water peak), 3.57-3.47 (m, 1H), 2.20-2.08 (m, 1H), 1.88-1.72 (m, 1H).

Step 5. Synthesis of 6-chloro-N-(3,3-difluorotetrahydro-2H-pyran-4-yl)-3-nitroquinolin-4-amine (C19)

N,N-Diisopropylethylamine (9.2 mL, 52.8 mmol) was added to a 10° C. solution of C7 (3.2 g, 13.2 mmol) and C18 (2.32 g, 13.4 mmol) in acetonitrile (40 mL) and the reaction mixture was stirred at 10° C. for 16 hours. It was then combined with two additional reactions carried out using C7 (1.2 g, 4.9 mmol and 90 mg, 0.37 mmol) and concentrated in vacuo. Silica gel chromatography (Gradient: 0% to 20% ethyl acetate in petroleum ether) provided the product as a yellow solid. Combined yield: 4.5 g, 13 mmol, 70%. LCMS m/z 344.0 (chlorine isotope pattern observed) [M+H]$^+$. $^1$H NMR (400 MHz, CDCl$_3$) δ 9.40 (s, 1H), 8.60 (br d, J=10.1 Hz, 1H), 8.05 (d, J=1.8 Hz, 1H), 8.05 (d, J=8.8 Hz, 1H), 7.77 (dd, J=9.2, 2.2 Hz, 1H), 4.40-4.26 (m, 1H), 4.17-4.02 (m, 2H), 3.59 (br ddd, J=12, 12, 1 Hz, 1H), 3.48 (dd, J=29.0, 12.8 Hz, 1H), 2.40-2.32 (m, 1H), 2.28-2.16 (m, 1H).

Step 6. Synthesis of 6-chloro-N$^4$-(3,3-difluorotetrahydro-2H-pyran-4-yl)quinoline-3,4-diamine (P5)

A mixture of C19 (4.40 g, 12.8 mmol) and platinum on carbon (5%; 250 mg) in tetrahydrofuran (50 mL) was degassed with nitrogen at 20° C., and then subjected to hydrogenation at 50 psi and 20° C. for 2 hours. The reaction mixture was filtered, and the filter cake was washed with tetrahydrofuran (3×10 mL). The combined filtrates were concentrated in vacuo, combined with the crude product from a similar reaction carried out using C19 (100 mg, 0.29 mmol), and purified via silica gel chromatography (Gradient: 0% to 20% methanol in dichloromethane) to provide the product as a yellow solid. Combined yield: 3.9 g, 12.4 mmol, 95%. LCMS m/z 314.1 [M+H]$^+$. $^1$H NMR (400 MHz, CDCl$_3$) δ 8.48 (s, 1H), 7.90 (d, J=9.3 Hz, 1H), 7.78 (d, J=2.0 Hz, 1H), 7.41 (dd, J=9.0, 2.2 Hz, 1H), 4.10-4.01 (m, 2H), 3.99-3.93 (br s, 2H), 3.85-3.69 (m, 2H), 3.51-3.42 (m, 1H), 3.44 (dd, J=31.3, 12.7 Hz, 1H), 2.10-1.95 (m, 2H).

Preparation P6

6-Chloro-N⁴-[(4S)-3,3-difluorotetrahydro-2H-pyran-4-yl]quinoline-3,4-diamine (P6)

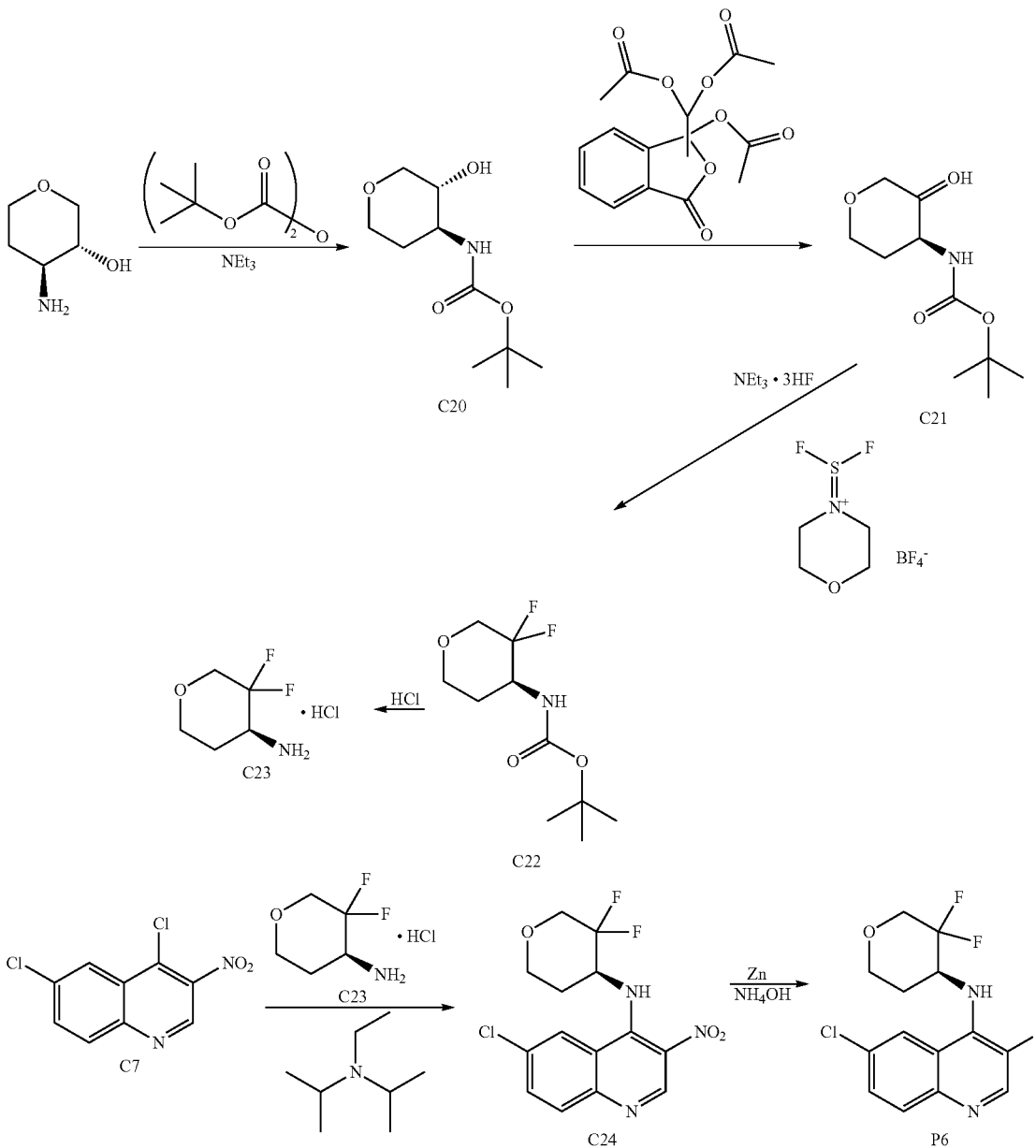

Step 1: Synthesis of tert-butyl [(3R,4S)-3-hydroxytetrahydro-2H-pyran-4-yl]carbamate (C20)

A solution of (3R,4S)-4-aminotetrahydro-2H-pyran-3-ol (see M. A. Brodney et al., in PCT International Pat. Appl. No. WO 2016009297 A1, published Jan. 21, 2016) (383 mg, 3.27 mmol) and di-tert-butyl dicarbonate (714 g, 3.27 mmol) in dichloromethane (33 mL) was treated with triethylamine (0.46 mL, 3.3 mmol) and the reaction mixture was stirred at room temperature overnight. Concentration in vacuo afforded the product as an off-white solid. Yield: 707 mg, 3.25 mmol, 99%. ¹H NMR (400 MHz, CDCl₃) δ 4.69-4.56 (br s, 1H), 4.02 (br dd, J=11.3, 4.7 Hz, 1H), 3.96-3.86 (m, 2H), 3.58-3.44 (m, 2H), 3.40 (ddd, J=12.1, 11.7, 2.3 Hz, 1H), 3.13 (dd, J=11.3, 9.4 Hz, 1H), 1.96-1.87 (m, 1H), 1.58-1.48 (m, 1H, assumed; partially obscured by water peak), 1.47 (s, 9H).

Step 2. Synthesis of tert-butyl [(4S)-3-oxotetrahydro-2H-pyran-4-yl]carbamate (C21)

A solution of C20 (707 mg, 3.25 mmol) in dichloromethane (40 mL) was treated with [1,1,1-tris(acetyloxy)-1,1-dihydro-1,2-benziodoxol-3-(1H)-one] (95%; 1.74 g, 3.90 mmol) and stirred at room temperature for 4 hours. The reaction mixture was quenched with saturated aqueous sodium bicarbonate solution (50 mL) and saturated aqueous sodium thiosulfate solution (50 mL) and stirred for 30 minutes. The aqueous layer was extracted twice with dichloromethane, and the combined organic layers were dried over magnesium sulfate, filtered, and concentrated in vacuo.

Silica gel chromatography (Gradient: 20% to 80% ethyl acetate in heptane) provided the product as a white solid. Yield: 546 mg, 2.54 mmol, 78%. GCMS m/z 215.1 [M+]. $^1$H NMR (400 MHz, CDCl$_3$) δ 5.49-5.36 (br s, 1H), 4.49-4.36 (m, 1H), 4.05 (AB quartet, J$_{AB}$=14.6 Hz, Δv$_{AB}$=38.1 Hz, 2H), 4.04-3.96 (m, 1H), 3.85 (ddd, J=12.1, 11.3, 3.1 Hz, 1H), 2.70-2.59 (m, 1H), 1.92-1.78 (m, 1H), 1.41 (s, 9H).

Step 3: Synthesis of tert-butyl [(4S)-3,3-difluorotetrahydro-2H-pyran-4-yl]carbamate (C22)

A solution of C21 (540 mg, 2.51 mmol) in dichloromethane (5 mL) was slowly added to a 0° C. suspension of difluoro-4-morpholinylsulfonium tetrafluoroborate (1.22 g, 5.02 mmol) and triethylamine trihydrofluoride (0.9 mL, 5.5 mmol) in dichloromethane (10 mL). The ice bath was removed and the reaction mixture was stirred at room temperature overnight, then at 40° C. for 90 minutes. After cooling to room temperature, the reaction mixture was carefully treated with saturated aqueous sodium bicarbonate solution {Caution: gas evolution}. The aqueous layer was extracted twice with dichloromethane, and the combined organic layers were washed with water, dried over magnesium sulfate, filtered, and concentrated in vacuo. Silica gel chromatography (Gradient: 15% to 45% ethyl acetate in heptane) provided the product as a yellow solid, which was used in the following step. By $^1$H NMR analysis, this material was somewhat impure. GCMS m/z 138.1 {[M-(2-methylprop-1-ene and carbon dioxide)]+H}$^+$. $^1$H NMR (400 MHz, CDCl$_3$), product peaks only: δ 4.93-4.81 (m, 1H), 4.16-3.93 (m, 3H), 3.51-3.43 (m, 1H), 3.45 (dd, J=30.4, 12.9 Hz, 1H), 2.05-1.96 (m, 1H), 1.83-1.71 (m, 1H), 1.45 (s, 9H).

Step 4: Synthesis of (4S)-3,3-difluorotetrahydro-2H-pyran-4-amine, hydrochloride salt (C23)

Concentrated hydrochloric acid (2 mL) was added to a solution of C22 (from the previous step; ≤2.51 mmol) in ethanol (10 mL), and the reaction mixture was stirred at room temperature overnight. Removal of solvents in vacuo provided the product as a brown solid. Yield: 155 mg, 0.893 mmol, 36% over two steps. GCMS m/z 137.1 [M$^+$]. $^1$H NMR (400 MHz, CD$_3$OD) δ 4.09-3.86 (m, 3H), 3.65 (dd, J=31.2, 12.9 Hz, 1H), 3.65-3.56 (m, 1H), 2.23-2.14 (m, 1H), 2.03-1.90 (m, 1H).

Step 5: Synthesis of 6-chloro-N-[(4S)-3,3-difluorotetrahydro-2H-pyran-4-yl]-3-nitroquinolin-4-amine (C24)

N,N-Diisopropylethylamine (0.41 mL, 2.4 mmol) was added to a mixture of C7 (190 mg, 0.782 mmol) and C23 (136 mg, 0.783 mmol) in acetonitrile (3 mL), and the reaction mixture was stirred at 60° C. overnight. After cooling to room temperature, the reaction mixture was concentrated in vacuo and partitioned between water and ethyl acetate. A small amount of saturated aqueous sodium bicarbonate solution was added to adjust the aqueous layer to pH 9, and the aqueous layer was extracted twice with ethyl acetate. The combined organic layers were dried over magnesium sulfate, filtered, concentrated in vacuo, and purified via silica gel chromatography (Gradient: 5% to 35% ethyl acetate in heptane), affording the product as a bright yellow solid. Yield: 164 mg, 0.477 mmol, 61%. LCMS m/z 344.4 [M+H]$^+$. $^1$H NMR (400 MHz, CDCl$_3$) δ 9.39 (s, 1H), 8.61 (br d, J=10.2 Hz, 1H), 8.04 (d, J=8.6 Hz, 1H), 8.04 (d, J=2.3 Hz, 1H), 7.77 (dd, J=9.0, 2.3 Hz, 1H), 4.40-4.26 (m, 1H), 4.17-4.02 (m, 2H), 3.59 (br ddd, J=12, 12, 1.5 Hz, 1H), 3.48 (dd, J=29.1, 12.7 Hz, 1H), 2.40-2.32 (m, 1H), 2.29-2.16 (m, 1H).

Step 6: Synthesis of 6-chloro-N$^4$-[(4S)-3,3-difluorotetrahydro-2H-pyran-4-yl]quinoline-3,4-diamine (P6)

Zinc powder (97.5%, 312 mg, 4.65 mmol) was added to a slurry of C24 (160 mg, 0.466 mmol) in methanol (3 mL) and concentrated ammonium hydroxide solution (3 mL). The reaction mixture was stirred at room temperature for 2 hours, whereupon it was filtered through diatomaceous earth. The filter pad was rinsed with dichloromethane and methanol, and the combined filtrates were concentrated in vacuo. The residue was diluted with half-saturated aqueous sodium chloride solution and extracted three times with dichloromethane. The combined organic layers were dried over magnesium sulfate, filtered, concentrated under reduced pressure, and purified via chromatography on silica gel (Gradient: 0% to 100% ethyl acetate in heptane) to provide the product as a pale tan oil. Yield: 78 mg, 0.249 mmol, 54%. LCMS m/z 314.4 [M+H]$^+$. $^1$H NMR (400 MHz, CDCl$_3$) δ 8.47 (s, 1H), 7.89 (d, J=9.0 Hz, 1H), 7.77 (d, J=2.3 Hz, 1H), 7.39 (dd, J=8.8, 2.1 Hz, 1H), 4.08-3.89 (m, 3H), 3.84-3.68 (m, 2H), 3.49-3.40 (m, 1H), 3.42 (dd, J=31.4, 12.7 Hz, 1H), 2.07-1.94 (m, 2H).

Preparation P7

$N^4$-[(2R,4R)-2-Methyltetrahydro-2H-pyran-4-yl]-6-(trifluoromethyl)quinoline-3,4-diamine

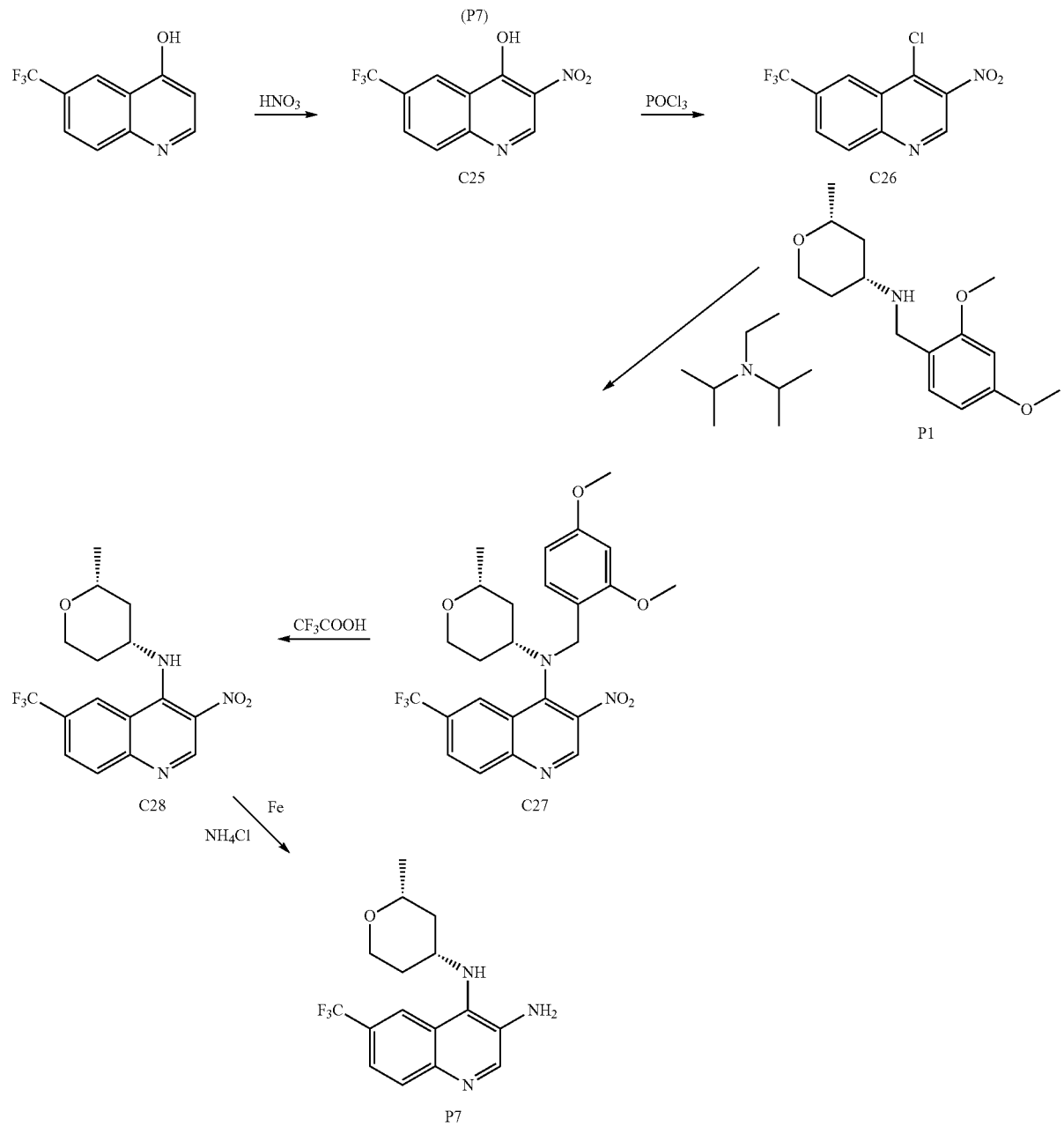

Step 1. Synthesis of 3-nitro-6-(trifluoromethyl)quinolin-4-ol (C25)

A solution of 6-(trifluoromethyl)quinolin-4-ol (2.00 g, 9.38 mmol) in concentrated nitric acid (10 mL) was stirred for 14 hours at 50° C., whereupon it was poured into water (50 mL). The resulting solid was isolated via filtration, providing the product as a pale yellow solid. Yield: 1.80 g, 6.97 mmol, 74%. $^1$H NMR (400 MHz, DMSO-$d_6$) δ 9.29 (s, 1H), 8.46 (s, 1H), 8.11 (d, J=9.0 Hz, 1H), 7.92 (d, J=8.5 Hz, 1H).

Step 2. Synthesis of 4-chloro-3-nitro-6-(trifluoromethyl)quinoline (C26)

Phosphorus oxychloride (3.25 mL, 34.9 mmol) was added to a 15° C. solution of compound C25 (3.00 g, 11.6 mmol) in N,N-dimethylformamide (10 mL), and the reaction mixture was stirred for 2 hours at 15° C. It was then poured into water (80 mL). Collection of the precipitate via filtration provided the product as a solid (2.40 g). This material was impure by $^1$H NMR analysis, and was taken directly into the following step. $^1$H NMR (400 MHz, DMSO-d$_6$), product peaks only: δ 9.22 (s, 1H), 8.40 (br s, 1H), 8.03 (br d, J=8.5 Hz, 1H), 7.92-7.97 (m, 1H).

Step 3. Synthesis of N-(2,4-dimethoxybenzyl)-N-[(2R,4R)-2-methyltetrahydro-2H-pyran-4-yl]-3-nitro-6-(trifluoromethyl)quinolin-4-amine (C27)

N,N-Diisopropylethylamine (3.36 g, 26.0 mmol) and P1 (2.43 g, 9.16 mmol) were slowly added to a 15° C. solution of C26 (from the previous step; 2.40 g, 8.68 mmol) in acetonitrile (30 mL), and the reaction mixture was stirred for 30 minutes at 80° C. Water (100 mL) was added, and the resulting mixture was extracted with ethyl acetate (3×100 mL). The combined organic layers were concentrated in vacuo, and the residue was purified via silica gel chromatography (Gradient: 9% to 25% ethyl acetate in petroleum ether) to provide the product as a yellow solid. Yield: 3.40 g, 6.73 mmol, 58% over 2 steps. $^1$H NMR (400 MHz, CDCl$_3$) δ 9.11 (s, 1H), 8.60 (br s, 1H), 8.15 (d, J=9.0 Hz, 1H), 7.92 (dd, J=8.8, 1.8 Hz, 1H), 6.84 (d, J=8.0 Hz, 1H), 6.22 (dd, J=8.3, 2.3 Hz, 1H), 6.16 (d, J=2.0 Hz, 1H), 4.33-4.44 (m, 2H), 4.02-4.10 (m, 1H), 3.77-3.87 (m, 1H), 3.68 (s, 3H), 3.50 (s, 3H), 3.36-3.46 (m, 2H), 1.95-2.10 (m, 3H), 1.67-1.78 (m, 1H), 1.23 (d, J=6.0 Hz, 3H).

Step 4. Synthesis of N-[(2R,4R)-2-methyltetrahydro-2H-pyran-4-yl]-3-nitro-6-(trifluoromethyl) quinolin-4-amine (C28)

Trifluoroacetic acid (7.67 g, 67.3 mmol) was added to a 15° C. solution of compound C27 (3.40 g, 6.73 mmol) in dichloromethane (30 mL), and the reaction mixture was stirred for 30 minutes at 15° C. Solvents were removed in vacuo, and the residue was diluted with water (100 mL) and extracted with ethyl acetate (3×100 mL). The combined organic layers were concentrated in vacuo to afford the product (2.50 g) as a pale yellow solid, a portion of which was used directly in the following step. LCMS m/z 355.8 [M+H]$^+$.

Step 5. Synthesis of N$^4$-[(2R,4R)-2-methyltetrahydro-2H-pyran-4-yl]-6-(trifluoromethyl) quinoline-3,4-diamine (P7)

Iron powder (314 mg, 5.62 mmol) and ammonium chloride (301 mg, 5.63 mmol) were added to a solution of C28 (from the previous step, 200 mg, ≤0.54 mmol) in ethanol (5 mL) and water (1 mL), and the reaction mixture was stirred for 1 hour at 80° C. It was then filtered through diatomaceous earth, and the filtrate was concentrated in vacuo. Silica gel chromatography (Gradient: 9% to 33% ethyl acetate in petroleum ether) afforded the product as a pale grey solid. Yield: 140 mg, 0.430 mmol, 80% over 2 steps. LCMS m/z 325.9 [M+H]$^+$.

Preparation P8

3-Amino-4-{[(2R,4R)-2-methyltetrahydro-2H-pyran-4-yl]amino}quinoline-6-carbonitrile (P8)

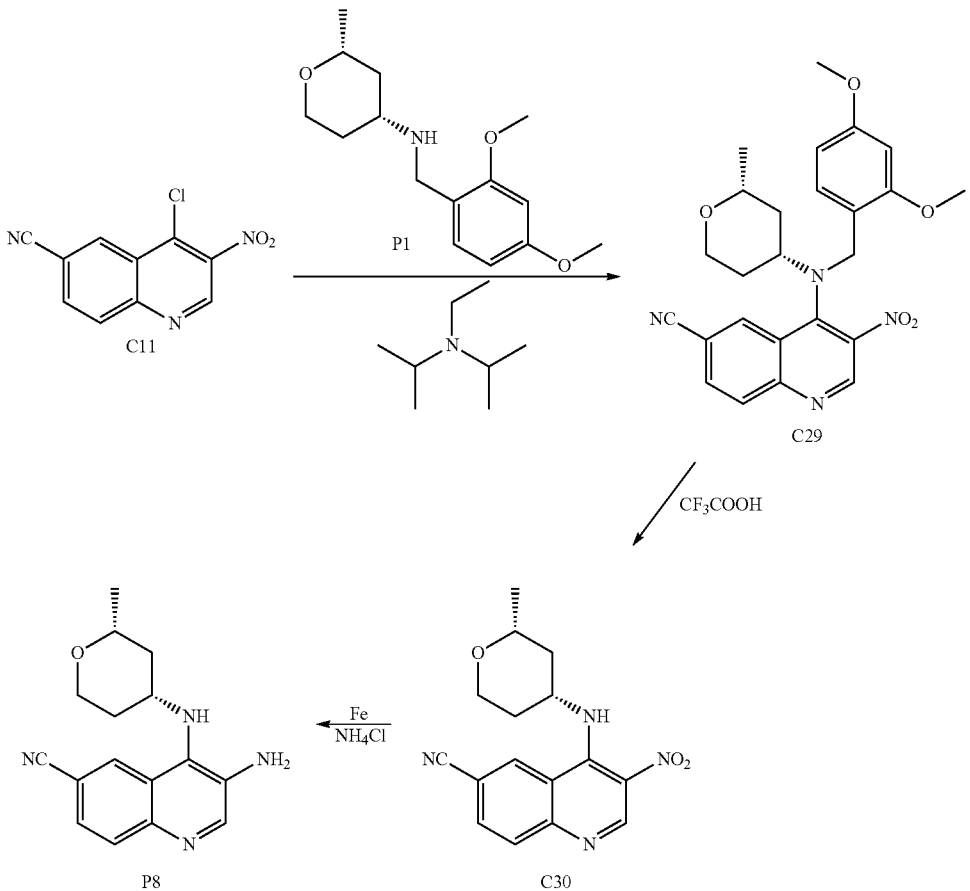

Step 1. Synthesis of 4-{(2,4-dimethoxybenzyl)[(2R, 4R)-2-methyltetrahydro-2H-pyran-4-yl]amino}-3-nitroquinoline-6-carbonitrile (C29)

To a solution of C11 (8.81 g, 37.7 mmol) in acetonitrile (80 mL) was added P1 (11.0 g, 41.5 mmol), followed by N,N-diisopropylethylamine (5.85 g, 45.3 mmol). The reaction mixture was stirred for 2 hours at room temperature, whereupon it was concentrated in vacuo and purified via silica gel chromatography (Eluent: 4:1 petroleum ether/ethyl acetate), affording the product as a viscous orange oil that slowly solidified. Yield: 15.0 g, 32.4 mmol, 86%. LCMS m/z 313.0 [M-(2,4-dimethoxybenzyl)+H]$^+$. $^1$H NMR (400 MHz, DMSO-d$_6$) δ 9.18 (s, 1H), 8.55 (br dd, J=1.3, 1 Hz, 1H), 8.15 (d, J=1.0 Hz, 2H), 6.88 (d, J=8.0 Hz, 1H), 6.24-6.30 (m, 2H), 4.33 (br AB quartet, J$_{AB}$=14.5 Hz, Δv$_{AB}$=12 Hz, 2H), 3.76-3.92 (m, 2H), 3.62 (s, 3H), 3.42 (s, 3H), 3.3-3.4 (m, 2H, assumed; largely obscured by water peak), 1.83-2.00 (m, 2H), 1.70-1.83 (m, 1H), 1.42-1.54 (m, 1H), 1.09 (d, J=6.0 Hz, 3H).

Step 2. Synthesis of 4-{[(2R,4R)-2-methyltetrahydro-2H-pyran-4-yl]amino}-3-nitro quinoline-6-carbonitrile (C30)

A mixture of C29 (15.0 g, 32.4 mmol) and trifluoroacetic acid (18.5 g, 162 mmol) in dichloromethane (150 mL) was stirred at room temperature for 30 minutes, whereupon it was concentrated to a volume of 20 mL and treated with saturated aqueous sodium bicarbonate solution (200 mL). The aqueous layer was extracted with dichloromethane (3×150 mL), and the combined organic layers were dried over sodium sulfate, filtered, and concentrated in vacuo to provide the product as a yellow solid. Yield: 5.68 g, 18.2 mmol, 56%. LCMS m/z 313.0 [M+H]$^+$. $^1$H NMR (400 MHz, DMSO-d$_6$) δ 9.06-9.09 (m, 2H), 8.30 (br d, J=9.0 Hz, 1H), 8.14 (dd, half of ABX pattern, J=8.7, 1.6 Hz, 1H), 8.01 (d, half of AB quartet, J=8.8 Hz, 1H), 3.87-3.93 (m, 1H), 3.69-3.82 (m, 1H), 3.3-3.5 (m, 2H, assumed; largely obscured by water peak), 1.87-2.03 (m, 2H), 1.60-1.72 (m, 1H), 1.36-1.47 (m, 1H), 1.11 (d, J=6.0 Hz, 3H).

Step 3. Synthesis of 3-amino-4-{[(2R,4R)-2-methyltetrahydro-2H-pyran-4-yl]amino}quinoline-6-carbonitrile (P8)

Ethanol (60 mL) and water (15 mL) were added to a mixture of C30 (5.68 g, 18.2 mmol), iron (10.2 g, 183 mmol), and ammonium chloride (9.73 g, 182 mmol). The reaction mixture was heated to 80° C. for 1 hour, whereupon it was diluted with ethanol (100 mL) and filtered. The filtrate was concentrated in vacuo, and the resulting solid was partitioned between saturated aqueous sodium bicarbonate solution (100 mL) and dichloromethane (300 mL). The organic layer was dried over sodium sulfate, filtered, and concentrated under reduced pressure to afford the product as a brown solid. Yield: 4.73 g, 16.8 mmol, 92%. LCMS m/z 282.9 [M+H]$^+$. $^1$H NMR (400 MHz, CD$_3$OD) δ 8.55 (d, J=1.2 Hz, 1H), 8.51 (s, 1H), 7.90 (d, J=8.8 Hz, 1H), 7.60 (dd, J=8.5, 1.8 Hz, 1H), 3.92-4.00 (m, 1H), 3.58-3.69 (m, 1H), 3.39-3.50 (m, 2H), 1.78-1.94 (m, 2H), 1.56-1.69 (m, 1H), 1.29-1.40 (m, 1H), 1.17 (d, J=6.0 Hz, 3H).

Preparation P9

3-Amino-4-{[(3R)-1-methylpyrrolidin-3-yl]amino}quinoline-6-carbonitrile (P9)

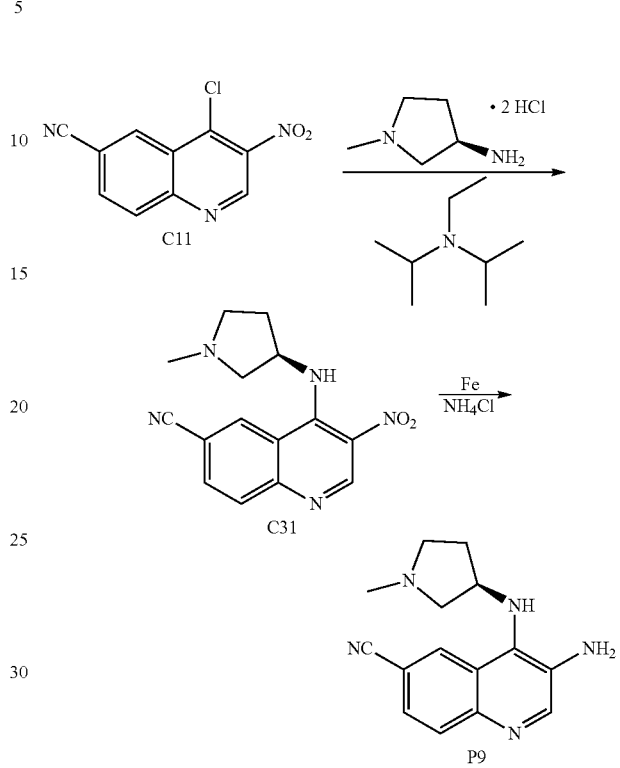

Step 1. Synthesis of 4-{[(3R)-1-methylpyrrolidin-3-yl]amino}-3-nitroquinoline-6-carbonitrile (C31)

N,N-Diisopropylethylamine (251 mg, 1.94 mmol) was added to a 20° C. solution of C11 (210 mg, 0.899 mmol) and (3R)-1-methylpyrrolidin-3-amine (77.9 mg, 0.778 mmol) in acetonitrile (3 mL). The reaction mixture was stirred at 20° C. for 2 hours, whereupon it was concentrated in vacuo. Purification of the residue via silica gel chromatography (Gradient: 0% to 1% methanol in dichloromethane) afforded the product as a yellow solid. Yield: 210 mg, 0.706 mmol, 91%. LCMS m/z 297.9 [M+H]$^+$. $^1$H NMR (400 MHz, CDCl$_3$) δ 10.04-10.15 (br m, 1H), 9.45 (s, 1H), 8.55 (d, J=1.5 Hz, 1H), 8.07 (d, half of AB quartet, J=8.5 Hz, 1H), 7.92 (dd, half of ABX pattern, J=8.5, 1.8 Hz, 1H), 4.65-4.74 (m, 1H), 3.02-3.10 (m, 1H), 2.84-2.90 (m, 1H), 2.80 (dd, half of ABX pattern, J=9.9, 5.6 Hz, 1H), 2.61-2.71 (m, 1H) 2.46 (s, 3H), 2.41-2.50 (m, 1H), 2.06-2.16 (m, 1H).

Step 2. Synthesis of 3-amino-4-{[(3R)-1-methylpyrrolidin-3-yl]amino}quinoline-6-carbonitrile (P9)

To a solution of C31 (100 mg, 0.336 mmol) in a mixture of ethanol (1 mL) and water (0.25 mL) were added ammonium chloride (36 mg, 0.673 mmol) and iron powder (75.1 mg, 1.34 mmol), and the reaction mixture was stirred at 80° C. for 1 hour. It was then filtered, and the filter cake was washed with methanol (30 mL). The organic layer from the combined filtrates was concentrated in vacuo and purified via silica gel chromatography (Gradient: 0% to 15% methanol in dichloromethane), affording the product as a yellow solid. Yield: 112 mg, assumed quantitative. $^1$H NMR (400 MHz, DMSO-d$_6$), characteristic peaks: δ 8.65-8.71 (br s, 1H), 8.58 (s, 1H), 7.89 (d, J=8.5 Hz, 1H), 7.62 (dd, J=8.5, 2.0 Hz, 1H), 5.56-5.70 (br s, 1H), 5.43 (d, J=10.5 Hz, 1H), 4.32-4.46 (br m, 1H), 2.81 (s, 3H), 1.84-1.95 (m, 1H).

Preparation P10

6-Chloro-N$^4$-[(2R,4R)-2-methyltetrahydro-2H-pyran-4-yl]quinoline-3,4-diamine (P10)

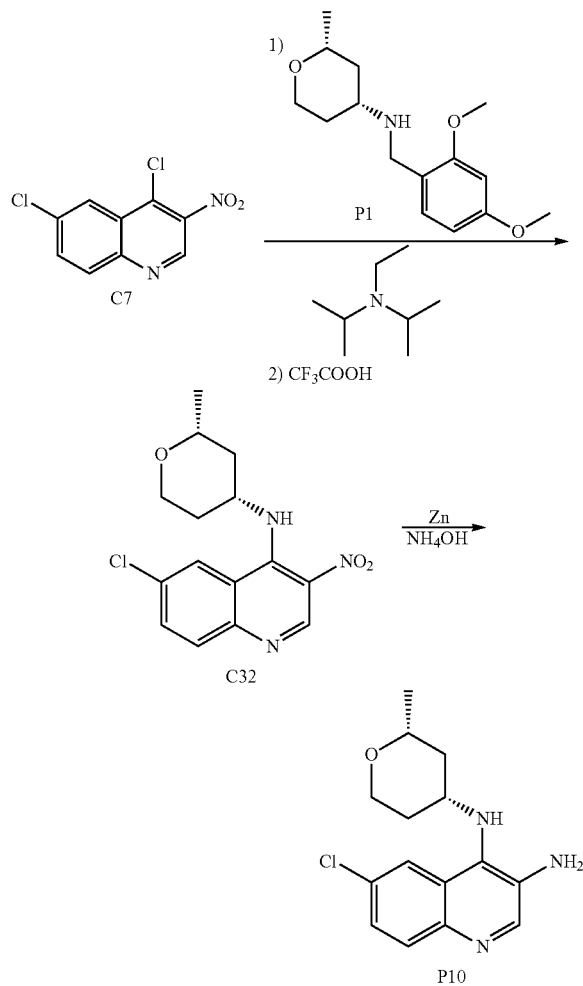

Step 1. Synthesis of 6-chloro-N-[(2R,4R)-2-methyl-tetrahydro-2H-pyran-4-yl]-3-nitroquinolin-4-amine (C32)

Compound C7 (12.2 g, 50.2 mmol) was added to a solution of P1 (13.3 g, 50.1 mmol) and N,N-diisopropylethylamine (13.1 mL, 75.2 mmol) in acetonitrile (250 mL), and the reaction mixture was heated to 55° C. overnight. After concentration in vacuo, the residue was partitioned between aqueous sodium bicarbonate solution (100 mL) and dichloromethane (150 mL). The aqueous layer was extracted with dichloromethane (2×50 mL) and the combined organic layers were treated with trifluoroacetic acid (25 mL). {Caution: exotherm!}. After 20 minutes, saturated aqueous sodium carbonate solution (150 mL) was added portionwise, and the mixture was allowed to stir for 10 minutes. The aqueous layer was extracted twice with dichloromethane, and the combined organic layers were concentrated in vacuo, providing a reddish solid (17.3 g); this was triturated with diethyl ether (230 mL) to afford a yellow solid (14.0 g). A portion of this solid (10 g) was subjected to purification via supercritical fluid chromatography (Column: Lux Amylose-2, 5 μm; Mobile phase: 65:35 carbon dioxide/methanol), providing the product as a crystalline solid. The indicated absolute configuration was determined via single crystal X-ray structural determination on this material: see below. Yield: 7.1 g, 22 mmol, 62% (yield corrected for material omitted from purification). $^1$H NMR (400 MHz, CDCl$_3$) δ 9.36 (s, 1H), 9.11 (br d, J=9 Hz, 1H), 8.12 (d, J=2.0 Hz, 1H), 7.98 (d, J=8.9 Hz, 1H), 7.73 (dd, J=8.9, 2.2 Hz, 1H), 4.21-4.33 (m, 1H), 4.08-4.15 (m, 1H), 3.50-3.60 (m, 2H), 2.11-2.22 (m, 2H), 1.77 (dddd, J=12, 12, 12, 5 Hz, 1H), 1.49 (ddd, J=12, 12, 11 Hz, 1H), 1.28 (d, J=6.2 Hz, 3H).

Single-Crystal X-Ray Structural Determination of C32

Single Crystal X-Ray Analysis

Data collection was performed on a Bruker APEX diffractometer at room temperature. Data collection consisted of omega and phi scans.

The structure was solved by direct methods using SHELX software suite in the space group P2$_1$2$_1$2$_1$. The structure was subsequently refined by the full-matrix least squares method. All non-hydrogen atoms were found and refined using anisotropic displacement parameters.

The hydrogen atom located on nitrogen was found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek, 2003). The results indicate that the absolute structure has been correctly assigned. The method calculates that the probability that the structure is correct is 100.0. The Hooft parameter is reported as 0.017 with an esd of 0.09.

The final R-index was 4.8%. A final difference Fourier revealed no missing or misplaced electron density.

Pertinent crystal, data collection and refinement information is summarized in Table A. Atomic coordinates, bond lengths, bond angles, and displacement parameters are listed in Tables B-E.

SOFTWARE AND REFERENCES

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Strayer, and A. L. Spek, *J. Appl. Cryst.* 2008, 41, 96-103.

H. D. Flack, *Acta Cryst.* 1983, A39, 867-881.

TABLE A

Crystal data and structure refinement for C32.

| | |
|---|---|
| Empirical formula | $C_{15}H_{16}ClN_3O_3$ |
| Formula weight | 321.76 |
| Temperature | 273(2) K |
| Wavelength | 1.54178 Å |
| Crystal system | Orthorhombic |
| Space group | $P2_12_12_1$ |
| Unit cell dimensions | a = 6.7882(13) Å   α = 90° |
| | b = 10.0703(19) Å  β = 90° |
| | c = 21.883(4) Å    γ = 90° |
| Volume | 1495.9(5) $Å^3$ |
| Z | 4 |
| Density (calculated) | 1.429 $Mg/m^3$ |
| Absorption coefficient | 2.415 $mm^{-1}$ |
| F(000) | 672 |
| Crystal size | 0.22 × 0.16 × 0.10 $mm^3$ |
| Theta range for data collection | 4.04 to 70.57° |
| Index ranges | -8 <= h <= 7, -12 <= k <= 12, -26 <= l <= 24 |
| Reflections collected | 12473 |
| Independent reflections | 2784 [$R_{int}$ = 0.1613] |
| Completeness to theta = 70.57° | 97.3% |
| Absorption correction | Empirical |
| Max. and min. transmission | 0.7943 and 0.6187 |
| Refinement method | Full-matrix least-squares on $F^2$ |
| Data/restraints/parameters | 2784/1/204 |
| Goodness-of-fit on $F^2$ | 1.130 |
| Final R indices [I > 2σ(I)] | R1 = 0.0481, wR2 = 0.1164 |
| R indices (all data) | R1 = 0.0514, wR2 = 0.1254 |
| Absolute structure parameter | -0.02(2) |
| Extinction coefficient | 0.0061(8) |
| Largest diff. peak and hole | 0.236 and -0.393 e · $Å^{-3}$ |

TABLE B

Atomic coordinates (×$10^4$) and equivalent isotropic displacement parameters ($Å^2$ × $10^3$) for C32. U(eq) is defined as one-third of the trace of the orthogonalized $U^{ij}$ tensor.

| | x | y | z | U(eq) |
|---|---|---|---|---|
| C(1) | 1294(3) | -465(2) | 8392(1) | 41(1) |
| C(2) | 2045(4) | -1731(2) | 8096(1) | 47(1) |
| C(3) | 5002(4) | -692(3) | 7811(1) | 59(1) |
| C(4) | 4408(4) | 620(3) | 8086(1) | 50(1) |
| C(5) | 2992(3) | 394(2) | 8615(1) | 37(1) |
| C(6) | 2190(3) | 2218(2) | 9392(1) | 33(1) |
| C(7) | 2088(3) | 3612(2) | 9478(1) | 36(1) |
| C(8) | 2116(3) | 4182(2) | 10060(1) | 41(1) |
| C(9) | 2196(3) | 2165(2) | 10525(1) | 36(1) |
| C(10) | 2142(3) | 1467(2) | 9960(1) | 33(1) |
| C(11) | 1948(3) | 75(2) | 9985(1) | 39(1) |
| C(12) | 1914(4) | -574(2) | 10537(1) | 47(1) |
| C(13) | 2053(4) | 111(2) | 11090(1) | 49(1) |
| C(14) | 2179(3) | 1449(2) | 11077(1) | 46(1) |
| C(15) | 394(5) | -2575(3) | 7835(1) | 72(1) |
| Cl(1) | 1654(2) | -2285(1) | 10550(1) | 79(1) |
| N(1) | 2317(3) | 1690(2) | 8834(1) | 44(1) |
| N(2) | 2029(3) | 4530(2) | 8976(1) | 46(1) |
| N(3) | 2205(3) | 3529(2) | 10573(1) | 44(1) |
| O(1) | 3340(3) | -1422(2) | 7603(1) | 56(1) |
| O(2) | 1960(3) | 4131(2) | 8443(1) | 59(1) |
| O(3) | 2016(4) | 5719(2) | 9091(1) | 78(1) |

TABLE C

Bond lengths [Å] and angles [°] for C32.

| | |
|---|---|
| C(1)—C(2) | 1.518 (3) |
| C(1)—C(5) | 1.521 (3) |
| C(2)—O(1) | 1.425 (3) |
| C(2)—C(15) | 1.517 (3) |
| C(3)—O(1) | 1.421 (3) |
| C(3)—C(4) | 1.507 (4) |
| C(4)—C(5) | 1.522 (3) |
| C(5)—N(1) | 1.464 (3) |
| C(6)—N(1) | 1.336 (2) |
| C(6)—C(7) | 1.418 (3) |
| C(6)—C(10) | 1.456 (3) |
| C(7)—C(8) | 1.396 (3) |
| C(7)—N(2) | 1.436 (3) |
| C(8)—N(3) | 1.304 (3) |
| C(9)—N(3) | 1.378 (3) |
| C(9)—C(14) | 1.406 (3) |
| C(9)—C(10) | 1.422 (3) |
| C(10)—C(11) | 1.409 (3) |
| C(11)—C(12) | 1.374 (3) |
| C(12)—C(13) | 1.395 (3) |
| C(12)—Cl(1) | 1.733 (2) |
| C(13)—C(14) | 1.351 (3) |
| N(2)—O(3) | 1.223 (2) |
| N(2)—O(2) | 1.236 (3) |
| C(2)—C(1)—C(5) | 111.09 (18) |
| O(1)—C(2)—C(15) | 107.09 (19) |
| O(1)—C(2)—C(1) | 110.31 (17) |
| C(15)—C(2)—C(1) | 112.5 (2) |
| O(1)—C(3)—C(4) | 111.7 (2) |
| C(3)—C(4)—C(5) | 109.98 (19) |
| N(1)—C(5)—C(1) | 112.00 (18) |
| N(1)—C(5)—C(4) | 108.27 (17) |
| C(1)—C(5)—C(4) | 108.68 (15) |
| N(1)—C(6)—C(7) | 121.25 (17) |
| N(1)—C(6)—C(10) | 125.16 (17) |
| C(7)—C(6)—C(10) | 113.60 (16) |
| C(8)—C(7)—C(6) | 121.78 (18) |
| C(8)—C(7)—N(2) | 115.67 (17) |
| C(6)—C(7)—N(2) | 122.51 (18) |
| N(3)—C(8)—C(7) | 125.41 (18) |
| N(3)—C(9)—C(14) | 116.46 (18) |
| N(3)—C(9)—C(10) | 123.97 (19) |
| C(14)—C(9)—C(10) | 119.54 (17) |
| C(11)—C(10)—C(9) | 117.44 (18) |
| C(11)—C(10)—C(6) | 123.46 (17) |
| C(9)—C(10)—C(6) | 119.03 (16) |
| C(12)—C(11)—C(10) | 120.51 (18) |
| C(11)—C(12)—C(13) | 121.77 (19) |
| C(11)—C(12)—Cl(1) | 119.23 (16) |
| C(13)—C(12)—Cl(1) | 119.00 (17) |
| C(14)—C(13)—C(12) | 118.66 (19) |
| C(13)—C(14)—C(9) | 121.96 (19) |
| C(6)—N(1)—C(5) | 132.47 (17) |
| O(3)—N(2)—O(2) | 120.82 (18) |
| O(3)—N(2)—C(7) | 118.24 (18) |
| O(2)—N(2)—C(7) | 120.93 (17) |
| C(8)—N(3)—C(9) | 115.92 (17) |
| C(3)—O(1)—C(2) | 111.14 (16) |

Symmetry transformations used to generate equivalent atoms.

TABLE D

Anisotropic displacement parameters ($Å^2$ × $10^3$) for C32. The anisotropic displacement factor exponent takes the form: $-2\pi^2[h^2 a^{*2} U^{11} + \ldots + 2 h k a^* b^* U^{12}]$.

| | U11 | U22 | U33 | U23 | U13 | U12 |
|---|---|---|---|---|---|---|
| C(1) | 48 (1) | 44(1) | 31(1) | 0 (1) | -2 (1) | -4 (1) |
| C(2) | 70 (2) | 38(1) | 33(1) | 0 (1) | -9 (1) | -3 (1) |
| C(3) | 62 (2) | 71(2) | 45(1) | -12 (1) | 15 (1) | 1 (1) |
| C(4) | 61 (1) | 54(1) | 36(1) | -7 (1) | 12 (1) | -13 (1) |
| C(5) | 50 (1) | 38(1) | 24(1) | -5 (1) | 1 (1) | -2 (1) |
| C(6) | 33 (1) | 38(1) | 30(1) | -4 (1) | 2 (1) | 0 (1) |
| C(7) | 36 (1) | 36(1) | 38(1) | 0 (1) | 4 (1) | -1 (1) |
| C(8) | 43 (1) | 35(1) | 44(1) | -9 (1) | 3 (1) | -1 (1) |
| C(9) | 34 (1) | 44(1) | 31(1) | -8 (1) | 2 (1) | 6 (1) |
| C(10) | 30 (1) | 41(1) | 28(1) | -4 (1) | 4 (1) | 2 (1) |

TABLE D-continued

Anisotropic displacement parameters (Å² × 10³) for C32. The anisotropic displacement factor exponent takes the form: $-2\pi^2[h^2 a^{*2}U^{11} + \ldots + 2 h k a^* b^* U^{12}]$.

|  | U11 | U22 | U33 | U23 | U13 | U12 |
|---|---|---|---|---|---|---|
| C(11) | 49 (1) | 40(1) | 28(1) | −4 (1) | 3 (1) | 2 (1) |
| C(12) | 60 (1) | 43(1) | 39(1) | 2 (1) | 6 (1) | 8 (1) |
| C(13) | 60 (1) | 57(1) | 29(1) | 6 (1) | 3 (1) | 15 (1) |
| C(14) | 53 (1) | 58(1) | 26(1) | −7 (1) | 2 (1) | 11 (1) |
| C(15) | 97 (2) | 53(2) | 65(2) | −7 (1) | −25 (2) | −21 (2) |
| Cl(1) | 138 (1) | 40(1) | 60(1) | 9 (1) | 18 (1) | 5 (1) |
| N(1) | 67 (1) | 36(1) | 29(1) | −3 (1) | 0 (1) | 3 (1) |
| N(2) | 49 (1) | 40(1) | 47(1) | 5 (1) | 2 (1) | −1 (1) |
| N(3) | 50 (1) | 44(1) | 37(1) | −12 (1) | 0 (1) | 2 (1) |
| O(1) | 82 (1) | 56(1) | 32(1) | −14 (1) | 6 (1) | −2 (1) |
| O(2) | 87 (1) | 53(1) | 38(1) | 8 (1) | 8 (1) | 3 (1) |
| O(3) | 127 (2) | 35(1) | 73(1) | 5 (1) | −4 (1) | −4 (1) |

TABLE E

Hydrogen coordinates (×10⁴) and isotropic displacement parameters (Å² × 10³) for C32.

|  | x | y | z | U(eq) |
|---|---|---|---|---|
| H(1A) | 451 | −690 | 8735 | 49 |
| H(1B) | 515 | 31 | 8099 | 49 |
| H(2A) | 2765 | −2251 | 8401 | 57 |
| H(3A) | 5887 | −535 | 7470 | 71 |
| H(3B) | 5704 | −1210 | 8114 | 71 |
| H(4A) | 3779 | 1166 | 7777 | 60 |
| H(4B) | 5569 | 1085 | 8231 | 60 |
| H(5) | 3684 | −67 | 8945 | 45 |
| H(8) | 2068 | 5104 | 10083 | 49 |
| H(11) | 1842 | −409 | 9624 | 47 |
| H(13) | 2060 | −345 | 11459 | 59 |
| H(14) | 2257 | 1911 | 11444 | 55 |
| H(15A) | −305 | −2077 | 7531 | 108 |
| H(15B) | −495 | −2820 | 8157 | 108 |
| H(15C) | 938 | −3361 | 7654 | 108 |
| H(111) | 2170(50) | 2330(30) | 8481(13) | 95 |

Step 2. Synthesis of 6-chloro-N⁴-[(2R,4R)-2-methyltetrahydro-2H-pyran-4-yl]quinoline-3,4-diamine (P10)

Zinc dust (97.5%, 12.3 g, 183 mmol) was added in one portion to a suspension of C32 (7.40 g, 23.0 mmol) in methanol (100 mL) and concentrated ammonium hydroxide (100 mL). After 1 hour, the reaction mixture was filtered through diatomaceous earth; the filter pad was rinsed with dichloromethane (70 mL). The combined filtrates were diluted with water, and the aqueous layer was extracted with dichloromethane (2×60 mL). The combined organic layers were dried over sodium sulfate, filtered, concentrated in vacuo, and purified via silica gel chromatography (Gradient: 40% to 100% ethyl acetate in heptane) to provide the product. Yield: 3.68 g, 12.6 mmol, 55%. ¹H NMR (400 MHz, CDCl₃) δ 8.48 (s, 1H), 7.91 (d, J=8.9 Hz, 1H), 7.74 (d, J=2.2 Hz, 1H), 7.40 (dd, J=8.9, 2.2 Hz, 1H), 4.02 (br dd, J=12, 5 Hz, 1H), 3.88 (br s, 2H), 3.29-3.56 (m, 4H), 1.82-1.96 (m, 2H), 1.56 (dddd, J=12, 12, 12, 5 Hz, 1H), 1.21-1.31 (m, 1H), 1.21 (d, J=6.2 Hz, 3H).

Preparation P11

6-(Difluoromethyl)-N⁴-[(2R,4R)-2-methyltetrahydro-2H-pyran-4-yl]quinoline-3,4-diamine (P11)

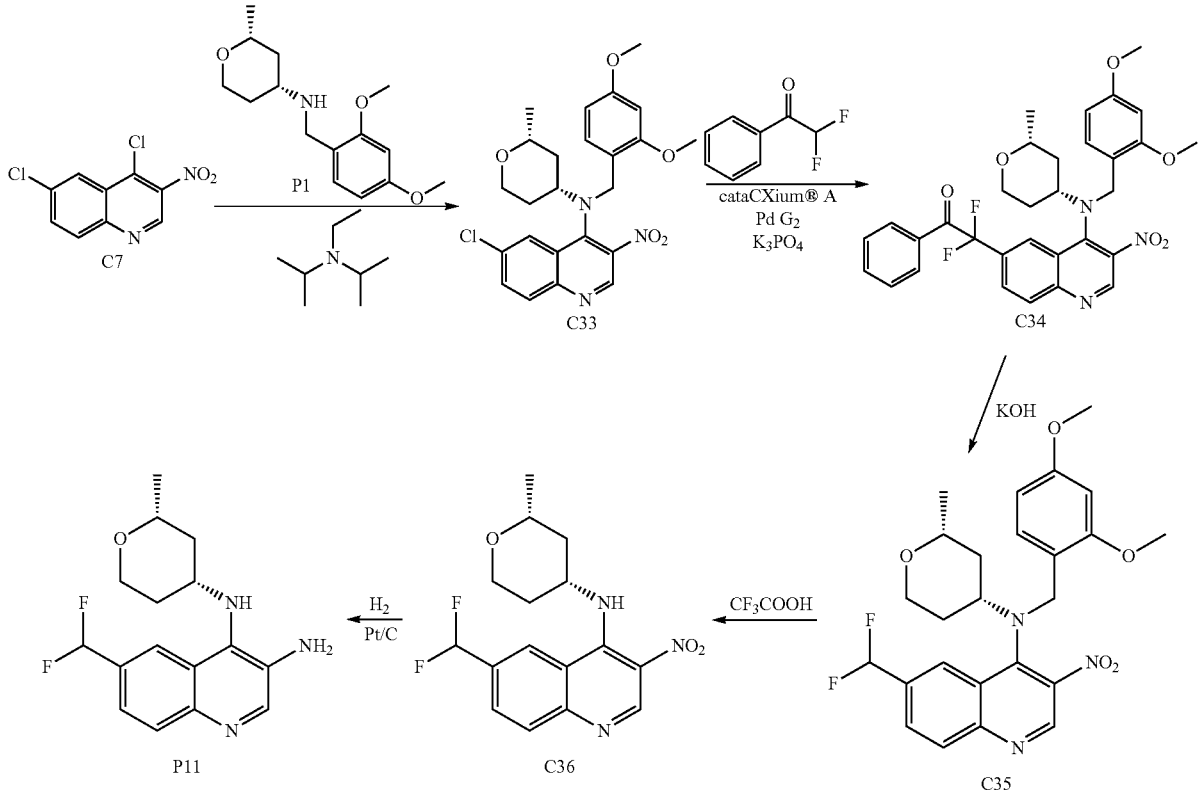

Step 1. Synthesis of 6-chloro-N-(2,4-dimethoxybenzyl)-N-[(2R,4R)-2-methyltetrahydro-2H-pyran-4-yl]-3-nitroquinolin-4-amine (C33)

To a solution of P1 (3.90 g, 14.7 mmol) and N,N-diisopropylethylamine (8.53 mL, 49.0 mmol) in acetonitrile (74 mL) was added C7 (4.00 g, 16.5 mmol), and the reaction mixture was heated at 50° C. for 16 hours. It was then concentrated in vacuo, and the residue was partitioned between ethyl acetate (100 mL) and saturated aqueous sodium bicarbonate solution (100 mL), whereupon the aqueous layer was extracted with ethyl acetate (2×150 mL), and the combined organic layers were washed with saturated aqueous sodium chloride solution (150 mL), dried over sodium sulfate, filtered, and concentrated under reduced pressure. Silica gel chromatography (Gradient: 0% to 80% ethyl acetate in heptane) afforded the product as an orange solid. Yield: 6.00 g, 12.7 mmol, 86%. LCMS m/z 472.5 [M+H]$^+$. $^1$H NMR (400 MHz, CDCl$_3$) δ 9.02 (s, 1H), 8.24 (d, J=2.4 Hz, 1H), 7.98 (d, J=9.0 Hz, 1H), 7.69 (dd, J=9.0, 2.4 Hz, 1H), 6.83 (d, J=8.2 Hz, 1H), 6.24-6.18 (m, 2H), 4.34 (br s, 2H), 4.08-4.00 (m, 1H), 3.82-3.70 (m, 1H), 3.69 (s, 3H), 3.55 (s, 3H), 3.49-3.38 (m, 2H), 2.02-1.85 (m, 3H), 1.66-1.52 (m, 1H, assumed; partially obscured by water peak), 1.21 (d, J=6.3 Hz, 3H).

Step 2. Synthesis of 2-(4-{(2,4-dimethoxybenzyl)[(2R,4R)-2-methyltetrahydro-2H-pyran-4-yl]amino}-3-nitroquinolin-6-yl)-2,2-difluoro-1-phenylethanone (C34)

A pressure tube (250 mL) was charged with chloro[(di(1-adamantyl)-N-butylphosphine)-2-(2-aminobiphenyl)]palladium(11) (cataCXium® A Pd G2; 85.0 mg, 0.127 mmol), C33 (3.00 g, 6.36 mmol), and potassium phosphate tribasic monohydrate (5.86 g, 25.4 mmol). The vial was then evacuated and charged with nitrogen. This evacuation cycle was repeated twice, whereupon a solution of 2,2-difluoro-1-phenylethanone (1.68 mL, 12.7 mmol) in toluene (37 mL) was added, and the reaction mixture was heated at 110° C. for 24 hours. After cooling to room temperature, the reaction mixture was partitioned between saturated aqueous ammonium chloride solution (250 mL) and ethyl acetate (250 mL). The organic layer was dried over sodium sulfate, filtered, concentrated in vacuo, and purified via chromatography on silica gel (Gradient: 0% to 100% ethyl acetate in heptane), providing the product as an orange solid. Yield: 2.07 g, 3.50 mmol, 55%. LCMS m/z 592.3 [M+H]$^+$. $^1$H NMR (400 MHz, CDCl$_3$) δ 9.07 (s, 1H), 8.49 (s, 1H), 8.17 (d, half of AB quartet, J=8.6 Hz, 1H), 8.08-7.99 (m, 3H), 7.65 (dd, J=8, 7 Hz, 1H), 7.50 (dd, J=8, 7 Hz, 2H), 6.83 (d, J=8.2 Hz, 1H), 6.20 (br d, J=8.6 Hz, 1H), 6.15 (s, 1H), 4.35 (br s, 2H), 4.04-3.96 (m, 1H), 3.81-3.70 (m, 1H), 3.69 (s, 3H), 3.47 (s, 3H), 3.30-3.18 (m, 2H), 2.07-1.87 (m, 3H), 1.76-1.64 (m, 1H), 1.21 (d, J=6.3 Hz, 3H).

Step 3. Synthesis of 6-(difluoromethyl)-N-(2,4-dimethoxybenzyl)-N-[(2R,4R)-2-methyltetrahydro-2H-pyran-4-yl]-3-nitroquinolin-4-amine (C35)

Potassium hydroxide (1.97 g, 35.1 mmol) and water (1.22 mL, 67.7 mmol) were added to a solution of C34 (2.0 g, 3.38 mmol) in toluene (20 mL), and the resulting biphasic reaction mixture was vigorously stirred at 100° C. for 11 hours. An aliquot of the reaction mixture was partitioned between saturated aqueous sodium bicarbonate solution and ethyl acetate; LCMS analysis of the organic layer indicated the presence of both starting material and product. The reaction mixture was cooled to room temperature and partitioned between saturated aqueous sodium bicarbonate solution (125 mL) and ethyl acetate (150 mL). The organic layer was dried over sodium sulfate, filtered, concentrated in vacuo, and subjected to silica gel chromatography (Gradient: 0% to 100% ethyl acetate in heptane), which failed to separate C35 from C34. The isolated mixture was resubjected to the reaction conditions for 24 hours, then worked up in the same manner; the crude residue (once again a mixture of C35 and C34) was again subjected to the original reaction conditions, this time for 48 hours. The reaction mixture was cooled to room temperature, and partitioned between saturated aqueous sodium bicarbonate solution (125 mL) and ethyl acetate (150 mL). The organic layer was dried over sodium sulfate, filtered, and concentrated under reduced pressure to afford an oily, orange residue (1.85 g) that contained both C35 and C34 by LCMS analysis. This material was used directly in step 4. LCMS m/z 488.5 [M+H]$^+$.

Improved conversion of C34 to 6-(difluoromethyl)-N-(2,4-dimethoxybenzyl)-N-[(2R,4R)-2-methyltetrahydro-2H-pyran-4-yl]-3-nitroquinolin-4-amine (C35).

Potassium hydroxide (267 mg, 4.76 mmol) was added to a solution of C34 (470 mg, 0.794 mmol) in toluene (4.7 mL) and water (0.28 mL, 16 mmol). The reaction mixture was heated to 100° C. for 24 hours, whereupon it was cooled to room temperature and partitioned between water (150 mL) and dichloromethane (150 mL). The aqueous layer was extracted with dichloromethane (2×100 mL), and the combined organic layers were dried over sodium sulfate, filtered, and concentrated in vacuo. Silica gel chromatography (Gradient: 0% to 80% ethyl acetate in heptane) afforded the product as an orange solid. Yield: 337 mg, 0.691 mmol, 87%. $^1$H NMR (400 MHz, CDCl$_3$) δ 9.10 (s, 1H), 8.45 (br s, 1H), 8.14 (d, J=8.6 Hz, 1H), 7.83 (br dd, J=8.6, 1 Hz, 1H), 6.86 (d, J=8.2 Hz, 1H), 6.81 (t, J$_{HF}$=56.3 Hz, 1H), 6.23 (dd, half of ABX pattern, J=8.2, 2.4 Hz, 1H), 6.17 (d, half of AB quartet, J=2.4 Hz, 1H), 4.38 (br AB quartet, J$_{AB}$=14 Hz, Δν$_{AB}$=8 Hz, 2H), 4.08-4.02 (m, 1H), 3.88-3.78 (m, 1H), 3.69 (s, 3H), 3.49 (s, 3H), 3.46-3.36 (m, 2H), 2.07-1.94 (m, 3H), 1.73-1.62 (m, 1H), 1.22 (d, J=6.3 Hz, 3H).

Step 4. Synthesis of 6-(difluoromethyl)-N-[(2R,4R)-2-methyltetrahydro-2H-pyran-4-yl]-3-nitroquinolin-4-amine (C36)

A solution of C35 and C34 (from step 3; 1.85 g, 3.38 mmol) in dichloromethane (25 mL) was cooled to 0° C. and treated with trifluoroacetic acid (1.16 mL, 15.1 mmol). The reaction mixture was allowed to warm to room temperature, and was stirred at room temperature for 20 minutes, whereupon it was cooled to 0° C., diluted with dichloromethane (20 mL) and basified to pH 8 via addition of saturated aqueous sodium bicarbonate solution (100 mL). The aqueous layer was extracted with dichloromethane (2×50 mL), and the combined organic layers were washed with saturated aqueous sodium chloride solution (150 mL), dried over magnesium sulfate, filtered, and concentrated in vacuo. The residue was purified via chromatography on silica gel (Gradient: 0% to 100% ethyl acetate in heptane) followed by trituration with diethyl ether (50 mL), providing the product as a yellow solid. Yield over two steps: 0.70 g, 2.1 mmol, 62%. LCMS m/z 338.3 [M+H]$^+$. $^1$H NMR (400 MHz, CDCl$_3$) δ 9.44 (s, 1H), 9.34 (br d, J=7.8 Hz, 1H), 8.37 (s, 1H), 8.11 (d, J=8.6 Hz, 1H), 7.86 (d, J=8.6 Hz, 1H), 6.84 (t, J$_{HF}$=56.5 Hz, 1H), 4.39-4.26 (m, 1H), 4.18-4.08 (m, 1H), 3.61-3.48 (m, 2H), 2.27-2.12 (m, 2H), 1.89-1.74 (m, 1H), 1.58-1.46 (m, 1H), 1.28 (d, J=6.3 Hz, 3H).

Step 5. Synthesis of 6-(difluoromethyl)-N⁴-[(2R,4R)-2-methyltetrahydro-2H-pyran-4-yl]quinoline-3,4-diamine (P11)

A Parr reactor was charged with a solution of C36 (0.70 g, 2.1 mmol) in tetrahydrofuran (150 mL), followed by platinum on carbon (5%; 600 mg). The mixture was purged three times with nitrogen, backfilling with hydrogen, whereupon it was hydrogenated for 2 hours at 30 psi. The reaction mixture was then diluted with tetrahydrofuran (50 mL), and filtered through a pad of diatomaceous earth. The filter pad was washed with tetrahydrofuran (3×50 mL), and the combined filtrates were concentrated in vacuo, dissolved in dichloromethane (15 mL), and filtered through an Acrodisc® filter. The filtrate was concentrated under reduced pressure to afford the product as a dark brown solid. The product was somewhat impure, as judged by ¹H NMR analysis. Yield: 547 mg. 1.78 mmol, 85%. LCMS m/z 308.4 [M+H]⁺. ¹H NMR (400 MHz, CDCl₃), characteristic peaks: δ 8.56 (s, 1H), 8.06 (d, J=8.6 Hz, 1H), 7.93 (br s, 1H), 7.57 (br d, J=8.6 Hz, 1H), 6.83 (t, J$_{HF}$=56.3 Hz, 1H), 4.03 (ddd, J=11.7, 4.7, 1.6 Hz, 1H), 3.87 (br s, 2H), 3.61-3.49 (m, 1H), 3.49-3.39 (m, 2H), 1.98-1.90 (m, 1H), 1.90-1.82 (m, 1H), 1.63-1.51 (m, 1H), 1.21 (d, J=6.3 Hz, 3H).

Preparation P12

N⁴-(4,4-Difluoro-1-methylpyrrolidin-3-yl)-6-fluoroquinoline-3,4-diamine (P12)

Step 1. Synthesis of tert-butyl 3,3-difluoro-4-[(6-fluoro-3-nitroquinolin-4-yl)amino]pyrrolidine-1-carboxylate (C37)

To a 15° C. solution of 4-chloro-6-fluoro-3-nitroquinoline (10.0 g, 44.1 mmol) in acetonitrile (50 mL) was added N,N-diisopropylethylamine (6.84 g, 52.9 mmol), followed by addition of tert-butyl 4-amino-3,3-difluoropyrrolidine-1-carboxylate (prepared using the method described by D. C. Behenna et al., in U.S. Patent Application 2015 0141402 A1, May 21, 2015; 9.81 g, 44.1 mmol). The reaction mixture was stirred at 20° C. for 48 hours, whereupon it was concentrated in vacuo and purified via chromatography on silica gel (Gradient: 9% to 17% tetrahydrofuran in petroleum ether) to afford the product as a pale yellow solid. Yield: 16.8 g, 40.7 mmol, 92%. ¹H NMR (400 MHz, CDCl₃) δ 9.39 (5, 1H), 8.87-8.69 (br m, 1H), 8.13 (dd, J=9.5, 5.5 Hz, 1H), 7.79-7.70 (br d, J=8 Hz, 1H), 7.63 (ddd, J=9.0, 7.5, 2.5 Hz, 1H), 4.87-4.71 (br m, 1H), 4.31-4.09 (br m, 1H), 4.04-3.84 (br m, 1H), 3.84-3.69 (m, 1H), 3.63-3.51 (br m, 1H), 1.50 (s, 9H).

Step 2. Synthesis of N-(4,4-difluoropyrrolidin-3-yl)-6-fluoro-3-nitroquinolin-4-amine (C38)

Trifluoroacetic acid (50 mL) was added to a 15° C. solution of C37 (16.8 g, 40.7 mmol) in dichloromethane (100 mL), and the reaction mixture was stirred for 3 hours at 15° C. LCMS analysis at this point indicated product formation (LCMS m/z 313.1 [M+H]⁺), and the reaction mixture was concentrated in vacuo. The residue was taken up in aqueous sodium bicarbonate solution (200 mL) and extracted with ethyl acetate (3×150 mL). Concentration of the combined organic layers under reduced pressure afforded the product as a pale yellow solid. Yield: 12.5 g, 40.0 mmol, 98%. ¹H NMR (400 MHz, DMSO-d₆) δ 9.07 (s, 1H), 8.30 (br d, J=9.2 Hz, 1H), 8.26 (dd, J=10.6, 2.6 Hz, 1H), 8.04 (dd, J=9.0, 5.9 Hz, 1H), 7.85-7.78 (m, 1H),

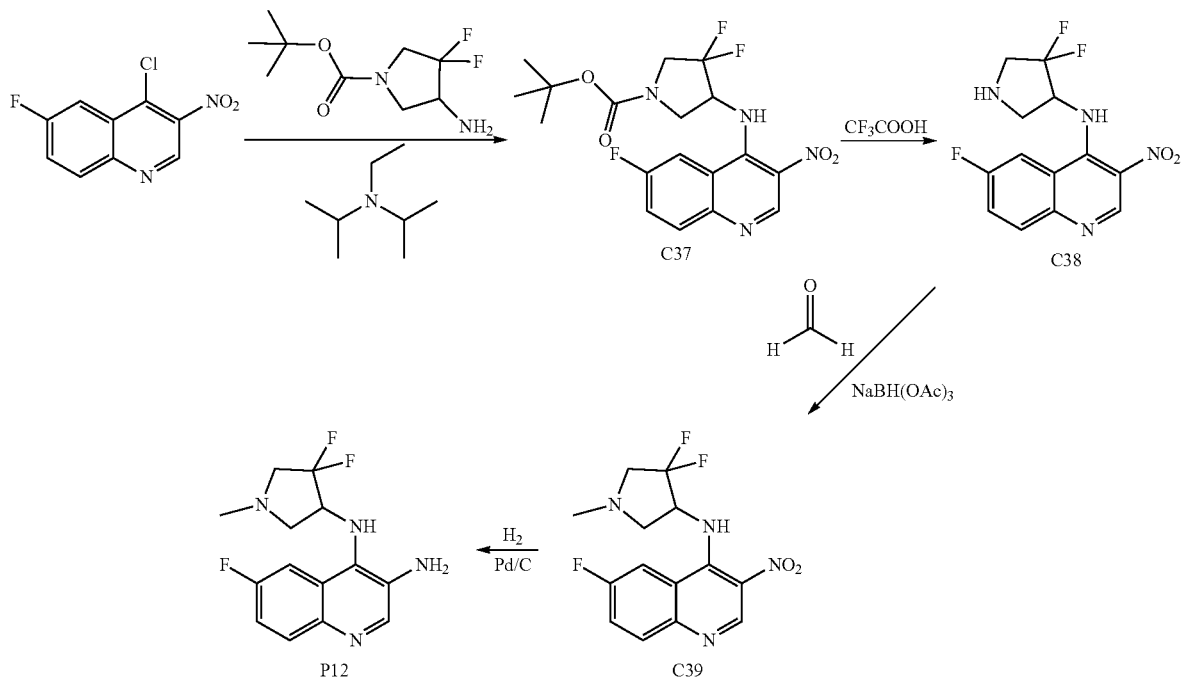

4.53-4.39 (m, 1H), 3.58 (dd, J=11.9, 7.5 Hz, 1H), 3.39-3.25 (m, 1H), 3.24-3.09 (m, 1H), 3.08 (dd, J=11.9, 7.5 Hz, 1H).

Step 3. Synthesis of N-(4,4-difluoro-1-methylpyrrolidin-3-yl)-6-fluoro-3-nitro quinolin-4-amine (C39)

Sodium triacetoxyborohydride (33.9 g, 160 mmol) was added to a 0° C. mixture of C38 (12.5 g, 40.0 mmol) in acetonitrile (150 mL). An aqueous solution of formaldehyde (37%; 13.0 g, 160 mmol) was slowly added over 20 minutes, and the reaction mixture was stirred at room temperature for 1 hour; LCMS analysis at this point indicated that the reaction was complete (LCMS m/z 327.1 [M+H]$^+$). After the reaction mixture had been concentrated to dryness, the residue was basified to pH 8 by addition of aqueous sodium bicarbonate solution. The resulting solid was collected via filtration to provide the product as a red solid. Yield: 11.8 g, 36.2 mmol, 90%. $^1$H NMR (400 MHz, CDCl$_3$), characteristic peaks: δ 9.35 (s, 1H), 9.22 (br d, J=9.2 Hz, 1H), 8.07 (dd, J=9.0, 5.5 Hz, 1H), 7.83 (dd, J=10.1, 2.6 Hz, 1H), 7.58 (ddd, J=9.2, 7.5, 2.6 Hz, 1H), 3.27 (dd, J=9.7, 6.2 Hz, 1H), 3.15-3.05 (m, 2H), 2.79 (ddd, J=9.9, 5.9, 2.0 Hz, 1H), 2.45 (s, 3H).

Step 4. Synthesis of N$^4$-(4,4-difluoro-1-methylpyrrolidin-3-yl)-6-fluoroquinoline-3,4-diamine (P12)

Palladium on carbon (10%, 3.85 g) was added to a solution of C39 (11.8 g, 36.2 mmol) in methanol (100 mL), and the resulting mixture was hydrogenated (30 psi) at 25° C. for 1 hour. This reaction mixture was combined with a similar reaction mixture employing C39 (3.60 g, 11.0 mmol) and filtered through diatomaceous earth. The filtrate was concentrated in vacuo and purified using chromatography on silica gel (Gradient: 9% to 17% tetrahydrofuran in petroleum ether). The product was obtained as a pale yellow solid. Combined yield: 8.40 g, 28.3 mmol, 60%. LCMS m/z 297.1 [M+H]$^+$. $^1$H NMR (400 MHz, CDCl$_3$) δ 8.45 (s, 1H), 7.95 (dd, J=9.0, 5.5 Hz, 1H), 7.43 (dd, J=10.6, 2.6 Hz, 1H), 7.23 (ddd, J=9.0, 8.1, 2.6 Hz, 1H), 4.26-4.12 (m, 1H), 4.05-3.89 (br s, 2H), 3.79 (br d, J=11.0 Hz, 1H), 3.23-2.93 (m, 3H), 2.63-2.55 (m, 1H), 2.38 (s, 3H).

Preparation P13

6-Chloro-N$^4$-(4,4-difluoro-1-methylpyrrolidin-3-yl) quinoline-3,4-diamine (P13)

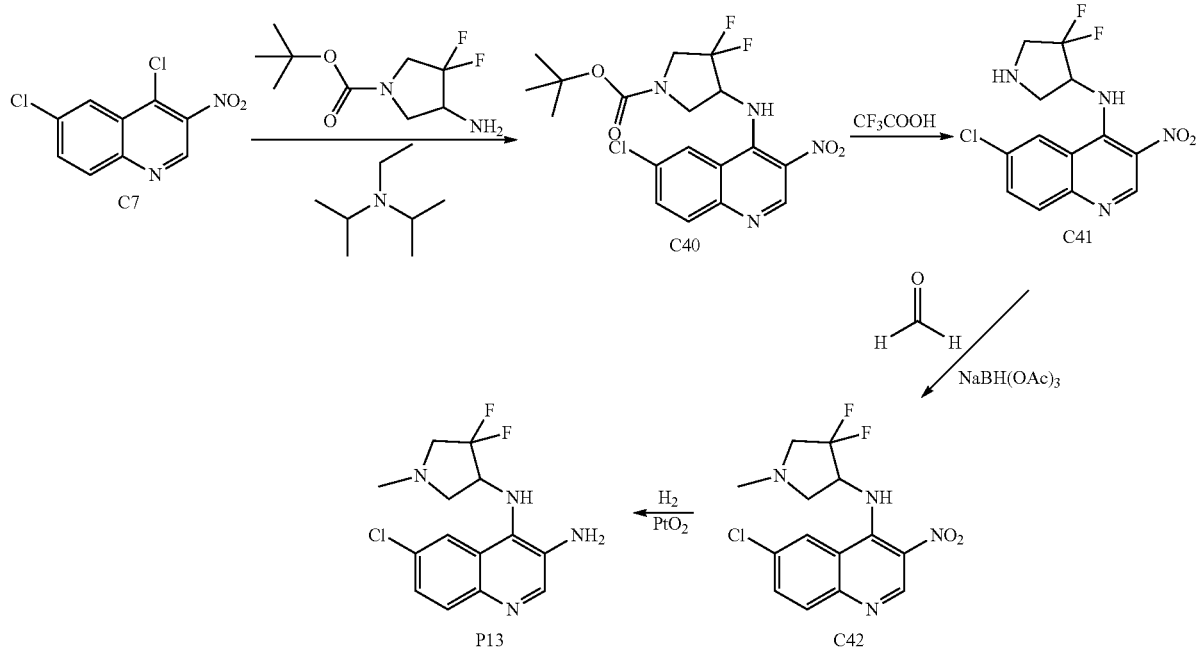

Step 1. Synthesis of tert-butyl 4-[(6-chloro-3-nitroquinolin-4-yl)amino]-3,3-difluoropyrrolidine-1-carboxylate (C40)

To a solution of C7 (13.1 g, 53.9 mmol) in acetonitrile (60 mL) was added N,N-diisopropylethylamine (11.3 mL, 64.9 mmol), followed by addition of a solution of tertbutyl 4-amino-3,3-difluoropyrrolidine-1-carboxylate (prepared using the method described by D. C. Behenna et al., in U.S. Patent Application 2015 0141402 A1, May 21, 2015; 12.0 g, 54.0 mmol) in acetonitrile (5 mL). After the reaction mixture had been stirred at 20° C. for 32 hours, it was diluted with water (100 mL). The resulting solid was collected by filtration and purified via chromatography on silica gel (Gradient: 0% to 25% tetrahydrofuran in petroleum ether), affording the product as a yellow solid. Yield: 12.0 g, 28.0 mmol, 52%. LCMS m/z 428.7 (chlorine isotope pattern observed) [M+H]$^+$. $^1$H NMR (400 MHz, CDCl$_3$) δ 9.41 (s, 1H), 8.91-8.78 (br m, 1H), 8.08 (br s, 1H), 8.06 (d, J=9.0 Hz, 1H), 7.79 (dd, J=9.0, 2.0 Hz, 1H), 4.86-4.72 (br m, 1H), 4.30-4.12 (br m, 1H), 4.03-3.86 (br m, 1H), 3.86-3.71 (m, 1H), 3.64-3.52 (br m, 1H), 1.51 (s, 9H).

Step 2. Synthesis of 6-chloro-N-(4,4-difluoropyrrolidin-3-yl)-3-nitroquinolin-4-amine (C41)

Trifluoroacetic acid (60 mL) was added to a solution of C40 (11.9 g, 27.8 mmol) in dichloromethane (100 mL), and the reaction mixture was stirred at 20° C. for 12 hours. Solvents were then removed via concentration in vacuo, and the residue was carefully basified by addition of aqueous sodium bicarbonate solution (500 mL). The resulting mixture was extracted with 2-methyltetrahydrofuran (2×200 mL), and the combined organic layers were dried over sodium sulfate, filtered, and concentrated under reduced pressure to provide the product as a yellow solid (10.9 g), which was used in the following step. LCMS m/z 328.5 (chlorine isotope pattern observed) [M+H]$^+$. $^1$H NMR (400 MHz, DMSO-d$_6$) δ 9.08 (s, 1H), 8.57 (s, 1H), 8.42-8.29 (br s, 1H), 7.94 (br AB quartet, J$_{AB}$=8 Hz, Δv$_{AB}$=26 Hz, 2H), 4.45-4.30 (br m, 1H), 3.57-3.46 (br m, 1H), 3.33-3.22 (m, 1H, assumed; partially obscured by water peak), 3.21-2.98 (m, 3H).

Step 3. Synthesis of 6-chloro-N-(4,4-difluoro-1-methylpyrrolidin-3-yl)-3-nitroquinolin-4-amine (C42)

Sodium triacetoxyborohydride (26.8 g, 126 mmol) was added to a 0° C. solution of C41 (from the previous step; 10.4 g, 26.5 mmol) in acetonitrile (110 mL). An aqueous solution of formaldehyde (37%; 10.3 g, 127 mmol) was added over 20 minutes, and the reaction mixture was stirred at room temperature for 1 hour. It was then combined with a similar reaction mixture derived from C41 (from the previous step; 500 mg, 1.27 mmol) and concentrated in vacuo. The residue was basified to pH 8 by addition of aqueous sodium bicarbonate solution, and the resulting solid was collection via filtration to afford the product as a red solid. Combined yield: 8.60 g, 25.1 mmol, 90% over two steps. LCMS m/z 342.6 (chlorine isotope pattern observed) [M+H]$^+$. $^1$H NMR (400 MHz, CDCl$_3$) δ 9.38 (s, 1H), 9.30 (br d, J=9.2 Hz, 1H), 8.18 (d, J=2.2 Hz, 1H), 8.01 (d, J=8.8 Hz, 1H), 7.75 (dd, J=9.2, 2.2 Hz, 1H), 4.83-4.71 (m, 1H), 3.27 (ddd, J=10.1, 6.2, 0.9 Hz, 1H), 3.16-3.07 (m, 2H), 2.81 (ddd, J=9.9, 5.7, 2.0 Hz, 1H), 2.46 (s, 3H).

Step 4. Synthesis of 6-chloro-N$^4$-(4,4-difluoro-1-methylpyrrolidin-3-yl)quinoline-3,4-diamine (P13)

Platinum(IV) oxide (5.0 g, 22 mmol) was added to a solution of C42 (8.50 g, 24.8 mmol) in methanol (100 mL), and the resulting mixture was hydrogenated at 25° C. for 4 hours, using a balloon of hydrogen. The reaction mixture was combined with a similar reaction mixture employing C42 (100 mg, 0.292 mmol), filtered through diatomaceous earth, and concentrated in vacuo. Chromatography on silica gel (Gradient: 17% to 100% tetrahydrofuran in petroleum ether) provided the product as a brown oil that solidified upon standing overnight. Combined yield: 5.02 g, 16.1 mmol, 64%. LCMS m/z 312.9 (chlorine isotope pattern observed) [M+H]$^+$. $^1$H NMR (400 MHz, CDCl$_3$) δ 8.48 (s, 1H), 7.90 (d, J=9.0 Hz, 1H), 7.81 (d, J=2.0 Hz, 1H), 7.41 (dd, J=8.8, 2.3 Hz, 1H), 4.29-4.16 (m, 1H), 3.95 (br s, 2H), 3.86 (br d, J=11.0 Hz, 1H), 3.19-2.96 (m, 3H), 2.61 (ddd, J=9, 7, 2 Hz, 1H), 2.41 (s, 3H).

Examples 1 and 2

[(2S,4R)-4-(8-Chloro-2-ethyl-1H-imidazo[4,5-c]quinolin-1-yl)tetrahydro-2H-pyran-2-yl]acetonitrile (1) and [(2R,4S)-4-(8-Chloro-2-ethyl-1H-imidazo[4,5-c]quinolin-1-yl)tetrahydro-2H-pyran-2-yl]acetonitrile (2)

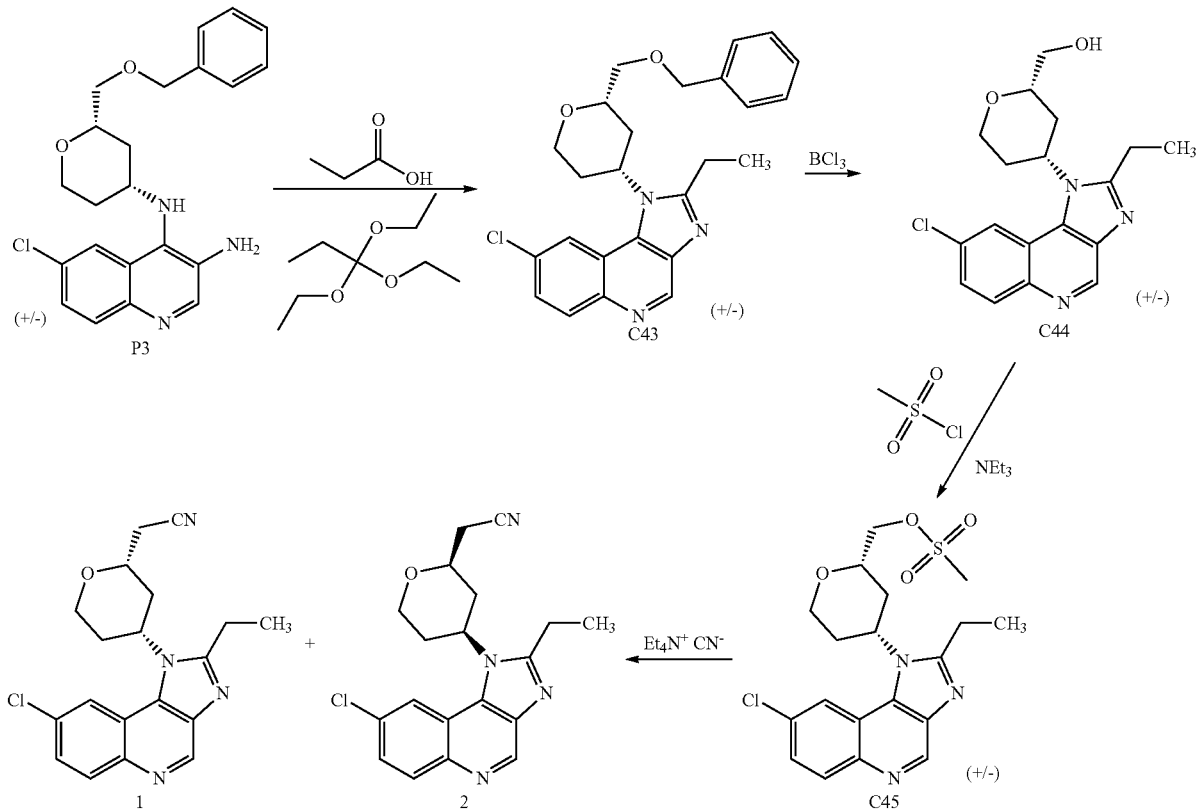

Step 1. Synthesis of 1-{cis-2-[(benzyloxy)methyl]tetrahydro-2H-pyran-4-yl}-8-chloro-2-ethyl-1H-imidazo[4,5-c]quinoline (C43)

A solution of P3 (800 mg, 2.01 mmol) in propanoic acid (10 mL) and 1,1,1-triethoxypropane (10 mL) was stirred at 110° C. for 2.5 hours, whereupon it was combined with a similar reaction carried out using P3 (100 mg, 0.251 mmol), and poured into water. The resulting mixture was neutralized with solid potassium carbonate and extracted with ethyl acetate (2×100 mL). The combined organic layers were dried over sodium sulfate, filtered, and concentrated in vacuo. Purification via silica gel chromatography (Gradient: 0% to 2% methanol in dichloromethane) provided the product as a yellow solid. Yield: 875 mg, 2.01 mmol, 89%. LCMS m/z 436.1 [M+H]$^+$.

Step 2. Synthesis of [cis-4-(8-chloro-2-ethyl-1H-imidazo[4,5-c]quinolin-1-yl)tetrahydro-2H-pyran-2-yl]methanol (C44)

A 0° C. solution of C43 (875 mg, 2.01 mmol) in dichloromethane (17 mL) was treated with boron trichloride (1 M solution; 6.02 mL, 6.02 mmol) and the reaction mixture was stirred at 20° C. for 2 hours, whereupon it was poured into aqueous sodium bicarbonate solution (50 mL) and extracted with ethyl acetate (2×50 mL). The combined organic layers were dried over sodium sulfate, filtered, concentrated under reduced pressure, and purified via silica gel chromatography (Gradient: 0% to 2.8% methanol in dichloromethane) to afford the product as an off-white, foamy solid. Yield: 490 mg, 1.42 mmol, 71%. LCMS m/z 346.0 [M+H]$^+$.

Step 3. Synthesis of [cis-4-(8-chloro-2-ethyl-1H-imidazo[4,5-c]quinolin-1-yl)tetrahydro-2H-pyran-2-yl]methyl methanesulfonate (C45)

To a 0° C. solution of C44 (490 mg, 1.42 mmol) in dichloromethane (10 mL) were added triethylamine (430 mg, 4.25 mmol) and methanesulfonyl chloride (195 mg, 1.70 mmol). The reaction mixture was stirred at 20° C. for 1 hour, whereupon it was poured into water (50 mL) and extracted with ethyl acetate (2×50 mL). The combined organic layers were dried over sodium sulfate, filtered, and concentrated in vacuo to provide the product as a yellow, foamy solid (640 mg), which was taken directly to the following step. LCMS m/z 423.8 (chlorine isotope pattern observed) [M+H]$^+$.

Step 4. Synthesis of [(2S,4R)-4-(8-chloro-2-ethyl-1H-imidazo[4,5-c]quinolin-1-yl)tetrahydro-2H-pyran-2-yl]acetonitrile (1) and [(2R,4S)-4-(8-chloro-2-ethyl-1H-imidazo[4,5-c]quinolin-1-yl)tetrahydro-2H-pyran-2-yl]acetonitrile (2)

To a solution of C45 (from the previous step; 1.42 mmol) in dimethyl sulfoxide (15 mL) was added tetraethylammonium cyanide (708 mg, 4.53 mmol). The reaction mixture was heated at 80° C. for 16 hours, whereupon it was cooled, poured into water, and extracted with ethyl acetate (2×100 mL). The combined organic layers were dried over sodium sulfate, filtered, and concentrated in vacuo. Chromatography on silica gel (Gradient: 0% to 2.8% methanol in dichloromethane) afforded a racemic mixture of 1 and 2 as an off-white, foamy solid. Yield of racemic product: 349 mg, 0.984 mmol, 69% over two steps.

This material was separated into its component enantiomers via supercritical fluid chromatography [Column: Chiral Technologies Chiralpak AD, 5 μm; Mobile phase: 7:3 carbon dioxide/(methanol containing 0.1% ammonium hydroxide)]. The first-eluting enantiomer was designated as 1, and the second-eluting enantiomer as 2; both were obtained as solids. The indicated absolute configurations for 1 and 2 were assigned on the basis of an X-ray structural determination carried out on 2 (see below).

For 1, Yield: 118 mg, 0.333 mmol, 34% for the separation. LCMS m/z 354.7 [M+H]$^+$. $^1$H NMR (400 MHz, CD$_3$OD) δ 9.12 (s, 1H), 8.83-8.63 (v br m, 1H), 8.18 (d, J=9.0 Hz, 1H), 7.72 (dd, J=9.0, 2.0 Hz, 1H), 5.37-5.13 (v br m, 1H), 4.45-4.31 (m, 1H), 4.06-3.97 (m, 1H), 3.88 (ddd, J=12.0, 12.0, 2.5 Hz, 1H), 3.21 (q, J=7.5 Hz, 2H), 2.94-2.44 (br m, 2H), 2.88 (dd, half of ABX pattern, J=17.1, 4.5 Hz, 1H), 2.78 (br dd, half of ABX pattern, J=17.1, 6.5 Hz, 1H), 2.31-2.14 (br m, 1H), 2.14-1.97 (br m, 1H), 1.52 (t, J=7.3 Hz, 3H).

For 2, Yield: 88.8 mg, 0.250 mmol, 25% yield for the separation. LCMS m/z 354.7 [M+H]$^+$. $^1$H NMR (400 MHz, CD$_3$OD) δ 9.11 (s, 1H), 8.82-8.59 (v br m, 1H), 8.17 (d, J=9.0 Hz, 1H), 7.71 (dd, J=9.0, 2.0 Hz, 1H), 5.39-5.12 (v br m, 1H), 4.44-4.31 (m, 1H), 4.06-3.96 (m, 1H), 3.88 (ddd, J=12, 12, 3 Hz, 1H), 3.20 (q, J=7.5 Hz, 2H), 2.88-2.69 (br m, 1H), 2.88 (dd, half of ABX pattern, J=17.1, 4.0 Hz, 1H), 2.78 (br dd, half of ABX pattern, J=17.1, 6.5 Hz, 1H), 2.67-2.46 (br m, 1H), 2.29-2.14 (br m, 1H), 2.14-1.97 (br m, 1H), 1.52 (t, J=7.3 Hz, 3H).

A sample of 2 was crystallized from 2-methyltetrahydrofuran/hexanes via vapor diffusion and used to determine the absolute configuration via X-ray crystallography:

Single-crystal X-ray structural determination of 2
Single Crystal X-Ray Analysis Data collection was performed on a Bruker APEX diffractometer at room temperature. Data collection consisted of omega and phi scans. Resolution was limited by diffraction of the crystal to approximately 0.9 angstroms.

The structure was solved by direct methods using SHELX software suite in the monoclinic space group P21. The structure was subsequently refined by the full-matrix least squares method. All non-hydrogen atoms were found and refined using anisotropic displacement parameters.

The hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The results indicate that the absolute structure has been correctly assigned. The method calculates that the probability that the structure is correct is 100.0. The Hooft parameter is reported as 0.045 with an Esd of 0.002.

The final R-index was 5.1%. A final difference Fourier revealed no missing or misplaced electron density.

Pertinent crystal, data collection and refinement information is summarized in Table F. Atomic coordinates, bond lengths, bond angles, and displacement parameters are listed in Tables G, H, and J.

SOFTWARE AND REFERENCES

SHELXTL, Version 5.1, Bruker A X S, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Strayer, and A. L. Spek, *J. Appl. Cryst.* 2008, 41, 96-103.

H. D. Flack, *Acta Cryst.* 1983, A39, 867-881.

TABLE F

Crystal data and structure refinement for 2.

| | |
|---|---|
| Empirical formula | $C_{19}H_{19}ClN_4O$ |
| Formula weight | 354.84 |
| Temperature | 296(2) K |
| Wavelength | 1.54178 Å |
| Crystal system | Monoclinic |
| Space group | P21 |
| Unit cell dimensions | a = 9.3184(7) Å, $\alpha = 90°$ |
| | b = 6.9545(5) Å, $\beta = 94.437(3)°$ |
| | c = 13.5545(9) Å, $\gamma = 90°$ |
| Volume | 875.76(11) Å$^3$ |
| Z | 2 |
| Density (calculated) | 1.346 Mg/m$^3$ |
| Absorption coefficient | 2.045 mm$^{-1}$ |
| F(000) | 372 |
| Crystal size | 0.120 × 0.120 × 0.060 mm$^3$ |
| Theta range for data collection | 17.720 to 69.948° |
| Index ranges | $-11 \le h \le 11$, $-8 \le k \le 8$, $-16 \le l \le 16$ |
| Reflections collected | 5772 |
| Independent reflections | 2717 [$R_{int}$ = 0.0396] |
| Completeness to theta = 70.57° | 94.9% |
| Absorption correction | Empirical |
| Refinement method | Full-matrix least-squares on $F^2$ |
| Data/restraints/parameters | 2717/1/228 |
| Goodness-of-fit on $F^2$ | 1.054 |
| Final R indices [$I > 2\sigma(I)$] | R1 = 0.0508, wR2 = 0.1118 |
| R indices (all data) | R1 = 0.0659, wR2 = 0.1203 |
| Absolute structure parameter | 0.04(2) |
| Extinction coefficient | 0.000(5) |
| Largest diff. peak and hole | 0.220 and −0.238 e · Å$^{-3}$ |

TABLE G

Atomic coordinates (×10$^4$) and equivalent isotropic displacement parameters (Å$^2$ × 10$^3$) for 2. U(eq) is defined as one-third of the trace of the orthogonalized U$^{ij}$ tensor.

| | x | y | z | U(eq) |
|---|---|---|---|---|
| Cl(1) | 5544(1) | 6289 (3) | 6228 (1) | 78(1) |
| O(1) | 5128(3) | 5926 (5) | 1381 (2) | 49(1) |
| N(1) | 11747(3) | 6220 (7) | 5643 (2) | 50(1) |
| N(2) | 11630(3) | 6286 (7) | 2918 (2) | 47(1) |
| N(3) | 9236(3) | 6080 (6) | 2976 (2) | 40(1) |
| N(4) | 2604(6) | 2224 (10) | 539 (4) | 95(2) |
| C(1) | 7761(4) | 6231 (8) | 5086 (2) | 44(1) |
| C(2) | 7371(4) | 6246 (9) | 6030 (3) | 49(1) |
| C(3) | 8389(5) | 6178 (9) | 6850 (3) | 53(1) |
| C(4) | 9805(4) | 6144 (9) | 6676 (3) | 50(1) |
| C(5) | 10282(4) | 6180 (8) | 5716 (2) | 41(1) |
| C(6) | 9224(3) | 6166 (7) | 4891 (2) | 38(1) |
| C(7) | 9817(4) | 6160 (8) | 3950 (2) | 38(1) |
| C(8) | 11288(3) | 6242 (8) | 3887 (2) | 41(1) |
| C(9) | 12213(4) | 6262 (9) | 4759 (3) | 50(1) |
| C(10) | 10387(4) | 6206 (9) | 2390 (3) | 44(1) |
| C(11) | 10260(4) | 6227 (12) | 1285 (3) | 61(1) |
| C(12) | 11494(7) | 7201 (11) | 842 (4) | 83(2) |
| C(13) | 7694(4) | 5811 (7) | 2668 (3) | 42(1) |
| C(14) | 6917(5) | 7699 (7) | 2409 (4) | 51(1) |
| C(15) | 5324(5) | 7311 (9) | 2160 (4) | 62(1) |

TABLE G-continued

Atomic coordinates (×10$^4$) and equivalent isotropic displacement parameters (Å$^2$ × 10$^3$) for 2. U(eq) is defined as one-third of the trace of the orthogonalized U$^{ij}$ tensor.

| | x | y | z | U(eq) |
|---|---|---|---|---|
| C(16) | 5752(5) | 4147 (7) | 1661 (3) | 46(1) |
| C(17) | 7371(5) | 4335 (7) | 1852 (4) | 51(1) |
| C(18) | 5357(5) | 2758 (9) | 813 (4) | 62(1) |
| C(19) | 3808(6) | 2452 (9) | 659 (4) | 66(1) |

TABLE H

Bond lengths [Å] and angles [°] for 2.

| | |
|---|---|
| Cl(1)—C(2) | 1.744 (4) |
| O(1)—C(16) | 1.406 (6) |
| O(1)—C(15) | 1.431 (6) |
| N(1)—C(9) | 1.306 (5) |
| N(1)—C(5) | 1.377 (5) |
| N(2)—C(10) | 1.315 (4) |
| N(2)—C(8) | 1.376 (5) |
| N(3)—C(10) | 1.386 (5) |
| N(3)—C(7) | 1.389 (4) |
| N(3)—C(13) | 1.477 (5) |
| N(4)—C(19) | 1.132 (7) |
| C(1)—C(2) | 1.357 (5) |
| C(1)—C(6) | 1.410 (5) |
| C(1)—H(1) | 0.9300 |
| C(2)—C(3) | 1.405 (5) |
| C(3)—C(4) | 1.359 (6) |
| C(3)—H(3) | 0.9300 |
| C(4)—C(5) | 1.407 (5) |
| C(4)—H(4) | 0.9300 |
| C(5)—C(6) | 1.432 (5) |
| C(6)—C(7) | 1.428 (5) |
| C(7)—C(8) | 1.381 (5) |
| C(8)—C(9) | 1.408 (5) |
| C(9)—H(9) | 0.9300 |
| C(10)—C(11) | 1.493 (5) |
| C(11)—C(12) | 1.499 (8) |
| C(11)—H(11A) | 0.9700 |
| C(11)—H(11B) | 0.9700 |
| C(12)—H(12A) | 0.9600 |
| C(12)—H(12B) | 0.9600 |
| C(12)—H(12C) | 0.9600 |
| C(13)—C(17) | 1.522 (6) |
| C(13)—C(14) | 1.527 (6) |
| C(13)—H(13) | 0.9800 |
| C(14)—C(15) | 1.520 (7) |
| C(14)—H(14A) | 0.9700 |
| C(14)—H(14B) | 0.9700 |
| C(15)—H(15A) | 0.9700 |
| C(15)—H(15B) | 0.9700 |
| C(16)—C(17) | 1.516 (6) |
| C(16)—C(18) | 1.524 (6) |
| C(16)—H(16) | 0.9800 |
| C(17)—H(17A) | 0.9700 |
| C(17)—H(17B) | 0.9700 |
| C(18)—C(19) | 1.458 (8) |
| C(18)—H(18A) | 0.9700 |
| C(18)—H(18B) | 0.9700 |
| C(16)—O(1)—C(15) | 111.5 (3) |
| C(9)—N(1)—C(5) | 117.9 (3) |
| C(10)—N(2)—C(8) | 105.0 (3) |
| C(10)—N(3)—C(7) | 106.3 (3) |
| C(10)—N(3)—C(13) | 128.7 (3) |
| C(7)—N(3)—C(13) | 125.0 (3) |
| C(2)—C(1)—C(6) | 120.7 (3) |
| C(2)—C(1)—H(1) | 119.6 |
| C(6)—C(1)—H(1) | 119.6 |
| C(1)—C(2)—C(3) | 122.1 (4) |
| C(1)—C(2)—Cl(1) | 118.8 (3) |
| C(3)—C(2)—Cl(1) | 119.1 (3) |
| C(4)—C(3)—C(2) | 117.9 (3) |
| C(4)—C(3)—H(3) | 121.0 |
| C(2)—C(3)—H(3) | 121.0 |

TABLE H-continued

Bond lengths [Å] and angles [°] for 2.

| | |
|---|---|
| C(3)—C(4)—C(5) | 122.7 (3) |
| C(3)—C(4)—H(4) | 118.6 |
| C(5)—C(4)—H(4) | 118.6 |
| N(1)—C(5)—C(4) | 116.9 (3) |
| N(1)—C(5)—C(6) | 124.8 (3) |
| C(4)—C(5)—C(6) | 118.3 (3) |
| C(1)—C(6)—C(7) | 127.9 (3) |
| C(1)—C(6)—C(5) | 118.0 (3) |
| C(7)—C(6)—C(5) | 114.0 (3) |
| C(8)—C(7)—N(3) | 105.0 (3) |
| C(8)—C(7)—C(6) | 120.6 (3) |
| N(3)—C(7)—C(6) | 134.4 (3) |
| C(7)—C(8)—N(2) | 111.4 (3) |
| C(7)—C(8)—C(9) | 119.7 (3) |
| N(2)—C(8)—C(9) | 129.0 (3) |
| N(1)—C(9)—C(8) | 122.9 (3) |
| N(1)—C(9)—H(9) | 118.5 |
| C(8)—C(9)—H(9) | 118.5 |
| N(2)—C(10)—N(3) | 112.2 (3) |
| N(2)—C(10)—C(11) | 122.9 (3) |
| N(3)—C(10)—C(11) | 124.8 (3) |
| C(10)—C(11)—C(12) | 113.7 (4) |
| C(10)—C(11)—H(11A) | 108.8 |
| C(12)—C(11)—H(11A) | 108.8 |
| C(10)—C(11)—H(11B) | 108.8 |
| C(12)—C(11)—H(11B) | 108.8 |
| H(11A)—C(11)—H(11B) | 107.7 |
| C(11)—C(12)—H(12A) | 109.5 |
| C(11)—C(12)—H(12B) | 109.5 |
| H(12A)—C(12)—H(12B) | 109.5 |
| C(11)—C(12)—H(12C) | 109.5 |
| H(12A)—C(12)—H(12C) | 109.5 |
| H(12B)—C(12)—H(12C) | 109.5 |
| N(3)—C(13)—C(17) | 115.1 (3) |
| N(3)—C(13)—C(14) | 112.9 (4) |
| C(17)—C(13)—C(14) | 110.4 (3) |
| N(3)—C(13)—H(13) | 105.8 |
| C(17)—C(13)—H(13) | 105.8 |
| C(14)—C(13)—H(13) | 105.8 |
| C(15)—C(14)—C(13) | 109.6 (4) |
| C(15)—C(14)—H(14A) | 109.7 |
| C(13)—C(14)—H(14A) | 109.7 |
| C(15)—C(14)—H(14B) | 109.7 |
| C(13)—C(14)—H(14B) | 109.7 |
| H(14A)—C(14)—H(14B) | 108.2 |
| O(1)—C(15)—C(14) | 110.5 (4) |
| O(1)—C(15)—H(15A) | 109.6 |
| C(14)—C(15)—H(15A) | 109.6 |
| O(1)—C(15)—H(15B) | 109.6 |
| C(14)—C(15)—H(15B) | 109.6 |
| H(15A)—C(15)—H(15B) | 108.1 |
| O(1)—C(16)—C(17) | 110.8 (4) |
| O(1)—C(16)—C(18) | 106.5 (3) |
| C(17)—C(16)—C(18) | 111.3 (4) |
| O(1)—C(16)—H(16) | 109.4 |
| C(17)—C(16)—H(16) | 109.4 |
| C(18)—C(16)—H(16) | 109.4 |
| C(16)—C(17)—C(13) | 108.7 (4) |
| C(16)—C(17)—H(17A) | 109.9 |
| C(13)—C(17)—H(17A) | 109.9 |
| C(16)—C(17)—H(17B) | 109.9 |
| C(13)—C(17)—H(17B) | 109.9 |
| H(17A)—C(17)—H(17B) | 108.3 |
| C(19)—C(18)—C(16) | 112.3 (4) |
| C(19)—C(18)—H(18A) | 109.1 |
| C(16)—C(18)—H(18A) | 109.1 |
| C(19)—C(18)—H(18B) | 109.1 |
| C(16)—C(18)—H(18B) | 109.1 |
| H(18A)—C(18)—H(18B) | 107.9 |
| N(4)—C(19)—C(18) | 179.6 (7) |

TABLE J

Anisotropic displacement parameters (Å$^2$ × 10$^3$) for 2.
The anisotropic displacement factor exponent takes the form: $-2\pi^2[h^2 a^{*2}U^{11} + \ldots + 2 h k a^* b^* U^{12}]$.

| | U$^{11}$ | U$^{22}$ | U$^{33}$ | U$^{23}$ | U$^{13}$ | U$^{12}$ |
|---|---|---|---|---|---|---|
| Cl(1) | 60(1) | 124 (1) | 52 (1) | −11 (1) | 13 (1) | 3 (1) |
| O(1) | 39(1) | 58 (2) | 49 (1) | −5 (2) | −7 (1) | 2 (2) |
| N(1) | 50(2) | 49 (2) | 48 (2) | 4 (2) | −16 (1) | −6 (2) |
| N(2) | 36(2) | 54 (2) | 50 (2) | 3 (2) | −2 (1) | 3 (2) |
| N(3) | 36(2) | 52 (2) | 33 (1) | 3 (2) | −4 (1) | −5 (2) |
| N(4) | 55(3) | 132 (5) | 96 (4) | −37 (3) | 0 (2) | −28 (3) |
| O(1) | 46(2) | 48 (2) | 38 (2) | −2 (2) | −6 (1) | −1 (3) |
| C(2) | 54(2) | 51 (3) | 42 (2) | −8 (3) | 2 (2) | −1 (3) |
| C(3) | 72(3) | 52 (3) | 35 (2) | −3 (3) | 0 (2) | −7 (3) |
| C(4) | 65(2) | 46 (2) | 37 (2) | 0 (2) | −15 (2) | −8 (3) |
| C(5) | 50(2) | 31 (2) | 41 (2) | 2 (2) | −12 (1) | −5 (2) |
| C(6) | 44(2) | 31 (2) | 36 (2) | −1 (2) | −7 (1) | −2 (2) |
| C(7) | 43(2) | 32 (2) | 37 (2) | 0 (2) | −9 (1) | 0 (2) |
| C(8) | 35(2) | 39 (2) | 46 (2) | 5 (2) | −6 (1) | 1 (2) |
| C(9) | 42(2) | 51 (3) | 54 (2) | −1 (3) | −12 (2) | −2 (3) |
| C(10) | 36 (2) | 52 (2) | 45 (2) | 2 (2) | 0 (1) | 1 (3) |
| C(11) | 43 (2) | 94 (4) | 46 (2) | 0 (3) | 2 (2) | 3 (4) |
| C(12) | 72 (4) | 119 (6) | 59 (3) | 21 (3) | 13 (2) | −10 (3) |
| C(13) | 37 (2) | 57 (3) | 32 (2) | 2 (2) | −3 (1) | −6 (2) |
| C(14) | 42 (2) | 51 (3) | 58 (3) | −10 (2) | −5 (2) | 2 (2) |
| C(15) | 39 (2) | 68 (4) | 79 (3) | −26 (3) | −8 (2) | 6 (2) |
| C(16) | 50 (2) | 51 (3) | 37 (2) | 3 (2) | −4 (2) | −12 (2) |
| C(17) | 49 (3) | 44 (3) | 58 (3) | −6 (2) | −16 (2) | 5 (2) |
| C(18) | 55 (3) | 61 (3) | 68 (3) | −14 (3) | −11 (2) | −4 (2) |
| C(19) | 63 (3) | 78 (4) | 55 (3) | −18 (3) | −3 (2) | −13 (3) |

Examples 3 and 4
1-(4,4-Difluoro-1-methylpyrrolidin-3-yl)-2-[(4-methyl-2H-1,2,3-triazol-2-yl)methyl]-1H-imidazo[4,5-c]quinoline-8-carbonitrile, ENT 1 (3) and 1-(4,4-Difluoro-1-methylpyrrolidin-3-yl)-2-[(4-methyl-2H-1,2,3-triazol-2-yl)methyl]-1H-imidazo[4,5-c]quinoline-8-carbonitrile, ENT 2 (4)
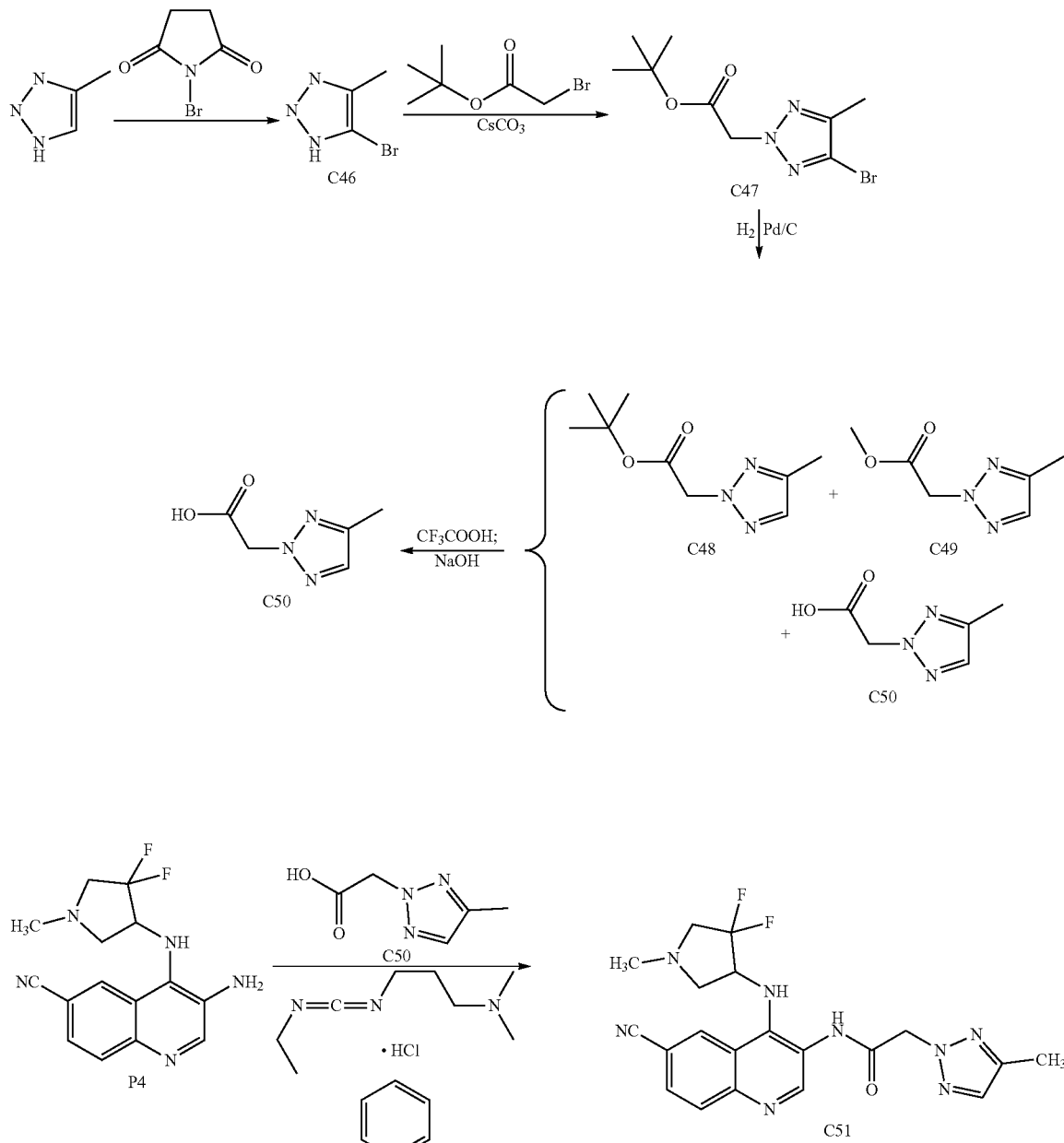
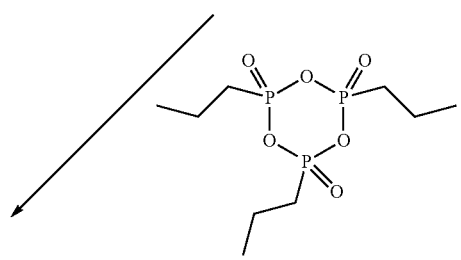

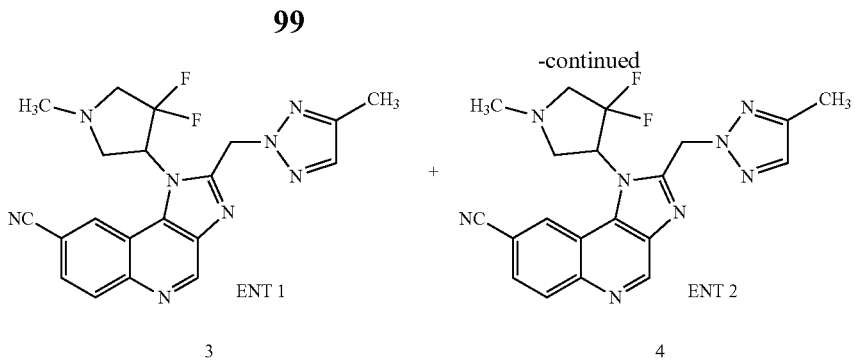

3

4

Step 1. Synthesis of 4-bromo-5-methyl-1H-1,2,3-triazole (C46)

N-Bromosuccinimide (5.89 g, 33.1 mmol) was added to a solution of 4-methyl-1H-1,2,3-triazole (2.50 g, 30.1 mmol) in chloroform (30 mL), and the reaction mixture was stirred for 16 hours at room temperature (15° C.). It was then diluted with dichloromethane (100 mL), washed with water (2×100 mL), dried over sodium sulfate, filtered, and concentrated in vacuo to provide the product as a white solid (4.9 g), which was used directly in the next step.

Step 2. Synthesis of tert-butyl (4-bromo-5-methyl-2H-1,2,3-triazol-2-yl)acetate (C47)

tert-Butyl bromoacetate (8.8 g, 45 mmol) was added in one portion to a mixture of C46 (from the previous step, 4.9 g, 30.1 mmol) and cesium carbonate (17.6 g, 54.0 mmol) in N,N-dimethylformamide (80 mL). The reaction mixture was stirred at room temperature (20° C.) for 16 hours, whereupon it was diluted with water (100 mL) and extracted with ethyl acetate (2×80 mL). The combined organic layers were washed with saturated aqueous sodium chloride solution (2×100 mL), dried over sodium sulfate, filtered, and concentrated in vacuo. Silica gel chromatography (Gradient: 0% to 15%, ethyl acetate in petroleum ether) provided the product as a colorless oil. Yield: 4.00 g, 14.5 mmol, 48% over 2 steps.

Step 3. Synthesis of tert-butyl (4-methyl-2H-1,2,3-triazol-2-yl)acetate (C48), methyl (4-methyl-2H-1,2,3-triazol-2-yl)acetate (C49), and (4-methyl-2H-1,2,3-triazol-2-yl)acetic Acid (C50)

A mixture of C47 (3.50 g, 12.7 mmol) and palladium on carbon (10%, 500 mg) in methanol (35 mL) was stirred under hydrogen (40 psi) for 4 hours at room temperature (17° C.). The reaction mixture was filtered, and the filtrate was concentrated in vacuo, providing a yellow oil (3.00 g). On the basis of $^1$H NMR, the product was assigned as a mixture of C48 (tert-butyl ester), C49 (methyl ester), and C50 (carboxylic acid); this material was taken directly to the following step for ester hydrolysis. $^1$H NMR peaks (400 MHz, CD$_3$OD) δ [7.50 (s) and 7.49 (s), total 1H], [5.23 (s), 5.17 (s), and 5.10 (s), total 2H], 3.75 (s, from methyl ester), 2.30 (s, 3H), 1.46 (s, from tert-butyl ester).

Step 4. Synthesis of (4-methyl-2H-1,2,3-triazol-2-yl)acetic Acid (C50)

A mixture of C48, C49, and C50 (from the previous step, 3.00 g, mmol) in trifluoroacetic acid (3 mL) was stirred for 2 hours at room temperature (17° C.). After removal of solvent in vacuo, the residue was dissolved in tetrahydrofuran (10 mL) and treated with aqueous sodium hydroxide solution (2 M, 10 mL). The reaction mixture was stirred for 1 hour at room temperature (17° C.), concentrated in vacuo, and partitioned between water (50 mL) and dichloromethane (20 mL). The aqueous layer was extracted with dichloromethane (2×20 mL), and then acidified with 1 M aqueous hydrochloric acid to a pH of 1. This acidic aqueous layer was extracted with ethyl acetate (3×40 mL), and the combined ethyl acetate layers were dried over sodium sulfate, filtered, and concentrated under reduced pressure to provide the product as a yellow solid. Yield: 1.9 g, 13 mmol, 100% over 2 steps. $^1$H NMR (400 MHz, CDCl$_3$) δ 7.46 (s, 1H), 5.25 (s, 2H), 2.34 (s, 3H).

Step 5. Synthesis of N-{6-cyano-4-[(4,4-difluoro-1-methylpyrrolidin-3-yl)amino]quinolin-3-yl}-2-(4-methyl-2H-1,2,3-triazol-2-yl)acetamide (C51)

This experiment was carried out in two identical batches. 1-[3-(Dimethylamino)propyl]-3-ethylcarbodiimide hydrochloride (139 mg, 0.725 mmol) was added to a solution of P4 (100 mg, 0.330 mmol) and C50 (55.8 mg, 0.395 mmol) in pyridine (1.0 mL). After the reaction mixture had been stirred at 25° C. for 1 hour, at which time LCMS analysis indicated conversion to the product: LCMS m/z 427.2 [M+H]$^+$, the two batches were combined, diluted with water (50 mL), and extracted with ethyl acetate (3×50 mL). The combined organic layers were concentrated in vacuo and purified via silica gel chromatography (Gradient: 17% to 50% ethyl acetate in petroleum ether) to provide the product as a white solid. Yield: 210 mg, 0.492 mmol, 75%. $^1$H NMR (400 MHz, CDCl$_3$) δ 8.84 (s, 1H), 8.29 (d, J=1.5 Hz, 1H), 8.11 (d, J=8.8 Hz, 1H), 8.08 (br s, 1H), 7.80 (dd, J=8.8, 1.5 Hz, 1H), 7.56 (s, 1H), 5.34 (s, 2H), 4.77 (br d, J=10.8 Hz, 1H), 4.30-4.17 (m, 1H), 3.10 (dd, J=9.8, 6.4 Hz, 1H), 3.07-2.95 (m, 2H), 2.68 (ddd, J=9.8, 5.9, 2.0 Hz, 1H), 2.42 (s, 3H), 2.40 (s, 3H).

Step 6. Synthesis of 1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 1 (3) and 1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 2 (4)

2,4,6-Tripropyl-1,3,5,2,4,6-trioxatriphosphinane 2,4,6-trioxide (50% solution in ethyl acetate; 0.92 mL, 1.5 mmol) was added to a 15° C. solution of C51 (210 mg, 0.492 mmol) in N,N-dimethylformamide (1 mL) and propyl acetate (4 mL). The reaction mixture was stirred for 14 hours at 110° C., whereupon it was cooled and treated with aqueous sodium bicarbonate solution (60 mL). The resulting mixture was extracted with ethyl acetate (3×60 mL), and the combined organic layers were concentrated in vacuo to provide a racemic mixture of 3 and 4 as a white solid. Yield of racemic product: 180 mg, 0.441 mmol, 90%.

This material was separated into its component enantiomers via supercritical fluid chromatography [Column: Regis Technologies, (S,S)-Whelk-0® 1, 10 μm; Mobile phase: 55:45 carbon dioxide/(2-propanol containing 0.1% ammonium hydroxide)]. The first-eluting product was designated as 3, and was obtained as a solid. Yield: 76.0 mg, 0.186 mmol, 42% for the separation. LCMS m/z 409.0 [M+H]$^+$. $^1$H NMR (400 MHz, CDCl$_3$) δ 10.2-9.4 (v br s, 1H), 9.44 (s, 1H), 8.33 (d, J=8.8 Hz, 1H), 7.86 (dd, J=8.6, 1.7 Hz, 1H), 7.43 (s, 1H), 6.41-6.09 (m, 2H), 5.96 (d, J=15.6 Hz, 1H), 3.75-3.57 (br m, 1H), 3.70 (dd, J=11.7, 11.7 Hz, 1H), 3.17-3.03 (m, 1H), 3.15 (dd, J=11.2, 11.2 Hz, 1H), 2.65 (br s, 3H), 2.32 (s, 3H).

The second-eluting product, also isolated as a solid, was designated as 4. Yield: 68.6 mg, 0.168 mmol, 38% for the separation. LCMS m/z 409.1 [M+H]$^+$. $^1$H NMR (400 MHz, CDCl$_3$) δ 10.1-9.5 (v br s, 1H), 9.44 (s, 1H), 8.33 (d, J=8.8 Hz, 1H), 7.86 (dd, J=8.8, 1.5 Hz, 1H), 7.43 (s, 1H), 6.36-6.10 (m, 2H), 5.96 (d, J=15.6 Hz, 1H), 3.75-3.57 (br m, 1H), 3.70 (dd, J=11.7, 11.2 Hz, 1H), 3.17-3.03 (m, 1H), 3.15 (dd, J=11.7, 11.2 Hz, 1H), 2.65 (br s, 3H), 2.32 (s, 3H).

Example 5

8-Chloro-1-[(4S)-3,3-difluorotetrahydro-2H-pyran-4-yl]-2-[(5-methyl-1,2-oxazol-3-yl)methyl]-1H-imidazo[4,5-c]quinoline (5)

A 0° C. solution of P6 (75 mg, 0.24 mmol), (5-methyl-1,2-oxazol-3-yl)acetic acid (57.4 mg, 0.407 mmol), and N,N-diisopropylethylamine (0.11 mL, 0.63 mmol) in tetrahydrofuran (4 mL) was treated drop-wise with 2,4,6-tripropyl-1,3,5,2,4,6-trioxatriphosphinane 2,4,6-trioxide (50% solution in ethyl acetate; 0.28 mL, 0.47 mmol), and the reaction mixture was allowed to warm to room temperature overnight. The resulting solution was concentrated in vacuo, and the residue was dissolved in toluene (5 mL) and stirred at 110° C. for 72 hours, whereupon it was cooled to room temperature and partitioned between saturated aqueous sodium chloride solution and ethyl acetate. The organic layer was washed with saturated aqueous sodium chloride solution, dried over magnesium sulfate, filtered, and concentrated. Silica gel chromatography (Gradient: 30% to 100% ethyl acetate in heptane) afforded the product as a pale tan foam. From analysis of the $^1$H NMR, this material was presumed to exist as a mixture of rotamers. Yield: 79 mg, 0.189 mmol, 79%. LCMS m/z 419.5 (chlorine isotope pattern observed) [M+H]$^+$. $^1$H NMR (400 MHz, CDCl$_3$) δ [9.27 (s) and 9.27 (s), total 1H], [8.52 (br s) and 8.11 (br s), total 1H], [8.22 (d, J=9.0 Hz) and 8.19 (d, J=9.0 Hz), total 1H], 7.66-7.57 (m, 1H), [6.11 (s) and 6.05 (s), total 1H], 5.69-5.43 (m, 1H), [4.59 (AB quartet, J$_{AB}$=16.8 Hz, Δv$_{AB}$=19.5 Hz) and 4.50 (AB quartet, J$_{AB}$=15.8 Hz, Δv$_{AB}$=11.8 Hz), total 2H], 4.43-4.27 (m, 2H), 3.92-3.63 (m, 2H), [3.30-3.17 (m) and 3.17-3.04 (m), total 1H], [2.40 (s) and 2.38 (s), total 3H], [2.23-2.14 (m) and 1.95-1.85 (m), total 1H].

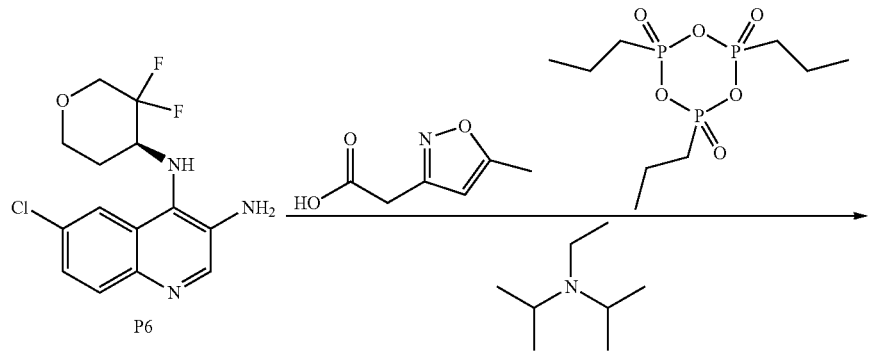

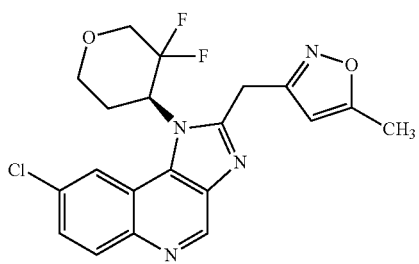

5

Example 6

2-[(6-Methylpyrimidin-4-yl)methyl]-1-[(3R)-1-methylpyrrolidin-3-yl]-1H-imidazo[4,5-c]quinoline-8-carbonitrile, formate salt (6)

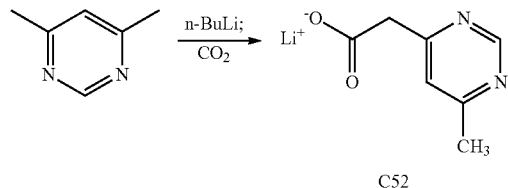

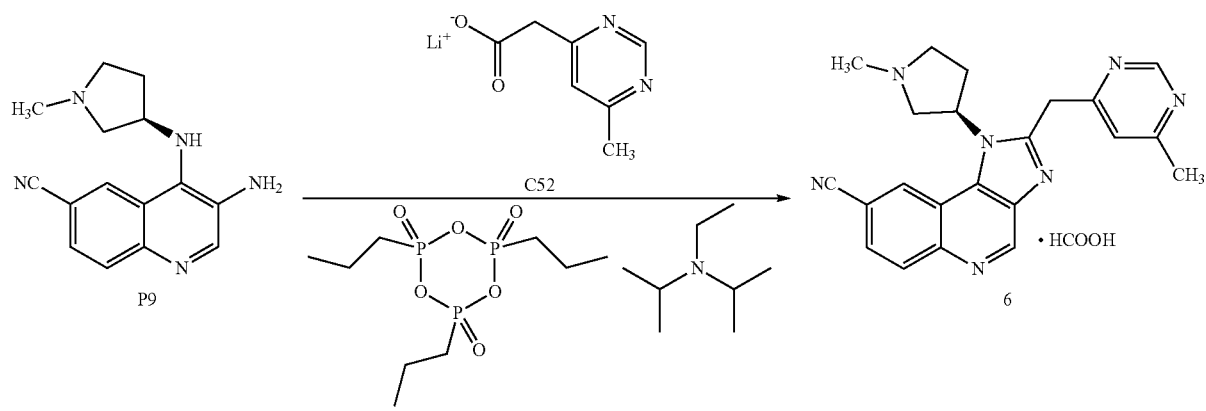

Step 1. Synthesis of lithium (6-methylpyrimidin-4-yl)acetate (C52)

n-Butyllithium (2.5 M in hexanes; 5.00 mL, 12.5 mmol) was slowly added dropwise to a −78° C. solution of 4,6-dimethylpyrimidine (1.08 g, 9.99 mmol) in tetrahydrofuran (20 mL). After the reaction mixture had been stirred for 20 minutes at −78° C., solid carbon dioxide (dry ice, 5.0 g) was added, and the reaction mixture was warmed to room temperature (15° C.) and stirred for 1 hour. Water (3.0 mL) was then added, and the resulting mixture was concentrated in vacuo to provide the product as a white solid. Yield: 1.53 g, 9.68 mmol, 97%. $^1$H NMR (400 MHz, D2O) δ 8.78 (s, 1H), 7.28 (s, 1H), [3.60 (s) and 3.59 (br s), total 2H], 2.43 (s, 3H).

Step 2. Synthesis of 2-[(6-methylpyrimidin-4-yl)methyl]-1-[(3R)-1-methylpyrrolidin-3-yl]-1H-imidazo[4,5-c]quinoline-8-carbonitrile, formate salt (6)

This synthesis was carried out in library format. A mixture of P9 (100 μmol), C52 (130 μmol), and 2,4,6-tripropyl-1,3,5,2,4,6-trioxatriphosphinane 2,4,6-trioxide (50% solution in ethyl acetate; 100 μL, 170 μmol) was treated with N,N-diisopropylethylamine (300 μmol) and 1,4-dioxane (1 mL), and the reaction vial was capped and shaken at 110° C. for 16 hours. After solvents had been removed using a Speed-vac® concentrator, the residue was purified via reversed-phase HPLC (Column: Agela Durashell C18, 5 μm; Mobile phase A: 0.225% formic acid in water; Mobile phase B: acetonitrile; Gradient: 0% to 31% B) to afford the product. Yield: 1.5 mg, 3.5 μmol, 4%. LCMS m/z 384 [M+H]$^+$. Retention time: 2.38 minutes (Conditions for analytical HPLC. Column: Waters XBridge C18, 2.1×50 mm, 5 μm; Mobile phase A: 0.05% ammonium hydroxide in water; Mobile phase B: acetonitrile; Gradient: 5% B for 0.5 minutes; 5% to 100% B over 2.9 minutes; 100% B for 0.8 minutes; Flow rate: 0.8 mL/minute).

Examples 7 and 8

8-Chloro-1-(3,3-difluorotetrahydro-2H-pyran-4-yl)-2-[(5-methylpyrazin-2-yl)methyl]-1H-imidazo[4,5-c]quinoline, ENT 1 (7) and 8-Chloro-1-(3,3-difluorotetrahydro-2H-pyran-4-yl)-2-[(5-methylpyrazin-2-yl)methyl]-1H-imidazo[4,5-c]quinoline, ENT 2 (8)

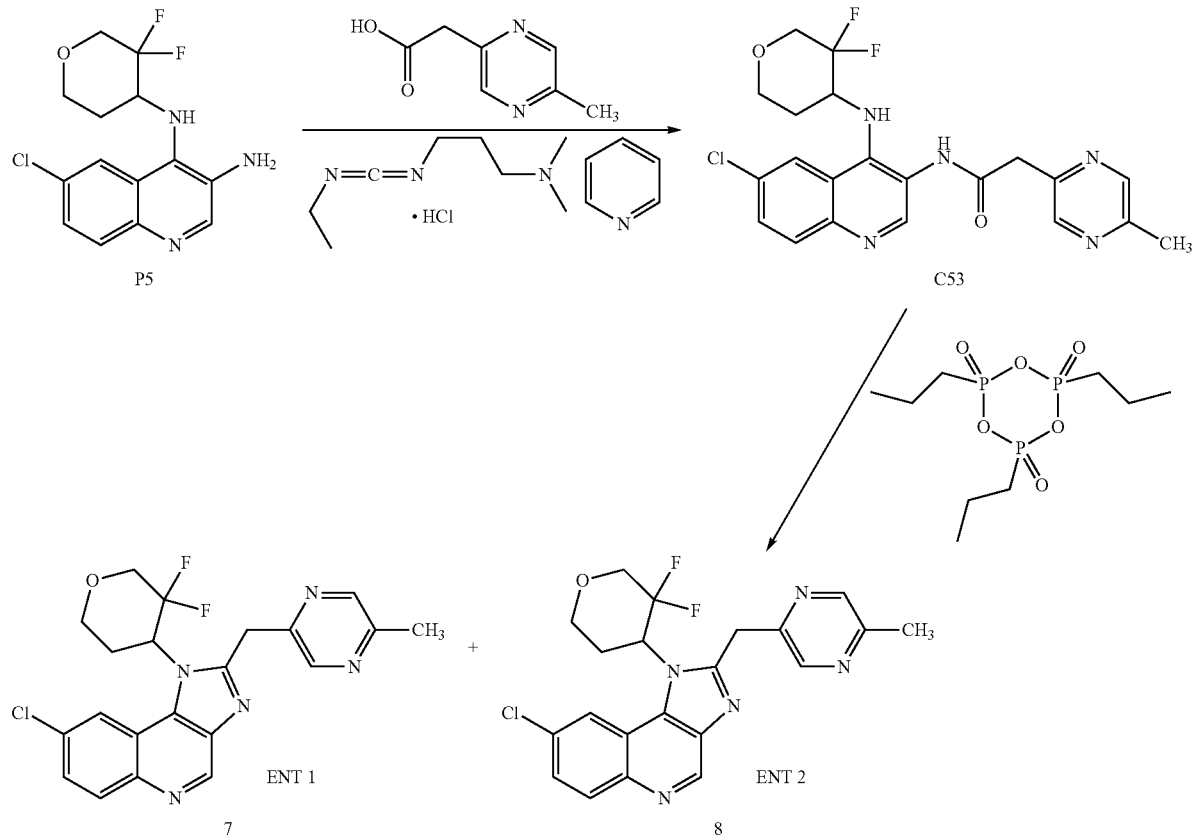

Step 1. Synthesis of N-{6-chloro-4-[(3,3-difluorotetrahydro-2H-pyran-4-yl)amino]quinolin-3-yl}-2-(5-methylpyrazin-2-yl)acetamide (C53)

1-[3-(Dimethylamino)propyl]-3-ethylcarbodiimide hydrochloride (183 mg, 0.955 mmol) was added to a solution of P5 (150 mg, 0.478 mmol) and (5-methylpyrazin-2-yl)acetic acid (94.6 mg, 0.622 mmol) in pyridine (0.80 mL). The reaction mixture was stirred at 25° C. for 4 hours, whereupon it was combined with a similar reaction carried out using P5 (10.0 mg, 31.9 µmol), diluted with water (2 mL), and extracted with ethyl acetate (3×3 mL). The combined organic layers were concentrated in vacuo to afford the product as a brown oil, which was used directly in the following step. Combined yield: 214 mg, 0.478 mmol, 94%. LCMS m/z 448.2 [M+H]$^+$.

Step 2. Synthesis of 8-chloro-1-(3,3-difluorotetrahydro-2H-pyran-4-yl)-2-[(5-methylpyrazin-2-yl)methyl]-1H-imidazo[4,5-c]quinoline, ENT 1 (7) and 8-chloro-1-(3,3-difluorotetrahydro-2H-pyran-4-yl)-2-[(5-methylpyrazin-2-yl)methyl]-1H-imidazo[4,5-c]quinoline, ENT 2 (8)

2,4,6-Tripropyl-1,3,5,2,4,6-trioxatriphosphinane 2,4,6-trioxide (50% solution in ethyl acetate; 608 mg, 0.955 mmol) was added to a 110° C. solution of C53 (214 mg, 0.478 mmol) in propyl acetate (1 mL), and the reaction mixture was stirred at 110° C. for 48 hours. It was then concentrated in vacuo and purified via silica gel chromatography (Gradient: 0% to 3% methanol in dichloromethane) to provide a racemic mixture of 7 and 8 as a yellow oil. Yield of racemic product: 150 mg, 0.349 mmol, 73%.

The enantiomers were separated using supercritical fluid chromatography ([Column: Chiral Technologies ChiralCel OD, 5 µm; Mobile phase: 7:3 carbon dioxide/(ethanol containing 0.1% ammonium hydroxide)]; each enantiomer was then individually subjected to reversed-phase HPLC purification (Column: Agela Durashell, 5 µm; Mobile phase A: 0.05% ammonium hydroxide in water; Mobile phase B: acetonitrile; Gradient: 32% to 52% B). The first-eluting enantiomer was designated as 7, and the second-eluting enantiomer as 8. Both 7 and 8 were obtained as solids, and from analysis of the $^1$H NMR spectra, both were presumed to exist as a mixture of rotamers.

For 7, yield: 21.3 mg, 49.6 µmol, 14% for the separation. LCMS m/z 429.8 (chlorine isotope pattern observed) [M+H]$^+$. $^1$H NMR (400 MHz, CD$_3$OD) δ [9.10 (s) and 9.06 (s), total 1H], 8.72-8.42 (m, 3H), [8.17 (d, J=8.8 Hz) and 8.15 (d, J=8.8 Hz), total 1H], 7.76-7.68 (m, 1H), [6.11-5.96 (m) and 5.96-5.80 (m), total 1H], 4.9-4.66 (m, 2H, assumed; partially obscured by water peak), 4.39-4.17 (m, 2H), 4.08-3.77 (m, 2H), [3.35-3.21 (m) and 3.17-3.04 (m), total 1H, assumed; partially obscured by solvent peak], [2.57 (s) and 2.54 (s), total 3H], [2.42-2.33 (m) and 2.32-2.21 (m), total 1H].

For 8, yield: 32.6 mg, 75.8 µmol, 22% for the separation. LCMS m/z 429.7 (chlorine isotope pattern observed)

[M+H]+. 1H NMR (400 MHz, CD3OD) δ [9.10 (s) and 9.06 (s), total 1H], 8.71-8.43 (m, 3H), [8.17 (d, J=8.8 Hz) and 8.15 (d, J=9 Hz), total 1H], 7.76-7.69 (m, 1H), [6.10-5.96 (m) and 5.96-5.81 (m), total 1H], 4.9-4.67 (m, 2H, assumed; partially obscured by water peak), 4.39-4.17 (m, 2H), 4.08-3.77 (m, 2H), [3.35-3.21 (m) and 3.17-3.04 (m), total 1H, assumed; partially obscured by solvent peak], [2.57 (s) and 2.54 (s), total 3H], [2.42-2.33 (m) and 2.32-2.22 (m), total 1H].
Example 9
1-[(2R,4R)-2-Methyltetrahydro-2H-pyran-4-yl]-2-[(1-methyl-1H-1,2,3-triazol-4-yl)methyl]-8-(trifluoromethyl)-1H-imidazo[4,5-c]quinoline (9)
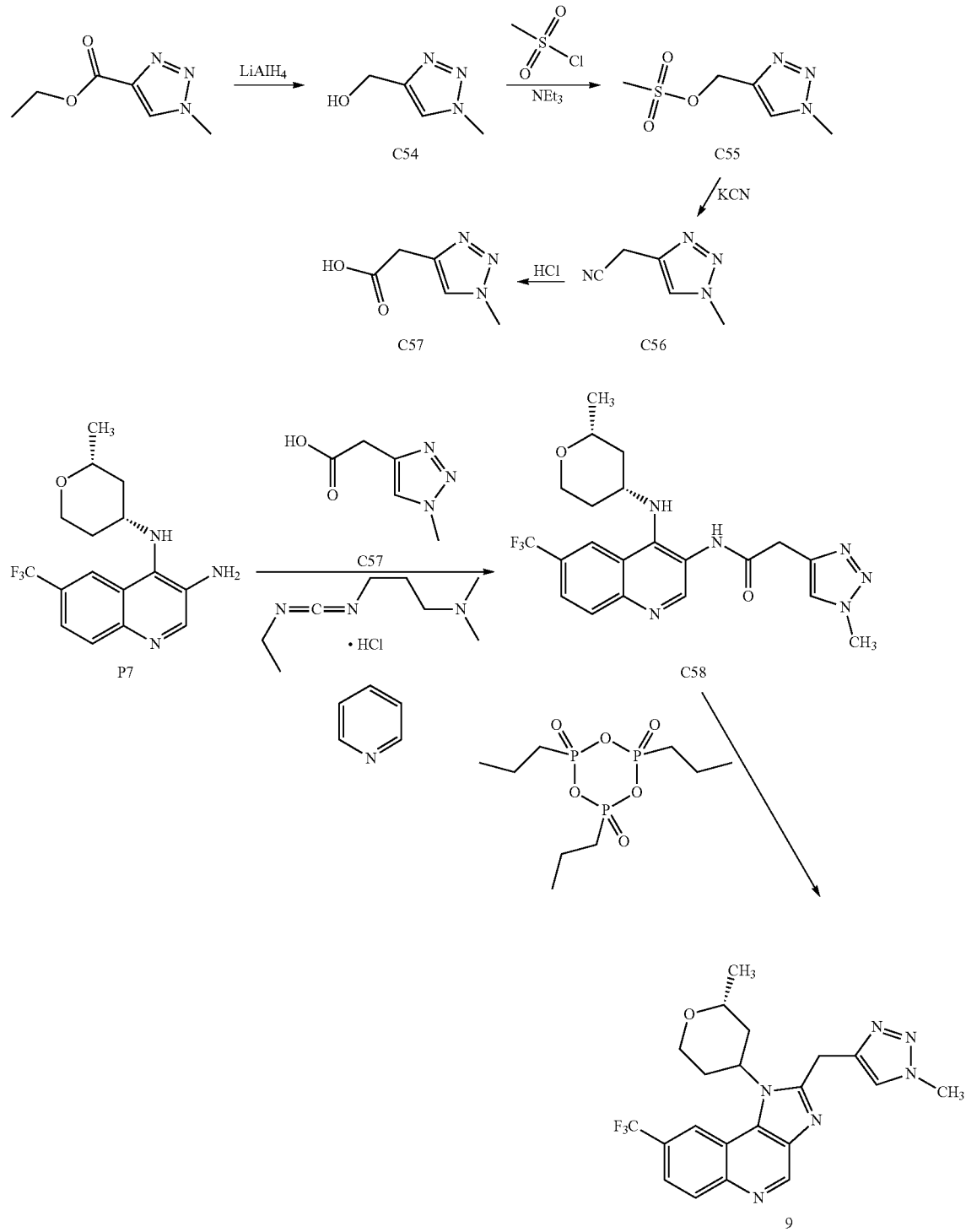

Step 1. Synthesis of (1-methyl-1H-1,2,3-triazol-4-yl)methanol (C54)

Lithium aluminum hydride (685 mg, 18.0 mmol) was added to a 0° C. suspension of ethyl 1-methyl-1H-1,2,3-triazole-4-carboxylate (1.40 g, 9.02 mmol) in tetrahydrofuran (20 mL) and the reaction mixture was stirred at 0° C. for 1 hour. Water was then added drop-wise at 0° C. until no further gas evolution was observed, whereupon sodium sulfate was added, and the mixture was stirred for 10 minutes. The mixture was then filtered, and the filtrate was concentrated in vacuo, affording the product as a yellow oil. Yield: 700 mg, 6.19 mmol, 69%. $^1$H NMR (400 MHz, DMSO-$d_6$) δ 7.90 (s, 1H), 5.15 (t, J=5.5 Hz, 1H), 4.49 (d, J=5.5 Hz, 2H), 4.01 (s, 3H).

Step 2. Synthesis of (1-methyl-1H-1,2,3-triazol-4-yl)methyl methanesulfonate (C55)

Methanesulfonyl chloride (851 mg, 7.43 mmol) was added to a 0° C. solution of C54 (700 mg, 6.19 mmol) and triethylamine (1.00 g, 9.88 mmol) in dichloromethane (20 mL). The reaction mixture was stirred at 0° C. for 2 hours, whereupon water (100 mL) was added, and the mixture was extracted with dichloromethane (2×100 mL). The combined organic layers were dried over sodium sulfate, filtered, and concentrated in vacuo to provide the product as a yellow oil, which was used directly in the next step. Yield: 800 mg, 4.18 mmol, 68%.

Step 3. Synthesis of (1-methyl-1H-1,2,3-triazol-4-yl)acetonitrile (C56)

To a solution of C55 (800 mg, 4.18 mmol) in acetonitrile (20 mL) was added potassium cyanide (1.50 g, 23.0 mmol). The reaction mixture was stirred at 60° C. overnight, whereupon it was treated with water (150 mL) and extracted with dichloromethane (3×100 mL). The combined organic layers were washed with saturated aqueous sodium chloride solution (80 mL), dried over sodium sulfate, filtered, and concentrated in vacuo to afford the product as a brown solid. Yield: 200 mg, 1.64 mmol, 39%. $^1$H NMR (400 MHz, CDCl$_3$) δ 7.61 (s, 1H), 4.13 (s, 3H), 3.89 (br s, 2H).

Step 4. Synthesis of (1-methyl-1H-1,2,3-triazol-4-yl)acetic acid (C57)

A solution of C56 (200 mg, 1.64 mmol) in concentrated hydrochloric acid (4 mL) was stirred at 60° C. for 2 hours. After the reaction mixture had cooled to room temperature, it was diluted with water (10 mL) and washed with tert-butyl methyl ether (2×20 mL). The aqueous layer was then concentrated to dryness, providing the product as a brown solid. Yield: 200 mg, 1.42 mmol, 87%. LCMS m/z 142.0 [M+H]$^+$. $^1$H NMR (400 MHz, DMSO-$d_6$) δ 7.94 (s, 1H), 4.01 (s, 3H), 3.66 (s, 2H).

Step 5. Synthesis of N-[4-{[(2R,4R)-2-methyltetrahydro-2H-pyran-4-yl]amino}-6-(trifluoromethyl)quinolin-3-yl]-2-(1-methyl-1H-1,2,3-triazol-4-yl)acetamide (C58)

1-[3-(Dimethylamino)propyl]-3-ethylcarbodiimide hydrochloride (118 mg, 0.615 mmol) was added in one portion to a solution of P7 (100 mg, 0.307 mmol) and C57 (52.1 mg, 0.369 mmol) in pyridine (0.8 mL), and the reaction mixture was stirred at 25° C. for 16 hours. It was then poured into water (50 mL) and extracted with ethyl acetate (3×30 mL); the combined organic layers were dried over sodium sulfate, filtered, and concentrated in vacuo to afford the product as a red oil (160 mg), which was used directly in the following step. LCMS m/z 449.2 [M+H]$^+$.

Step 6. Synthesis of 1-[(2R,4R)-2-methyltetrahydro-2H-pyran-4-yl]-2-[(1-methyl-1H-1,2,3-triazol-4-yl)methyl]-8-(trifluoromethyl)-1H-imidazo[4,5-c]quinoline (9)

2,4,6-Tripropyl-1,3,5,2,4,6-trioxatriphosphinane 2,4,6-trioxide (1.6 M solution in ethyl acetate; 0.669 mL, 1.07 mmol) was added to a solution of C58 (from the previous step; ≤0.307 mmol) in N,N-dimethylformamide (1 mL) and propyl acetate (4 mL). The reaction mixture was stirred at 110° C. for 16 hours, whereupon it was poured into water (40 mL) and extracted with ethyl acetate (2×30 mL). The combined organic layers were dried over sodium sulfate, filtered, and concentrated in vacuo. Silica gel chromatography (Gradient: 0% to 1.5% methanol in dichloromethane), followed by reversed-phase HPLC (Column: Agela Durashell C18, 5 μm; Mobile phase A: 0.05% ammonium hydroxide in water; Mobile phase B: acetonitrile; Gradient: 5% to 95% B) afforded the product as a solid. Yield: 29.5 mg, 68.5 μmol, 22% over two steps. LCMS m/z 431.1 [M+H]$^+$. $^1$H NMR (400 MHz, CDCl$_3$) δ 9.35 (s, 1H), 9.13-8.89 (br s, 1H), 8.38 (d, J=9.0 Hz, 1H), 7.86 (br d, J=8.5 Hz, 1H), 7.64-7.54 (br s, 1H), 5.53-5.38 (m, 1H), 4.62 (s, 2H), 4.29 (dd, J=12.0, 5.0 Hz, 1H), 4.07 (s, 3H), 3.83-3.68 (m, 2H), 2.77-2.57 (m, 1H), 2.50-2.31 (m, 1H), 2.0-1.59 (m, 2H, assumed; partially obscured by water peak), 1.32 (d, J=6.5 Hz, 3H).

Examples 10 and 11

[cis-4-(8-Chloro-2-cyclobutyl-1H-imidazo[4,5-c]quinolin-1-yl)tetrahydro-2H-pyran-2-yl]acetonitrile, ENT 1 (10) and [cis-4-(8-Chloro-2-cyclobutyl-1H-imidazo[4,5-c]quinolin-1-yl)tetrahydro-2H-pyran-2-yl]acetonitrile, ENT 2 (11)

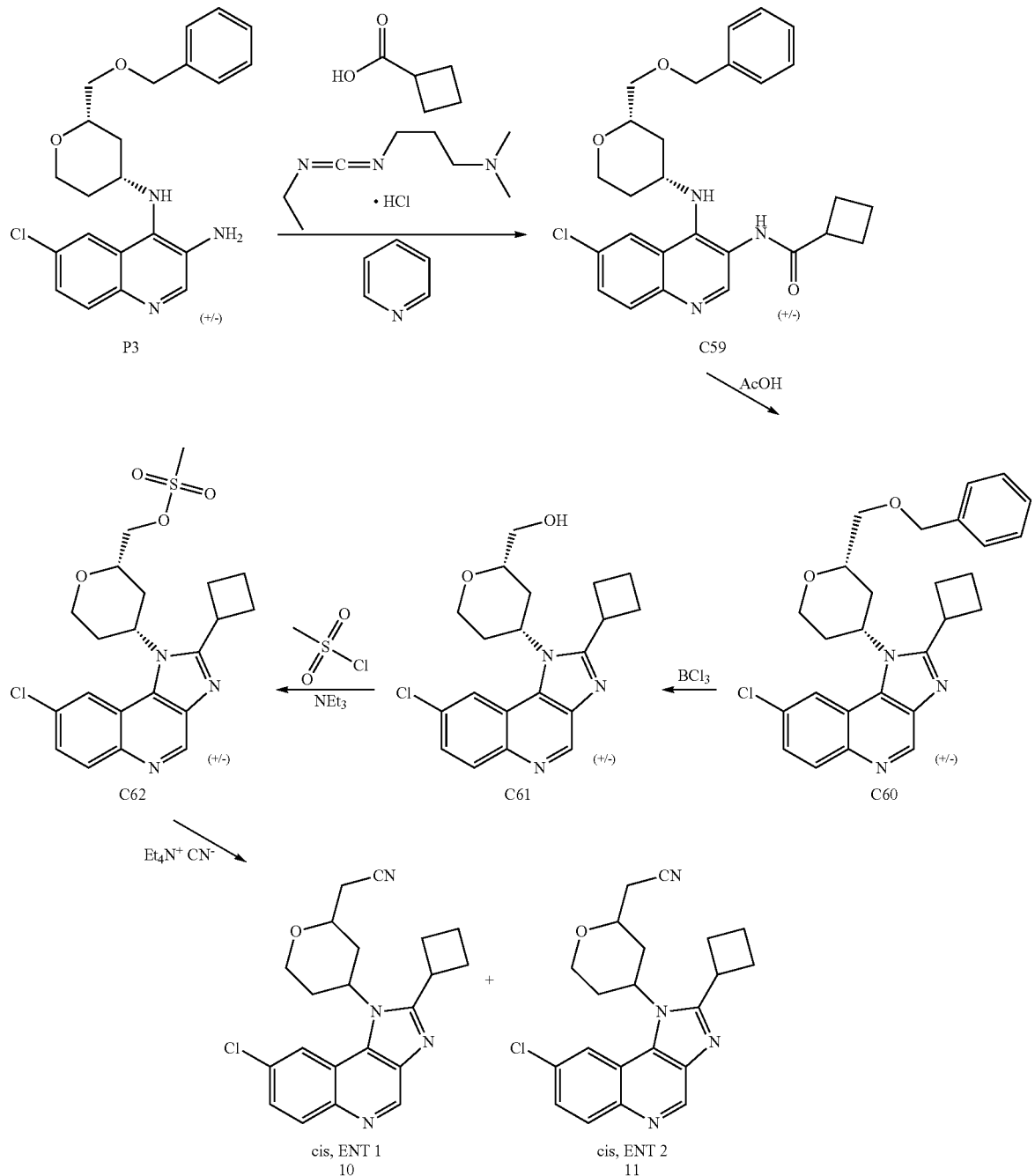

Step 1. Synthesis of N-[4-({cis-2-[(benzyloxy)methyl]tetrahydro-2H-pyran-4-yl}amino)-6-chloro-quinolin-3-yl]cyclobutanecarboxamide (C59)

1-[3-(Dimethylamino)propyl]-3-ethylcarbodiimide hydrochloride (771 mg, 4.02 mmol) was added to a solution of P3 (800 mg, 2.01 mmol) and cyclobutanecarboxylic acid (221 mg, 2.21 mmol) in pyridine (20 mL). The reaction mixture was stirred at 25° C. for 40 hours, whereupon it was concentrated in vacuo and partitioned between water (80 mL) and ethyl acetate (80 mL). The aqueous layer was extracted with ethyl acetate (80 mL), and the combined organic layers were dried over sodium sulfate, filtered, and concentrated under reduced pressure to provide the product as a foamy, orange solid (1.01 g), which was used directly in the following step. LCMS m/z 479.9 (chlorine isotope pattern observed) [M+H]$^+$.

Step 2. Synthesis of 1-{cis-2-[(benzyloxy)methyl]tetrahydro-2H-pyran-4-yl}-8-chloro-2-cyclobutyl-1H-imidazo[4,5-c]quinoline (C60)

A solution of C59 (from the previous step; 2.01 mmol) in acetic acid (20 mL) was stirred at 110° C. for 16 hours. This was combined with a similar reaction carried out using C59 (154 mg, 0.321 mmol) and concentrated in vacuo. The residue was mixed with half-saturated aqueous sodium bicarbonate solution (100 mL) and extracted with ethyl acetate (100 mL); the organic layer was dried over sodium sulfate, filtered, and concentrated under reduced pressure to afford the product as a yellow solid. Combined yield: 1.07 g, 2.32 mmol, quantitative over two steps. LCMS m/z 462.0 (chlorine isotope pattern observed) [M+H]$^+$.

Step 3. Synthesis of [cis-4-(8-chloro-2-cyclobutyl-1H-imidazo[4,5-c]quinolin-1-yl)tetrahydro-2H-pyran-2-yl]methanol (C61)

Boron trichloride (1 M solution; 6.95 mL, 6.95 mmol) was added in portions to a 10° C. solution of C60 (1.07 g, 2.32 mmol) in dichloromethane (30 mL). The reaction mixture was stirred at 25° C. for 1 hour, whereupon it was poured into saturated aqueous sodium bicarbonate solution (80 mL) and extracted with dichloromethane (2×50 mL). The combined organic layers were dried over sodium sulfate, filtered, concentrated in vacuo, and purified using silica gel chromatography (Gradient: 0% to 2% methanol in dichloromethane) to provide the product as an off-white solid. Yield: 643 mg, 1.73 mmol, 75%. LCMS m/z 371.9 (chlorine isotope pattern observed) [M+H]$^+$.

Step 4. Synthesis of [cis-4-(8-chloro-2-cyclobutyl-1H-imidazo[4,5-c]quinolin-1-yl)tetrahydro-2H-pyran-2-yl]methyl methanesulfonate (C62)

Triethylamine (525 mg, 5.19 mmol) and methanesulfonyl chloride (0.160 mL, 2.07 mmol) were added to a solution of C61 (643 mg, 1.73 mmol) in dichloromethane (20 mL). The reaction mixture was stirred at 25° C. for 1 hour, whereupon it was poured into water (50 mL) and extracted with ethyl acetate (2×50 mL). The combined organic layers were dried over sodium sulfate, filtered, and concentrated in vacuo to provide the product as a foamy, light yellow solid. Yield: 750 mg, 1.67 mmol, 96%. LCMS m/z 449.8 (chlorine isotope pattern observed) [M+H]$^+$.

Step 5. Synthesis of [cis-4-(8-chloro-2-cyclobutyl-1H-imidazo[4,5-c]quinolin-1-yl)tetrahydro-2H-pyran-2-yl]acetonitrile, ENT 1 (10) and [cis-4-(8-chloro-2-cyclobutyl-1H-imidazo[4,5-c]quinolin-1-yl)tetrahydro-2H-pyran-2-yl]acetonitrile, ENT 2 (11)

Tetraethylammonium cyanide (781 mg, 5.00 mmol) was added to a solution of C62 (750 mg, 1.67 mmol) in dimethyl sulfoxide (15 mL), and the reaction mixture was heated at 80° C. for 16 hours. It was then diluted with tert-butyl methyl ether (100 mL), and washed sequentially with water (2×50 mL) and saturated aqueous sodium chloride solution (50 mL). The combined aqueous layers were extracted with tert-butyl methyl ether (50 mL), whereupon the combined organic layers were dried over sodium sulfate, filtered, and concentrated in vacuo. Chromatography on silica gel (Gradient: 0% to 2% methanol in dichloromethane) afforded a racemic mixture of 10 and 11 as a light yellow, foamy solid. Yield of racemic product: 613 mg, 1.61 mmol, 96%.

A portion of this material (300 mg, 0.788 mmol) was separated into its component enantiomers via supercritical fluid chromatography [Column: Chiral Technologies Chiralpak AS, 5 μm; Mobile phase: 3:2 carbon dioxide/(ethanol containing 0.1% ammonium hydroxide)]. The first-eluting enantiomer was designated as 10, and was obtained as a solid. Yield: 91.1 mg, 0.239 mmol, 30% for the separation. LCMS m/z 381.0 (chlorine isotope pattern observed) [M+H]$^+$. $^1$H NMR (400 MHz, CD$_3$OD) δ 9.14 (s, 1H), 8.72-8.55 (br s, 1H), 8.17 (d, J=8.5 Hz, 1H), 7.71 (dd, J=9.0, 2.0 Hz, 1H), 5.23-4.97 (v br m, 1H), 4.36 (dd, J=11.8, 5.3 Hz, 1H), 4.18-4.08 (m, 1H), 4.03-3.95 (m, 1H), 3.86 (ddd, J=12.0, 12.0, 2.5 Hz, 1H), 2.88 (dd, half of ABX pattern, J=17.1, 4.0 Hz, 1H), 2.77 (dd, half of ABX pattern, J=17.1, 6.5 Hz, 1H), 2.73-2.42 (m, 6H), 2.33-1.93 (m, 4H).

The second-eluting enantiomer, also isolated as a solid, was designated as 11. Yield: 93.9 mg, 0.247 mmol, 31% for the separation. LCMS m/z 381.0 (chlorine isotope pattern observed) [M+H]$^+$. $^1$H NMR (400 MHz, CD$_3$OD) δ 9.14 (s, 1H), 8.72-8.54 (br s, 1H), 8.17 (d, J=9 Hz, 1H), 7.71 (d, J=9 Hz, 1H), 5.25-4.96 (v br m, 1H), 4.36 (dd, J=12, 5 Hz, 1H), 4.19-4.07 (m, 1H), 4.03-3.95 (m, 1H), 3.86 (br dd, J=12, 12 Hz, 1H), 2.88 (dd, half of ABX pattern, J=17.1, 4.0 Hz, 1H), 2.77 (dd, half of ABX pattern, J=17.1, 6.0 Hz, 1H), 2.73-2.42 (m, 6H), 2.33-1.92 (m, 4H).

Example 12

8-(Difluoromethyl)-2-[(4-methoxy-1H-pyrazol-1-yl)methyl]-1-[(2R,4R)-2-methyltetrahydro-2H-pyran-4-yl]-1H-imidazo[4,5-c]quinoline (12)

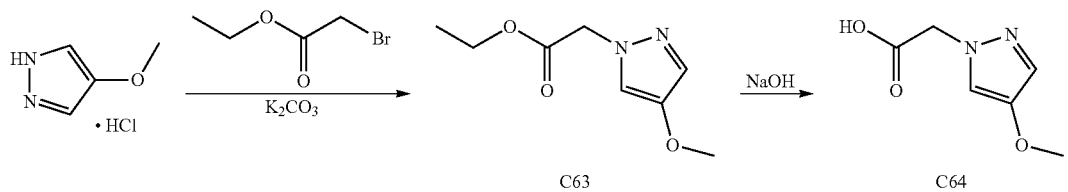

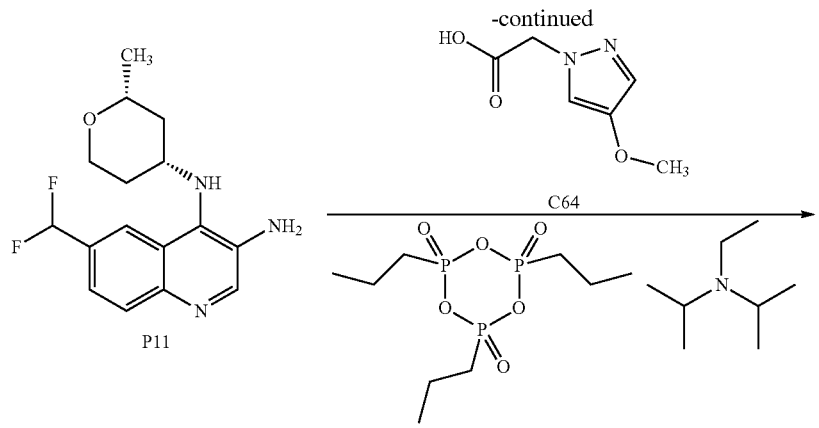

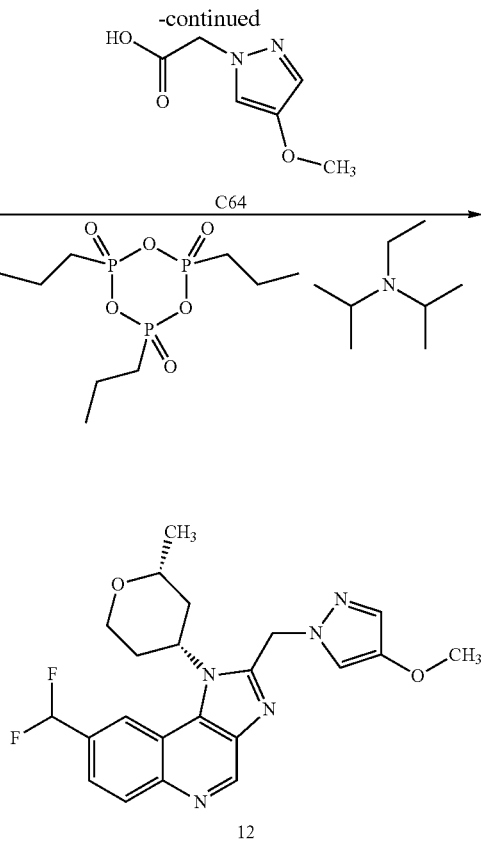

12

Step 1. Synthesis of ethyl (4-methoxy-1H-pyrazol-1-yl)acetate (C63)

Ethyl bromoacetate (5.46 g, 32.7 mmol) was added in one portion to a mixture of 4-methoxy-1H-pyrazole, hydrochloride salt (4.00 g, 29.7 mmol) and potassium carbonate (8.62 g, 62.4 mmol) in N,N-dimethylformamide (40 mL) at room temperature (30° C.). The reaction mixture was stirred at room temperature (30° C.) for 16 hours, whereupon it was diluted with water (200 mL) and extracted with ethyl acetate (3×100 mL). The combined organic layers were washed with saturated aqueous sodium chloride solution (2×150 mL), dried over sodium sulfate, filtered and concentrated in vacuo. Silica gel chromatography (Gradient: 0% to 30% ethyl acetate in petroleum ether) afforded the product as a colorless oil. Yield: 4.45 g, 24.2 mmol, 81%. $^1$H NMR (400 MHz, CDCl$_3$) δ 7.30 (d, J=0.8 Hz, 1H), 7.15 (d, J=0.8 Hz, 1H), 4.80 (s, 2H), 4.24 (q, J=7.2 Hz, 2H), 3.76 (s, 3H), 1.29 (t, J=7.2 Hz, 3H).

Step 2. Synthesis of (4-methoxy-1H-pyrazol-1-yl)acetic acid (C64)

Aqueous sodium hydroxide solution (2 M; 24.2 mL, 48.4 mmol) was added in one portion to a solution of C63 (4.45 g, 24.2 mmol) in tetrahydrofuran (30 mL) at room temperature (29° C.), and the reaction mixture was stirred at room temperature (29° C.) for 3 hours. It was then concentrated under reduced pressure, diluted with water (50 mL), and extracted with dichloromethane (2×30 mL). The organic layers were discarded, and the aqueous layer was acidified to pH 1 with 1 M hydrochloric acid, and extracted with ethyl acetate (4×50 mL). After the combined ethyl acetate layers had been dried over sodium sulfate, they were filtered and concentrated in vacuo, providing the product as a white solid. Yield: 2.80 g, 17.9 mmol, 74%. $^1$H NMR (400 MHz, DMSO-d$_6$) δ 7.44 (s, 1H), 7.21 (s, 1H), 4.80 (s, 2H), 3.65 (s, 3H).

Step 3. Synthesis of 8-(difluoromethyl)-2-[(4-methoxy-1H-pyrazol-1-yl)methyl]-1-[(2R,4R)-2-methyltetrahydro-2H-pyran-4-yl]-1H-imidazo[4,5-c]quinoline (12)

To a solution of P11 (50 mg, 0.16 mmol) in toluene (1.5 mL) were added C64 (26.7 mg, 0.171 mmol) and N,N-diisopropylethylamine (31.2 μL, 0.179 mmol), followed by 2,4,6-tripropyl-1,3,5,2,4,6-trioxatriphosphinane 2,4,6-trioxide (50% solution in ethyl acetate; 0.107 mL, 0.180 mmol). The reaction mixture was heated at 60° C. for 90 minutes, and then at 100° C. for 4 hours, whereupon it was partitioned between ethyl acetate (10 mL) and saturated aqueous sodium bicarbonate solution (10 mL). The organic layer was dried over sodium sulfate, filtered, concentrated in vacuo, and purified via silica gel chromatography (Gradient: 0% to 15% methanol in dichloromethane), providing the product as an off-white solid. Yield: 51 mg, 0.12 mmol, 75%. LCMS m/z 428.5 [M+H]$^+$. $^1$H NMR (400 MHz, CD$_3$OD) δ 9.28 (s, 1H), 8.98-8.81 (br s, 1H), 8.34 (d, J=8.6 Hz, 1H), 7.92 (d, J=9.0 Hz, 1H), 7.48 (s, 1H), 7.30 (s, 1H), 7.08 (t, J$_{HF}$=56.0 Hz, 1H), 5.82 (s, 2H), 5.44-5.29 (br m, 1H), 4.23 (dd, J=11.7, 5.1 Hz, 1H), 3.81-3.66 (m, 2H), 3.71 (s, 3H), 2.76-2.55 (br m, 1H), 2.47-2.24 (br m, 1H), 1.90-1.56 (br m, 2H), 1.28 (d, J=6.3 Hz, 3H).

Example 13

8-(Difluoromethyl)-2-[(5-methylpyrazin-2-yl)methyl]-1-[(2R,4R)-2-methyl tetrahydro-2H-pyran-4-yl]-1H-imidazo[4,5-c]quinoline (13)

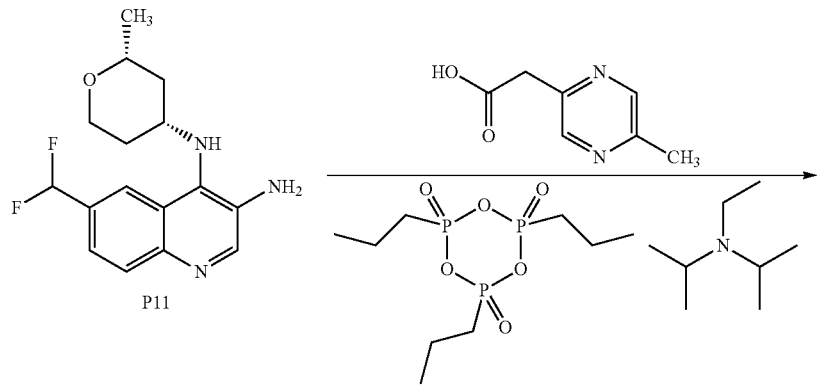

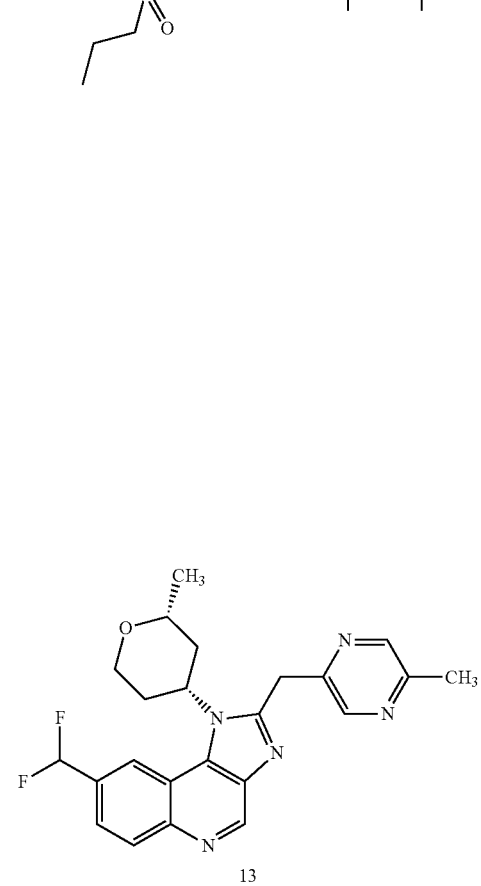

Reaction of P11 (50 mg, 0.16 mmol) with (5-methylpyrazin-2-yl)acetic acid was carried out using the method described for synthesis of 12 from P11 in Example 12. In this case, silica gel chromatography was carried out twice (Gradient: 0% to 15% methanol in dichloromethane), affording the product as a light orange solid. Yield: 39 mg, 92 μmol, 58%. LCMS m/z 424.5 [M+H]$^+$. $^1$H NMR (400 MHz, CD$_3$OD) δ 9.19 (s, 1H), 9.03-8.87 (br s, 1H), 8.64 (s, 1H), 8.48 (s, 1H), 8.33 (d, J=8.6 Hz, 1H), 7.90 (d, J=8.6 Hz, 1H), 7.08 (t, J$_{HF}$=56.0 Hz, 1H), 5.51-5.31 (br m, 1H), 4.80 (s, 2H), 4.26 (dd, J=12.1, 5.1 Hz, 1H), 3.84-3.66 (m, 2H), 2.84-2.65 (br m, 1H), 2.55 (s, 3H), 2.52-2.35 (br m, 1H), 2.13-1.84 (br m, 2H), 1.31 (d, J=5.9 Hz, 3H).

Examples 14 and 15

{8-Chloro-1-[(2R,4R)-2-methyltetrahydro-2H-pyran-4-yl]-1H-imidazo[4,5-c]quinolin-2-yl}(5-methylpyrazin-2-yl)methanol, DIAST 1 (14) and {8-Chloro-1-[(2R,4R)-2-methyl tetrahydro-2H-pyran-4-yl]-1H-imidazo[4,5-c]quinolin-2-yl}(5-methylpyrazin-2-yl) methanol, DIAST 2 (15)

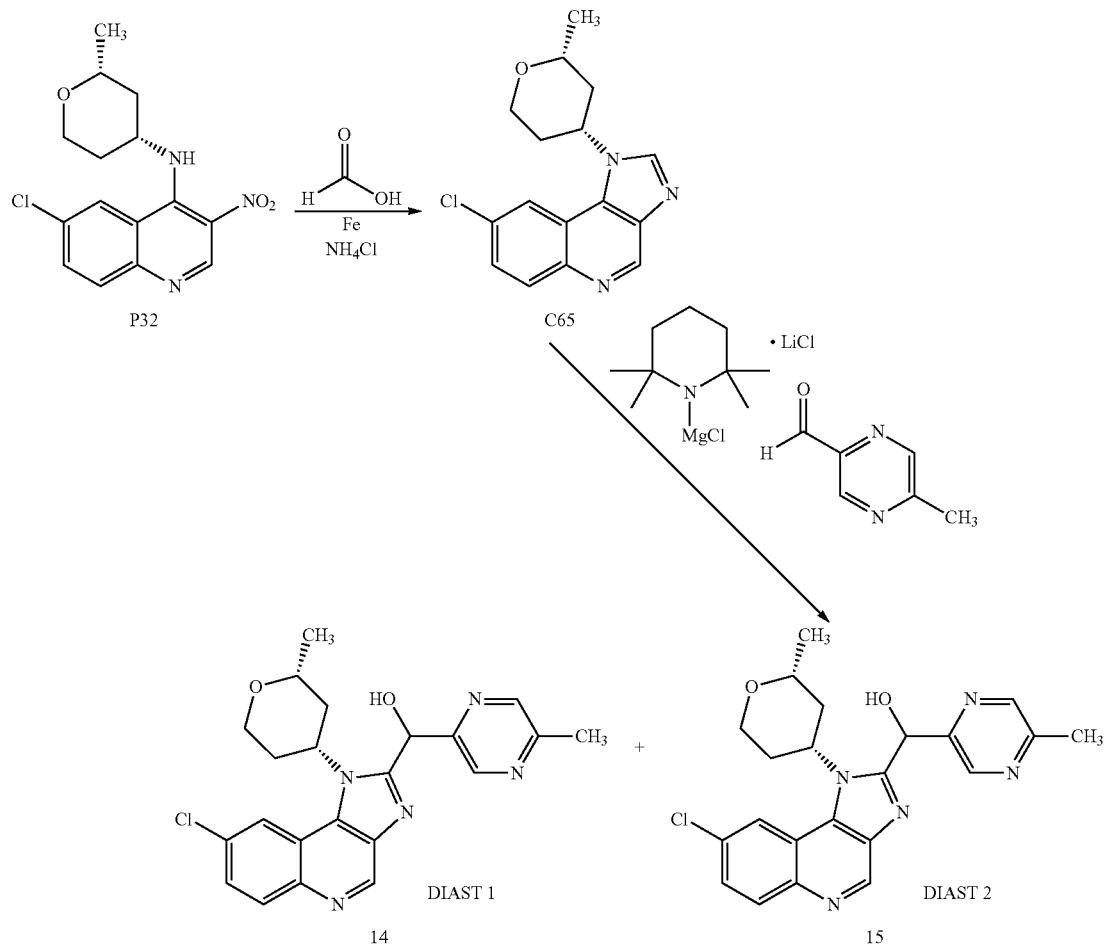

Step 1. Synthesis of 8-chloro-1-[(2R,4R)-2-methyltetrahydro-2H-pyran-4-yl]-1H-imidazo[4,5-c]quinoline (C65)

Formic acid (310 mL) was added to a mixture of iron powder (34.7 g, 621 mmol), ammonium chloride (33.2 g, 621 mmol), and C32 (20 g, 62.2 mmol) in 2-propanol (310 mL) at room temperature (14° C.). The reaction mixture was heated at 80° C. for 16 hours, whereupon it was diluted with ethanol (300 mL), and filtered. The collected solids were washed with 2-propanol (200 mL) and dichloromethane (100 mL), and the combined filtrates were concentrated in vacuo, then co-evaporated with ethanol (200 mL). The residue was diluted with dichloromethane (300 mL), basified via addition of saturated aqueous sodium bicarbonate solution (500 mL), and then filtered through diatomaceous earth; the filter pad was washed with dichloromethane (300 mL). The aqueous layer of the combined filtrates was extracted with dichloromethane (4×100 mL), and the combined organic layers were washed with saturated aqueous sodium chloride solution (100 mL), dried over sodium sulfate, filtered, and concentrated under reduced pressure. Silica gel chromatography (Gradient: 0% to 5% methanol in dichloromethane) afforded a solid, which was washed with a mixture of petroleum ether and ethyl acetate (3:1, 100 mL) and with petroleum ether (50 mL) to provide the product as a beige solid. Yield: 10.05 g, 33.3 mmol, 54%. LCMS m/z 301.8 (chlorine isotope pattern observed) [M+H]$^+$. $^1$H NMR (400 MHz, CDCl$_3$) δ 9.35 (s, 1H), 8.25 (d, J=9.0 Hz, 1H), 8.19 (s, 1H), 8.09 (d, J=2.3 Hz, 1H), 7.66 (dd, J=8.8, 2.3 Hz, 1H), 5.02 (tt, J=12.0, 3.8 Hz, 1H), 4.30 (ddd, J=11.9, 4.6, 1.6 Hz, 1H), 3.77-3.89 (m, 2H), 2.33-2.46 (m, 2H), 2.09-2.22 (m, 1H), 1.83-1.95 (m, 1H), 1.38 (d, J=6.3 Hz, 3H).

Step 2. Synthesis of {8-chloro-1-[(2R,4R)-2-methyltetrahydro-2H-pyran-4-yl]-1H-imidazo[4,5-c]quinolin-2-yl}(5-methylpyrazin-2-yl)methanol, DIAST 1 (14) and {8-chloro-1-[(2R,4R)-2-methyltetrahydro-2H-pyran-4-yl]-1H-imidazo[4,5-c]quinolin-2-yl}(5-methylpyrazin-2-yl)methanol, DIAST 2 (15)

A vial was charged with C65 (100 mg, 0.33 mmol), and the vial was evacuated and flushed with nitrogen; this procedure was repeated twice, tetrahydrofuran (1.6 mL) was added, and the solution was cooled to −78° C. 2,2,6,6-Tetramethylpiperidinylmagnesium chloride, lithium chloride complex (1 M solution in tetrahydrofuran and toluene; 0.497 mL, 0.497 mmol) was added, and the reaction mixture was allowed to stir for 1 hour at −78° C. In a separate vial, 5-methylpyrazine-2-carbaldehyde (80.9 mg, 0.662 mmol) was dissolved in tetrahydrofuran (1.6 mL), and the resulting solution was cooled in a dry ice/acetone bath for 10 minutes. This solution was then added to the reaction mixture, which was subsequently allowed to stir while slowly warming to 15° C. After 1 hour, it was combined with two similar reaction mixtures derived from C65 (50 mg, 0.17 mmol; 100 mg, 0.33 mmol), and the resulting mixture was diluted with water (20 mL) and extracted with ethyl acetate (3×15 mL). The combined organic layers were concentrated in vacuo and subjected to reversed-phase HPLC (Column: Phenomenex Synergi Max-RP, 10 μm; Mobile phase A: 0.1% trifluoroacetic acid in water; Mobile phase B: acetonitrile; Gradient: 15% to 45% B), affording a diastereomeric mixture of 14 and 15 as a viscous, brick-red oil. Combined yield of diastereomeric mixture: 180 mg, 0.425 mmol, 51%.

This material was separated into its component diastereomers via supercritical fluid chromatography [Column: Regis Technologies, (S,S)-Whelk-0® 1, 10 μm; Mobile phase: 3:2 carbon dioxide/(ethanol containing 0.1% ammonium hydroxide)]. The first-eluting diastereomer, obtained as a light yellow solid, was designated as 14. Yield: 58.6 mg, 0.138 mmol, 32% for the separation. LCMS m/z 423.9 (chlorine isotope pattern observed) [M+H]+. 1H NMR (400 MHz, CD3OD) δ 9.12 (br s, 1H), 8.92 (s, 1H), 8.83-8.74 (br s, 1H), 8.48 (s, 1H), 8.18 (d, J=9.0 Hz, 1H), 7.74 (dd, J=9.0, 2.0 Hz, 1H), 6.51 (s, 1H), 5.58-5.46 (m, 1H), 4.29 (dd, J=11.8, 5.3 Hz, 1H), 3.80-3.66 (br m, 1H), 3.66-3.52 (br m, 1H), 2.79-2.66 (m, 1H), 2.60 (s, 3H), 2.42-2.27 (br m, 1H), 2.13-2.00 (br m, 1H), 1.77-1.63 (br m, 1H), 1.28 (br d, J=5.5 Hz, 3H).

The second-eluting diastereomer, also isolated as a light yellow solid, was designated as 15. Yield: 56.8 mg, 0.134 mmol, 32% for the separation. LCMS m/z 423.9 (chlorine isotope pattern observed) [M+H]+. 1H NMR (400 MHz, CD3OD) δ 9.12 (br s, 1H), 8.92 (s, 1H), 8.82-8.74 (br s, 1H), 8.47 (br s, 1H), 8.18 (d, J=8.5 Hz, 1H), 7.74 (dd, J=9.0, 2.0 Hz, 1H), 6.50 (s, 1H), 5.57-5.46 (m, 1H), 4.21 (dd, J=11.8, 4.8 Hz, 1H), 3.82-3.70 (br m, 1H), 3.62-3.47 (br m, 1H), 2.71-2.57 (br m, 1H), 2.59 (s, 3H), 2.48-2.35 (m, 1H), 2.24-2.13 (br m, 1H), 1.63-1.50 (br m, 1H), 1.34 (d, J=6.0 Hz, 3H).

Examples 16 and 17

1-(4,4-Difluoro-1-methylpyrrolidin-3-yl)-8-fluoro-2-(1H-1,2,4-triazol-1-ylmethyl)-1H-imidazo[4,5-c]quinoline, ENT 1 (16) and 1-(4,4-Difluoro-1-methylpyrrolidin-3-yl)-8-fluoro-2-(1H-1,2,4-triazol-1-ylmethyl)-1H-imidazo[4,5-c]quinoline, ENT 2 (17)

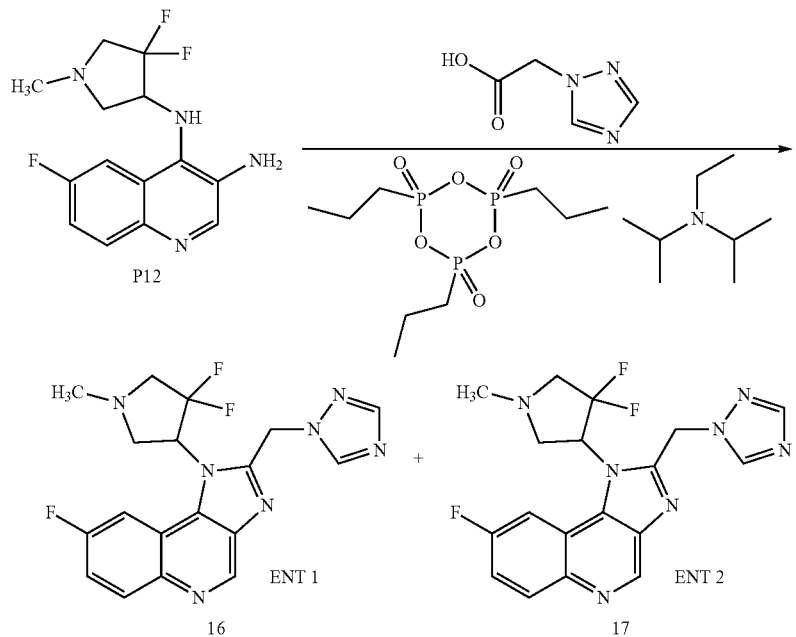

This reaction was carried out in library format. N,N-Diisopropylethylamine (52 μL, 30 μmol) was added to a mixture of 1H-1,2,4-triazol-1-ylacetic acid (100 μmol) and P12 (29.6 mg, 100 μmol) in a 3:2 mixture of ethyl acetate and toluene (0.5 mL). 2,4,6-Tripropyl-1,3,5,2,4,6-trioxatriphosphinane 2,4,6-trioxide (50% solution in ethyl acetate; 0.19 mL, 0.32 mmol) was added, and the reaction vial was shaken and heated at 70° C. for 10 hours, then at 110° C. for 3 hours. It was then partitioned between half-saturated aqueous sodium bicarbonate solution (1.5 mL) and ethyl acetate (2.4 mL) and subjected to vortexing. The organic layer was eluted through a solid phase extraction cartridge (6 mL) charged with sodium sulfate (~1 g); this extraction procedure was repeated twice, and the combined eluents were concentrated in vacuo. Purification via reversed-phase HPLC (Column: Waters Sunfire C18, 5 μm; Mobile phase A: 0.05% trifluoroacetic acid in water; Mobile phase B: 0.05% trifluoroacetic acid in acetonitrile; Gradient: 5% B for 1.0 minute, followed by 5.0% to 75% B over 7.5 minutes, followed by 75% to 100% B) provided a racemic mixture of the two products. Separation into the component enantiomers was carried out using supercritical fluid chromatography [Column: Chiral Technologies Chiralpak AD-H, 5 μm;

Mobile phase: 85:15 carbon dioxide/(methanol containing 0.2% ammonium hydroxide)]. The first-eluting enantiomer was designated as 16. Yield: 4.9 mg, 13 μmol, 13%. LCMS m/z 388.5 [M+H]$^+$. Retention time: 2.91 minutes [Analytical conditions, Column: Chiral Technologies Chiralpak AD-H, 4.6×100 mm, 5 μm; Mobile phase: 80:20 carbon dioxide/(methanol containing 0.2% ammonium hydroxide); Back pressure: 150 bar; Flow rate: 1.5 mL/minute].

The second-eluting enantiomer was designated as 17. Yield: 2.0 mg, 5.2 μmol, 5%. LCMS m/z 388.3 [M+H]$^+$. Retention time: 3.31 minutes, using the same analytical conditions.

Examples 18 and 19

1-(4,4-Difluoro-1-methylpyrrolidin-3-yl)-8-fluoro-2-[(4-methyl-1H-1,2,3-triazol-1-yl) methyl]-1H-imidazo[4,5-c]quinoline, ENT 1 (18) and 1-(4,4-Difluoro-1-methylpyrrolidin-3-yl)-8-fluoro-2-[(4-methyl-1H-1,2,3-triazol-1-yl)methyl]-1H-imidazo[4, 5-c]quinoline, ENT 2 (19)

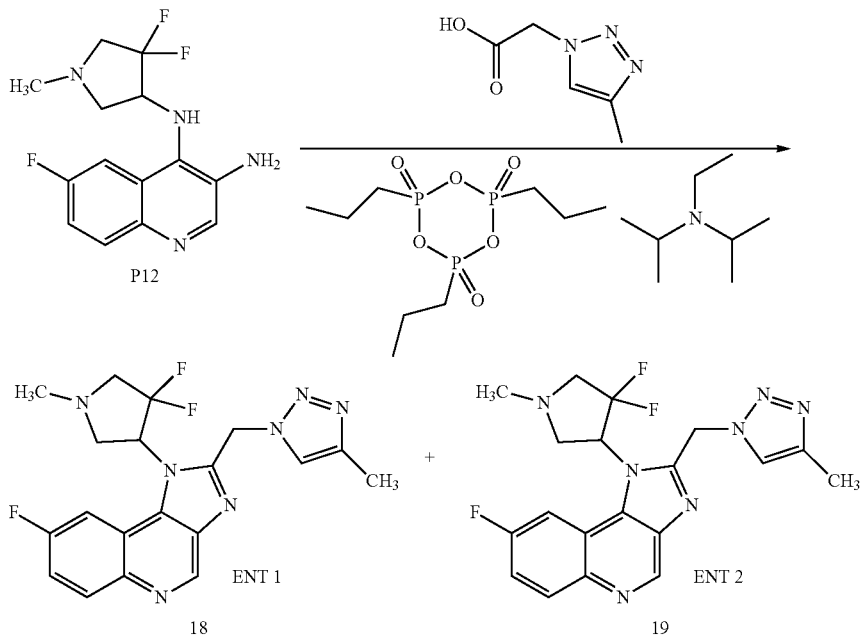

(4-Methyl-1H-1,2,3-triazol-1-yl)acetic acid and P12 were used to generate a racemic mixture of 18 and 19, using the method described in Examples 16 and 17. Separation into the component enantiomers was carried out using supercritical fluid chromatography [Column: Chiral Technologies Chiralpak AD-H, 5 μm; Mobile phase: 3:2 carbon dioxide/(methanol containing 0.2% ammonium hydroxide)]. The first-eluting enantiomer was designated as 18. Yield: 4.0 mg, 10 μmol, 10%. LCMS m/z 402.8 [M+H]$^+$. Retention time: 1.68 minutes [Analytical conditions, Column: Chiral Technologies Chiralpak AD-H, 4.6×100 mm, 5 μm; Mobile phase: 3:2 carbon dioxide/(methanol containing 0.2% ammonium hydroxide); Back pressure: 150 bar; Flow rate: 1.5 mL/minute].

The second-eluting enantiomer was designated as 19. Yield: 3.7 mg, 9.2 μmol, 9%. LCMS m/z 402.6 [M+H]$^+$. Retention time: 4.1 minutes, using the same analytical conditions.

Examples 20 and 21

1-(4,4-Difluoro-1-methylpyrrolidin-3-yl)-8-fluoro-2-[(5-methylpyrazin-2-yl)methyl]-1H-imidazo[4,5-c]quinoline, ENT 1 (20) and 1-(4,4-Difluoro-1-methylpyrrolidin-3-yl)-8-fluoro-2-[(5-methylpyrazin-2-yl)methyl]-1H-imidazo[4,5-c]quinoline, ENT 2 (21)

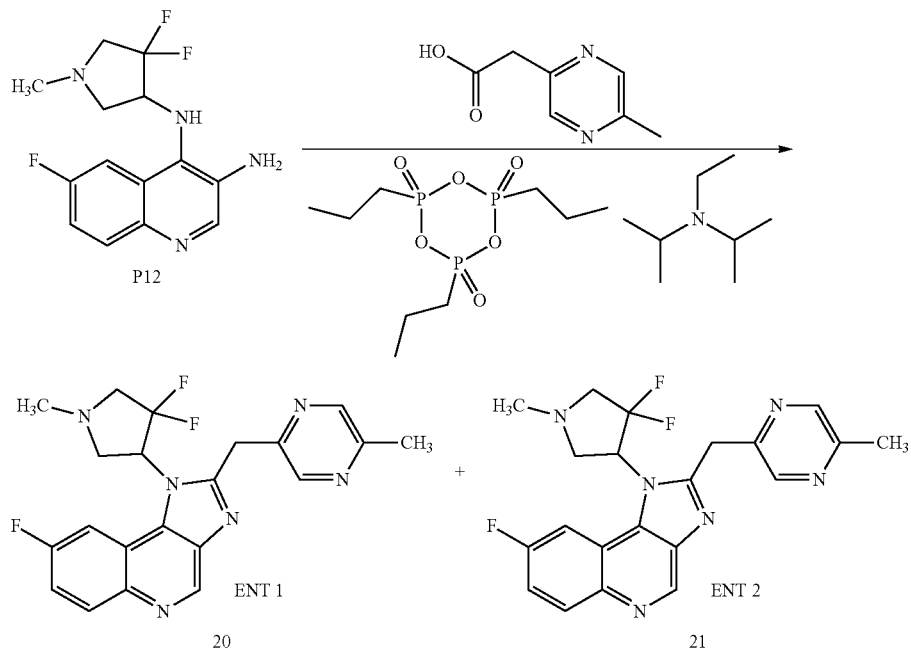

(5-Methylpyrazin-2-yl)acetic acid and P12 were used to generate a racemic mixture of 20 and 21, using the method described in Examples 16 and 17. Separation into the component enantiomers was carried out using supercritical fluid chromatography [Column: Chiral Technologies Chiralpak AD-H, 5 μm; Mobile phase: 85:15 carbon dioxide/(methanol containing 0.2% ammonium hydroxide)]. The first-eluting enantiomer was designated as 20. Yield: 2.0 mg, 4.8 μmol, 5%. LCMS m/z 413.9 [M+H]+. Retention time: 2.66 minutes [Analytical conditions, Column: Chiral Technologies Chiralpak AD-H, 4.6×100 mm, 5 μm; Mobile phase: 80:20 carbon dioxide/(methanol containing 0.2% ammonium hydroxide); Back pressure: 200 bar; Flow rate: 1.5 mL/minute].

The second-eluting enantiomer was designated as 21. Yield: 1.8 mg, 4.4 μmol, 4%. LCMS m/z 413.9 [M+H]+. Retention time: 3.3 minutes, using the same analytical conditions.

Examples 22 and 23

8-Chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 1 (22) and 8-Chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 2 (23)

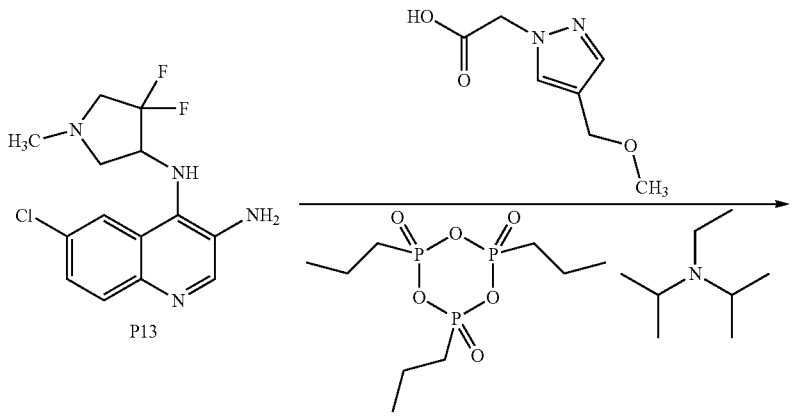

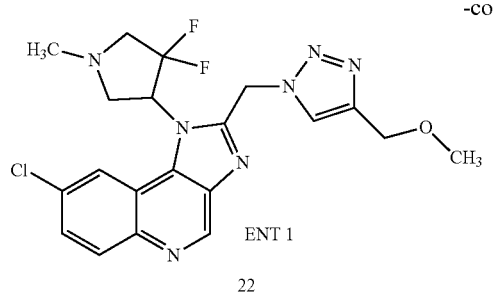
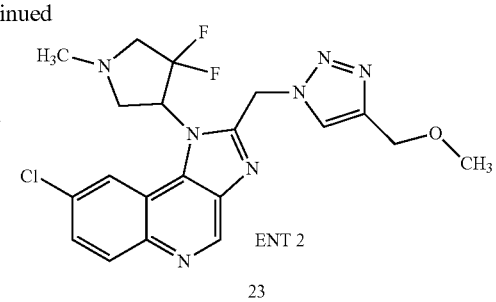

This reaction was carried out in library format. N,N-Diisopropylethylamine (52 μL, 300 μmol) was added to a mixture of [4-(methoxymethyl)-1H-1,2,3-triazol-1-yl]acetic acid (this may be synthesized according to the method described by M. D. Andrews et al., PCT International Application WO 2014053967 A1, Apr. 10, 2014; 100 μmol) and P13 (31.2 mg, 100 μmol) in a 3:2 mixture of ethyl acetate and toluene (0.5 mL). 2,4,6-Tripropyl-1,3,5,2,4,6-trioxatriphosphinane 2,4,6-trioxide (50% solution in ethyl acetate; 0.19 mL, 0.32 mmol) was then added, and the reaction vial was shaken and heated at 70° C. for 10 hours, then at 110° C. for 3 hours. The reaction mixture was then partitioned between half-saturated aqueous sodium bicarbonate solution (1.5 mL) and ethyl acetate (2.4 mL) and subjected to vortexing. The organic layer was eluted through a solid phase extraction cartridge (6 mL) charged with sodium sulfate (~1 g); this extraction procedure was repeated twice, and the combined eluents were concentrated in vacuo. Purification via reversed-phase HPLC (Column: Waters Sunfire C18, 5 μm; Mobile phase A: 0.05% trifluoroacetic acid in water; Mobile phase B: 0.05% trifluoroacetic acid in acetonitrile; Gradient: 5% B for 1.0 minute, followed by 5.0% to 75% B over 7.5 minutes, followed by 75% to 100% B) provided a racemic mixture of the two products. Separation into the component enantiomers was carried out using supercritical fluid chromatography [Column: Chiral Technologies Chiralpak AD-H, 5 μm; Mobile phase: 3:1 carbon dioxide/(methanol containing 0.2% ammonium hydroxide)]. The first-eluting enantiomer was designated as 22. Yield: 4.9 mg, 11 μmol, 11%. LCMS m/z 447.9 [M+H]$^+$. Retention time: 2.4 minutes [Analytical conditions, Column: Chiral Technologies Chiralpak AD-H, 4.6×100 mm, 5 μm; Mobile phase: 3:2 carbon dioxide/(methanol containing 0.2% ammonium hydroxide); Back pressure: 150 bar; Flow rate: 1.5 m L/minute].

The second-eluting enantiomer was designated as 23. Yield: 4.8 mg, 11 μmol, 11%. LCMS m/z 448.2 (chlorine isotope pattern observed) [M+H]$^+$. Retention time: 2.95 minutes, using the same analytical conditions.

Examples 24 and 25

8-Chloro-1-(4,4-difluoro-1-methylpyrrolidin-3-yl)-2-(1H-1,2,4-triazol-1-ylmethyl)-1H-imidazo[4,5-c]quinoline, ENT 1 (24) and 8-Chloro-1-(4,4-difluoro-1-methylpyrrolidin-3-yl)-2-(1H-1,2,4-triazol-1-ylmethyl)-1H-imidazo[4,5-c]quinoline, ENT 2 (25)

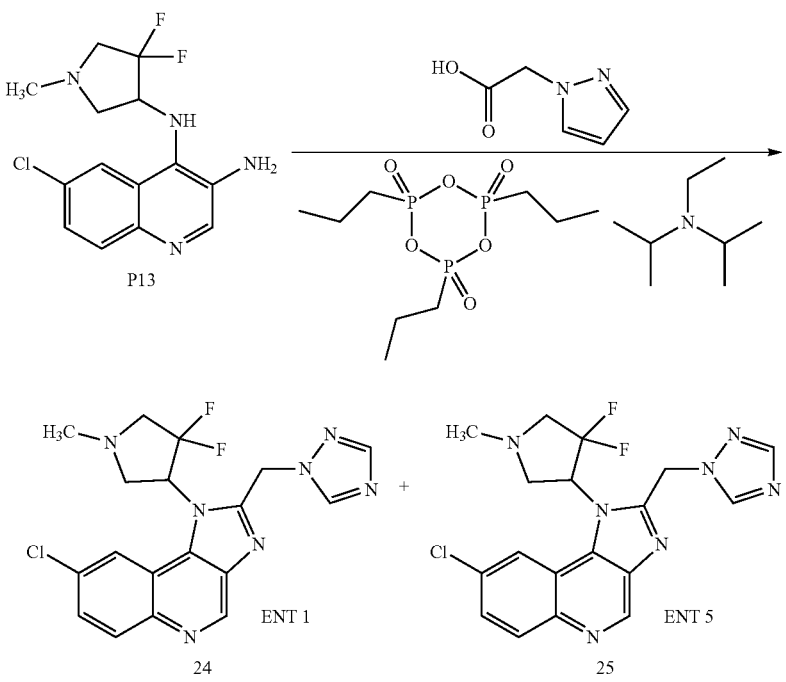

1H-1,2,4-Triazol-1-ylacetic acid and P13 were used to generate a racemic mixture of 24 and 25, using the method described in Examples 22 and 23. Separation into the component enantiomers was carried out using supercritical fluid chromatography [Column: Chiral Technologies Chiralpak AD-H, 5 μm; Mobile phase: 85:15 carbon dioxide/(methanol containing 0.2% ammonium hydroxide)]. In this case, the enantiomers were not fully separated, but the samples described are enriched in the indicated enantiomer. The first-eluting enantiomer was designated as 24. Yield: 2.3 mg, 5.7 μmol, 6%. LCMS m/z 404.5 (chlorine isotope pattern observed) [M+H]$^+$. Retention time: 3.7 minutes [Analytical conditions, Column: Chiral Technologies Chiralpak AD-H, 4.6×100 mm, 5 μm; Mobile phase: 75:25 carbon dioxide/(methanol containing 0.2% ammonium hydroxide); Back pressure: 150 bar; Flow rate: 1.5 mL/minute].

The second-eluting enantiomer was designated as 25. Yield: 1.0 mg, 2.5 μmol, 2%. LCMS m/z 403.9 [M+H]$^+$. Retention time: 3.9 minutes, using the same analytical conditions.

Examples 26 and 27

8-Chloro-1-(3,3-difluorotetrahydro-2H-pyran-4-yl)-2-[(4-methoxy-1H-pyrazol-1-yl) methyl]-1H-imidazo[4,5-c]quinoline, ENT 1 (26) and 8-Chloro-1-(3,3-difluorotetrahydro-2H-pyran-4-yl)-2-[(4-methoxy-1H-pyrazol-1-yl)methyl]-1H-imidazo[4,5-c]quinoline, ENT 2 (27)

This reaction was carried out in library format. N,N-Diisopropylethylamine (52 μL, 300 μmol) was added to a mixture of C64 (100 μmol) and P5 (31.2 mg, 99 μmol) in a 3:2 mixture of ethyl acetate and toluene (0.5 mL). 2,4,6-Tripropyl-1,3,5,2,4,6-trioxatriphosphinane 2,4,6-trioxide (50% solution in ethyl acetate; 0.19 mL, 0.32 mmol) was then added, and the reaction vial was shaken and heated at 70° C. for 2 hours, then at 110° C. for 6 hours. The reaction mixture was then partitioned between half-saturated aqueous sodium bicarbonate solution (1.5 mL) and ethyl acetate (2.4 mL) and subjected to vortexing. The organic layer was eluted through a solid phase extraction cartridge (6 mL) charged with sodium sulfate (~1 g); this extraction procedure was repeated twice, and the combined eluents were concentrated in vacuo. Purification via reversed-phase HPLC (Column: Waters XBridge C18, 5 μm; Mobile phase A: 0.03% ammonium hydroxide in water; Mobile phase B: 0.03% ammonium hydroxide in acetonitrile; Gradient: 5% to 100% B) provided a racemic mixture of the two products. Separation into the component enantiomers was carried out using supercritical fluid chromatography [Column: Chiral Technologies Chiralcel OJ-H, 5 μm; Mobile phase: 92:8 carbon dioxide/(methanol containing 0.2% ammonium hydroxide)]. The first-eluting enantiomer was designated as 26. Yield: 1.8 mg, 4.1 μmol, 4%. LCMS m/z 434.5 (chlorine isotope pattern observed) [M+H]$^+$. Retention time: 1.98 minutes [Analytical conditions, Chiral Technologies Chiralcel OJ-H, 4.6×100 mm, 5 μm; Mobile phase: 90:10 carbon dioxide/(methanol containing 0.2% ammonium hydroxide); Back pressure: 150 bar; Flow rate: 1.5 mL/minute].

The second-eluting enantiomer was designated as 27. Yield: 1.8 mg, 4.1 μmol, 4%. LCMS m/z 435.5 [M+H]$^+$. Retention time: 2.25 minutes, using the same analytical conditions.

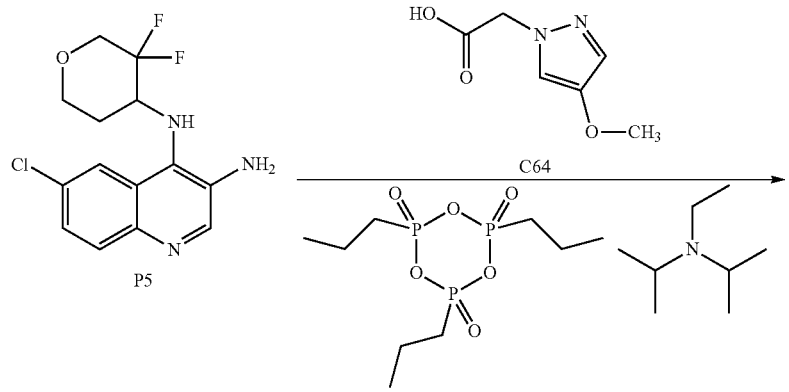

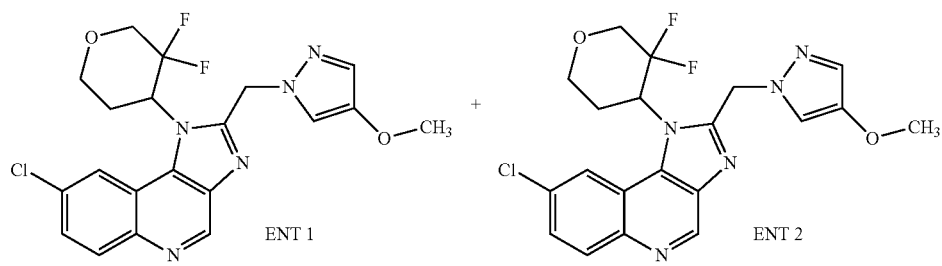

TABLE 1

Method of preparation, structure, and physicochemical data for Examples 28-55.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 28 | Example 6[1] | 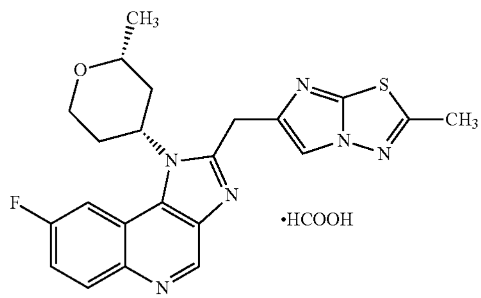 [SMILES: Cc1nn2cc(Cc3nc4cnc5ccc(F)cc5c4n3[C@@H]3CCO[C@H](C)C3)nc2s1 ; "·HCOOH"] | 2.33 minutes[2]; 437 |
| 29 | P7[3] | 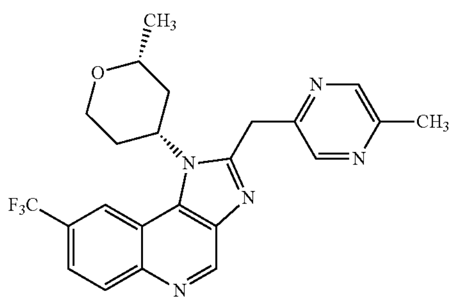 [SMILES: Cc1cnc(Cc2nc3cnc4ccc(C(F)(F)F)cc4c3n2[C@@H]2CCO[C@H](C)C2)cn1] | 9.39 (s, 1H), 9.09-8.91 (br s, 1H), 8.60 (s, 1H), 8.44-8.36 (m, 2H), 7.88 (dd, J = 8.8, 1.3 Hz, 1H), 5.39-5.23 (m, 1H), 4.68 (s, 2H), 4.30 (dd, J = 12.1, 5.1 Hz, 1H), 3.77-3.62 (m, 2H), 2.82-2.61 (br m, 1H), 2.57 (s, 3H), 2.54-2.36 (br m, 1H), 1.97-1.6 (br m, 2H, assumed; partially obscured by water peak), 1.33 (d, J = 6.2 Hz, 3H); 442.0 |
| 30 | Examples 10 and 11[4]; P8 | 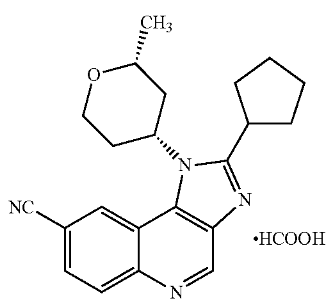 [SMILES: C[C@@H]1C[C@H](n2c(C3CCCC3)nc3cnc4ccc(C#N)cc4c32)CCO1 ; "·HCOOH"] | 2.80 minutes[2]; 361 |
| 31 | Examples 1 and 2[5]; P3 | cis, ENT 1 | $^1$H NMR (400 MHz, CD$_3$OD) δ 9.08 (s, 1H), 8.8-8.4 (v br s, 1H), 8.17 (d, J = 9.0 Hz, 1H), 7.72 (d, J = 9.0 Hz, 1H), 5.6-5.1 (v br s, 1H), 4.42-4.30 (m, 1H), 4.06-3.96 (m, 1H), 3.88 (br dd, J = 12, 12 Hz, 1H), 2.92-2.83 (m, 1H), 2.86 (s, 3H), 2.78 (dd, half of ABX pattern, J = 17.1, 6.5 Hz, 1H), 2.75-2.37 (v br m, 2H), 2.33-2.19 (br m, 1H), 2.17-2.05 (br m, 1H); 340.9 (chlorine isotope pattern observed) |

TABLE 1-continued

Method of preparation, structure, and physicochemical data for Examples 28-55.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 32 | Examples 3 and 4[6]; P4 | 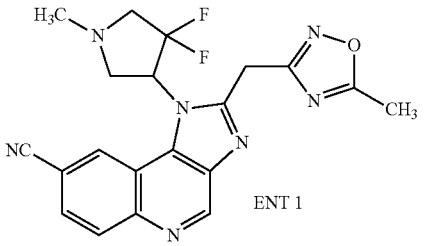 [SMILES: Cc1nc(Cc2nc3cnc4ccc(C#N)cc4c3n2C2CN(C)CC2(F)F)no1] ENT 1 | 10.0-9.45 (v br s, 1H), 9.40 (s, 1H), 8.33 (d, J = 8.8 Hz, 1H), 7.85 (dd, J = 8.8, 1.8 Hz, 1H), 5.95-5.78 (m, 1H), 5.02-4.78 (br m, 1H), 4.57 (d, J = 16.3 Hz, 1H), 3.70-3.61 (m, 1H), 3.69 (dd, J = 11.9, 11.4 Hz, 1H), 3.23 (dd, J = 11.4, 11.4 Hz, 1H), 3.08 (ddd, J = 23.8, 11.0, 7.0 Hz, 1H), 2.64 (br s, 3H), 2.60 (s, 3H); 409.8 |
| 33 | Examples 7 and 8; P9 | 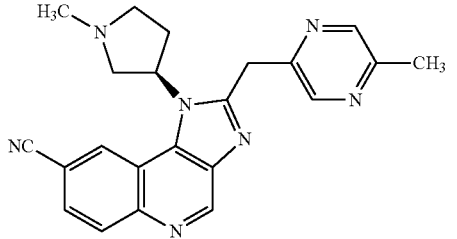 [SMILES: Cc1cnc(Cc2nc3cnc4ccc(C#N)cc4c3n2[C@@H]2CCN(C)C2)cn1] | 10.33-10.20 (br s, 1H), 9.38 (s, 1H), 8.58 (br s, 1H), 8.39 (br s, 1H), 8.31 (d, J = 8.8 Hz, 1H), 7.82 (dd, J = 8.6, 1.7 Hz, 1H), 5.77-5.65 (m, 1H), 4.72 (s, 2H), 3.43 (dd, J = 8.8, 6.8 Hz, 1H), 3.37 (dd, J = 11.2, 4.4 Hz, 1H), 2.80 (dd, J = 10.8, 10.8 Hz, 1H), 2.62-2.53 (m, 1H), 2.57 (s, 6H), 2.52-2.40 (m, 1H), 2.25-2.15 (m, 1H); 384.2 |
| 34 | Example 6[7]; P9 | 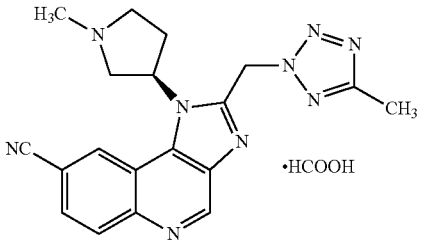 [SMILES: Cc1nnn(Cc2nc3cnc4ccc(C#N)cc4c3n2[C@@H]2CCN(C)C2)n1 ; "·HCOOH"] •HCOOH | 2.50 minutes[8]; 374 |
| 35 | Example 6; P9 | 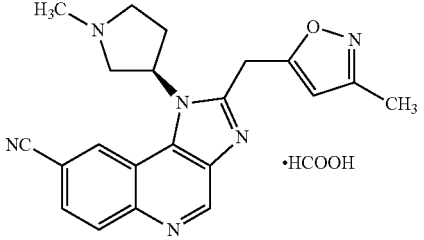 [SMILES: Cc1cc(Cc2nc3cnc4ccc(C#N)cc4c3n2[C@@H]2CCN(C)C2)on1 ; "·HCOOH"] •HCOOH | 1.98 minutes[2]; 373 |
| 36 | Example 6; P9, C64 | 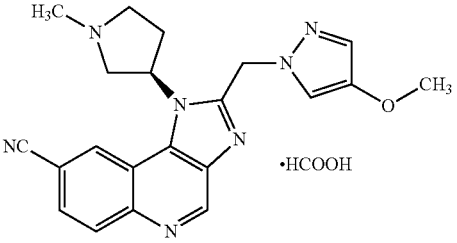 [SMILES: COc1cnn(Cc2nc3cnc4ccc(C#N)cc4c3n2[C@@H]2CCN(C)C2)c1 ; "·HCOOH"] •HCOOH | 2.56 minutes[8]; 388 |

TABLE 1-continued

Method of preparation, structure, and physicochemical data for Examples 28-55.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 37 | Examples 3 and 4; P9 | (structure) | 10.15-9.86 (v br s, 1H), 9.40 (s, 1H), 8.34 (d, J = 8.5 Hz, 1H), 7.86 (dd, J = 9.0, 1.5 Hz, 1H), 5.92-5.77 (br m, 1H), 5.04 (AB quartet, downfield doublet is broadened, $J_{AB}$ = 16.6 Hz, $\Delta_{vAB}$ = 22.7 Hz, 2H), 3.47 (dd, J = 8.5, 8.5 Hz, 1H), 3.40 (dd, J = 11.0, 5.0 Hz, 1H), 3.14-2.96 (br m, 1H), 2.89-2.73 (m, 1H), 2.77 (s, 3H), 2.64 (br s, 3H), 2.55-2.31 (m, 2H); 390.0 |
| 38 | Examples 3 and 4[9]; P9 | (structure) | 10.33-10.19 (br s, 1H), 9.40 (s, 1H), 8.31 (d, J = 8.4 Hz, 1H), 7.83 (dd, J = 8.8, 1.3 Hz, 1H), 6.71 (br s, 1H), 5.66-5.55 (m, 1H), 4.69 (AB quartet, $J_{AB}$ = 16.7 Hz, $\Delta_{vAB}$ = 12.2 Hz, 2H), 3.43 (dd, J = 8.8, 7.5 Hz, 1H), 3.38 (dd, J = 11.2, 4.2 Hz, 1H), 2.83 (dd, J = 11.0, 10.6 Hz, 1H), 2.62-2.54 (m, 1H), 2.57 (s, 3H), 2.51-2.39 (m, 1H), 2.31-2.21 (m, 1H), 2.29 (br s, 3H); 373.0 |
| 39 | Example 6; P8 | (structure) •HCOOH | 2.94 minutes[2]; 453 |
| 40 | Examples 3 and 4[10]; C7, C52 | (structure) | 9.66-9.52 (br s, 1H), 9.26 (s, 1H), 9.04 (br s, 1H), 8.17 (d, J = 9.0 Hz, 1H), 7.61 (dd, J = 9.0, 2.5 Hz, 1H), 7.21 (br s, 1H), 5.71-5.59 (m, 1H), 4.67 (AB quartet, downfield doublet is broadened, $J_{AB}$ = 15.8 Hz, $\Delta_{vAB}$ =11.1 Hz, 2H), 3.39-3.30 (m, 2H), 2.76 (dd, J = 10.5, 10.5 Hz, 1H), 2.58 (ddd, half of ABXY pattern, J = 11.0, 9.0, 5.5 Hz, 1H), 2.54-2.41 (m, 1H), 2.51 (s, 3H), 2.50 (s, 3H), 2.26-2.14 (br m, 1H); 393.0 (chlorine isotope pattern observed) |

TABLE 1-continued

Method of preparation, structure, and physicochemical data for Examples 28-55.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 41 | P7, C64[3] | *structure* | 9.43 (s, 1H), 9.07-8.91 (br s, 1H), 8.42 (d, J = 8.8 Hz, 1H), 7.91 (dd, J = 8.6, 1.5 Hz, 1H), 7.29 (s, 1H), 7.14 (s, 1H), 5.72 (s, 2H), 5.45-5.33 (m, 1H), 4.27 (dd, J = 12.1, 5.1 Hz, 1H), 3.77-3.62 (m, 2H), 3.67 (s, 3H), 2.71-2.54 (br m, 1H), 2.45-2.28 (br m, 1H), 1.73-1.42 (br m, 2H, assumed; partially obscured by water peak), 1.31 (d, J = 6.2 Hz, 3H); 446.1 |
| 42 | Examples 3 and 4[10] | *structure* | $^1$H NMR (400 MHz, CD$_3$OD) δ 9.89-9.76 (br s, 1H), 9.08 (s, 1H), 8.13 (d, J = 9.2 Hz, 1H), 7.70 (dd, J = 8.8, 2.2 Hz, 1H), 5.79-5.67 (m, 1H), 4.80 (s, 2H), 3.43-3.33 (m, 2H), 2.93 (dd, J = 11.0, 10.6 Hz, 1H), 2.66-2.55 (m, 1H), 2.59 (s, 3H), 2.54-2.43 (m, 2H), 2.52 (s, 3H); 383.0 (chlorine isotope pattern observed) |
| 43 | Example 12; P13 | *structure* | 3.00 minutes[11]; 404.2 (chlorine isotope pattern observed) |
| 44 | Example 12[12]; P13 | *structure* | 3.08 minutes[11]; 448.3 (chlorine isotope pattern observed) |
| 45 | Example 12; P13 | *structure* | 3.13 minutes[11]; 419.3 (chlorine isotope pattern observed) |

TABLE 1-continued

Method of preparation, structure, and physicochemical data for Examples 28-55.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 46 | Examples 3 and 4[13]; P5 | 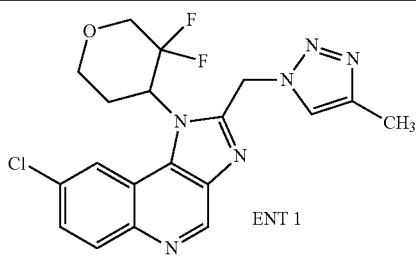 ENT 1 | From analysis of the $^1$H NMR, this Example was presumed to exist as a mixture of rotamers; [9.31 (s) and 9.30 (s), total 1H], [8.53 (br s) and 8.13 (br s), total 1H], [8.27 (d, J = 9.0 Hz) and 8.20 (d, J = 9.0 Hz), total 1H], 7.72-7.64 (m, 1H), [7.68 (s) and 7.56 (s), total 1H], [6.28 (d, J = 15.6 Hz) and 6.13 (d, J = 15.6 Hz), total 1H], [6.04-5.89 (m) and 5.72-5.59 (m), total 1H], [5.84 (d, J = 15.6 Hz) and 5.82 (d, J = 15.6 Hz), total 1H], 4.47-4.32 (m, 2H), 3.94-3.70 (m, 2H), 3.31-3.16 (m, 1H), [2.36 (s) and 2.33 (s), total 3H], [2.15-2.07 (m) and 1.84-1.75 (m), total 1H]; 419.0 (chlorine isotope pattern observed) |
| 47 | Examples 22 and 23[14]; P13 | 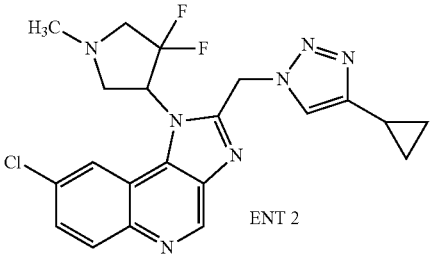 [SMILES: CN1CC(n2c(Cn3cc(C4CC4)nn3)nc3cnc4ccc(Cl)cc4c32)C(F)(F)C1] ENT 2 | 2.51 minutes[15]; 446.5 |
| 48 | Examples 22 and 23[16]; P13 | 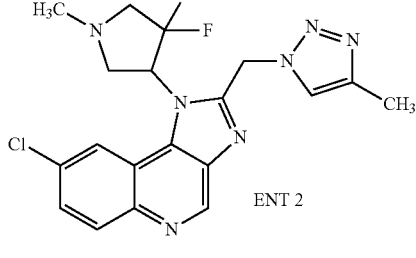 ENT 2 | 2.55 minutes[17]; 420.2 |
| 49 | Examples 22 and 23[7,18]; P13 | 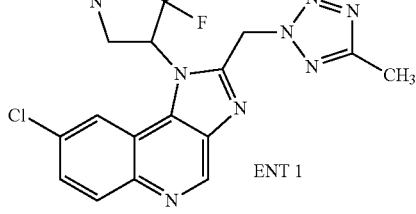 ENT 1 | 1.45 minutes[19]; 421.2 |

TABLE 1-continued

Method of preparation, structure, and physicochemical data for Examples 28-55.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 50 | Examples 22 and 23[20]; P13 | 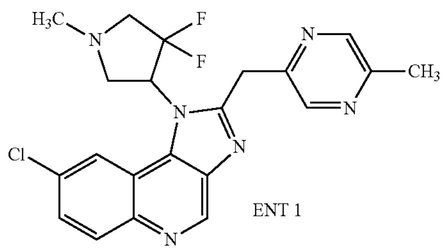 [SMILES: Cc1cnc(Cc2nc3cnc4ccc(Cl)cc4c3n2C2CN(C)CC2(F)F)cn1] | 1.9 minutes[17]; 429.6 |
| 51 | Examples 22 and 23[21]; P13 | 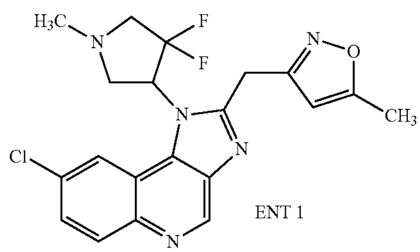 [SMILES: Cc1cc(Cc2nc3cnc4ccc(Cl)cc4c3n2C2CN(C)CC2(F)F)no1] | 1.65 minutes[17]; 420.1 |
| 52 | Examples 22 and 23[21]; P13 | 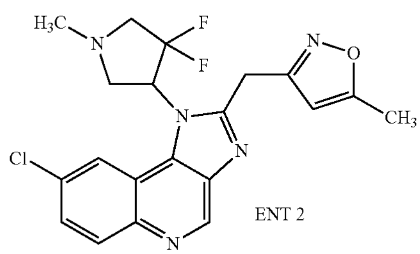 [SMILES: Cc1cc(Cc2nc3cnc4ccc(Cl)cc4c3n2C2CN(C)CC2(F)F)no1] | 1.91 minutes[17]; 419.5 |
| 53 | Examples 16 and 17[12,22]; P12 | 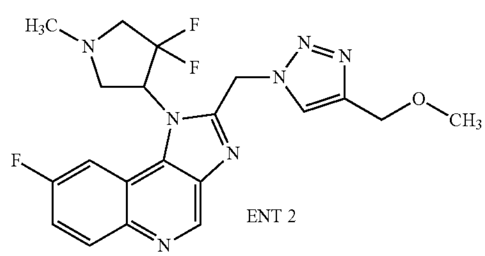 [SMILES: COCc1cn(Cc2nc3cnc4ccc(F)cc4c3n2C2CN(C)CC2(F)F)nn1] | 4.8 minutes[19]; 432.5 |
| 54 | Examples 26 and 27[23]; P5 | 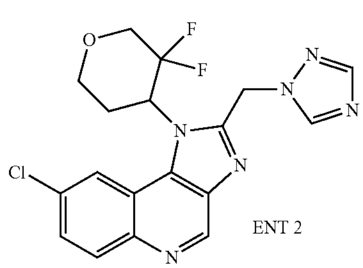 [SMILES: FC1(F)COCCC1n1c(Cn2cncn2)nc2cnc3ccc(Cl)cc3c21] | 3.31 minutes[24]; 405.6 |

TABLE 1-continued

Method of preparation, structure, and physicochemical data for Examples 28-55.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 55 | Examples 26 and 27[12,25]; P5 | (structure shown) ENT 1 | 2.43 minutes[26]; 449.5 |

1. The requisite 6-fluoro-N$^4$-[(2R,4R)-2-methyltetrahydro-2H-pyran-4-yl]quinoline-3,4-diamine was synthesized from 6-fluoro-3-nitroquinolin-4-ol using the general method described in Preparation P7 for synthesis of P7 from C25, except that the final reduction was carried out via hydrogenation over platinum on carbon, rather than treatment with iron powder and ammonium chloride.

2. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute.

3. In this case, the amide formation and ring closure were carried out in separate steps: condensation of the appropriate amine and carboxylic acid was effected with 2,4,6-tripropyl-1,3,5,2,4,6-trioxatriphosphinane 2,4,6-trioxide and either triethylamine or N,N-diisopropylethylamine. The intermediate amide was cyclized via heating with 2,4,6-tripropyl-1,3,5,2,4,6-trioxatriphosphinane 2,4,6-trioxide and N,N-diisopropylethylamine in N,N-dimethylformamide.

4. Amide formation between P8 and cyclopentanecarboxylic acid was effected using dimethyl carbonate and N,N-diisopropylethylamine, affording N-(6-cyano-4-{[(2R,4R)-2-methyltetrahydro-2H-pyran-4-yl]amino}quinolin-3-yl) acetamide. This material was converted to Example 30 using the method described for synthesis of C60 from C59 in Examples 10 and 11.

5. The racemate of Example 31 was separated into its component enantiomers via supercritical fluid chromatography [(Column: Chiral Technologies Chiralpak AD, 5 μm; Mobile phase: 3:1 carbon dioxide/(ethanol containing 0.1% ammonium hydroxide)]. The first-eluting compound was Example 31. The enantiomer of Example 31, [cis-4-(8-chloro-2-methyl-1H-imidazo[4,5-c]quinolin-1-yl)tetrahydro-2H-pyran-2-yl]acetonitrile, ENT 2, was the second-eluting enantiomer, LCMS m/z 341.0 (chlorine isotope pattern observed) [M+H]$^+$, and exhibited the following biological data: LRRK2, WT IC$_{50}$, 1660 nM.

6. The racemate of Example 32 was separated into its component enantiomers via supercritical fluid chromatography [Column: Chiral Technologies Chiralpak AD, 5 μm; Mobile phase: 7:3 carbon dioxide/(methanol containing 0.1% ammonium hydroxide)]. The first-eluting compound was Example 32. The enantiomer of Example 32, 1-(4,4-difluoro-1-methylpyrrolidin-3-yl)-2-[(5-methyl-1,2,4-oxadiazol-3-yl)methyl]-1H-imidazo[4,5-c]quinoline-8-carbonitrile, ENT 2, was the second-eluting enantiomer, LCMS m/z 409.8 [M+H]$^+$, and exhibited the following biological data: LRRK2, WT IC$_{50}$, 473 nM.

7. Reaction of 5-methyl-1H-tetrazole with methyl bromoacetate in the presence of triethylamine afforded methyl (5-methyl-2H-tetrazol-2-yl)acetate, which was hydrolyzed with lithium hydroxide to provide the requisite (5-methyl-2H-tetrazol-2-yl)acetic acid.

8. Conditions for analytical HPLC. Column: Waters XBridge C18, 2.1×50 mm, 5 μm; Mobile phase A: 0.05% ammonium hydroxide in water; Mobile phase B: acetonitrile; Gradient: 5% B for 0.5 minutes; 5% to 100% B over 2.9 minutes; 100% B for 0.8 minutes; Flow rate: 0.8 mL/minute.

9. Methyl (5-methyl-1,3-oxazol-2-yl)acetate was synthesized using the procedure described by A. S. K. Hashmi et al., Organic Letters 2004, 6, 4391-4394. Ester hydrolysis was carried out using hydrochloric acid, to provide the requisite (5-methyl-1,3-oxazol-2-yl)acetic acid.

10. The requisite 6-chloro-N$^4$-[(3R)-1-methylpyrrolidin-3-yl]quinoline-3,4-diamine was synthesized from C7, using the method described in Preparation P9. The reduction of the nitro group in this case was carried out via hydrogenation over platinum(IV) oxide.

11. Conditions for analytical HPLC. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% B for 1 minute, then linear from 5.0% to 95% B over 3.0 minutes, then 95% B for 1 minute. Flow rate: 2 mL/minute.

12. The requisite [4-(methoxymethyl)-1H-1,2,3-triazol-1-yl]acetic acid may be synthesized according to the method described by M. D. Andrews et al., PCT International Application WO 2014053967 A1, Apr. 10, 2014.

13. The racemate of Example 46 was separated into its component enantiomers via supercritical fluid chromatography [Column: Chiral Technologies ChiralCel OD, 5 μm; Mobile phase: 7:3 carbon dioxide/(ethanol containing 0.1% ammonium hydroxide)]. The first-eluting compound was Example 46. The enantiomer of Example 46, 8-chloro-1-(3,3-difluorotetrahydro-2H-pyran-4-yl)-2-[(4-methyl-1H-1,2, 3-triazol-1-yl)methyl]-1H-imidazo[4,5-c]quinoline, ENT 2, was the second-eluting enantiomer, LCMS m/z 419.1 (chlorine isotope pattern observed) [M+H]$^+$, and exhibited the following biological data: LRRK2, WT IC$_{50}$, 21.4 nM; LRRK2, G2019S mutant 1050, 16.1 nM.

14. The racemate of Example 47 was separated into its component enantiomers via supercritical fluid chromatography [Column: Chiral Technologies Chiralpak AD-H, 5 µm; Mobile phase: 65:35 carbon dioxide/(methanol containing 0.2% ammonium hydroxide)]. The second-eluting compound was Example 47. The enantiomer of Example 47, 8-chloro-2-[(4-cyclopropyl-1H-1,2,3-triazol-1-yl)methyl]-1-(4,4-difluoro-1-methylpyrrolidin-3-yl)-1H-imidazo[4,5-c]quinoline, ENT 1, was the first-eluting enantiomer, LCMS m/z 444.3 [M+H]$^+$, and exhibited the following biological data: LRRK2, WT IC$_{50}$, 97.3 nM.

15. Conditions for analytical HPLC. Column: Chiral Technologies Chiralpak ADH, 4.6×100 mm, 5 µm; Mobile phase: 7:3 carbon dioxide/(methanol containing 0.2% ammonium hydroxide); Back pressure: 200 bar; Flow rate: 1.5 mL/minute.

16. The racemate of Example 48 (Example 82) was separated into its component enantiomers via supercritical fluid chromatography [Column: Chiral Technologies Chiralpak AD-H, 5 µm; Mobile phase: 4:1 carbon dioxide/(methanol containing 0.2% ammonium hydroxide)]. The second-eluting compound was Example 48. The enantiomer of Example 48, 8-chloro-1-(4,4-difluoro-1-methylpyrrolidin-3-yl)-2-[(4-methyl-1H-1,2,3-triazol-1-yl)methyl]-1H-imidazo[4,5-c]quinoline, ENT 1, was the first-eluting enantiomer, LCMS m/z 420.1 [M+H]$^+$, and exhibited the following biological data: LRRK2, WT IC$_{50}$, 145 nM.

17. Conditions for analytical HPLC. Column: Chiral Technologies Chiralpak ADH, 4.6×100 mm, 5 µm; Mobile phase: 3:2 carbon dioxide/(methanol containing 0.2% ammonium hydroxide); Back pressure: 120 bar; Flow rate: 1.5 mL/minute.

18. The racemate of Example 49 was separated into its component enantiomers via supercritical fluid chromatography [Column: Chiral Technologies Chiralpak AD-H, 5 µm; Mobile phase: 3:1 carbon dioxide/(methanol containing 0.2% ammonium hydroxide)]. The first-eluting compound was Example 49. The enantiomer of Example 49, 8-chloro-1-(4,4-difluoro-1-methylpyrrolidin-3-yl)-2-[(5-methyl-2H-tetrazol-2-yl)methyl]-1H-imidazo[4,5-c]quinoline, ENT 2, was the second-eluting enantiomer, LCMS m/z 421.1 [M+H]$^+$, and exhibited the following biological data: LRRK2, WT IC50, 46.2 nM; LRRK2.

19. Conditions for analytical HPLC. Column: Chiral Technologies Chiralpak ADH, 4.6×100 mm, 5 µm; Mobile phase: 1:1 carbon dioxide/(methanol containing 0.2% ammonium hydroxide); Back pressure: 120 bar; Flow rate: 1.5 mL/minute.

20. The racemate of Example 50 was separated into its component enantiomers via supercritical fluid chromatography [Column: Chiral Technologies Chiralpak AD-H, 5 µm; Mobile phase: 3:1 carbon dioxide/(methanol containing 0.2% ammonium hydroxide)]. The first-eluting compound was Example 50. The enantiomer of Example 50, 8-chloro-1-(4,4-difluoro-1-methylpyrrolidin-3-yl)-2-[(5-methylpyrazin-2-yl)methyl]-1H-imidazo[4,5-c]quinoline, ENT 2, was the second-eluting enantiomer, LCMS m/z 429.2 (chlorine isotope pattern observed) [M+H]$^+$, and exhibited the following biological data: LRRK2, WT IC$_{50}$, 181 nM.

21. The racemate of Examples 51 and 52 was separated into its component enantiomers via supercritical fluid chromatography [Column: Chiral Technologies Chiralpak AD-H, 5 µm; Mobile phase: 3:1 carbon dioxide/(methanol containing 0.2% ammonium hydroxide)]. The first-eluting compound was Example 51, and the second-eluting enantiomer was Example 52.

22. The racemate of Example 53 was separated into its component enantiomers via supercritical fluid chromatography [Column: Chiral Technologies Chiralpak AD-H, 5 µm; Mobile phase: 55:45 carbon dioxide/(methanol containing 0.2% ammonium hydroxide)]. The second-eluting compound was Example 53. The enantiomer of Example 53, 1-(4,4-difluoro-1-methylpyrrolidin-3-yl)-8-fluoro-2-{[4-(methoxymethyl)-1H-1,2,3-triazol-1-yl]methyl}-1H-imidazo[4,5-c]quinoline, ENT 1, was the first-eluting enantiomer, LCMS m/z 432.7 [M+H]$^+$, and exhibited the following biological data: LRRK2, WT IC$_{50}$, 229 nM.

23. The racemate of Example 54 was separated into its component enantiomers via supercritical fluid chromatography [Chiral Technologies Chiralpak AD-H, 5 µm; Mobile phase: 4:1 carbon dioxide/(methanol containing 0.2% ammonium hydroxide)]. The second-eluting compound was Example 54. The enantiomer of Example 54, 8-chloro-1-(3,3-difluorotetrahydro-2H-pyran-4-yl)-2-(1H-1,2,4-triazol-1-ylmethyl)-1H-imidazo[4,5-c]quinoline, ENT 1 (Example 93), was the first-eluting enantiomer, LCMS m/z 405.3 [M+H]$^+$, and exhibited the following biological data: LRRK2, WT IC$_{50}$, 11.0 nM; LRRK2.

24. Conditions for analytical HPLC. Column: Phenomenex Lux Amylose-1, 4.6×100 mm, 5 µm; Mobile phase: 7:3 carbon dioxide/(methanol containing 0.2% ammonium hydroxide); Back pressure: 150 bar; Flow rate: 1.5 mL/minute.

25. The racemate of Example 55 was separated into its component enantiomers via supercritical fluid chromatography [Column: Chiral Technologies ChiralCel OD-H, 5 µm; Mobile phase: 7:3 carbon dioxide/(methanol containing 0.2% ammonium hydroxide)]. The first-eluting compound was Example 55. The enantiomer of Example 55, 8-chloro-1-(3,3-difluorotetrahydro-2H-pyran-4-yl)-2-{[4-(methoxymethyl)-1H-1,2,3-triazol-1-yl]methyl}-1H-imidazo[4,5-c]quinoline, ENT 2, was the second-eluting enantiomer, LCMS m/z 449.3 (chlorine isotope pattern observed) [M+H]$^+$, and exhibited the following biological data: LRRK2, WT IC$_{50}$, 15.3 nM.

26. Conditions for analytical HPLC. Column: Chiral Technologies ChiralCel ODH, 4.6×100 mm, 5 µm; Mobile phase: 3:2 carbon dioxide/(methanol containing 0.2% ammonium hydroxide); Back pressure: 120 bar; Flow rate: 1.5 mL/minute.

TABLE 2

Structure and mass spectral data for Examples 56-94.

| Example Number | Structure | $^1$H NMR (400 MHz, CDCl$_3$) δ and Mass spectrum m/z [M + H]$^+$; or HPLC or SFC retention time and Mass spectrum m/z [M + H]$^+$ (unless otherwise indicated) |
|---|---|---|
| 56 | 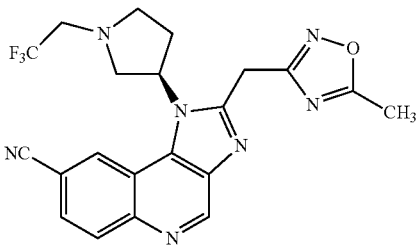 [SMILES: Cc1nc(Cc2nc3cnc4ccc(C#N)cc4c3n2[C@@H]2CCN(CC(F)(F)F)C2)no1] | 9.52 (br s, 1H), 9.39 (s, 1H), 8.35 (d, J = 8.8 Hz, 1H), 7.87 (br d, J = 8.4 Hz, 1H), 5.72-5.59 (m, 1H), 4.71 (AB quartet, J$_{AB}$ = 16.5 Hz, Δ$_{vAB}$ = 12.1 Hz, 2H), 3.70-3.61 (m, 2H), 3.56-3.42 (m, 1H), 3.31-3.15 (m, 2H), 3.02-2.92 (m, 1H), 2.69-2.55 (m, 1H), 2.59 (s, 3H), 2.50-2.38 (m, 1H); 442.1$^1$ |
| 57 | 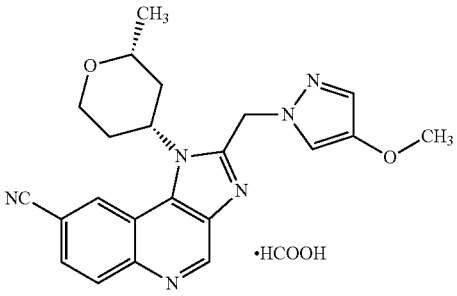 [SMILES: COc1cnn(Cc2nc3cnc4ccc(C#N)cc4c3n2[C@@H]2CCO[C@H](C)C2)c1 ; "·HCOOH"] ·HCOOH | 2.61 minutes$^2$; 403 |
| 58 | 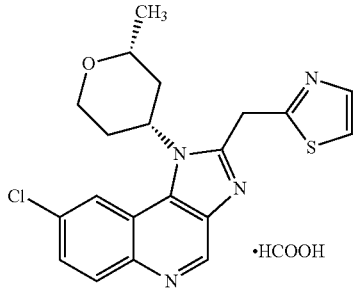 [SMILES: C[C@@H]1C[C@H](n2c(Cc3nccs3)nc3cnc4ccc(Cl)cc4c32)CCO1 ; "·HCOOH"] ·HCOOH | 2.48 minutes$^2$; 399 |
| 59 | 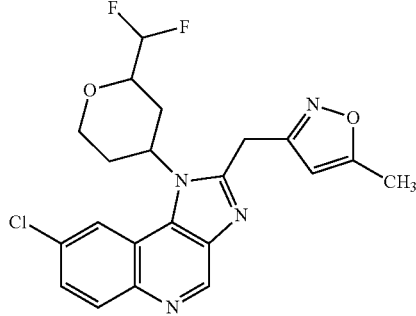 cis, ENT 1 | 9.29 (s, 1H), 8.61-8.47 (br m, 1H), 8.23 (d, J = 8.8 Hz, 1H), 7.65 (dd, J = 9.0, 1.5 Hz, 1H), 6.00 (br s, 1H), 5.86 (td, J = 55.5, 3.1 Hz, 1H), 5.32-5.18 (br m, 1H), 4.52 (s, 2H), 4.42 (dd, J = 11.9, 5.3 Hz, 1H), 3.95-3.82 (m, 1H), 3.77 (br dd, J = 11.9, 11.0 Hz, 1H), 2.89-2.58 (br m, 2H), 2.39 (s, 3H), 1.91-1.68 (br m, 2H); 433.0 (chlorine isotope pattern observed)$^{3,4}$ |
| 60 | 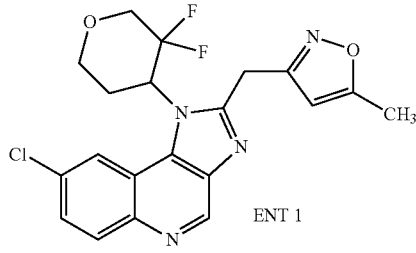 [SMILES: Cc1cc(Cc2nc3cnc4ccc(Cl)cc4c3n2C2CCOCC2(F)F)no1] ENT 1 | From analysis of $^1$H and 2-dimensional NMR data, this Example was presumed to exist as a mixture of rotamers. $^1$H NMR (600 MHz, CDCl$_3$), characteristic peaks: δ 9.29 (s, 1H), [8.54 (br s) and 8.13 (br s), total 1H], [8.26 (d, J = 8.8 Hz) and 8.22 (d, J = 9.4 Hz), total 1H], 7.67-7.62 (m, 1H), [6.12 (s) and 6.07 (s), total 1H], 5.67-5.48 (m, 1H), [4.61 (AB quartet, J$_{AB}$ = 16.7 Hz, Δ$_{vAB}$ = 30.6 Hz) and 4.52 (AB |

TABLE 2-continued

Structure and mass spectral data for Examples 56-94.

| Example Number | Structure | $^1$H NMR (400 MHz, CDCl$_3$) δ and Mass spectrum m/z [M + H]$^+$; or HPLC or SFC retention time and Mass spectrum m/z [M + H]$^+$ (unless otherwise indicated) |
|---|---|---|
|  |  | quartet, J$_{AB}$ = 15.8 Hz, Δ$_{vAB}$ = 14.8 Hz), total 2H], 4.42-4.30 (m, 2H), 3.90-3.67 (m, 2H), [3.28-3.19 (m) and 3.17-3.08 (m), total 1H], [2.41 (s) and 2.39 (s), total 3H]; 419.3 (chlorine isotope pattern observed)$^5$ |
| 61 | [Structure: NC-substituted imidazoquinoline with methyl-tetrahydropyran and thiazolylmethyl substituents; •HCOOH] | 2.44 minutes$^2$; 390 |
| 62 | [Structure: Cl-substituted imidazoquinoline with N-methylpyrrolidinyl and methyltriazolylmethyl substituents] | From analysis of the $^1$H NMR, this Example was presumed to exist as a mixture of rotamers. $^1$H NMR (400 MHz, CD$_3$OD) δ 9.85-9.71 (br m, 1H), [9.14 (s) and 9.13 (s), total 1H], 8.17-8.11 (m, 1H), 7.86 (s, 1H), 7.75-7.69 (m, 1H), 6.27 (AB quartet, J$_{AB}$ = 15.6 Hz, Δ$_{vAB}$ = 16.4 Hz, 2H), 5.89-5.78 (m, 1H), 3.41-3.3 (m, 3H, assumed; partially obscured by solvent peak), 2.86 (dd, J = 11.0, 10.6 Hz, 1H), 2.64-2.55 (m, 1H), 2.52 (s, 3H), 2.47-2.28 (m, 1H), 2.33 (s, 3H); 382.2 (chlorine isotope pattern observed) |
| 63 | [Structure: F$_3$C-substituted imidazoquinoline with methyl-tetrahydropyran and thiadiazolylmethyl substituents; •HCOOH] | 2.73 minutes$^2$; 434$^6$ |
| 64 | [Structure: F-substituted imidazoquinoline with methyl-tetrahydropyran and thiazolylmethyl substituents; •HCOOH] | 2.30 minutes$^2$; 383 |

TABLE 2-continued

Structure and mass spectral data for Examples 56-94.

| Example Number | Structure | $^1$H NMR (400 MHz, CDCl$_3$) δ and Mass spectrum m/z [M + H]$^+$; or HPLC or SFC retention time and Mass spectrum m/z [M + H]$^+$ (unless otherwise indicated) |
|---|---|---|
| 65 | 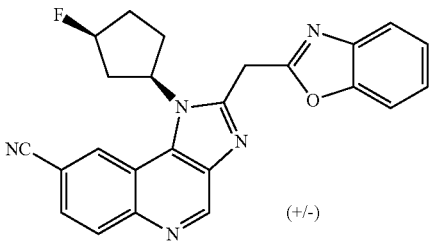 [SMILES: N#Cc1ccc2ncc3nc(Cc4nc5ccccc5o4)n([C@@H]4CC[C@H](F)C4)c3c2c1] (+/−) | 2.80 minutes$^2$; 412 |
| 66 | 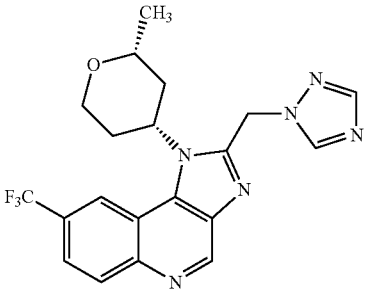 [SMILES: C[C@@H]1C[C@H](n2c(Cn3cncn3)nc3cnc4ccc(C(F)(F)F)cc4c32)CCO1] | 9.41 (s, 1H), 9.10-8.94 (br m, 1H), 8.43 (d, J = 9.0 Hz, 1H), 8.32 (s, 1H), 8.01 (s, 1H), 7.93 (dd, J = 8.8, 1.8 Hz, 1H), 5.88 (s, 2H), 5.48-5.36 (m, 1H), 4.37-4.30 (m, 1H), 3.82-3.69 (m, 2H), 2.80-2.62 (br m, 1H), 2.53-2.35 (br m, 1H), 1.95-1.59 (br m, 2H, assumed; partially obscured by water peak), 1.35 (d, J = 6.0 Hz, 3H); 417.1 |
| 67 | 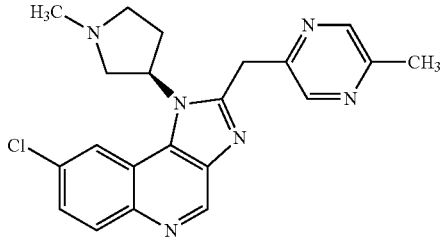 [SMILES: Cc1cnc(Cc2nc3cnc4ccc(Cl)cc4c3n2[C@@H]2CCN(C)C2)cn1] | 9.64-9.49 (br m, 1H), 9.25 (s, 1H), 8.58-8.55 (m, 1H), 8.39 (br s, 1H), 8.17 (d, J = 8.8 Hz, 1H), 7.60 (dd, J = 9.0, 2.0 Hz, 1H), 5.73-5.62 (m, 1H), 4.78-4.67 (m, 2H), 3.40-3.32 (m, 2H), 2.78 (dd, J = 11.0, 10.6 Hz, 1H), 2.64-2.42 (m, 2H), 2.56 (s, 3H), 2.52 (s, 3H), 2.27-2.17 (m, 1H); 393.1 (chlorine isotope pattern observed) |
| 68 | 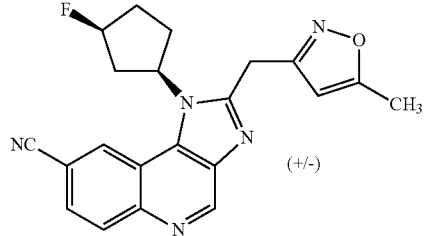 (+/−) | From analysis of the $^1$H NMR, this Example was presumed to exist as a mixture of rotamers. 9.41 (s, 1H), [8.95 (d, J = 1.2 Hz) and 8.94 (d, J = 1.6 Hz), total 1H], 8.35 (d, J = 8.6 Hz, 1H), 7.85 (dd, J = 8.6, 2.0 Hz, 1H), 6.01-5.99 (m, 1H), [5.54-5.49 (m) and 5.44-5.32 (m), total 2H], 4.53 (s, 2H), 2.76-2.46 (m, 4H), 2.40 (br s, 3H), 2.15-1.92 (m, 2H); 376.4 |
| 69 | 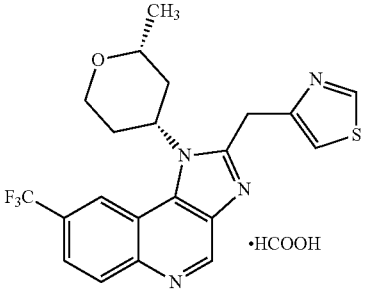 [SMILES: C[C@@H]1C[C@H](n2c(Cc3cscn3)nc3cnc4ccc(C(F)(F)F)cc4c32)CCO1 ; "·HCOOH"] ·HCOOH | 2.70 minutes$^2$; 433 |

TABLE 2-continued

Structure and mass spectral data for Examples 56-94.

| Example Number | Structure | ¹H NMR (400 MHz, CDCl₃) δ and Mass spectrum m/z [M + H]⁺; or HPLC or SFC retention time and Mass spectrum m/z [M + H]⁺ (unless otherwise indicated) |
|---|---|---|
| 70 | 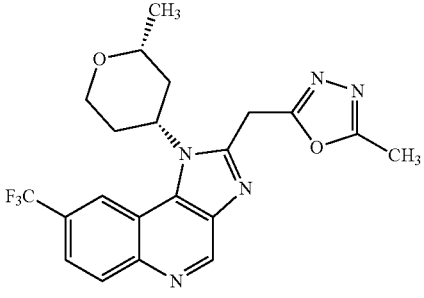 [SMILES: Cc1nnc(Cc2nc3cnc4ccc(C(F)(F)F)cc4c3n2[C@@H]2CCO[C@H](C)C2)o1] | 9.40 (s, 1H), 9.16-8.87 (br m, 1H), 8.42 (d, J = 8.8 Hz, 1H), 7.91 (br d, J = 8.8 Hz, 1H), 5.31-5.10 (br m, 1H), 4.75 (s, 2H), 4.33 (dd, J = 12.1, 5.1 Hz, 1H), 3.82-3.67 (m, 2H), 2.86-2.33 (br m, 2H), 2.54 (s, 3H), 2.07-1.78 (br m, 2H), 1.35 (d, J = 6.2 Hz, 3H); 432.1 |
| 71 | 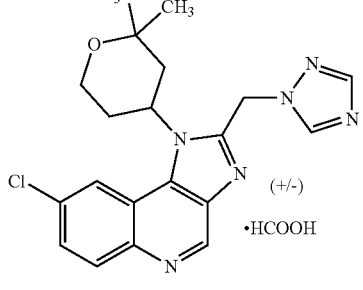 | 2.42 minutes²; 397 |
| 72 | 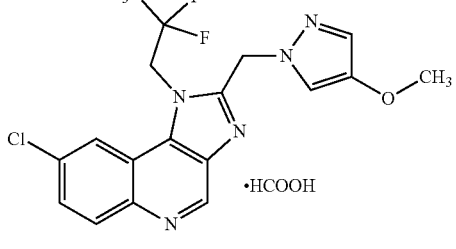 | 2.36 minutes⁷; 392 |
| 73 | 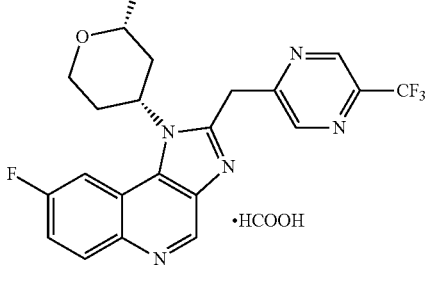 | 2.77 minutes²; 446 |
| 74 | 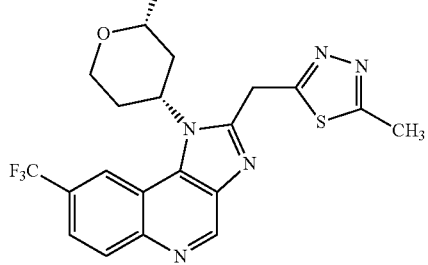 | 9.41 (s, 1H), 9.11-8.88 (br m, 1H), 8.42 (d, J = 8.8 Hz, 1H), 7.90 (dd, J = 8.8, 1.3 Hz, 1H), 5.40-5.29 (m, 1H), 4.96 (s, 2H), 4.31 (dd, J = 11.9, 4.8 Hz, 1H), 3.81-3.69 (m, 2H), 2.82-2.62 (br m, 1H), 2.77 (s, 3H), 2.51-2.34 (br m, 1H), 1.99-1.7 (m, 2H, assumed; largely obscured by water peak), 1.34 (d, J = 6.2 Hz, 3H); 448.0 |

TABLE 2-continued

Structure and mass spectral data for Examples 56-94.

| Example Number | Structure | $^1$H NMR (400 MHz, CDCl$_3$) δ and Mass spectrum m/z [M + H]$^+$; or HPLC or SFC retention time and Mass spectrum m/z [M + H]$^+$ (unless otherwise indicated) |
|---|---|---|
| 75 | ENT 1 | From analysis of the $^1$H NMR, this Example was presumed to exist as a mixture of rotamers. $^1$H NMR (400 MHz, CD$_3$OD) δ [9.13 (s) and 9.09 (s), total 1H], [8.71-8.67 (m) and 8.49-8.45 (m), total 1H], [8.18 (d, J = 8.8 Hz) and 8.17 (d, J = 8.8 Hz), total 1H], 7.78-7.70 (m, 1H), [6.11-5.97 (m) and 5.81-5.65 (m), total 1H], 4.78-4.58 (m, 2H), 4.40-4.20 (m, 2H), 4.09-3.79 (m, 2H), [3.36-3.22 (m) and 3.11-2.98 (m), total 1H, assumed; partially obscured by solvent peak], [2.62 (s) and 2.59 (s), total 3H], [2.48-2.39 (m) and 2.38-2.30 (m), total 1H]; 420.1 (chlorine isotope pattern observed)[8] |
| 76 | 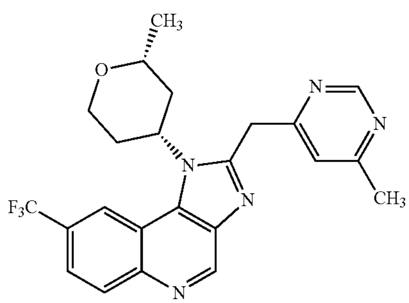 [SMILES: Cc1cc(Cc2nc3cnc4ccc(C(F)(F)F)cc4c3n2[C@@H]2CCO[C@H](C)C2)ncn1] | $^1$H NMR (400 MHz, CD$_3$OD) δ 9.26 (s, 1H), 9.21-9.07 (br m, 1H), 8.94 (br s, 1H), 8.39 (d, J = 8.8 Hz, 1H), 7.99 (dd, J = 8.8, 1.5 Hz, 1H), 7.53 (s, 1H), 5.43-5.28 (br m, 1H), 4.77 (s, 2H), 4.25 (dd, J = 12.0, 5.1 Hz, 1H), 3.79-3.66 (m, 2H), 2.78-2.61 (br m, 1H), 2.54 (s, 3H), 2.48-2.32 (br m, 1H), 2.14-1.88 (br m, 2H), 1.29 (d, J = 6.4 Hz, 3H); 442.2 |
| 77 | (+/−) •HCOOH | 2.31 minutes[7]; 396 |
| 78 | DIAST 2 | Characteristic $^1$H NMR peaks: δ 9.27 (s, 1H), 8.24 (d, J = 9.0 Hz, 1H), 7.66 (dd, J = 8.8, 2.3 Hz, 1H), 4.42-4.32 (br m, 1H), 3.84-3.59 (m, 3H), 3.52-3.40 (m, 1H), 3.29-3.21 (m, 1H), 2.25-2.04 (br m, 2H), 1.64-1.6 (m, 3H, assumed; partially obscured by water peak), 1.40 (d, J = 6.0 Hz, 3H); 369.0 (chlorine isotope pattern observed)[9,10] |

TABLE 2-continued

Structure and mass spectral data for Examples 56-94.

| Example Number | Structure | $^1$H NMR (400 MHz, CDCl$_3$) δ and Mass spectrum m/z [M + H]$^+$; or HPLC or SFC retention time and Mass spectrum m/z [M + H]$^+$ (unless otherwise indicated) |
|---|---|---|
| 79 | cis, ENT 2 | 9.24 (s, 1H), 8.58 (s, 1H), 8.27 (dd, J = 9.0, 6.0 Hz, 1H), 8.17-8.11 (m, 1H), 7.45 (ddd, J = 9.3, 7.8, 2.8 Hz, 1H), 5.62-5.51 (m, 1H), [5.52-5.46 (m) and 5.38-5.33 (m), J$_{HF}$ = 54 Hz, total 1H], 5.06 (s, 2H), 2.81-2.67 (m, 2H), 2.66-2.60 (m, 1H), 2.56-2.42 (m, 1H), 2.16-1.93 (m, 2H); 372.0[6,11] |
| 80 | ·HCOOH | 2.40 minutes[2]; 355 |
| 81 | ·HCOOH | 2.87 minutes[7]; 432[12] |
| 82 | (+/-) ·CF$_3$COOH | 3.08 minutes[13]; 418.3 (chlorine isotope pattern observed) |
| 83 | (+/-) ·CF$_3$COOH | 3.07 minutes[13]; 405.2 (chlorine isotope pattern observed) |

TABLE 2-continued

Structure and mass spectral data for Examples 56-94.

| Example Number | Structure | $^1$H NMR (400 MHz, CDCl$_3$) δ and Mass spectrum m/z [M + H]$^+$; or HPLC or SFC retention time and Mass spectrum m/z [M + H]$^+$ (unless otherwise indicated) |
|---|---|---|
| 84 | (structure; (+/−) •CF$_3$COOH) | 2.93 minutes[13]; 418.3 (chlorine isotope pattern observed) |
| 85 | (structure; ENT 1) | 3.03 minutes[14]; 458.5[15] |
| 86 | (structure; ENT 2) | 1.92 minutes[16]; 405.6[17] |
| 87 | (structure; ENT 1) | 1.78 minutes[18]; 420.2[19] |
| 88 | (structure; ENT 1) | 1.44 minutes[20]; 420.5[21] |

TABLE 2-continued

Structure and mass spectral data for Examples 56-94.

| Example Number | Structure | $^1$H NMR (400 MHz, CDCl$_3$) δ and Mass spectrum m/z [M + H]$^+$; or HPLC or SFC retention time and Mass spectrum m/z [M + H]$^+$ (unless otherwise indicated) |
|---|---|---|
| 89 | 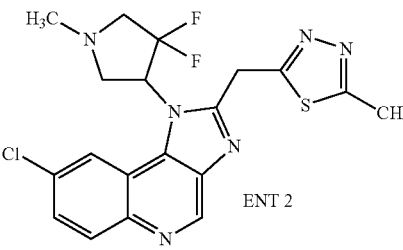 ENT 2 | 3.14 minutes[22]; 435.2 (chlorine isotope pattern observed)[23] |
| 90 | 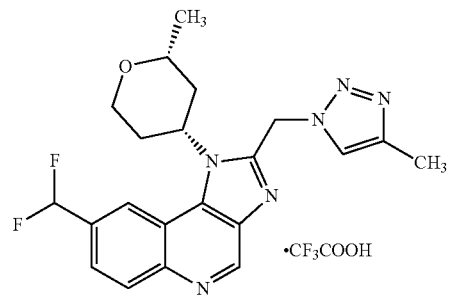 ·CF$_3$COOH | 3.04 minutes[13]; 413.4 |
| 91 | 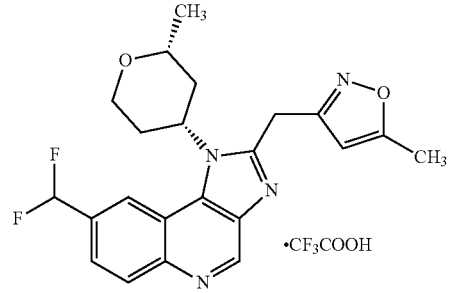 ·CF$_3$COOH | 3.19 minutes[13]; 413.4 |
| 92 | 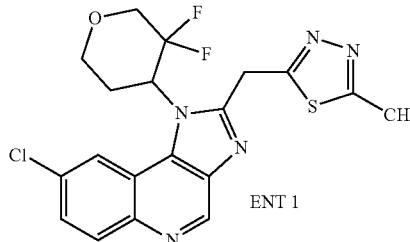 ENT 1 | 3.35 minutes[24]; 436.5 (chlorine isotope pattern observed)[25] |
| 93 | 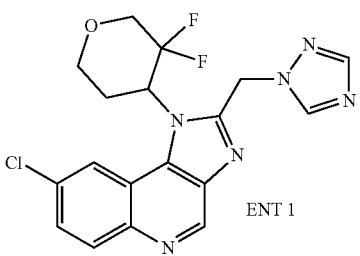 ENT 1 | 2.44 minutes[26]; 405.3 (chlorine isotope pattern observed)[27] |

TABLE 2-continued

Structure and mass spectral data for Examples 56-94.

| Example Number | Structure | $^1$H NMR (400 MHz, CDCl$_3$) δ and Mass spectrum m/z [M + H]$^+$; or HPLC or SFC retention time and Mass spectrum m/z [M + H]$^+$ (unless otherwise indicated) |
|---|---|---|
| 94 | 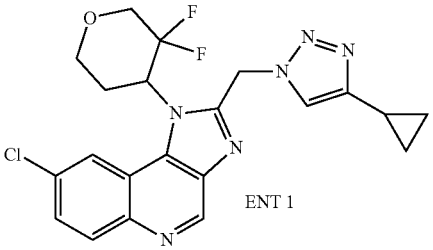 ENT 1 | 3.53 minutes[24]; 445.5 (chlorine isotope pattern observed)[28] |

1. tert-Butyl (3R)-3-aminopyrrolidine-1-carboxylate and C11 were used to synthesize tert-butyl (3R)-3-[(3-amino-6-cyanoquinolin-4-yl)amino]pyrrolidine-1-carboxylate, according to the method described for synthesis of P9 in Preparation P9. This material was converted to tert-butyl (3R)-3-{8-cyano-2-[(5-methyl-1,2,4-oxadiazol-3-yl)methyl]-1H-imidazo[4,5-c]quinolin-1-yl}pyrrolidine-1-carboxylate using the method described for synthesis of 3 and 4 in Examples 3 and 4. Removal of the protecting group with trifluoroacetic acid was followed by alkylation with 2,2,2-trifluoroethyl trifluoromethanesulfonate and N,N-diisopropylethylamine, providing Example 56.

2. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute.

3. Reaction of P3 with (5-methyl-1,2-oxazol-3-yl)acetic acid, 2,4,6-tripropyl-1,3,5,2,4,6-trioxatriphosphinane 2,4,6-trioxide, and N,N-diisopropylethylamine afforded 1-{cis-2-[(benzyloxy)methyl]tetrahydro-2H-pyran-4-yl}-8-chloro-2-[(5-methyl-1,2-oxazol-3-yl)methyl]-1H-imidazo[4,5-c]quinoline, which was debenzylated with boron trichloride and oxidized using Dess-Martin periodinane [1,1,1-tris(acetyloxy)-1,1-dihydro-1,2-benziodoxol-3-(1H)-one]. The resulting cis-4-{8-chloro-2-[(5-methyl-1,2-oxazol-3-yl)methyl]-1H-imidazo[4,5-c]quinolin-1-yl}tetrahydro-2H-pyran-2-carbaldehyde was converted to racemic 8-chloro-1-[cis-2-(difluoromethyl)tetrahydro-2H-pyran-4-yl]-2-[(5-methyl-1,2-oxazol-3-yl)methyl]-1H-imidazo[4,5-c]quinoline via treatment with (diethylamino)sulfur trifluoride.

4. Example 59 was isolated from the corresponding racemic mixture via supercritical fluid chromatography (Column: Chiral Technologies Chiralpak AD, 5 μm; Mobile phase: 7:3 carbon dioxide/methanol). Example 59 was the first-eluting enantiomer. The enantiomer of Example 59, 8-chloro-1-[cis-2-(difluoromethyl)tetrahydro-2H-pyran-4-yl]-2-[(5-methyl-1,2-oxazol-3-yl)methyl]-1H-imidazo[4,5-c]quinoline, ENT 2, was the second-eluting enantiomer, LCMS m/z 433.0 [M+H]$^+$, and exhibited the following biological data: LRRK2, WT IC$_{50}$, 631 nM.

5. Example 60 was isolated from the corresponding racemic mixture via supercritical fluid chromatography [Column: Chiral Technologies Chiralcel OJ-H, 5 μm; Mobile phase: 85:15 carbon dioxide/(ethanol containing 0.2% ammonium hydroxide)]. Example 60 was the first-eluting enantiomer. The enantiomer of Example 60, 8-chloro-1-(3,3-difluorotetrahydro-2H-pyran-4-yl)-2-[(5-methyl-1,2-oxazol-3-yl)methyl]-1H-imidazo[4,5-c]quinoline, ENT 2, was the second-eluting enantiomer, LCMS m/z 419.3 [M+H]$^+$, and exhibited the following biological data: LRRK2, WT IC$_{50}$, 42.2 nM.

6. Reaction of 1,2,3-thiadiazol-4-ylmethanol with methanesulfonyl chloride and triethylamine, followed by displacement using potassium cyanide and hydrolysis in concentrated hydrochloric acid, provided the requisite 1,2,3-thiadiazol-4-ylacetic acid.

7. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 10% to 100% B over 4.0 minutes; Flow rate: 0.8 mL/minute.

8. Example 75 was isolated from the corresponding racemic mixture via supercritical fluid chromatography [Column: Chiral Technologies Chiralpak IC, 10 μm; Mobile phase: 55:45 carbon dioxide/(2-propanol containing 0.1% ammonium hydroxide)]. Example 75 was the first-eluting enantiomer. The enantiomer of Example 75, 8-chloro-1-(3, 3-difluorotetrahydro-2H-pyran-4-yl)-2-[(5-methyl-1,2,4-oxadiazol-3-yl) methyl]-1H-imidazo[4,5-c]quinoline, ENT 2, was the second-eluting enantiomer, LCMS m/z 420.0 (chlorine isotope pattern observed) [M+H]$^+$, and exhibited the following biological data: LRRK2, WT IC$_{50}$, not determined.

9. Treatment of ethyl 3-oxobutanoate with lithium trifluoromethanesulfonate, trifluoromethanesulfonic anhydride, and N,N-diisopropylethylamine provided ethyl 3-{[(trifluoromethyl)sulfonyl]oxy}but-2-enoate. This was reacted with zinc cyanide in the presence of tetrakis(triphenylphosphine) palladium(0) to afford ethyl 3-cyanobut-2-enoate, which was subjected to hydrogenation over palladium on carbon, followed by hydrolysis with sodium hydroxide, to yield the requisite 3-cyanobutanoic acid.

10. Example 78 was isolated from the corresponding diastereomeric mixture via supercritical fluid chromatography [Column: Phenomenex Lux Cellulose-2, 10 μm; Mobile phase: 3:2 carbon dioxide/(2-propanol containing 0.1% ammonium hydroxide)]. Example 78 was the second-eluting diastereomer. The diastereomer of Example 78, 3-{8-chloro-1-[(2R,4R)-2-methyltetrahydro-2H-pyran-4-yl]-1H-imidazo[4,5-c]quinolin-2-yl}-2-methylpropanenitrile, DIAST 1, was the first-eluting diastereomer, LCMS m/z 369.0

(chlorine isotope pattern observed) [M+H]⁺, and exhibited the following biological data: LRRK2, WT $IC_{50}$, 37.2 nM.

11. Example 79 was isolated from the corresponding racemic mixture via supercritical fluid chromatography [Column: Chiral Technologies Chiralpak AY, 10 μm; Mobile phase: 3:2 carbon dioxide/(ethanol containing 0.1% ammonium hydroxide)]. Example 79 was the second-eluting enantiomer. The enantiomer of Example 79, 8-fluoro-1-[cis-3-fluorocyclopentyl]-2-(1,2,3-thiadiazol-4-ylmethyl)-1H-imidazo[4,5-c]quinoline, ENT 1, was the first-eluting enantiomer, LCMS m/z 372.0 [M+H]⁺, and exhibited the following biological data: LRRK2, WT $IC_{50}$, 7.54 nM.

12. Reaction of 5-methyl-1H-tetrazole with methyl bromoacetate in the presence of triethylamine afforded methyl (5-methyl-2H-tetrazol-2-yl)acetate, which was hydrolyzed with lithium hydroxide to provide the requisite (5-methyl-2H-tetrazol-2-yl)acetic acid.

13. Conditions for analytical HPLC. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% B for 1 minute, then linear from 5.0% to 95% B over 3.0 minutes, then 95% B for 1 minute. Flow rate: 2 mL/minute.

14. Conditions for analytical HPLC. Column: Chiral Technologies Chiralpak ADH, 4.6×100 mm, 5 μm; Mobile phase: 75:25 carbon dioxide/(methanol containing 0.2% ammonium hydroxide); Back pressure: 200 bar; Flow rate: 1.5 mL/minute.

15. Example 85 was isolated from the corresponding racemic mixture via supercritical fluid chromatography [Column: Chiral Technologies Chiralpak AD-H, 5 μm; Mobile phase: 4:1 carbon dioxide/(methanol containing 0.2% ammonium hydroxide)]. Example 85 was the first-eluting enantiomer. The enantiomer of Example 85, 1-(4,4-difluoro-1-methylpyrrolidin-3-yl)-8-fluoro-2-[(2-methyl-imidazo[2,1-b][1,3,4]thiadiazol-6-yl)methyl]-1H-imidazo[4,5-c]quinoline, ENT 2, was the second-eluting enantiomer, LCMS m/z 458.3 [M+H]⁺, and exhibited the following biological data: LRRK2, WT $IC_{50}$, 55.9 nM.

16. Conditions for analytical HPLC. Column: Chiral Technologies Chiralpak ADH, 4.6×100 mm, 5 μm; Mobile phase: 70:30 carbon dioxide/(methanol containing 0.2% ammonium hydroxide); Back pressure: 150 bar; Flow rate: 1.5 mL/minute.

17. Example 83 was separated into its component enantiomers via supercritical fluid chromatography [Column: Chiral Technologies Chiralpak AD-H, 5 μm; Mobile phase: 4:1 carbon dioxide/(methanol containing 0.2% ammonium hydroxide)]. Example 86 was the second-eluting enantiomer. The enantiomer of Example 86, 8-chloro-1-(4,4-difluoro-1-methylpyrrolidin-3-yl)-2-(1H-tetrazol-1-ylmethyl)-1H-imidazo[4,5-c]quinoline, ENT 1, was the first-eluting enantiomer, LCMS m/z 407.1 [M+H]⁺, and exhibited the following biological data: LRRK2, WT $IC_{50}$, 271 nM.

18. Conditions for analytical HPLC. Column: Chiral Technologies Chiralcel ODH, 4.6×100 mm, 5 μm; Mobile phase: 7:3 carbon dioxide/(methanol containing 0.2% ammonium hydroxide); Back pressure: 150 bar; Flow rate: 1.5 mL/minute.

19. Example 87 was isolated from the corresponding racemic mixture via supercritical fluid chromatography [Column: Chiral Technologies ChiralCel OD-H, 5 μm; Mobile phase: 4:1 carbon dioxide/(methanol containing 0.2% ammonium hydroxide)]. Example 87 was the first-eluting enantiomer. The enantiomer of Example 87, 8-chloro-1-(4,4-difluoro-1-methylpyrrolidin-3-yl)-2-[(4-methyl-2H-1,2,3-triazol-2-yl)methyl]-1H-imidazo[4,5-c]quinoline, ENT 2, was the second-eluting enantiomer, LCMS m/z 420.2 [M+H]⁺, and exhibited the following biological data: LRRK2, WT $IC_{50}$, 37.8 nM.

20. Conditions for analytical HPLC. Column: Chiral Technologies Chiralpak ADH, 4.6×100 mm, 5 μm; Mobile phase: 60:40 carbon dioxide/(methanol containing 0.2% ammonium hydroxide); Back pressure: 120 bar; Flow rate: 1.5 mL/minute.

21. Example 88 was isolated from the corresponding racemic mixture via supercritical fluid chromatography [Column: Chiral Technologies Chiralpak AD-H, 5 μm; Mobile phase: 3:2 carbon dioxide/(methanol containing 0.2% ammonium hydroxide)]. Example 88 was the first-eluting enantiomer. The enantiomer of Example 88, 8-chloro-1-(4,4-difluoro-1-methylpyrrolidin-3-yl)-2-[(5-methyl-1,2,4-oxadiazol-3-yl)methyl]-1H-imidazo[4,5-c]quinoline, ENT 2, was the second-eluting enantiomer, LCMS m/z 420.5 [M+H]⁺, and exhibited the following biological data: LRRK2, WT $IC_{50}$, 261 nM.

22. Conditions for analytical HPLC. Column: Chiral Technologies Chiralpak ADH, 4.6×100 mm, 5 μm; Mobile phase: 7:3 carbon dioxide/(methanol containing 0.2% ammonium hydroxide); Back pressure: 200 bar; Flow rate: 1.5 mL/minute.

23. Example 89 was isolated from the corresponding racemic mixture via supercritical fluid chromatography [Column: Chiral Technologies Chiralpak AD-H, 5 μm; Mobile phase: 85:15 carbon dioxide/(methanol containing 0.2% ammonium hydroxide)]. Example 89 was the second-eluting enantiomer. The enantiomer of Example 89, 8-chloro-1-(4,4-difluoro-1-methylpyrrolidin-3-yl)-2-[(5-methyl-1,3,4-thiadiazol-2-yl)methyl]-1H-imidazo[4,5-c]quinoline, ENT 1, was the first-eluting enantiomer, LCMS m/z 434.8 [M+H]⁺, and exhibited the following biological data: LRRK2, WT $IC_{50}$, not determined.

24. Conditions for analytical HPLC. Column: Chiral Technologies Chiralcel OJ-H, 4.6×100 mm, 5 μm; Mobile phase: 9:1 carbon dioxide/(methanol containing 0.2% ammonium hydroxide); Back pressure: 150 bar; Flow rate: 1.5 mL/minute.

25. Example 92 was isolated from the corresponding racemic mixture via supercritical fluid chromatography [Column: Chiral Technologies Chiralcel OJ-H, 5 μm; Mobile phase: 95:5 carbon dioxide/(methanol containing 0.2% ammonium hydroxide)]. Example 92 was the first-eluting enantiomer. The enantiomer of Example 92, 8-chloro-1-(3,3-difluorotetrahydro-2H-pyran-4-yl)-2-[(5-methyl-1,3,4-thiadiazol-2-yl) methyl]-1H-imidazo[4,5-c]quinoline, ENT 2, was the second-eluting enantiomer, LCMS m/z 436.5 (chlorine isotope pattern observed) [M+H]⁺, and exhibited the following biological data: LRRK2, WT $IC_{50}$, 33.7 nM.

26. Conditions for analytical HPLC. Column: Phenomenex Lux Amylose-1, 4.6×100 mm, 5 μm; Mobile phase: 7:3 carbon dioxide/(methanol containing 0.2% ammonium hydroxide); Back pressure: 150 bar; Flow rate: 1.5 mL/minute.

27. Example 93 was isolated from the corresponding racemic mixture via supercritical fluid chromatography [Column: Chiral Technologies Chiralpak AD-H, 5 μm; Mobile phase: 4:1 carbon dioxide/(methanol containing 0.2% ammonium hydroxide)]. Example 93 was the first-eluting enantiomer. The enantiomer of Example 93, 8-chloro-1-(3,3-difluorotetrahydro-2H-pyran-4-yl)-2-(1H-1,2,4-triazol-1-ylmethyl)-1H-imidazo[4,5-c]quinoline, ENT 2, was the second-eluting enantiomer, LCMS m/z 405.6 [M+H]+, and exhibited the following biological data: LRRK2, WT IC50, 10.3 nM.

28. Example 94 was isolated from the corresponding racemic mixture via supercritical fluid chromatography [Column: Chiral Technologies Chiralpak AD-H, 5 μm; Mobile phase: 3:1 carbon dioxide/(methanol containing 0.2% ammonium hydroxide)]. Example 94 was the first-eluting enantiomer. The enantiomer of Example 94, 8-chloro-2-[(4-cyclopropyl-1H-1,2,3-triazol-1-yl)methyl]-1-(3,3-difluorotetrahydro-2H-pyran-4-yl)-1H-imidazo[4,5-c]quinoline, ENT 2, was the second-eluting enantiomer, LCMS m/z 445.3 (chlorine isotope pattern observed) [M+H]+, and exhibited the following biological data: LRRK2, WT IC50, 9.35 nM.

Example 95

[5-({8-chloro-1-[(2R,4R)-2-methyltetrahydro-2H-pyran-4-yl]-1H-imidazo[4,5-c]quinolin-2-yl}methyl)pyrazin-2-yl]methanol (95)

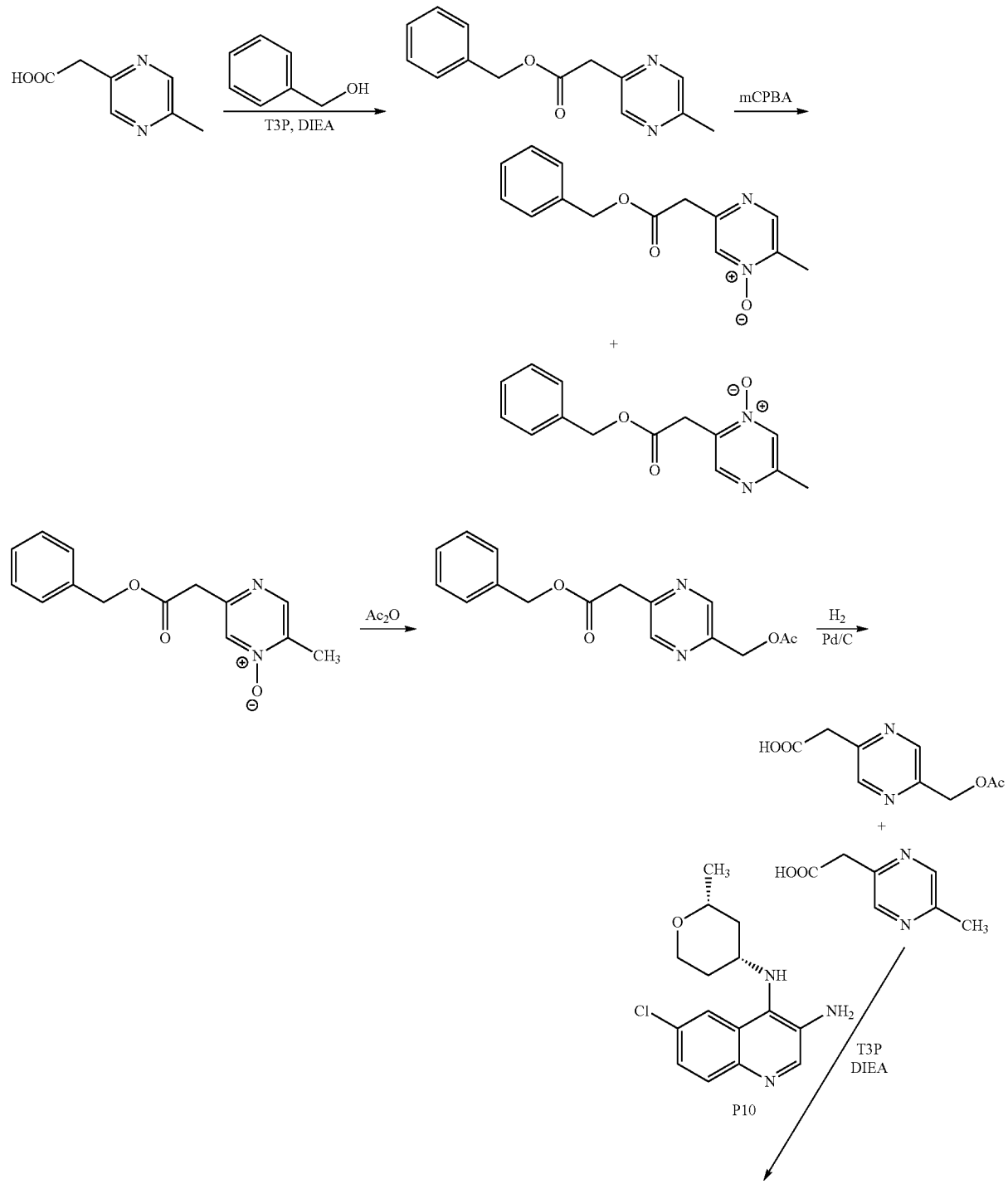

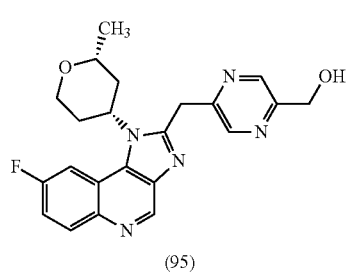 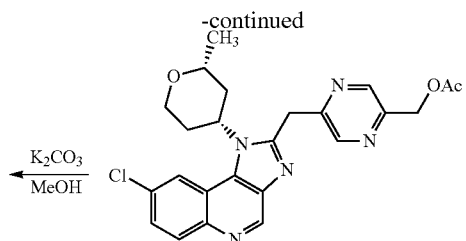 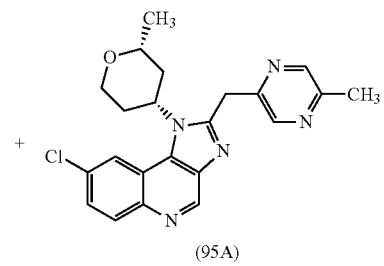

Step 1. Synthesis of benzyl 2-(5-methylpyrazin-2-yl)acetate

A suspension containing 2-(5-methylpyrazin-2-yl)acetic acid (1.00 g, 6.57 mmol) and benzyl alcohol (853 mg, 7.89 mmol, 0.820 mL) in tetrahydrofuran (26.3 mL) was treated with N,N-diisopropylethylamine (1.72 mL, 9.86 mmol) and 2,4,6-tripropyl-1,3,5,2,4,6-trioxatriphosphinane 2,4,6-trioxide (50% solution in N,N-dimethylformamide; 4.69 mL, 7.89 mmol). The solids slowly dissolved as the reaction mixture was stirred at room temperature for 20 hours. The reaction was quenched with saturated aqueous sodium bicarbonate solution, and then extracted with ethyl acetate. The combined organic layers were dried over sodium sulfate, filtered, and concentrated in vacuo. Silica gel chromatography (Gradient: 0% to 80% ethyl acetate in heptane) afforded the product as a yellow oil. Yield: 1.2 g, 76%. LCMS m/z 243.4 [M+H]$^+$. $^1$H NMR (400 MHz, CDCl$_3$) δ 8.48 (d, J=1.5 Hz, 1H), 8.43 (d, J=1.5 Hz, 1H), 7.43-7.30 (m, 5H), 5.20 (s, 2H), 3.91 (s, 2H), 2.58 (s, 3H).

Step 2. Synthesis of benzyl (5-methyl-4-oxidopyrazin-2-yl)acetate

A solution of benzyl 2-(5-methylpyrazin-2-yl)acetate (1.22 g, 5.03 mmol) in dichloromethane (50 mL) was placed under house vacuum and the reaction flask was refilled with nitrogen; this procedure was carried out three times. The solution was cooled to 0° C. and m-chloroperbenzoic acid (mCPBA; 886 mg, 5.13 mmol) was added in one portion, while keeping the solution temperature at 0° C. The reaction mixture was allowed to slowly warm to room temperature and was stirred for 20 hours, whereupon it was quenched with saturated aqueous sodium bicarbonate solution. The aqueous layer was extracted with dichloromethane, and the combined organic layers were dried over sodium sulfate, filtered, and concentrated in vacuo. The residue was purified via silica gel chromatography (Gradient: 0% to 80% ethyl acetate in heptane) to afford the product as a colorless oil, which became a white solid upon standing. Two-dimensional NMR NOE studies indicated that this material was the desired regioisomer. Yield: 616 mg, 47%. LCMS m/z 259.2 [M+H]$^+$. $^1$H NMR (400 MHz, CDCl$_3$) δ 8.41 (s, 1H), 8.20 (s, 1H), 7.44-7.31 (m, 5H), 5.20 (s, 2H), 3.84 (s, 2H), 2.47 (s, 3H).

The regioisomeric N-oxide was also isolated (200 mg, 15%), as well as some starting material (205 mg, 17%).

Step 3. Synthesis of benzyl {5-[(acetyloxy)methyl]pyrazin-2-yl}acetate

A solution of benzyl (5-methyl-4-oxidopyrazin-2-yl)acetate (591 mg, 2.29 mmol) in acetic anhydride (9.15 mL) was heated to 70° C. for 1 hour, and then at 100° C. for 24 hours. The reaction mixture was then cooled to room temperature, and the acetic anhydride and acetic acid were removed under vacuum on a rotary evaporator. The residue was dissolved in ethyl acetate and washed with saturated aqueous sodium bicarbonate solution. The organic layer was dried over sodium sulfate, filtered, and concentrated in vacuo. Chromatography on silica gel (Gradient: 0% to 70% ethyl acetate in heptane) provided the product as a yellow oil. Yield: 392 mg, 57%. LCMS m/z 301.2 [M+H]$^+$. $^1$H NMR (400 MHz, CDCl$_3$) δ 8.62 (d, J=1.5 Hz, 1H), 8.59 (d, J=1.5 Hz, 1H), 7.44-7.31 (m, 5H), 5.27 (s, 2H), 5.20 (s, 2H), 3.96 (s, 2H), 2.19 (s, 3H).

Step 4. Synthesis of {5-[(acetyloxy)methyl]pyrazin-2-yl}acetic acid

A mixture of benzyl {5-[(acetyloxy)methyl]pyrazin-2-yl}acetate (390 mg, 1.30 mmol) and palladium on carbon (150 mg, 10% Pd basis) in ethyl acetate (13.0 mL) was placed in a Hastelloy reactor and the atmosphere was purged three times with nitrogen, and then purged three times with hydrogen. The reaction mixture was stirred at room temperature under 30 psi hydrogen for 2 hours, whereupon it was filtered. The filter cake was washed with ethyl acetate, and the combined filtrates were concentrated in vacuo to provide the product as a yellow oil. Yield: 186 mg, 68% mass recovery. Spectral data and thin-layer chromatographic analysis indicated that the product was contaminated with the product of hydrogenolysis of the acetoxy group (~3:4 methyl to acetoxymethyl by NMR). This mixture was carried to the next step without further purification.

Step 5. Synthesis of [5-({8-chloro-1-[(2R,4R)-2-methyltetrahydro-2H-pyran-4-yl]-1H-imidazo[4,5-c]quinolin-2-yl}methyl)pyrazin-2-yl]methyl acetate A mixture of P10 (246 mg, 0.843 mmol) and {5-[(acetyloxy)methyl]pyrazin-2-yl}acetic acid (186 mg, 0.885 mmol, as a mixture from the previous step) in toluene (17.7 mL) was treated with N,N-diisopropylethylamine (176 µL, 1.01 mmol) and 2,4,6-tripropyl-1,3,5,2,4,6-trioxatriphosphinane 2,4,6-trioxide (50% solution in ethyl acetate; (1.51 mL, 2.53 mmol). The reaction mixture was heated to 70° C. for 1 hour, and then at 110° C. for 4 hours. The reaction mixture was allowed to cool to ambient temperature and was then quenched by addition of saturated aqueous sodium bicarbonate solution, and extracted with ethyl acetate. The combined organic layers were dried over sodium sulfate, filtered, and concentrated in vacuo. Silica gel chromatography (Gradient: 0% to 10% methanol in dichloromethane) afforded two products. The desired product was obtained as a light brown oil. Yield: 206 mg, 50%. LCMS m/z 466.2 [M+H]$^+$. $^1$H NMR (400 MHz, CDCl$_3$) δ 9.28 (s, 1H), 8.73 (s, 1H), 8.67 (s, 1H), 8.59 (s, 1H), 8.24 (d, J=9.0 Hz, 1H), 7.66 (dd, J=8.9, 2.1 Hz, 1H), 5.30 (br s, 1H), 5.27 (s, 2H), 4.73 (s, 2H), 4.34 (dd, J=12.0, 5.1 Hz, 1H), 3.73 (br s, 2H), 2.75 (br s, 1H), 2.48 (br s, 1H), 2.17 (s, 3H), 1.85 (br s, 1H), 1.74 (br s, 1H), 1.38 (d, J=6.1 Hz, 3H). Also obtained was a light yellow solid identified as the desacetoxy product 8-chloro-2-[(5-methylpyrazin-2-yl)methyl]-1-[(2R,4R)-2-methyltetrahydro-2H-pyran-4-yl]-1H-imidazo[4,5-c]quinoline (95A). Yield: 131 mg, 36%.

Step 6. Synthesis of [5-({8-chloro-1-[(2R,4R)-2-methyltetrahydro-2H-pyran-4-yl]-1H-imidazo[4,5-c]quinolin-2-yl}methyl)pyrazin-2-yl]methanol (95)

To a solution of [5-({8-chloro-1-[(2R,4R)-2-methyltetrahydro-2H-pyran-4-yl]-1H-imidazo[4,5-c]quinolin-2-yl}methyl)pyrazin-2-yl]methyl acetate (206 mg, 0.442 mmol) in methanol (10 mL) was added potassium carbonate (61.1 mg, 0.442 mmol). The resulting white suspension was stirred at room temperature for 30 minutes, whereupon it was diluted with water and extracted with dichloromethane. The organic layer was dried over sodium sulfate, filtered, and concentrated in vacuo. Chromatography on silica gel (Gradient: 0% to 20% methanol in dichloromethane) afforded a light yellow foam (151 mg). This material was recrystallized from diethyl ether and heptane to provide the product as a light yellow solid. Yield: 130 mg, 69%. LCMS m/z 424.2 [M+H]$^+$. $^1$H NMR (400 MHz, CDCl$_3$) δ 9.29 (s, 1H), 8.72-8.67 (m, 2H), 8.59 (s, 1H), 8.24 (d, J=8.9 Hz, 1H), 7.66 (dd, J=8.9, 2.1 Hz, 1H), 5.31 (br s, 1H), 4.87 (d, J=5.4 Hz, 2H), 4.73 (s, 2H), 4.34 (dd, J=12.1, 5.2 Hz, 1H), 3.74 (br s, 2H), 2.91 (br s, 1H), 2.76 (br s, 1H), 2.48 (br s, 1H), 1.88 (br s, 1H), 1.75 (br s, 1H), 1.38 (d, J=6.1 Hz, 3H).

Example 96

8-chloro-2-{[5-($^2$H$_3$)methylpyrazin-2-yl]methyl}-1-[(2R,4R)-2-methyltetrahydro-2H-pyran-4-yl]-1H-imidazo[4,5-c]quinoline (96); [5-({8-chloro-1-[(2R, 4R)-2-methyltetrahydro-2H-pyran-4-yl]-1H-imidazo [4,5-c]quinolin-2-yl}(2H3)methyl)pyrazine-2-yl]methanol (96B)

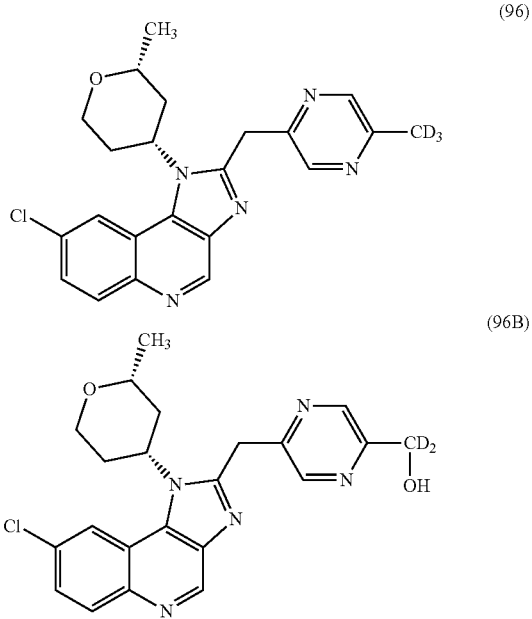

To 1.2 g of 8-chloro-2-[(5-methylpyrazin-2-yl)methyl]-1-[(2R,4R)-2-methyltetrahydro-2H-pyran-4-yl]-1H-imidazo[4,5-c]quinoline (95A) (yellow solid) was added 5.7 g of deuterated acetic acid (CD$_3$CO$_2$D) in a first container. The mixture was stirred at 120° C. for 20 hours and then concentrated. Proton NMR suggested >90% D/H exchange on the pyrazine methyl group.

In a second container, to 3.0 g of 8-chloro-2-[(5-methylpyrazin-2-yl)methyl]-1-[(2R,4R)-2-methyltetrahydro-2H-pyran-4-yl]-1H-imidazo[4,5-c]quinolone was added 50 mL deuterated acetic acid. The mixture was stirred at 120° C. for 24 hours and then concentrated.

The concentrated residues from the first and second containers were combined and dissolved in 75 mL of deuterated acetic acid. This solution was stirred at 120° C. for 24 hours and then concentrated. The residue was dissolved in 50 mL of deuterated acetic acid and stirred at 120° C. for 24 hours and then concentrated. The residue was dissolved in 120 mL ethyl acetate and washed with 60 mL saturated aqueous sodium carbonate solution. The organic layer was dried over magnesium sulfate and concentrated to furnish 4.4 g of a dark solid.

Part of this sample, 2.4 g, was dissolved in 100 mL acetic acid and stirred at room temperature for 24 hours and then concentrated. The residue was dissolved in 100 mL of acetic acid and stirred at room temperature for 24 hours and the concentrated. The residue was dissolved in 150 mL ethyl acetate, washed with 80 mL of 3:1 brine/ammonium hydroxide. Organic layer was dried over magnesium sulfate, concentrated to furnish 2.4 g of a dark color, which was purified using a step gradient method (20% B hold from 0 to 1.5 minutes, 20% to 70% B from 1.5 to 10 minutes, and finally 70 to 100% from 10 to 12 minutes; with mobile phase A being 0.05% formic acid in water and mobile phase B 0.05% formic acid in acetonitrile) on a Phenomenex Gemini NX C18 150 mm×21.2 mm 5 um column at a flow rate of 27 mL/min. The collected fractions were lyophilized to furnish off-white fluffy solid samples with a combined weight of 2.12 g.

Analytical data: [M+H]$^+$ observed 411.178 (predicted 411.178); HPLC retention time 4.12 min on a C$^{18}$ 100 mm×3.0 mm 2.6 um column with 5% B from 0 to 1.5 min, 5 to 100% B from 1.5 to 4.0 min and hold at 100% from 4.0 to 5.4 min (A 0.1% formic acid in water, B 0.1% formic acid in acetonitrile); $^1$H NMR (600 MHz, DMSO-d$_6$) δ 9.17 (s, 1H), 8.66 (s, 2H), 8.46 (d, J=1.5 Hz, 1H), 8.19 (d, J=8.9 Hz, 1H), 7.74 (dd, J=8.9, 2.2 Hz, 1H), 5.27 (m, 1H), 4.77 (s, 2H), 4.16 (m, 1H), 3.69 (m, 1H), 3.60 (m, 1H), 2.47 (m, 1H), 2.21 (m, 1H), 2.09-1.92 (m, 1H), 1.85 (m, 1H), 1.22 (d, J=6.1 Hz, 3H).

Biological Assays

LRRK2 Assay

LRRK2 kinase activity was measured using Lantha Screen technology from Invitrogen. GST-tagged truncated LRRK2 from Invitrogen (Cat #PV4874) was incubated with a fluorescein-labeled peptide substrate based upon ezrin/radixin/moesin (ERM), also known as LRRKtide (Invitrogen cat #PR8976A), in the presence of a dose response of compound. Upon completion, the assay was stopped and detected with a terbium labeled anti-phospho-ERM antibody (Invitrogen, cat #PR8975A). The assay was carried out under the following protocol: The compound dose response was prepared by diluting compound to a top concentration of 0.3 mM in 100% DMSO and serial diluted by half-log in DMSO to give an 11 point curve, 100× final assay concentration. Using Echo acoustic dispensing, 60 nL of compound was transferred to a low volume Corning 384-well assay plate. 3 µL of a working solution of substrate (200 nM LRRKtide, 2 mM ATP) prepared in assay buffer (50 mM HEPES, pH 7.5, 3 mM MgCl$_2$, with 2 mM DTT and 0.01% Brij35 added fresh) was added to the 60 nL compound assay plate. The kinase reaction was started with 3 µL of a working solution of LRRK2 enzyme at a concentration of 4 µg/m L. The final reaction concentrations were 100 nM LRRKtide, 1 mM ATP, 2 µg/mL LRRK2 enzyme and a compound dose response with a top dose of 3 µM. The reaction was allowed to progress at room temperature for 30 minutes and then stopped with the addition of 6 µL of detection buffer (20 mM Tris pH 7.6, 0.01% NP-40, 6 mM EDTA with 2 nM terbium labeled antiphospho-ERM). After an incubation of 1 hour at room temperature, the plate was read on an Envision with an excitation wavelength of 340 nm and a reading emission at both 520 nm and 495 nm. The ratio of the 520 nm and 495 nm emission was used to analyze the data. Inhibition of mutant G2019S LRRK2 (Invitrogen cat #PV4881) was measured in the exact same method. All final concentrations of substrate ATP and enzyme were the same.

TABLE 3

IUPAC name and biological data for Examples 1-96

| Example Number | IUPAC Name | LRRK2, WT IC$_{50}$ (nM); (Number of determinations) | LRRK2, G2019S IC$_{50}$ (nM); (Number of determinations) |
|---|---|---|---|
| 1 | [(2S,4R)-4-(8-chloro-2-ethyl-1H-imidazo[4,5-c]quinolin-1-yl)tetrahydro-2H-pyran-2-yl]acetonitrile | 10.2 (2) | 8.87 (1) |
| 2 | [(2R,4S)-4-(8-chloro-2-ethyl-1H-imidazo[4,5-c]quinolin-1-yl)tetrahydro-2H-pyran-2-yl]acetonitrile | 1530 (2) | N.D.$^a$ |
| 3 | 1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 1 | 31.8 (5) | N.D. |
| 4 | 1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 2 | 17.6 (5) | 3.31 (1) |
| 5 | 8-chloro-1-[(4S)-3,3-difluorotetrahydro-2H-pyran-4-yl]-2-[(5-methyl-1,2-oxazol-3-yl)methyl]-1H-imidazo[4,5-c]quinoline | 14.6 (2) | 9.41 (1) |
| 6 | 2-[(6-methylpyrimidin-4-yl)methyl]-1-[(3R)-1-methylpyrrolidin-3-yl]-1H-imidazo[4,5-c]quinoline-8-carbonitrile, formate salt | 6.39 (2) | 11.3 (1) |
| 7 | 8-chloro-1-(3,3-difluorotetrahydro-2H-pyran-4-yl)-2-[(5-methylpyrazin-2-yl)methyl]-1H-imidazo[4,5-c]quinoline, ENT 1 | 47.9 (2) | 39.7 (1) |
| 8 | 8-chloro-1-(3,3-difluorotetrahydro-2H-pyran-4-yl)-2-[(5-methylpyrazin-2-yl)methyl]-1H-imidazo[4,5-c]quinoline, ENT 2 | 11.8 (2) | 11.6 (1) |
| 9 | 1-[(2R,4R)-2-methyltetrahydro-2H-pyran-4-yl]-2-[(1-methyl-1H-1,2,3-triazol-4-yl)methyl]-8-(trifluoromethyl)-1H-imidazo[4,5-c]quinoline | 11.8 (2) | 5.55 (1) |
| 10 | [cis-4-(8-chloro-2-cyclobutyl-1H-imidazo[4,5-c]quinolin-1-yl)tetrahydro-2H-pyran-2-yl]acetonitrile, ENT 1 | 1790 (2) | N.D. |
| 11 | [cis-4-(8-chloro-2-cyclobutyl-1H-imidazo[4,5-c]quinolin-1-yl)tetrahydro-2H-pyran-2-yl]acetonitrile, ENT 2 | 18.0 (2) | 5.06 (1) |
| 12 | 8-(difluoromethyl)-2-[(4-methoxy-1H-pyrazol-1-yl)methyl]-1-[(2R,4R)-2-methyltetrahydro-2H-pyran-4-yl]-1H-imidazo[4,5-c]quinoline | 8.77 (2) | 4.38 (1) |
| 13 | 8-(difluoromethyl)-2-[(5-methylpyrazin-2-yl)methyl]-1-[(2R,4R)-2-methyltetrahydro-2H-pyran-4-yl]-1H-imidazo[4,5-c]quinoline | 9.72 (3) | 7.77 (2) |
| 14 | {8-chloro-1-[(2R,4R)-2-methyltetrahydro-2H-pyran-4-yl]-1H-imidazo[4,5-c]quinolin-2-yl}(5-methylpyrazin-2-yl)methanol, DIAST 1 | 14.2 (3) | 12.8 (3) |
| 15 | {8-chloro-1-[(2R,4R)-2-methyltetrahydro-2H-pyran-4-yl]-1H-imidazo[4,5-c]quinolin-2-yl}(5-methylpyrazin-2-yl)methanol, DIAST 2 | 16.3 (3) | 18.4 (3) |
| 16 | 1-(4,4-difluoro-1-methylpyrrolidin-3-yl)-8-fluoro-2-(1H-1,2,4-triazol-1-ylmethyl)-1H-imidazo[4,5-c]quinoline, ENT 1 | 731 (2) | N.D. |
| 17 | 1-(4,4-difluoro-1-methylpyrrolidin-3-yl)-8-fluoro-2-(1H-1,2,4-triazol-1-ylmethyl)-1H-imidazo[4,5-c]quinoline, ENT 2 | 6.49 (2) | 7.57 (1) |
| 18 | 1-(4,4-difluoro-1-methylpyrrolidin-3-yl)-8-fluoro-2-[(4-methyl-1H-1,2,3-triazol-1-yl)methyl]-1H-imidazo[4,5-c]quinoline, ENT 1 | 263 (2) | N.D. |

TABLE 3-continued

IUPAC name and biological data for Examples 1-96

| Example Number | IUPAC Name | LRRK2, WT IC$_{50}$ (nM); (Number of determinations) | LRRK2, G2019S IC$_{50}$ (nM); (Number of determinations) |
|---|---|---|---|
| 19 | 1-(4,4-difluoro-1-methylpyrrolidin-3-yl)-8-fluoro-2-[(4-methyl-1H-1,2,3-triazol-1-yl) methyl]-1H-imidazo[4,5-c]quinoline, ENT 2 | 5.43 (2) | 8.12 (1) |
| 20 | 1-(4,4-difluoro-1-methylpyrrolidin-3-yl)-8-fluoro-2-[(5-methylpyrazin-2-yl)methyl]-1H-imidazo[4,5-c]quinoline, ENT 1 | 4.12 (2) | 3.31 (1) |
| 21 | 1-(4,4-difluoro-1-methylpyrrolidin-3-yl)-8-fluoro-2-[(5-methylpyrazin-2-yl)methyl]-1H-imidazo[4,5-c]quinoline, ENT 2 | 235 (2) | N.D. |
| 22 | 8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 1 | 138 (3) | N.D. |
| 23 | 8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 2 | 2.35 (2) | 1.35 (1) |
| 24 | 8-chloro-1-(4,4-difluoro-1-methylpyrrolidin-3-yl)-2-(1H-1,2,4-triazol-1-ylmethyl)-1H-imidazo[4,5-c]quinoline, ENT 1 | 2.77 (3) | 1.19 (1) |
| 25 | 8-chloro-1-(4,4-difluoro-1-methylpyrrolidin-3-yl)-2-(1H-1,2,4-triazol-1-ylmethyl)-1H-imidazo[4,5-c]quinoline, ENT 2 | 318 (2) | N.D. |
| 26 | 8-chloro-1-(3,3-difluorotetrahydro-2H-pyran-4-yl)-2-[(4-methoxy-1H-pyrazol-1-yl)methyl]-1H-imidazo[4,5-c]quinoline, ENT 1 | 5.90 (1) | N.D. |
| 27 | 8-chloro-1-(3,3-difluorotetrahydro-2H-pyran-4-yl)-2-[(4-methoxy-1H-pyrazol-1-yl)methyl]-1H-imidazo[4,5-c]quinoline, ENT 2 | 29.1 (3) | 20.3 (1) |
| 28 | 8-fluoro-2-[(2-methylimidazo[2,1-b][1,3,4]thiadiazol-6-yl)methyl]-1-[(2R,4R)-2-methyltetrahydro-2H-pyran-4-yl]-1H-imidazo[4,5-c]quinoline, formate salt | 7.18 (2) | 4.59 (1) |
| 29 | 2-[(5-methylpyrazin-2-yl)methyl]-1-[(2R,4R)-2-methyltetrahydro-2H-pyran-4-yl]-8-(trifluoromethyl)-1H-imidazo[4,5-c]quinoline | 6.47 (6) | 4.13 (5) |
| 30 | 2-cyclopentyl-1-[(2R,4R)-2-methyltetrahydro-2H-pyran-4-yl]-1H-imidazo[4,5-c]quinoline-8-carbonitrile, formate salt | 20.6 (2) | 22.0 (2) |
| 31 | [cis-4-(8-chloro-2-methyl-1H-imidazo[4,5-c]quinolin-1-yl)tetrahydro-2H-pyran-2-yl]acetonitrile, ENT 1 | 7.86 (2) | 8.67 (1) |
| 32 | 1-(4,4-difluoro-1-methylpyrrolidin-3-yl)-2-[(5-methyl-1,2,4-oxadiazol-3-yl)methyl]-1H-imidazo[4,5-c]quinoline-8-carbonitrile, ENT 1 | 4.59 (2) | 5.98 (1) |
| 33 | 2-[(5-methylpyrazin-2-yl)methyl]-1-[(3R)-1-methylpyrrolidin-3-yl]-1H-imidazo[4,5-c]quinoline-8-carbonitrile | 8.35$^b$ (2) | 6.82$^b$ (1) |
| 34 | 1-[(3R)-1-methylpyrrolidin-3-yl]-2-[(5-methyl-2H-tetrazol-2-yl)methyl]-1H-imidazo[4,5-c]quinoline-8-carbonitrile, formate salt | 5.53 (2) | 5.04 (1) |
| 35 | 2-[(3-methyl-1,2-oxazol-5-yl)methyl]-1-[(3R)-1-methylpyrrolidin-3-yl]-1H-imidazo[4,5-c]quinoline-8-carbonitrile, formate salt | 7.57 (2) | 6.17 (1) |
| 36 | 2-[(4-methoxy-1H-pyrazol-1-yl)methyl]-1-[(3R)-1-methylpyrrolidin-3-yl]-1H-imidazo[4,5-c]quinoline-8-carbonitrile, formate salt | 5.00 (2) | 4.63 (1) |
| 37 | 1-[(3R)-1-methylpyrrolidin-3-yl]-2-[(5-methyl-1,3,4-thiadiazol-2-yl)methyl]-1H-imidazo[4,5-c]quinoline-8-carbonitrile | 5.26 (2) | 12.6 (1) |
| 38 | 2-[(5-methyl-1,3-oxazol-2-yl)methyl]-1-[(3R)-1-methylpyrrolidin-3-yl]-1H-imidazo[4,5-c]quinoline-8-carbonitrile | 7.49 (2) | 12.9 (1) |
| 39 | 1-[(2R,4R)-2-methyltetrahydro-2H-pyran-4-yl]-2-{[5-(trifluoromethyl)pyrazin-2-yl]methyl}-1H-imidazo[4,5-c]quinoline-8-carbonitrile, formate salt | 17.4 (4) | 9.30 (3) |
| 40 | 8-chloro-2-[(6-methylpyrimidin-4-yl)methyl]-1-[(3R)-1-methylpyrrolidin-3-yl]-1H-imidazo[4,5-c]quinoline | 9.73 (2) | 13.9 (1) |

TABLE 3-continued

IUPAC name and biological data for Examples 1-96

| Example Number | IUPAC Name | LRRK2, WT IC$_{50}$ (nM); (Number of determinations) | LRRK2, G2019S IC$_{50}$ (nM); (Number of determinations) |
|---|---|---|---|
| 41 | 2-[(4-methoxy-1H-pyrazol-1-yl)methyl]-1-[(2R,4R)-2-methyltetrahydro-2H-pyran-4-yl]-8-(trifluoromethyl)-1H-imidazo[4,5-c]quinoline | 11.1 (2) | 3.87 (1) |
| 42 | 8-chloro-2-[(5-methyl-1,2,4-oxadiazol-3-yl)methyl]-1-[(3R)-1-methylpyrrolidin-3-yl]-1H-imidazo[4,5-c]quinoline | 12.9 (2) | 26.0 (1) |
| 43 | 8-chloro-1-(4,4-difluoro-1-methylpyrrolidin-3-yl)-2-(1H-1,2,4-triazol-1-ylmethyl)-1H-imidazo[4,5-c]quinoline, trifluoroacetate salt | 5.87 (2) | 8.53 (1) |
| 44 | 8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, trifluoroacetate salt | 6.02 (2) | 4.53 (1) |
| 45 | 8-chloro-1-(4,4-difluoro-1-methylpyrrolidin-3-yl)-2-[(5-methyl-1,2,4-oxadiazol-3-yl)methyl]-1H-imidazo[4,5-c]quinoline, trifluoroacetate salt | 8.13 (2) | 5.82 (1) |
| 46 | 8-chloro-1-(3,3-difluorotetrahydro-2H-pyran-4-yl)-2-[(4-methyl-1H-1,2,3-triazol-1-yl)methyl]-1H-imidazo[4,5-c]quinoline, ENT 1 | 9.31 (2) | 7.66 (1) |
| 47 | 8-chloro-2-[(4-cyclopropyl-1H-1,2,3-triazol-1-yl)methyl]-1-(4,4-difluoro-1-methylpyrrolidin-3-yl)-1H-imidazo[4,5-c]quinoline, ENT 2 | 2.80 (2) | 1.42 (1) |
| 48 | 8-chloro-1-(4,4-difluoro-1-methylpyrrolidin-3-yl)-2-[(4-methyl-1H-1,2,3-triazol-1-yl)methyl]-1H-imidazo[4,5-c]quinoline, ENT 2 | 3.27 (2) | 0.938 (1) |
| 49 | 8-chloro-1-(4,4-difluoro-1-methylpyrrolidin-3-yl)-2-[(5-methyl-2H-tetrazol-2-yl)methyl]-1H-imidazo[4,5-c]quinoline, ENT 1 | 4.48 (2) | 1.34 (1) |
| 50 | 8-chloro-1-(4,4-difluoro-1-methylpyrrolidin-3-yl)-2-[(5-methylpyrazin-2-yl)methyl]-1H-imidazo[4,5-c]quinoline, ENT 1 | 5.06 (2) | 1.11 (1) |
| 51 | 8-chloro-1-(4,4-difluoro-1-methylpyrrolidin-3-yl)-2-[(5-methyl-1,2-oxazol-3-yl)methyl]-1H-imidazo[4,5-c]quinoline, ENT 1 | 5.78 (2) | 3.49 (1) |
| 52 | 8-chloro-1-(4,4-difluoro-1-methylpyrrolidin-3-yl)-2-[(5-methyl-1,2-oxazol-3-yl)methyl]-1H-imidazo[4,5-c]quinoline, ENT 2 | 15.1 (2) | 12.9 (1) |
| 53 | 1-(4,4-difluoro-1-methylpyrrolidin-3-yl)-8-fluoro-2-{[4-(methoxymethyl)-1H-1,2,3-triazol-1-yl]methyl}-1H-imidazo[4,5-c] quinoline, ENT 2 | 7.51 (2) | 7.49 (1) |
| 54 | 8-chloro-1-(3,3-difluorotetrahydro-2H-pyran-4-yl)-2-(1H-1,2,4-triazol-1-ylmethyl)-1H-imidazo[4,5-c]quinoline, ENT 2 | 10.3 (1) | N.D. |
| 55 | 8-chloro-1-(3,3-difluorotetrahydro-2H-pyran-4-yl)-2-{[4-(methoxymethyl)-1H-1,2,3-triazol-1-yl]methyl}-1H-imidazo[4,5-c]quinoline, ENT 1 | 11.3 (3) | 6.49 (1) |
| 56 | 2-[(5-methyl-1,2,4-oxadiazol-3-yl)methyl]-1-[(3R)-1-(2,2,2-trifluoroethyl)pyrrolidin-3-yl]-1H-imidazo[4,5-c]quinoline-8-carbonitrile | 6.46 (2) | 6.48 (1) |
| 57 | 2-[(4-methoxy-1H-pyrazol-1-yl)methyl]-1-[(2R,4R)-2-methyltetrahydro-2H-pyran-4-yl]-1H-imidazo[4,5-c]quinoline-8-carbonitrile, formate salt | 7.43 (2) | 5.40 (1) |
| 58 | 8-chloro-1-[(2R,4R)-2-methyltetrahydro-2H-pyran-4-yl]-2-(1,3-thiazol-2-ylmethyl)-1H-imidazo[4,5-c]quinoline, formate salt | 5.35 (2) | 3.00 (1) |
| 59 | 8-chloro-1-[cis-2-(difluoromethyl)tetrahydro-2H-pyran-4-yl]-2-[(5-methyl-1,2-oxazol-3-yl)methyl]-1H-imidazo[4,5-c]quinoline, ENT 1 | 6.60 (2) | 8.16 (1) |
| 60 | 8-chloro-1-(3,3-difluorotetrahydro-2H-pyran-4-yl)-2-[(5-methyl-1,2-oxazol-3-yl)methyl]-1H-imidazo[4,5-c]quinoline, ENT 1 | 11.4 (2) | 16.3 (1) |
| 61 | 1-[(2R,4R)-2-methyltetrahydro-2H-pyran-4-yl]-2-(1,3-thiazol-2-ylmethyl)-1H-imidazo[4,5-c]quinoline-8-carbonitrile, formate salt | 5.79 (2) | 4.17 (1) |
| 62 | 8-chloro-1-[(3R)-1-methylpyrrolidin-3-yl]-2-[(4-methyl-1H-1,2,3-triazol-1-yl)methyl]-1H-imidazo[4,5-c]quinoline | 5.78 (3) | 6.50 (1) |

TABLE 3-continued

IUPAC name and biological data for Examples 1-96

| Example Number | IUPAC Name | LRRK2, WT IC$_{50}$ (nM); (Number of determinations) | LRRK2, G2019S IC$_{50}$ (nM); (Number of determinations) |
|---|---|---|---|
| 63 | 1-[(2R,4R)-2-methyltetrahydro-2H-pyran-4-yl]-2-(1,2,3-thiadiazol-4-ylmethyl)-8-(trifluoromethyl)-1H-imidazo[4,5-c]quinoline, formate salt | 6.96 (2) | 3.04 (1) |
| 64 | 8-fluoro-1-[(2R,4R)-2-methyltetrahydro-2H-pyran-4-yl]-2-(1,3-thiazol-2-ylmethyl)-1H-imidazo[4,5-c]quinoline, formate salt | 9.80 (2) | 6.87 (1) |
| 65 | 2-(1,3-benzoxazol-2-ylmethyl)-1-[cis-3-fluorocyclopentyl]-1H-imidazo[4,5-c]quinoline-8-carbonitrile | 8.56 (2) | 6.33 (1) |
| 66 | 1-[(2R,4R)-2-methyltetrahydro-2H-pyran-4-yl]-2-(1H-1,2,4-triazol-1-ylmethyl)-8-(trifluoromethyl)-1H-imidazo[4,5-c]quinoline | 8.32 (2) | 8.01 (1) |
| 67 | 8-chloro-2-[(5-methylpyrazin-2-yl)methyl]-1-[(3R)-1-methylpyrrolidin-3-yl]-1H-imidazo [4,5-c]quinoline | 8.03 (3) | 8.55 (1) |
| 68 | 1-[cis-3-fluorocyclopentyl]-2-[(5-methyl-1,2-oxazol-3-yl)methyl]-1H-imidazo[4,5-c] quinoline-8-carbonitrile | 8.32$^b$ (2) | 12.3$^b$ (2) |
| 69 | 1-[(2R,4R)-2-methyltetrahydro-2H-pyran-4-yl]-2-(1,3-thiazol-4-ylmethyl)-8-(trifluoromethyl)-1H-imidazo[4,5-c]quinoline, formate salt | 7.39 (2) | 3.33 (1) |
| 70 | 2-[(5-methyl-1,3,4-oxadiazol-2-yl)methyl]-1-[(2R,4R)-2-methyltetrahydro-2H-pyran-4-yl]-8-(trifluoromethyl)-1H-imidazo[4,5-c] quinoline | 13.7 (2) | 7.59 (1) |
| 71 | 8-chloro-1-(2,2-dimethyltetrahydro-2H-pyran-4-yl)-2-(1H-1,2,4-triazol-1-ylmethyl)-1H-imidazo [4,5-c]quinoline, formate salt | 13.7 (2) | 11.9 (2) |
| 72 | 8-chloro-1-(2,2-difluoropropyl)-2-[(4-methoxy-1H-pyrazol-1-yl)methyl]-1H-imidazo[4,5-c] quinoline, formate salt | 12.1 (2) | 7.17 (1) |
| 73 | 8-fluoro-1-[(2R,4R)-2-methyltetrahydro-2H-pyran-4-yl]-2-{[5-(trifluoromethyl)pyrazin-2-yl]methyl}-1H-imidazo[4,5-c]quinoline, formate salt | 16.9 (2) | 13.0 (1) |
| 74 | 1-[(2R,4R)-2-methyltetrahydro-2H-pyran-4-yl]-2-[(5-methyl-1,3,4-thiadiazol-2-yl)methyl]-8-(trifluoromethyl)-1H-imidazo[4,5-c] quinoline | 26.1 (2) | 13.5 (1) |
| 75 | 8-chloro-1-(3,3-difluorotetrahydro-2H-pyran-4-yl)-2-[(5-methyl-1,2,4-oxadiazol-3-yl) methyl]-1H-imidazo[4,5-c]quinoline, ENT 1 | 25.7 (2) | 26.5 (1) |
| 76 | 2-[(6-methylpyrimidin-4-yl)methyl]-1-[(2R,4R)-2-methyltetrahydro-2H-pyran-4-yl]-8-(trifluoromethyl)-1H-imidazo[4,5-c]quinoline | 17.3 (2) | 12.0 (1) |
| 77 | 8-chloro-1-[cis-3-fluorocyclopentyl]-2-[(5-methylpyrazin-2-yl)methyl]-1H-imidazo[4,5-c] quinoline, formate salt | 13.0 (2) | 11.8 (1) |
| 78 | 3-{8-chloro-1-[(2R,4R)-2-methyltetrahydro-2H-pyran-4-yl]-1H-imidazo[4,5-c]quinolin-2-yl}-2-methylpropanenitrile, DIAST 2 | 25.8 (2) | 13.2 (1) |
| 79 | 8-fluoro-1-[cis-3-fluorocyclopentyl]-2-(1,2,3-thiadiazol-4-ylmethyl)-1H-imidazo[4,5-c] quinoline, ENT 2 | 9.73 (3) | 9.75 (1) |
| 80 | 3-{8-chloro-1-[(2R,4R)-2-methyltetrahydro-2H-pyran-4-yl]-1H-imidazo[4,5-c]quinolin-2-yl}propanenitrile, formate salt | 9.40 (2) | 11.3 (2) |
| 81 | 1-[(2R,4R)-2-methyltetrahydro-2H-pyran-4-yl]-2-[(5-methyl-2H-tetrazol-2-yl)methyl]-8-(trifluoromethyl)-1H-imidazo[4,5-c]quinoline, formate salt | 16.9 (2) | 7.50 (1) |
| 82 | 8-chloro-1-(4,4-difluoro-1-methylpyrrolidin-3-yl)-2-[(4-methyl-1H-1,2,3-triazol-1-yl)methyl]-1H-imidazo[4,5-c]quinoline, trifluoroacetate salt | 6.33 (2) | 4.64 (1) |
| 83 | 8-chloro-1-(4,4-difluoro-1-methylpyrrolidin-3-yl)-2-(1H-tetrazol-1-ylmethyl)-1H-imidazo[4,5-c]quinoline, trifluoroacetate salt | 7.91 (2) | 11.6 (1) |
| 84 | 8-chloro-1-(4,4-difluoro-1-methylpyrrolidin-3-yl)-2-[(1-methyl-1H-1,2,4-triazol-3-yl)methyl]-1H-imidazo[4,5-c]quinoline, trifluoroacetate salt | 10.2 (2) | 18.2 (1) |

TABLE 3-continued

IUPAC name and biological data for Examples 1-96

| Example Number | IUPAC Name | LRRK2, WT IC$_{50}$ (nM); (Number of determinations) | LRRK2, G2019S IC$_{50}$ (nM); (Number of determinations) |
|---|---|---|---|
| 85 | 1-(4,4-difluoro-1-methylpyrrolidin-3-yl)-8-fluoro-2-[(2-methylimidazo[2,1-b][1,3,4] thiadiazol-6-yl)methyl]-1H-imidazo[4,5-c] quinoline, ENT 1 | 2.62 (2) | 3.31 (1) |
| 86 | 8-chloro-1-(4,4-difluoro-1-methylpyrrolidin-3-yl)-2-(1H-tetrazol-1-ylmethyl)-1H-imidazo [4,5-c]quinoline, ENT 2 | 6.66 (2) | 4.40 (1) |
| 87 | 8-chloro-1-(4,4-difluoro-1-methylpyrrolidin-3-yl)-2-[(4-methyl-2H-1,2,3-triazol-2-yl)methyl]-1H-imidazo[4,5-c]quinoline, ENT 1 | 7.04 (2) | 4.51 (1) |
| 88 | 8-chloro-1-(4,4-difluoro-1-methylpyrrolidin-3-yl)-2-[(5-methyl-1,2,4-oxadiazol-3-yl)methyl]-1H-imidazo[4,5-c]quinoline, ENT 1 | 9.25 (2) | 8.16 (1) |
| 89 | 8-chloro-1-(4,4-difluoro-1-methylpyrrolidin-3-yl)-2-[(5-methyl-1,3,4-thiadiazol-2-yl)methyl]-1H-imidazo[4,5-c]quinoline, ENT 2 | 13.9 (2) | 8.03 (1) |
| 90 | 8-(difluoromethyl)-1-[(2R,4R)-2-methyltetrahydro-2H-pyran-4-yl]-2-[(4-methyl-1H-1,2,3-triazol-1-yl)methyl]-1H-imidazo[4,5-c]quinoline, trifluoroacetate salt | 14.7 (2) | 7.32 (1) |
| 91 | 8-(difluoromethyl)-2-[(5-methyl-1,2-oxazol-3-yl)methyl]-1-[(2R,4R)-2-methyltetrahydro-2H-pyran-4-yl]-1H-imidazo[4,5-c]quinoline, trifluoroacetate salt | 18.0 (4) | 8.40 (3) |
| 92 | 8-chloro-1-(3,3-difluorotetrahydro-2H-pyran-4-yl)-2-[(5-methyl-1,3,4-thiadiazol-2-yl) methyl]-1H-imidazo[4,5-c]quinoline, ENT 1 | 10.9 (3) | 6.91 (1) |
| 93 | 8-chloro-1-(3,3-difluorotetrahydro-2H-pyran-4-yl)-2-(1H-1,2,4-triazol-1-ylmethyl)-1H-imidazo[4,5-c]quinoline, ENT 1 | 11.9 (3) | 8.70 (1) |
| 94 | 8-chloro-2-[(4-cyclopropyl-1H-1,2,3-triazol-1-yl)methyl]-1-(3,3-difluorotetrahydro-2H-pyran-4-yl)-1H-imidazo[4,5-c]quinoline, ENT-1 | 6.35 (3) | 6.48 (1) |
| 95 | [5-({8-chloro-1-[(2R,4R)-2-methyltetrahydro-2H-pyran-4-yl]-1H-imidazo[4,5-c]quinolin-2-yl}methyl)pyrazin-2-yl]methanol | 4.60 (13) | 3.50 (4) |
| 95A | 8-chloro-2-[(5-methylpyrazin-2-yl)methyl]-1-[(2R,4R)-2-methyltetrahydro-2H-pyran-4-yl]-1H-imidazo[4,5-c]quinoline | 7.32 (6) | 6.06 (5) |
| 96 | 8-chloro-2-{[5-($^2$H$_3$)methylpyrazin-2-yl]methyl}-1-[(2R,4R)-2-methyltetrahydro-2H-pyran-4-yl]-1H-imidazo[4,5-c]quinoline | 3.21 (1) | 2.16 (1) |

$^a$Not determined
$^b$In this case, the biological data was obtained using the formate salt of the Example.

Intrinsic Clearance (CL$_{int}$) in Human Liver Microsomes

Incubations (in duplicate) contained either 95A or 96, or both 95A and 96 at final concentrations of 1 µM, human liver microsomes (BD Biosciences Bedford, Mass., 0.25 µM CYP protein equivalent to 0.801 mg/mL protein concentration), NADPH (1.3 mM), MgCl$_2$ (3.3 mM) and potassium phosphate buffer (100 mM, pH 7.4). The final reaction volume (500 µL) contained 0.003% DMSO, 0.5% acetonitrile. The incubations were conducted at 37° C. and aliquots (50 µL) were removed at 0, 5, 10, 15, 20, 30, 45 and 60 minutes and quenched by addition to cold acetonitrile containing mass spectrometry (MS) internal standard (200 µL). Quenched incubations were vortex for 1 minute followed by centrifugation at 3000 rpm for 5 minutes at room temperature (Allegra X-12R, Beckman Coulter, Fullerton, Calif.). The supernatant (150 µL) was then removed and added to a 96-deep well injection plate containing 150 µL of water with 0.1% formic acid (v/v), the plates were capped and vortex for 1 minute and subsequently analyzed using LC-MS/MS as described below. Control incubations were prepared similar without adding the NADPH cofactor to monitor for any non-CYP/FMO metabolism. Discrete standard curves (0.5-2000 nM) were prepared, processed, and analyzed as described above.

The amount of substrate (95A or 96) and metabolite (95 or 96B) were measured and the results are shown in Tables 4a and Table 4b. Example 96 has a decreased intrinsic clearance (increased half-life=T$_{1/2}$) in comparison to its corresponding undeuterated form (95A) which can be beneficial (e.g., decreased dosage) while maintaining beneficial properties. In addition, Example 96 has a lower rate of metabolite (96B) formation in comparison to the undeuterated metabolite (95) formed from Example 95A. In the combined substrates (competition) experiment, Example 96 shows a decreased intrinsic clearance (increased T$_{1/2}$) in comparison to its corresponding undeuterated form (95A), and has a lower rate of metabolite formation in comparison to the undeuterated form (95A).

TABLE 4a

CL$_{int}$ in the human liver microsome assay using individual substrates

| Example | CLint (μL/min/mg) | T½ (min) | Rate of metabolite (nmol/min/mg) |
|---|---|---|---|
| 95A | 15.98 | 54.4 | 8.54 |
| 96 | 6.68 | 90.4 | 1.10 |

TABLE 4b

CL$_{int}$ in the human liver microsome assay using combined substrates - competition

| Example | CLint (μL/min/mg) | T½ (min) | Rate of metabolite (nmol/min/mg) |
|---|---|---|---|
| 95A and 96 (for 95A) | 13.98 | 65.9 | 7.39 |
| 95A and 96 (for 96) | 6.86 | 126.6 | 1.65 |

TABLE 5a

CL$_{int}$ in the monkey liver microsome assay using individual substrates

| Example | CLint (μL/min/mg) | T½ (min) | Rate of metabolite (nmol/min/mg) |
|---|---|---|---|
| 95A | 215.1 | 15.3 | 109.05 |
| 96 | 150.7 | 21.9 | 22.83 |

TABLE 5b

CL$_{int}$ in the monkey liver microsome assay using combined substrates - competition

| Example | CLint (μL/min/mg) | T½ (min) | Rate of metabolite (nmol/min/mg) |
|---|---|---|---|
| 95A and 96 (for 95A) | 192.8 | 17.2 | 97.19 |
| 95A and 96 (for 96) | 110.4 | 29.9 | 25.19 |

Intrinsic Clearance (CL$_{int}$) in Cynomolgus Monkey Liver Microsomes

Incubations (in duplicate) contained either 95A or 96, or both 95A and 96 at final concentrations of 1 μM, pooled cynomolgus monkey liver microsomes (Xenotech, LLC, Lenexa, Kans., 0.25 μM CYP protein equivalent to 0.21 mg/mL protein concentration), NADPH (1.3 mM), magnesium chloride (3.3 mM) and potassium phosphate buffer (100 mM, pH 7.4). The final reaction volume (500 μL) contained 0.003% DMSO, 0.5% acetonitrile. The incubations were conducted at 37° C. and aliquots (50 μL) were removed at 0, 5, 10, 15, 20, 30, 45 and 60 minutes and quenched by addition to cold acetonitrile containing mass spectrometry (MS) internal standard (200 μL). Quenched incubations were vortexed for 1 minute followed by centrifugation at 3000 rpm for 5 minutes at room temperature (Allegra X-12R, Beckman Coulter, Fullerton, Calif.). The supernatant (150 μL) was then removed and added to a 96-deep well injection plate containing 150 μL of water with 0.1% formic acid (v/v). The plates were capped and vortexed for 1 minute and subsequently analyzed using LC-MS/MS as described below. Control incubations were prepared similar without adding the NADPH cofactor to monitor for any non-CYP/FMO metabolism. Discrete standard curves (0.5-2000 nM) were prepared, processed, and analyzed as described above.

The amount of substrate (95A or 96) and metabolite (95 or 96B) were measured and the results are shown in Tables 5a and Table 5b. Example 96 has a decreased intrinsic clearance (increased half-life=T$_{1/2}$) in comparison to its corresponding undeuterated form (95A) which can be beneficial (e.g., decreased dosage) while maintaining beneficial properties. In addition, Example 96 has a lower rate of metabolite (96B) formation in comparison to the undeuterated form (95A). In the combined substrates (competition) experiment, Example 96 showed a similar trend when compared to the individual substrate incubations. Example 96 showed a decreased intrinsic clearance (increased half-life=T$_{1/2}$) in comparison to its corresponding undeuterated form (95A), and has a lower rate of metabolite formation in comparison to the undeuterated form (95A).

Human Liver Microsomes Enzyme Kinetics

Incubations (in triplicate) contained 95A or 96 (1-1000 μM, final concentrations), pooled human liver microsomes (BD Biosciences, Bedford, Mass., 0.25 protein concentration, NADPH (1.3 mM), magnesium chrolide (5 mM) and potassium phosphate buffer (100 mM, pH 7.4). The final reaction volume (100 μL) contained 1 acetonitrile. The incubations were conducted at 37° C. At time points of 15 minutes for 95A, or 30 min for 96, 50 μL of incubate was quenched by the addition of 200 μL of cold acetonitrile containing 0.1% formic acid (v/v) and mass spectrometry (MS) internal standard. Quenched samples were vortexed for 1 minute followed by centrifugation at 3000 rpm for 5 minutes at room temperature (Allegra X-12R, Beckman Coulter, Fullerton, Calif.). The supernatant (150 μL) was placed into a clean injection sample block and dried down under nitrogen gas, then reconstituted with 150 μL of water containing 0.1% formic acid (v/v). The plates were capped and vortexed for 1 minute and subsequently analyzed using LC-MS/MS as described below. Formation of metabolites 95 (from substrate 95A) and 96B (from substrate 96) was quantitated using a standard curve (0.5-5000 nM) generated using a synthetic standard of substrate 95. Standard curve samples were prepared, processed, and analyzed as described above.

The kinetics of metabolite 95 or 96B formation determined in human liver microsomes are shown in Table 6. Again in this example, Example 96 has a decreased intrinsic clearance in comparison to its corresponding undeuterated form (95A) which can be beneficial (e.g., decreased dosage) while maintaining beneficial properties.

TABLE 6

Kinetic parameters for formation of Metabolites 95 or 96B from Substrates 95A or 96, respectively, in the human liver microsomes

| Example | K$_m$ (μM) | V$_{max}$ (nmol/min/mg) | CLint (μL/min/mg) |
|---|---|---|---|
| 95A | 15.23 | 0.229 | 15.06 |
| 96 | 64.93 | 0.0554 | 0.85 |

LC-MS/MS Analyses for Data Reported in Tables 4a, 4b, 5a, 5b and 6

Disappearance of substrates 95A and 96 and formation of metabolites 95 or 96B were determined using an LC-MS/MS system which is comprised of an AB Sciex 6500 triple quadrupole mass spectrometer equipped with an electrospray source (AB Sciex, Framingham, Mass.) and Agilent Technologies Infinity 1290 (Santa Clara, Calif.). A binary gradient was employed with a flow rate of 0.500 mL/min, using 0.1% formic acid in water as the aqueous mobile phase (solvent A) and 0.1% formic acid in acetonitrile (solvent B) as the organic phase. The LC gradient profile begins at 5% solvent B which was ramped to 98% B over 2 minutes and then held for 0.20 minutes and returned to initial conditions (5% B) over 0.5 minutes, for a total run time of 3.00 minutes. The analytical column used was a Phenomenex Kinetex 2.6 µm, 2.1×50 mm (Phenomenex, Torrance, Calif.), with an injection volume of 10 µL. The mass spectrometer was run under positive mode with the source temperature set to 500° C., ionization voltage set to 4.5 kV. The following MS/MS transitions were utilized: for substrate 95A (408→310), substrate 96 (411→313), metabolite 95 (424→326), and metabolite 96B (426→328). Analytes were quantified using Analyst software, version 1.6.2 or earlier (AB Sciex, Framingham, Mass.).

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A compound of Formula I

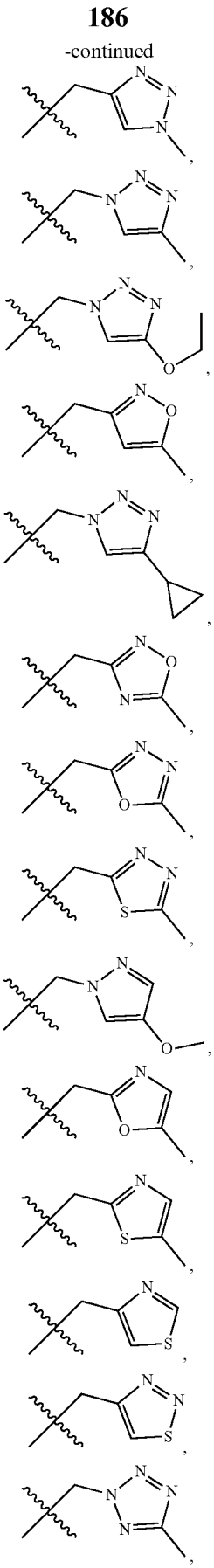

wherein
R¹ is selected from the group consisting of methyl, ethyl, cyclobutyl, cyclopentyl,

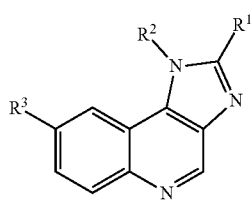

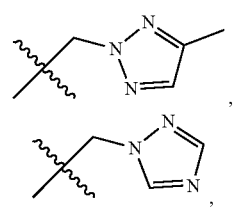

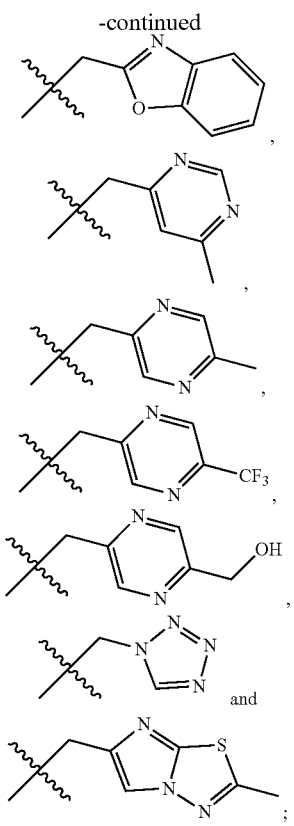

$R^2$ is selected from the group consisting of 2,2-difluoropropyl,

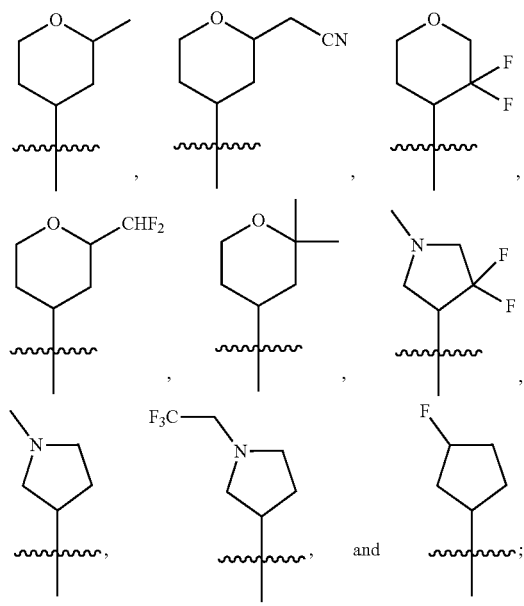

and $R^3$ is selected from the group consisting of fluoro, chloro, cyano, difluoromethyl and trifluoromethyl;

or a pharmaceutically acceptable salt, isotopically labeled derivative, or isotopically labeled derivative of the pharmaceutically acceptable salt thereof.

2. A compound selected from the group consisting of:
[(2S,4R)-4-(8-chloro-2-ethyl-1H-imidazo[4,5-c]quinolin-1-yl)tetrahydro-2H-pyran-2-yl]acetonitrile;
[(2R,4S)-4-(8-chloro-2-ethyl-1H-imidazo[4,5-c]quinolin-1-yl)tetrahydro-2H-pyran-2-yl]acetonitrile;
1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 1;
1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 2;
8-chloro-1-[(4S)-3,3-difluorotetrahydro-2H-pyran-4-yl]-2-[(5-methyl-1,2-oxazol-3-yl)methyl]-1H-imidazo[4,5-c]quinoline;
2-[(6-methylpyrimidin-4-yl)methyl]-1-[(3R)-1-methylpyrrolidin-3-yl]-1H-imidazo [4,5-c]quinoline-8-carbonitrile;
8-chloro-1-(3,3-difluorotetrahydro-2H-pyran-4-yl)-2-[(5-methylpyrazin-2-yl) methyl]-1H-imidazo[4,5-c]quinoline, ENT 1;
8-chloro-1-(3,3-difluorotetrahydro-2H-pyran-4-yl)-2-[(5-methylpyrazin-2-yl) methyl]-1H-imidazo[4,5-c]quinoline, ENT 2;
1-[(2R,4R)-2-methyltetrahydro-2H-pyran-4-yl]-2-[(1-methyl-1H-1,2,3-triazol-4-yl) methyl]-8-(trifluoromethyl)-1H-imidazo[4,5-c]quinoline;
[cis-4-(8-chloro-2-cyclobutyl-1H-imidazo[4,5-c]quinolin-1-yl)tetrahydro-2H-pyran-2-yl]acetonitrile, ENT 1;
[cis-4-(8-chloro-2-cyclobutyl-1H-imidazo[4,5-c]quinolin-1-yl)tetrahydro-2H-pyran-2-yl]acetonitrile, ENT 2;
8-(difluoromethyl)-2-[(4-methoxy-1H-pyrazol-1-yl) methyl]-1-[(2R,4R)-2-methyl tetrahydro-2H-pyran-4-yl]-1H-imidazo[4,5-c]quinoline;
8-(difluoromethyl)-2-[(5-methylpyrazin-2-yl)methyl]-1-[(2R,4R)-2-methyltetrahydro-2H-pyran-4-yl]-1H-imidazo[4,5-c]quinoline;
{8-chloro-1-[(2R,4R)-2-methyltetrahydro-2H-pyran-4-yl]-1H-imidazo[4,5-c] quinolin-2-yl}(5-methylpyrazin-2-yl)methanol, DIAST 1;
{8-chloro-1-[(2R,4R)-2-methyltetrahydro-2H-pyran-4-yl]-1H-imidazo[4,5-c]quinolin-2-yl}(5-methylpyrazin-2-yl)methanol, DIAST 2;
1-(4,4-difluoro-1-methylpyrrolidin-3-yl)-8-fluoro-2-(1H-1,2,4-triazol-1-ylmethyl)-1H-imidazo[4,5-c]quinoline, ENT 1;
1-(4,4-difluoro-1-methylpyrrolidin-3-yl)-8-fluoro-2-(1H-1,2,4-triazol-1-ylmethyl)-1H-imidazo[4,5-c]quinoline, ENT 2;
1-(4,4-difluoro-1-methylpyrrolidin-3-yl)-8-fluoro-2-[(4-methyl-1H-1,2,3-triazol-1-yl) methyl]-1H-imidazo[4,5-c]quinoline, ENT 1;
1-(4,4-difluoro-1-methylpyrrolidin-3-yl)-8-fluoro-2-[(4-methyl-1H-1,2,3-triazol-1-yl) methyl]-1H-imidazo[4,5-c]quinoline, ENT 2;
1-(4,4-difluoro-1-methylpyrrolidin-3-yl)-8-fluoro-2-[(5-methylpyrazin-2-yl)methyl]-1H-imidazo[4,5-c]quinoline, ENT 1;
1-(4,4-difluoro-1-methylpyrrolidin-3-yl)-8-fluoro-2-[(5-methylpyrazin-2-yl)methyl]-1H-imidazo[4,5-c]quinoline, ENT 2;
8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 1;
8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 2;

8-chloro-1-(4,4-difluoro-1-methylpyrrolidin-3-yl)-2-(1H-1,2,4-triazol-1-ylmethyl)-1H-imidazo[4,5-c]quinoline, ENT 1;

8-chloro-1-(4,4-difluoro-1-methylpyrrolidin-3-yl)-2-(1H-1,2,4-triazol-1-ylmethyl)-1H-imidazo[4,5-c]quinoline, ENT 2;

8-chloro-1-(3,3-difluorotetrahydro-2H-pyran-4-yl)-2-[(4-methoxy-1H-pyrazol-1-yl) methyl]-1H-imidazo[4,5-c]quinoline, ENT 1;

8-chloro-1-(3,3-difluorotetrahydro-2H-pyran-4-yl)-2-[(4-methoxy-1H-pyrazol-1-yl) methyl]-1H-imidazo[4,5-c]quinoline, ENT 2;

8-fluoro-2-[(2-methylimidazo[2,1-b][1,3,4]thiadiazol-6-yl)methyl]-1-[(2R,4R)-2-methyltetrahydro-2H-pyran-4-yl]-1H-imidazo[4,5-c]quinoline;

2-[(5-methylpyrazin-2-yl)methyl]-1-[(2R,4R)-2-methyltetrahydro-2H-pyran-4-yl]-8-(trifluoromethyl)-1H-imidazo[4,5-c]quinoline;

2-cyclopentyl-1-[(2R,4R)-2-methyltetrahydro-2H-pyran-4-yl]-1H-imidazo[4,5-c] quinoline-8-carbonitrile;

[cis-4-(8-chloro-2-methyl-1H-imidazo[4,5-c]quinolin-1-yl)tetrahydro-2H-pyran-2-yl]acetonitrile, ENT 1;

1-(4,4-difluoro-1-methylpyrrolidin-3-yl)-2-[(5-methyl-1,2,4-oxadiazol-3-yl)methyl]-1H-imidazo[4,5-c]quinoline-8-carbonitrile, ENT 1;

2-[(5-methylpyrazin-2-yl)methyl]-1-[(3R)-1-methylpyrrolidin-3-yl]-1H-imidazo[4,5-c]quinoline-8-carbonitrile;

1-[(3R)-1-methylpyrrolidin-3-yl]-2-[(5-methyl-2H-tetrazol-2-yl)methyl]-1H-imidazo [4,5-c]quinoline-8-carbonitrile;

2-[(3-methyl-1,2-oxazol-5-yl)methyl]-1-[(3R)-1-methylpyrrolidin-3-yl]-1H-imidazo [4,5-c]quinoline-8-carbonitrile;

2-[(4-methoxy-1H-pyrazol-1-yl)methyl]-1-[(3R)-1-methylpyrrolidin-3-yl]-1H-imidazo[4,5-c]quinoline-8-carbonitrile;

1-[(3R)-1-methylpyrrolidin-3-yl]-2-[(5-methyl-1,3,4-thiadiazol-2-yl)methyl]-1H-imidazo[4,5-c]quinoline-8-carbonitrile;

2-[(5-methyl-1,3-oxazol-2-yl)methyl]-1-[(3R)-1-methylpyrrolidin-3-yl]-1H-imidazo [4,5-c]quinoline-8-carbonitrile;

1-[(2R,4R)-2-methyltetrahydro-2H-pyran-4-yl]-2-{[5-(trifluoromethyl)pyrazin-2-yl]methyl}-1H-imidazo[4,5-c]quinoline-8-carbonitrile;

8-chloro-2-[(6-methylpyrimidin-4-yl)methyl]-1-[(3R)-1-methylpyrrolidin-3-yl]-1H-imidazo[4,5-c]quinoline;

2-[(4-methoxy-1H-pyrazol-1-yl)methyl]-1-[(2R,4R)-2-methyltetrahydro-2H-pyran-4-yl]-8-(trifluoromethyl)-1H-imidazo[4,5-c]quinoline;

8-chloro-2-[(5-methyl-1,2,4-oxadiazol-3-yl)methyl]-1-[(3R)-1-methylpyrrolidin-3-yl]-1H-imidazo[4,5-c]quinoline;

8-chloro-1-(4,4-difluoro-1-methylpyrrolidin-3-yl)-2-(1H-1,2,4-triazol-1-ylmethyl)-1H-imidazo[4,5-c]quinoline;

8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline;

8-chloro-1-(4,4-difluoro-1-methylpyrrolidin-3-yl)-2-[(5-methyl-1,2,4-oxadiazol-3-yl) methyl]-1H-imidazo[4,5-c]quinoline;

8-chloro-1-(3,3-difluorotetrahydro-2H-pyran-4-yl)-2-[(4-methyl-1H-1,2,3-triazol-1-yl)methyl]-1H-imidazo[4,5-c]quinoline, ENT 1;

8-chloro-2-[(4-cyclopropyl-1H-1,2,3-triazol-1-yl)methyl]-1-(4,4-difluoro-1-methylpyrrolidin-3-yl)-1H-imidazo[4,5-c]quinoline, ENT 2;

8-chloro-1-(4,4-difluoro-1-methylpyrrolidin-3-yl)-2-[(4-methyl-1H-1,2,3-triazol-1-yl) methyl]-1H-imidazo[4,5-c]quinoline, ENT 2;

8-chloro-1-(4,4-difluoro-1-methylpyrrolidin-3-yl)-2-[(5-methyl-2H-tetrazol-2-yl) methyl]-1H-imidazo[4,5-c]quinoline, ENT 1;

8-chloro-1-(4,4-difluoro-1-methylpyrrolidin-3-yl)-2-[(5-methylpyrazin-2-yl)methyl]-1H-imidazo[4,5-c]quinoline, ENT 1;

8-chloro-1-(4,4-difluoro-1-methylpyrrolidin-3-yl)-2-[(5-methyl-1,2-oxazol-3-yl) methyl]-1H-imidazo[4,5-c]quinoline, ENT 1;

8-chloro-1-(4,4-difluoro-1-methylpyrrolidin-3-yl)-2-[(5-methyl-1,2-oxazol-3-yl) methyl]-1H-imidazo[4,5-c]quinoline, ENT 2;

1-(4,4-difluoro-1-methylpyrrolidin-3-yl)-8-fluoro-2-{[4-(methoxymethyl)-1H-1,2,3-triazol-1-yl]methyl}-1H-imidazo[4,5-c]quinoline, ENT 2;

8-chloro-1-(3,3-difluorotetrahydro-2H-pyran-4-yl)-2-(1H-1,2,4-triazol-1-ylmethyl)-1H-imidazo[4,5-c]quinoline, ENT 2;

8-chloro-1-(3,3-difluorotetrahydro-2H-pyran-4-yl)-2-{[4-(methoxymethyl)-1H-1,2,3-triazol-1-yl]methyl}-1H-imidazo[4,5-c]quinoline, ENT 1;

2-[(5-methyl-1,2,4-oxadiazol-3-yl)methyl]-1-[(3R)-1-(2,2,2-trifluoroethyl)pyrrolidin-3-yl]-1H-imidazo[4,5-c]quinoline-8-carbonitrile;

2-[(4-methoxy-1H-pyrazol-1-yl)methyl]-1-[(2R,4R)-2-methyltetrahydro-2H-pyran-4-yl]-1H-imidazo[4,5-c]quinoline-8-carbonitrile;

8-chloro-1-[(2R,4R)-2-methyltetrahydro-2H-pyran-4-yl]-2-(1,3-thiazol-2-ylmethyl)-1H-imidazo[4,5-c]quinoline;

8-chloro-1-[cis-2-(difluoromethyl)tetrahydro-2H-pyran-4-yl]-2-[(5-methyl-1,2-oxazol-3-yl)methyl]-1H-imidazo[4,5-c]quinoline, ENT 1;

8-chloro-1-(3,3-difluorotetrahydro-2H-pyran-4-yl)-2-[(5-methyl-1,2-oxazol-3-yl) methyl]-1H-imidazo[4,5-c]quinoline, ENT 1;

1-[(2R,4R)-2-methyltetrahydro-2H-pyran-4-yl]-2-(1,3-thiazol-2-ylmethyl)-1H-imidazo[4,5-c]quinoline-8-carbonitrile;

8-chloro-1-[(3R)-1-methylpyrrolidin-3-yl]-2-[(4-methyl-1H-1,2,3-triazol-1-yl) methyl]-1H-imidazo[4,5-c]quinoline;

1-[(2R,4R)-2-methyltetrahydro-2H-pyran-4-yl]-2-(1,2,3-thiadiazol-4-ylmethyl)-8-(trifluoromethyl)-1H-imidazo[4,5-c]quinoline;

8-fluoro-1-[(2R,4R)-2-methyltetrahydro-2H-pyran-4-yl]-2-(1,3-thiazol-2-ylmethyl)-1H-imidazo[4,5-c]quinoline;

2-(1,3-benzoxazol-2-ylmethyl)-1-[cis-3-fluorocyclopentyl]-1H-imidazo[4,5-c] quinoline-8-carbonitrile;

1-[(2R,4R)-2-methyltetrahydro-2H-pyran-4-yl]-2-(1H-1,2,4-triazol-1-ylmethyl)-8-(trifluoromethyl)-1H-imidazo[4,5-c]quinoline;

8-chloro-2-[(5-methylpyrazin-2-yl)methyl]-1-[(3R)-1-methylpyrrolidin-3-yl]-1H-imidazo[4,5-c]quinoline;

1-[cis-3-fluorocyclopentyl]-2-[(5-methyl-1,2-oxazol-3-yl)methyl]-1H-imidazo[4,5-c]quinoline-8-carbonitrile;

1-[(2R,4R)-2-methyltetrahydro-2H-pyran-4-yl]-2-(1,3-thiazol-4-ylmethyl)-8-(trifluoromethyl)-1H-imidazo[4,5-c]quinoline;

2-[(5-methyl-1,3,4-oxadiazol-2-yl)methyl]-1-[(2R,4R)-2-methyltetrahydro-2H-pyran-4-yl]-8-(trifluoromethyl)-1H-imidazo[4,5-c]quinoline;

8-chloro-1-(2,2-dimethyltetrahydro-2H-pyran-4-yl)-2-(1H-1,2,4-triazol-1-ylmethyl)-1H-imidazo[4,5-c]quinoline;

8-chloro-1-(2,2-difluoropropyl)-2-[(4-methoxy-1H-pyrazol-1-yl)methyl]-1H-imidazo[4,5-c]quinoline;

8-fluoro-1-[(2R,4R)-2-methyltetrahydro-2H-pyran-4-yl]-2-{[5-(trifluoromethyl)pyrazin-2-yl]methyl}-1H-imidazo[4,5-c]quinoline;

1-[(2R,4R)-2-methyltetrahydro-2H-pyran-4-yl]-2-[(5-methyl-1,3,4-thiadiazol-2-yl) methyl]-8-(trifluoromethyl)-1H-imidazo[4,5-c]quinoline;

8-chloro-1-(3,3-difluorotetrahydro-2H-pyran-4-yl)-2-[(5-methyl-1,2,4-oxadiazol-3-yl)methyl]-1H-imidazo[4,5-c]quinoline, ENT 1;

2-[(6-methylpyrimidin-4-yl)methyl]-1-[(2R,4R)-2-methyltetrahydro-2H-pyran-4-yl]-8-(trifluoromethyl)-1H-imidazo[4,5-c]quinoline;

8-chloro-1-[cis-3-fluorocyclopentyl]-2-[(5-methylpyrazin-2-yl)methyl]-1H-imidazo[4,5-c]quinoline;

3-{8-chloro-1-[(2R,4R)-2-methyltetrahydro-2H-pyran-4-yl]-1H-imidazo[4,5-c]quinolin-2-yl}-2-methylpropanenitrile, DIAST 2;

8-fluoro-1-[cis-3-fluorocyclopentyl]-2-(1,2,3-thiadiazol-4-ylmethyl)-1H-imidazo[4,5-c]quinoline, ENT 2;

3-{8-chloro-1-[(2R,4R)-2-methyltetrahydro-2H-pyran-4-yl]-1H-imidazo[4,5-c]quinolin-2-yl}propanenitrile;

1-[(2R,4R)-2-methyltetrahydro-2H-pyran-4-yl]-2-[(5-methyl-2H-tetrazol-2-yl)methyl]-8-(trifluoromethyl)-1H-imidazo[4,5-c]quinoline;

8-chloro-1-(4,4-difluoro-1-methylpyrrolidin-3-yl)-2-[(4-methyl-1H-1,2,3-triazol-1-yl)methyl]-1H-imidazo[4,5-c]quinoline;

8-chloro-1-(4,4-difluoro-1-methylpyrrolidin-3-yl)-2-(1H-tetrazol-1-ylmethyl)-1H-imidazo[4,5-c]quinoline;

8-chloro-1-(4,4-difluoro-1-methylpyrrolidin-3-yl)-2-[(1-methyl-1H-1,2,4-triazol-3-yl) methyl]-1H-imidazo[4,5-c]quinoline;

1-(4,4-difluoro-1-methylpyrrolidin-3-yl)-8-fluoro-2-[(2-methylimidazo[2,1-b][1,3,4]thiadiazol-6-yl)methyl]-1H-imidazo[4,5-c]quinoline, ENT 1;

8-chloro-1-(4,4-difluoro-1-methylpyrrolidin-3-yl)-2-(1H-tetrazol-1-ylmethyl)-1H-imidazo[4,5-c]quinoline, ENT 2;

8-chloro-1-(4,4-difluoro-1-methylpyrrolidin-3-yl)-2-[(4-methyl-2H-1,2,3-triazol-2-yl) methyl]-1H-imidazo[4,5-c]quinoline, ENT 1;

8-chloro-1-(4,4-difluoro-1-methylpyrrolidin-3-yl)-2-[(5-methyl-1,2,4-oxadiazol-3-yl) methyl]-1H-imidazo[4,5-c]quinoline, ENT 1;

8-chloro-1-(4,4-difluoro-1-methylpyrrolidin-3-yl)-2-[(5-methyl-1,3,4-thiadiazol-2-yl)methyl]-1H-imidazo[4,5-c]quinoline, ENT 2;

8-(difluoromethyl)-1-[(2R,4R)-2-methyltetrahydro-2H-pyran-4-yl]-2-[(4-methyl-1H-1,2,3-triazol-1-yl)methyl]-1H-imidazo[4,5-c]quinoline;

8-(difluoromethyl)-2-[(5-methyl-1,2-oxazol-3-yl)methyl]-1-[(2R,4R)-2-methyltetrahydro-2H-pyran-4-yl]-1H-imidazo[4,5-c]quinoline;

8-chloro-1-(3,3-difluorotetrahydro-2H-pyran-4-yl)-2-[(5-methyl-1,3,4-thiadiazol-2-yl)methyl]-1H-imidazo[4,5-c]quinoline, ENT 1;

8-chloro-1-(3,3-difluorotetrahydro-2H-pyran-4-yl)-2-(1H-1,2,4-triazol-1-ylmethyl)-1H-imidazo[4,5-c]quinoline, ENT 1;

8-chloro-2-[(4-cyclopropyl-1H-1,2,3-triazol-1-yl)methyl]-1-(3,3-difluorotetrahydro-2H-pyran-4-yl)-1H-imidazo[4,5-c]quinoline; and

[5-({8-chloro-1-[(2R,4R)-2-methyltetrahydro-2H-pyran-4-yl]-1H-imidazo[4,5-c]quinolin-2-yl} methyl)pyrazin-2-yl]methanol or a pharmaceutically acceptable salt thereof.

3. The compound of claim 2 which is selected from the group consisting of 8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 2;

8-chloro-1-(4,4-difluoro-1-methylpyrrolidin-3-yl)-2-(1H-1,2,4-triazol-1-ylmethyl)-1H-imidazo[4,5-c]quinoline, ENT 1;

2-[(6-methylpyrimidin-4-yl)methyl]-1-[(3R)-1-methylpyrrolidin-3-yl]-1H-imidazo[4,5-c]quinoline-8-carbonitrile;

8-chloro-1-(3,3-difluorotetrahydro-2H-pyran-4-yl)-2-[(5-methylpyrazin-2-yl)methyl]-1H-imidazo[4,5-c]quinoline, ENT 2;

1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 2;

1-[(2R,4R)-2-methyltetrahydro-2H-pyran-4-yl]-2-[(1-methyl-1H-1,2,3-triazol-4-yl)methyl]-8-(trifluoromethyl)-1H-imidazo[4,5-c]quinoline;

[(2S,4R)-4-(8-chloro-2-ethyl-1H-imidazo[4,5-c]quinolin-1-yl)tetrahydro-2H-pyran-2-yl]acetonitrile;

8-(difluoromethyl)-2-[(5-methylpyrazin-2-yl)methyl]-1-[(2R,4R)-2-methyltetrahydro-2H-pyran-4-yl]-1H-imidazo[4,5-c]quinoline;

8-chloro-1-[(4S)-3,3-difluorotetrahydro-2H-pyran-4-yl]-2-[(5-methyl-1,2-oxazol-3-yl)methyl]-1H-imidazo[4,5-c]quinoline;

1-(4,4-difluoro-1-methylpyrrolidin-3-yl)-2-[(5-methyl-1,2,4-oxadiazol-3-yl)methyl]-1H-imidazo[4,5-c]quinoline-8-carbonitrile, ENT 1;

8-fluoro-2-[(2-methylimidazo[2,1-b][1,3,4]thiadiazol-6-yl)methyl]-1-[(2R,4R)-2-methyltetrahydro-2H-pyran-4-yl]-1H-imidazo[4,5-c]quinoline;

2-[(5-methylpyrazin-2-yl)methyl]-1-[(3R)-1-methylpyrrolidin-3-yl]-1H-imidazo[4,5-c]quinoline-8-carbonitrile;

1-[(3R)-1-methylpyrrolidin-3-yl]-2-[(5-methyl-1,3,4-thiadiazol-2-yl)methyl]-1H-imidazo[4,5-c]quinoline-8-carbonitrile;

1-[(3R)-1-methylpyrrolidin-3-yl]-2-[(5-methyl-2H-tetrazol-2-yl)methyl]-1H-imidazo[4,5-c]quinoline-8-carbonitrile;

2-[(5-methylpyrazin-2-yl)methyl]-1-[(2R,4R)-2-methyltetrahydro-2H-pyran-4-yl]-8-(trifluoromethyl)-1H-imidazo[4,5-c]quinoline;

[cis-4-(8-chloro-2-cyclobutyl-1H-imidazo[4,5-c]quinolin-1-yl)tetrahydro-2H-pyran-2-yl]acetonitrile, ENT 2;

1-(4,4-difluoro-1-methylpyrrolidin-3-yl)-8-fluoro-2-[(5-methylpyrazin-2-yl)methyl]-1H-imidazo[4,5-c]quinoline, ENT 1;

1-(4,4-difluoro-1-methylpyrrolidin-3-yl)-8-fluoro-2-[(4-methyl-1H-1,2,3-triazol-1-yl)methyl]-1H-imidazo[4,5-c]quinoline, ENT 2; and 1-(4,4-difluoro-1-methylpyrrolidin-3-yl)-8-fluoro-2-(1H-1,2,4-triazol-1-ylmethyl)-1H-imidazo[4,5-c]quinoline, ENT 2;

or a pharmaceutically acceptable salt thereof.

4. The compound of claim 3 which is selected from the group consisting of 8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 2;

8-chloro-1-(4,4-difluoro-1-methylpyrrolidin-3-yl)-2-(1H-1,2,4-triazol-1-ylmethyl)-1H-imidazo[4,5-c]quinoline, ENT 1;

2-[(6-methylpyrimidin-4-yl)methyl]-1-[(3R)-1-methylpyrrolidin-3-yl]-1H-imidazo[4,5-c]quinoline-8-carbonitrile;

8-chloro-1-(3,3-difluorotetrahydro-2H-pyran-4-yl)-2-[(5-methylpyrazin-2-yl)methyl]-1H-imidazo[4,5-c]quinoline, ENT 2;

1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 2;

1-[(2R,4R)-2-methyltetrahydro-2H-pyran-4-yl]-2-[(1-methyl-1H-1,2,3-triazol-4-yl)methyl]-8-(trifluoromethyl)-1H-imidazo[4,5-c]quinoline;

[(2S,4R)-4-(8-chloro-2-ethyl-1H-imidazo[4,5-c]quinolin-1-yl)tetrahydro-2H-pyran-2-yl]acetonitrile;

8-(difluoromethyl)-2-[(5-methylpyrazin-2-yl)methyl]-1-[(2R,4R)-2-methyltetrahydro-2H-pyran-4-yl]-1H-imidazo[4,5-c]quinoline;

8-chloro-1-[(4S)-3,3-difluorotetrahydro-2H-pyran-4-yl]-2-[(5-methyl-1,2-oxazol-3-yl)methyl]-1H-imidazo[4,5-c]quinoline; and 1-(4,4-difluoro-1-methylpyrrolidin-3-yl)-2-[(5-methyl-1,2,4-oxadiazol-3-yl)methyl]-1H-imidazo[4,5-c]quinoline-8-carbonitrile, ENT 1;

or a pharmaceutically acceptable salt thereof.

5. The compound of claim 4 which is selected from the group consisting of 8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 2;

8-chloro-1-(4,4-difluoro-1-methylpyrrolidin-3-yl)-2-(1H-1,2,4-triazol-1-ylmethyl)-1H-imidazo[4,5-c]quinoline, ENT 1;

2-[(6-methylpyrimidin-4-yl)methyl]-1-[(3R)-1-methylpyrrolidin-3-yl]-1H-imidazo[4,5-c]quinoline-8-carbonitrile;

8-chloro-1-(3,3-difluorotetrahydro-2H-pyran-4-yl)-2-[(5-methylpyrazin-2-yl)methyl]-1H-imidazo[4,5-c]quinoline, ENT 2; and 1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 2;

or a pharmaceutically acceptable salt thereof.

6. The compound according to claim 2, wherein the compound is 8-chloro-1-(4,4-difluoro-1-methylpyrrolidin-3-yl)-2-{[4-(methoxymethyl)-1H-1,2,3-triazol-1-yl]methyl}-1H-imidazo[4,5-c]quinoline, ENT 2;

or a pharmaceutically acceptable salt thereof.

7. The compound according to claim 2, wherein the compound is 8-chloro-1-(4,4-difluoro-1-methylpyrrolidin-3-yl)-2-(1H-1,2,4-triazol-1-ylmethyl)-1H-imidazo[4,5-c]quinoline, ENT 1;

or a pharmaceutically acceptable salt thereof.

8. The compound according to claim 2, wherein the compound is 2-[(6-methylpyrimidin-4-yl)methyl]-1-[(3R)-1-methyl pyrrolidin-3-yl]-1H-imidazo[4,5-c]quinoline-8-carbonitrile;

or a pharmaceutically acceptable salt thereof.

9. The compound according to claim 2, wherein the compound is 8-chloro-1-(3,3-difluorotetrahydro-2H-pyran-4-yl)-2-[(5-methyl pyrazin-2-yl)methyl]-1H-imidazo[4,5-c]quinoline, ENT 2;

or a pharmaceutically acceptable salt thereof.

10. The compound according to claim 2, wherein the compound is 1-(4,4-difluoro-1-methylpyrrolidin-3-yl)-2-[(4-methyl-2H-1,2,3-triazol-2-yl)methyl]-1H-imidazo[4,5-c]quinoline-8-carbonitrile, ENT 2;

or a pharmaceutically acceptable salt thereof.

11. The compound according to claim 1, wherein R¹ is ethyl,

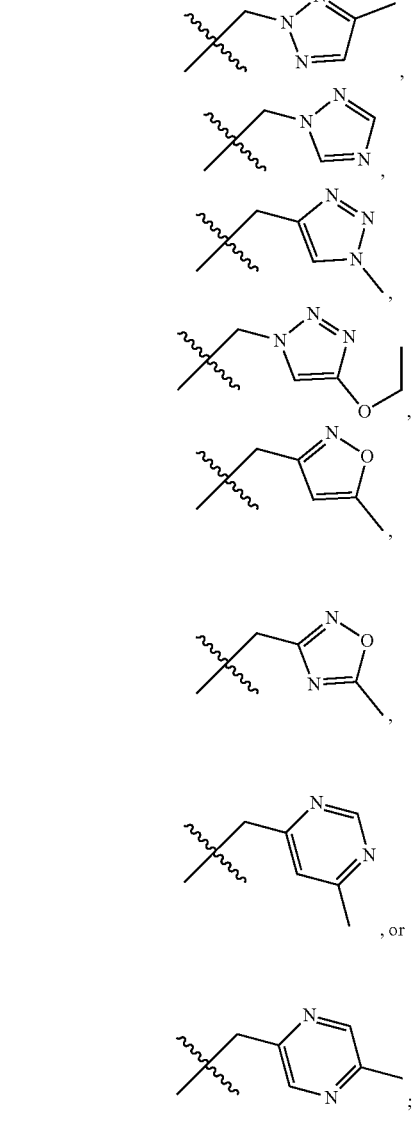

R² is

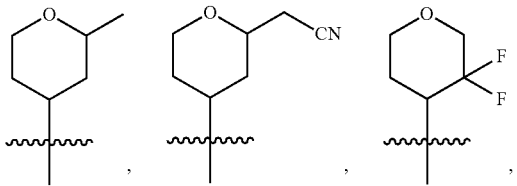

-continued

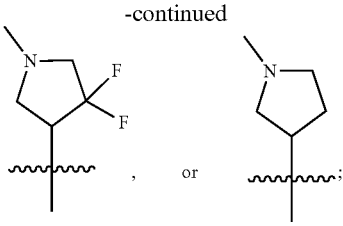

and
R³ is chloro, cyano, difluoromethyl, or trifluoromethyl,
or a pharmaceutically acceptable salt, isotopically labeled derivative, or isotopically labeled derivative of the pharmaceutically acceptable salt thereof.

12. The compound according to claim 1, wherein
R¹ is

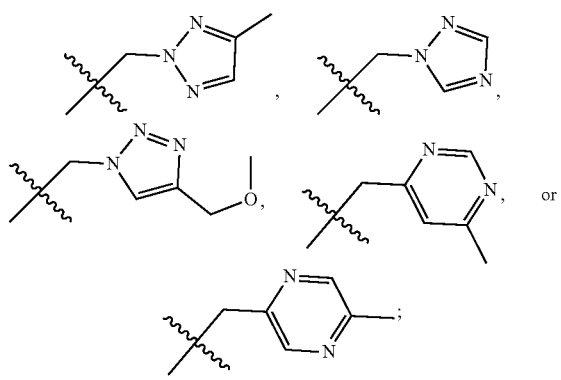

R² is

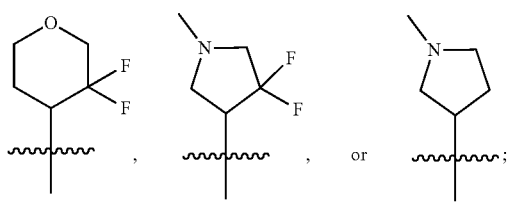

and
R³ is chloro or cyano,
or a pharmaceutically acceptable salt, isotopically labeled derivative, or isotopically labeled derivative of the pharmaceutically acceptable salt thereof.

13. The compound of claim 11, wherein
R¹ is

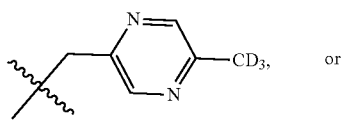

-continued

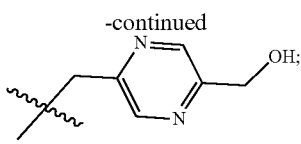

R² is

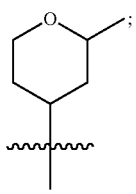 [SMILES: *C1CCOC(C)C1]

and
R³ is chloro,
or a pharmaceutically acceptable salt thereof.

14. The compound according to claim 2, wherein the compound is [5-({8-chloro-1-[(2R,4R)-2-methyltetrahydro-2H-pyran-4-yl]-1H-imidazo[4,5-c]quinolin-2-yl}methyl)pyrazin-2-yl]methanol; or a pharmaceutically acceptable salt thereof.

15. The compound according to claim 1, wherein the compound is 8-chloro-2-{[5-($^2$H$_3$)methylpyrazin-2-yl]methyl}-1-[(2R,4R)-2-methyltetrahydro-2H-pyran-4-yl]-1H-imidazo[4,5-c]quinoline; or a pharmaceutically acceptable salt thereof.

16. A pharmaceutical composition comprising a therapeutically effective amount of a compound according to claim 1, 2 or 15, or a pharmaceutically acceptable salt thereof together with a pharmaceutically acceptable carrier.

17. A method of treating a LRRK2-mediated (or LRRK2-associated) disease or disorder selected from the group consisting of Crohn's disease, Parkinson's disease, Lewy body dementia, frontotemporal dementia, corticobasal dementia, progressive supranuclear palsy, leprosy, Alzheimer's disease, tauopathy disease and Alpha-synucleinopathy in a patient, the method comprising administering to a patient in need of treatment thereof a therapeutically effective amount of a compound or pharmaceutically acceptable salt thereof according to claim 1, 2 or 15, or a pharmaceutical composition of claim 16.

18. A method of treating a LRRK2-mediated (or LRRK2-associated) disease or disorder selected from the group consisting of Crohn's disease, Parkinson's disease, Lewy body dementia, frontotemporal dementia, corticobasal dementia, progressive supranuclear palsy, leprosy, Alzheimer's disease, tauopathy disease and Alpha-synucleinopathy in a patient, the method comprising administering to a patient in need of treatment thereof a pharmaceutical composition of claim 16.

* * * * *